(12) United States Patent
Chapoux et al.

(10) Patent No.: US 10,106,544 B2
(45) Date of Patent: Oct. 23, 2018

(54) 1,2-DIHYDRO-3H-PYRROLO[1,2-C] IMIDAZOL-3-ONE DERIVATIVES AND THEIR USE AS ANTIBACTERIAL AGENTS

(71) Applicant: IDORSIA PHARMACEUTICALS LTD, Allschwil (CH)

(72) Inventors: Gaelle Chapoux, Allschwil (CH); Jean-Christophe Gauvin, Allschwil (CH); Azely Mirre, Allschwil (CH); Philippe Panchaud, Allschwil (CH); Christine Schmitt, Allschwil (CH); Jean-Luc Specklin, Allschwil (CH); Jean-Philippe Surivet, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 15/123,184

(22) PCT Filed: Mar. 3, 2015

(86) PCT No.: PCT/EP2015/054358
§ 371 (c)(1),
(2) Date: Sep. 1, 2016

(87) PCT Pub. No.: WO2015/132228
PCT Pub. Date: Sep. 11, 2015

(65) Prior Publication Data
US 2017/0107223 A1   Apr. 20, 2017

(30) Foreign Application Priority Data

Mar. 4, 2014  (EP) ..................................... 14157636

(51) Int. Cl.
C07D 487/04  (2006.01)
(52) U.S. Cl.
CPC .................. C07D 487/04 (2013.01)
(58) Field of Classification Search
None
See application file for complete search history.

(56) References Cited

U.S. PATENT DOCUMENTS 8,809,333 B2 * 8/2014 Brown ................. C07D 231/12
514/249
2007/0287708 A1  12/2007 Cole et al.

FOREIGN PATENT DOCUMENTS

| EP | 2 418 203 A1 | 2/2012 |
|---|---|---|
| JP | 2008-001635 A | 1/2008 |
| WO | WO 2003/077914 A1 | 9/2003 |
| WO | WO 2005/103032 A2 | 11/2005 |
| WO | WO 2006/063281 A2 | 6/2006 |
| WO | WO 2010/135536 A2 | 11/2010 |
| WO | WO 2011/021209 A1 | 2/2011 |
| WO | WO 2011/045703 A2 | 4/2011 |
| WO | WO 2011/073845 A1 | 6/2011 |
| WO | WO 2012/093809 A2 | 7/2012 |
| WO | WO 2012/120397 A1 | 9/2012 |
| WO | WO 2012/137094 A1 | 10/2012 |
| WO | WO 2012/137099 A1 | 10/2012 |
| WO | WO 2012/154204 A1 | 11/2012 |
| WO | WO 2013/092674 A1 | 6/2013 |
| WO | WO 2013/170030 A1 | 11/2013 |
| WO | WO 2013/170165 A1 | 11/2013 |
| WO | WO 2014/165075 A1 | 10/2014 |
| WO | WO 2015/036964 A1 | 3/2015 |
| WO | WO 2015/091741 A1 | 6/2015 |
| WO | WO 2015/173329 A1 | 11/2015 |
| WO | WO 2017/025562 A1 | 2/2017 |
| WO | WO 2017/036968 A1 | 3/2017 |
| WO | WO 2017/037039 A1 | 3/2017 |
| WO | WO 2017/037221 A1 | 3/2017 |
| WO | WO 2017/098440 A1 | 6/2017 |

OTHER PUBLICATIONS

Abdel-Magid et al., "Reductive Amination of Aldehydes and Ketones with Sodium Triacetoxyborohydride. Studies on Direct and Indirect Reductive Amination Procedures," J. Org. Chem., vol. 61, 1996, pp. 3849-3862.

(Continued)

*Primary Examiner* — Po-Chih Chen
(74) *Attorney, Agent, or Firm* — Arent Fox LLP

(57) ABSTRACT

The invention relates to antibacterial compounds of formula I

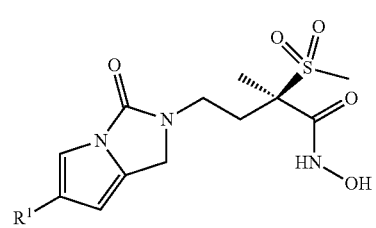

wherein $R^1$ is one of the groups represented below

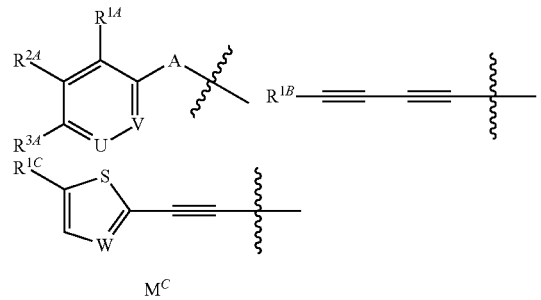

wherein A is a bond, CH=CH or C≡C; U is N or CH; V is N or CH; W represents N or CH;
and $R^{1A}$, $R^{2A}$, $R^{3A}$, $R^{1B}$ and $R^{1C}$ are as defined in the claims; and salts thereof.

15 Claims, No Drawings

(56) References Cited

OTHER PUBLICATIONS

Allen et al., "Oxaziridine-Mediated Intramolecular Amination of sp3-Hybridized C—H Bonds," J. Am. Chem. Soc. vol. 131, 2009, pp. 12560-12561.
Bellina et al., "Palladium Catalysts for the Suzuki Cross-Coupling Reaction: An Overview of Recent Advances," Synthesis, 2004, pp. 2419-2440.
Benz, "Synthesis of Amides and Related Compounds," Comprehensive Organic Synthesis, B.M. Trost, I. Fleming, Eds; Pergamon Press: New York (1991), vol. 6, pp. 381-417.
Chai et al., "Gas-Phase Nucleophilic Aromatic Substitution between Piperazine and Halobenzyl Cations: Reactivity of the Methylene Arenium Form of Benzyl Cations," Chem. Eur. J., vol. 17, 2011, pp. 10820-10824.
Fu, "The Development of Versatile Methods for Palladium-Catalyzed Coupling Reactions of Aryl Electrophiles through the Use of P(t-BU)3 and PCY3 as Ligands," Accounts of Chemical Research, vol. 41, Nov. 2008, pp. 1555-1564.
International Search Report issued in PCT/EP2015/054358 dated Apr. 2, 2015.
Kantchev et al., "Pd-N-Heterocyclic Carbene (NHC) Catalysts for Cross-Coupling Reactions," Aldrichimica ACTA, vol. 39, 2006, pp. 97-111.
Larock, Comprehensive Organic Transformations. A guide to Functional Group Preparations, 2nd Edition (1999), sectional nitriles, carboxylic acids and derivatives, p. 1941-1949 (Wiley-VC; New York, Chichester, Weinheim, Brisbane, Singapore, Toronto).
Marmer et al., "The Preparation and Reactions of Novel O-Acylhydroxylamines," J. Org. Chem., vol. 37, 1972, pp. 3520-3523.
Mauger et al., "Synthetic Applications of Buchwald's Phosphines in Palladium-Catalyzed Aromatic-Bond-Forming Reactions," Aldrichimica ACTA, vol. 39, 2006, pp. 17-24.
Methods of Dilution Antimicrobial Susceptibility Tests for Bacteria that Grow Aerobically, Approved Standard, 7th ed., Clinical and Laboratory Standards Institute (CLSI) Document M7-A7, Wayne, PA, USA (2006).
Miyaura et al., "Palladium-Catalyzed Cross-Coupling Reactions of Organoboron Compounds," Chem. Rev., vol. 95, 1995, pp. 2457-2483.
Montgomery et al., "Pyridone Methylsulfone Hydroxamate LpxC inhibitors for the Treatment of Serious Gram-Negative Infections," Journal of Medical Chemistry, 2012, vol. 55, pp. 1662-1670.
Perner et al., "Synthesis and biological evaluation of 6,7-disubstitued 4-aminopyrido [2,3-d]pyrimidines as adenosine kinase inhibitors," Bioorganic & Medicinal Chemistry Letters, vol. 15, 2015, pp. 2803-2807.
Reddy et al., "Mild and efficient oxy-iodination of alkynes and phenols and potassium iodide and tert-butyl hydroperoxide," Tetrahedron Letters, vol. 51, 2010, pp. 2170-2173.
Sakagami et al., "Synthesis, in vitro pharmacology, and pharmacokinetic profiles of 2-[1 amino-1-carboxy-2-(9H-xanthen-9-yb-ethyl]-1-fluoro-cyclopropanecarboxlic acid and its 6-heptyl ester, a potent mGluR2 antagonist," Bioorg., Med. Chem., vol. 16, 2008, pp. 4359-4366.
Sanford et al, "The Sanford Guide to Antimicrobial Therapy", 26th Edition, (Antimicrobial Therapy, Inc., 1996), pp. 1-4.
Sleveland et al, "Synthesis of Phenylboroic Acids in Continuous Flow by Means of a Multijet Oscillating Disc Reactor System Operating at Cryogenic Temperature," Organic Process Research & Development (2012), 16, 1121-1130.
Smith III et al, Tetrahedron (2009), 65(33), 6470-6488.
Sonogashira, K. In Metal-Catalyzed Reactions, Diederich, F., Stang, P.J., Eds.; Wiley-VCH: New York (1998), pp. 203-229.
Stahl et al., Handbook of Pharmaceutical Salts, 2008, pp. 329-350.
Surivet et al, J. Med. Chem. (2013), 56, 7396-7415.
T.W. Greene, P.G.M. Wuts, Protecting Groups in Organic Synthesis, 3rd Ed, 1999, pp. 23-441 (Publisher: John Wiley and Songs, Inc., New York, N.Y.).
Tsuda et al., Chem. Pharm. Bull. (2003), 51, 448-451.
Wang et al., J. Org. Chem. (2001), 66, 2146-2148.
Wouters et al, Pharmaceutical Salts and Co-crystals, RSC Publishing (2012), pp. 1-10.
Co-pending U.S. Appl. No. 15/528,407, filed May 19, 2017.
U.S. Appl. No. 15/311,758, filed Nov. 16, 2016.
Co-pending U.S. Appl. No. 15/751,596, filed Feb. 9, 2018.
Co-pending U.S. Appl. No. 15/755,411, filed Feb. 26, 2018.
Co-pending U.S. Appl. No. 15/755,893, filed Feb. 27, 2018.
Co-pending U.S. Appl. No. 15/756,366, filed Feb. 28, 2018.

* cited by examiner

1,2-DIHYDRO-3H-PYRROLO[1,2-C] IMIDAZOL-3-ONE DERIVATIVES AND THEIR USE AS ANTIBACTERIAL AGENTS

CROSS REFERENCE TO RELATED APPLICATION

This application is a 35 U.S.C. 371 National Phase of PCT Application No. PCT/EP2015/054358 filed Mar. 3, 2015, which claims priority to European Patent Application No. 14157636.3 filed Mar. 4, 2014.

The present invention concerns antibacterial 1,2-dihydro-3H-pyrrolo[1,2-c]imidazol-3-one derivatives, pharmaceutical compositions containing them and uses of these compounds in the manufacture of medicaments for the treatment of bacterial infections. These compounds are useful antimicrobial agents effective against a variety of human and veterinary pathogens, especially Gram-negative aerobic and anaerobic bacteria. The compounds of the present invention can optionally be employed in combination, either sequentially or simultaneously, with one or more therapeutic agents effective against bacterial infections.

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immune-compromised patients.

In hospital settings, an increasing number of strains of *Staphylococcus aureus, Streptococcus pneumoniae, Enterococcus* spp., Enterobacteriaceae such as *Klebsiella pneumonia, Acinetobacter baumannii* and *Pseudomonas aeruginosa*, major sources of infections, are becoming multi-drug resistant and therefore difficult if not impossible to treat. This is particularly the case for Gram-negative organisms where the situation is getting worrisome since no novel agents have been approved for decades and the development pipeline looks empty.

Therefore, there is an important medical need for new antibacterial compounds addressing Gram-negative resistant bacteria, in particular third generation cephalosporins- and carbapenem-resistant *Klebsiella pneumoniae* and multi-drug-resistant *Pseudomonas aeruginosa* and *Acinetobacter baumannii*. One way to tackle the problem of cross resistance to established classes of antibiotics is to inhibit a new target. In this respect, LpxC, which is an essential enzyme in the biosynthesis of lipopolysaccharides (a major constituent of the outer membrane of Gram-negative bacteria), has received some attention and several patent applications relating to LpxC inhibitors have been published recently.

For example, WO 2011/045703 describes antibacterial compounds of formula (A1)

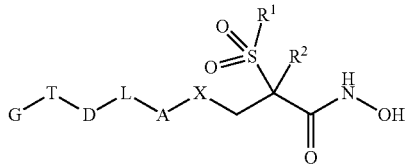

(A1)

wherein $R^1$ is $(C_1-C_3)$alkyl; $R^2$ is H or $(C_1-C_3)$alkyl; X is $CH_2$, O, NH, S or $SO_2$; A is an optionally substituted phenyl or a 6-membered heteroaryl group; L is absent or is S, SH, OH, —$(CH_2)_p$—O—$(CH_2)_n$—, —$(CH_2)_p$—O—$(CH_2)_z$—O—$(CH_2)_n$—, —S—$(CH_2)_z$— or —$(CH_2)_z$—S—; D is absent or is an optionally substituted group containing a carbocyclic or heterocyclic component with optionally a $(C_1-C_3)$alkyl chain appended; T is absent or is —$(CH_2)_z$—, —$(CH_2)_z$—O— or —O—$(CH_2)_p$—C(O)—$(CH_2)_n$—; G is absent or is an optionally substituted carbocyclic or heterocyclic group; and n and p are integers each ranging from 0 to 3 and z is an integer ranging from 1 to 3.

WO 2011/073845 and WO 2012/120397 describe antibacterial compounds with a structural formula similar to formula (A1), whereby the group corresponding to the group A of formula (A1) however respectively represents a pyridin-2-one or a fluoropyridin-2-one residue.

WO 2012/137094 describes antibacterial compounds of formulae (A2) and (A3)

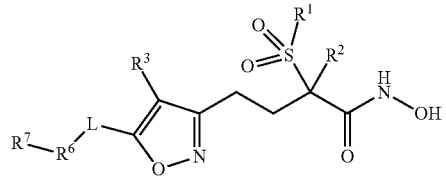

(A2)

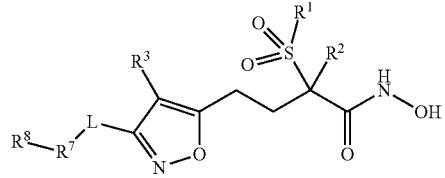

(A3)

wherein $R^1$ is $(C_1-C_3)$alkyl; $R^2$ is H or $(C_1-C_3)$alkyl; $R^3$ is H, $(C_1-C_3)$alkoxy, $(C_1-C_3)$alkyl, cyano, $(C_1-C_3)$haloalkoxy, $(C_1-C_3)$haloalkyl, halogen or hydroxy; L is a bond, —$(CH_2)_n$—, —$(CH_2)_n O(CH_2)_p$—, —$(CH_2)_n NR^4(CH_2)_p$—, —$(CH_2)_n SO_2 NR^4(CH_2)_p$—, —$(CH_2)_n CONR^4(CH_2)_p$— or —$(CH_2)_n NR^4 CO(CH_2)_p$—; $R^4$ and $R^5$ are independently H, $(C_1-C_6)$alkyl, $(C_1-C_6)$alkylcarbonyl, $(C_3-C_8)$cycloalkyl, $(C_3-C_8)$cycloalkyl$(C_1-C_6)$alkyl or formyl; n is 0, 1, 2, 3 or 4; p is 0, 1, 2, 3 or 4; $R^6$ is $(C_1-C_6)$alkoxy$(C_1-C_6)$alkyl, $(C_1-C_6)$alkoxycarbonyl, $(C_1-C_6)$alkyl-$NR^4$—$(C_1-C_6)$alkyl, $(C_1-C_6)$alkylthio$(C_1-C_6)$alkyl, $(C_1-C_6)$alkylthiocarbonyl, $(C_6-C_{12})$aryl, $(C_6-C_{12})$aryloxy, $(C_6-C_{12})$arylthio, $(C_6-C_{12})$aryl-$NR^4$—, $(C_3-C_8)$cycloalkyl, $(C_3-C_8)$cycloalkyloxy, $(C_3-C_8)$cycloalkylthio, $(C_5-C_8)$cycloalkyl-$NR^4$—, $(C_5-C_{12})$heteroaryl, $(C_5-C_{12})$heteroaryloxy, $(C_5-C_{12})$heteroarylthio, $(C_5-C_{12})$heteroaryl-$NR^4$—, $(C_3-C_{13})$heterocyclyl, $(C_3-C_{13})$heterocyclyloxy, $(C_3-C_{13})$heterocyclylthio, $(C_3-C_{13})$heterocycle-$NR^4$—, hydroxy$(C_1-C_{10})$alkyl, mercapto$(C_1-C_6)$alkyl, $(NR^4R^5)$alkyl, or $(NR^4R^5)$carbonyl; and $R^7$ is absent or is $(C_6-C_{12})$aryl, $(C_6-C_{12})$aryl$(C_1-C_6)$alkyl, $(C_3-C_8)$cycloalkyl, $(C_3-C_8)$cycloalkyl$(C_1-C_6)$alkyl, $(C_5-C_{12})$heteroaryl, $(C_5-C_{12})$heteroaryl$(C_1-C_6)$alkyl, $(C_3-C_{13})$heterocyclyl or $(C_3-C_{13})$heterocyclyl$(C_1-C_6)$alkyl.

WO 2012/137099 describes antibacterial compounds of formula (A4)

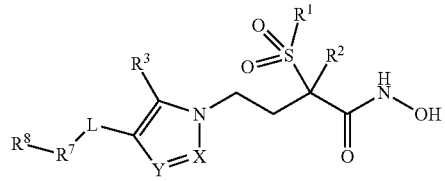

(A4)

wherein $R^1$ is $(C_1-C_3)$alkyl; $R^2$ is H or $(C_1-C_3)$alkyl; $R^3$ is H or $(C_1-C_3)$alkyl; X is N or $CR^4$; Y is N or $CR^4$; $R^4$ is H or $(C_1-C_3)$alkyl; L is a bond, $(C_2-C_6)$alkenylene, $(C_1-C_6)$ alkylene, $(C_2-C_6)$alkynylene, $—(CH_2)_nO(CH_2)_p—$, $—(CH_2)_nS(CH_2)_p—$, $—(CH_2)_nNR^5(CH_2)_p—$, $—(CH_2)_n SO_2NR^5(CH_2)_p—$, $—(CH_2)_nNR^5SO_2(CH_2)_p—$, $—(CH_2)_n CONR^5(CH_2)_p—$ or $—(CH_2)_nNR^5CO(CH_2)_p—$; $R^5$ and $R^6$ are independently H, $(C_1-C_6)$alkyl, $(C_1-C_6)$alkylcarbonyl, $(C_3-C_8)$cycloalkyl, $(C_3-C_8)$cycloalkyl$(C_1-C_6)$alkyl or formyl; n is 0, 1, 2, 3 or 4; p is 0, 1, 2, 3 or 4; $R^7$ is $(C_2-C_6)$alkenyl, $(C_1-C_6)$alkoxy, $(C_1-C_6)$alkoxy$(C_1-C_6)$alkyl, $(C_1-C_6)$alkoxycarbonyl, $(C_1-C_6)$alkyl, $(C_1-C_6)$alkylcarbonyl, $(C_1-C_6)$alkyl-$NR^5$—$(C_1-C_6)$alkyl, $(C_1-C_6)$alkylthio, $(C_1-C_6)$alkylthio$(C_1-C_6)$alkyl, $(C_1-C_6)$alkylthiocarbonyl, $(C_2-C_6)$alkynyl, $(C_6-C_{12})$aryl, $(C_6-C_{12})$aryloxy, $(C_6-C_{12})$arylthio, $(C_6-C_{12})$aryl-$NR^5$—, cyano, cyano$(C_1-C_6)$alkyl, $(C_5-C_8)$cycloalkenyl, $(C_3-C_8)$cycloalkyl, $(C_3-C_8)$cycloalkyloxy, $(C_3-C_8)$cycloalkylthio, $(C_5-C_8)$cycloalkyl-$NR^5$—$(C_5-C_{12})$heteroaryl, $(C_5-C_{12})$heteroaryloxy, $(C_5-C_{12})$heteroarylthio, $(C_5-C_{12})$heteroaryl-$NR^5$—, $(C_3-C_{13})$heterocyclyl, $(C_3-C_{13})$heterocyclyloxy, $(C_3-C_{13})$heterocyclylthio, $(C_3-C_{13})$heterocyclyl-$NR^5$—, hydroxy$(C_1-C_{10})$alkyl, mercapto$(C_1-C_6)$alkyl, $(NR^5R^6)$alkyl, or $(NR^5R^6)$carbonyl; and $R^8$ is absent or is $(C_6-C_{12})$aryl, $(C_6-C_{12})$aryl$(C_1-C_6)$alkyl, $(C_3-C_8)$cycloalkyl, $(C_3-C_8)$cycloalkyl$(C_1-C_6)$alkyl, $(C_5-C_{12})$heteroaryl, $(C_5-C_{12})$heteroaryl$(C_1-C_6)$alkyl, $(C_3-C_{13})$heterocyclyl or $(C_3-C_{13})$heterocyclyl$(C_1-C_6)$alkyl.

WO 2013/170165 describes notably antibacterial compounds of formula (A5)

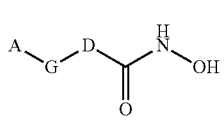
(A5)

wherein A is a substituted alkyl group, wherein at least one substituent is hydroxy, or A is a substituted cycloalkyl group, wherein at least one substituent is hydroxy or hydroxyalkyl; G is a group comprising at least one carbon-carbon double or triple bond and/or a phenyl ring; D represents a group selected from

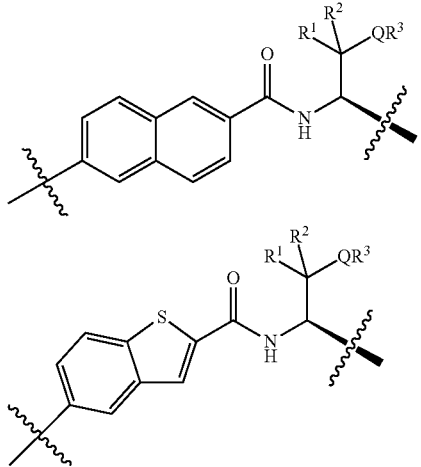

Q is O or NR, wherein R is H or an unsubstituted $(C_1-C_3)$alkyl; $R^1$ and $R^2$ independently are selected from the group consisting of H and substituted or unsubstituted $(C_1-C_3)$alkyl, or $R^1$ and $R^2$, together with the carbon atom to which they are attached, form an unsubstituted $(C_3-C_4)$ cycloalkyl group or an unsubstituted 4-6 membered heterocyclic group; and $R^3$ is selected from the group consisting of hydrogen, substituted or unsubstituted $(C_1-C_3)$alkyl, substituted or unsubstituted cycloalkyl, substituted or unsubstituted cycloalkylalkyl, substituted or unsubstituted aryl, substituted or unsubstituted arylalkyl, substituted or unsubstituted heterocyclyl, substituted or unsubstituted heterocyclylalkyl, substituted or unsubstituted heteroaryl, and substituted or unsubstituted heteroarylalkyl.

In a previous, yet unpublished patent application, we have reported antibacterial 2H-indazole derivatives of general formula (A6)

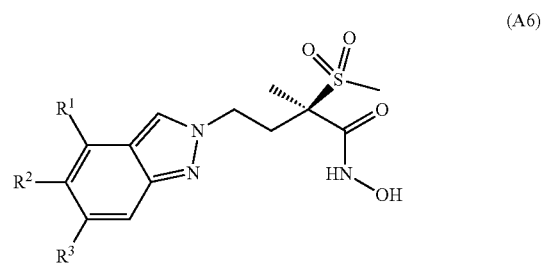
(A6)

wherein
$R^1$ is H or halogen; $R^2$ is $(C_3-C_4)$alkynyloxy or the group M; $R^3$ is H or halogen; M is one of the groups $M^A$ and $M^B$ represented below

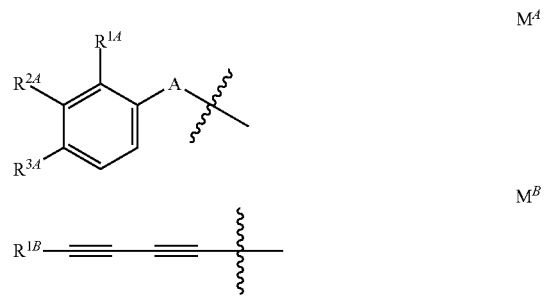

wherein A is a bond, $CH_2CH_2$, $CH=CH$ or $C\equiv C$; $R^{1A}$ represents H or halogen; $R^{2A}$ represents H, alkoxy or halogen; $R^{3A}$ represents H, alkoxy, hydroxyalkoxy, thioalkoxy, trifluoromethoxy, amino, dialkylamino, hydroxyalkyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxyalkyl)oxetan-3-yl, 3-aminooxetan-3-yl, 3-(dialkylamino)oxetan-3-yl, 3-hydroxythietan-3-yl, morpholin-4-ylalkoxy, morpholin-4-ylalkyl, oxazol-2-yl or [1,2,3]triazol-2-yl; and $R^{1B}$ represents 3-hydroxyoxetan-3-yl, 3-hydroxythietan-3-yl, hydroxyalkyl, aminoalkyl, trans-2-hydroxymethyl-cycloprop-1-yl or 4-hydroxytetrahydro-2H-pyran-4-yl.

In another previous, yet unpublished patent application, we have reported antibacterial 1H-indazole derivatives of general formula (A7)

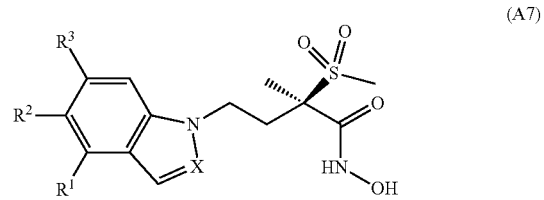
(A7)

wherein
X represents N or CH;
R¹ represents H or halogen;
R² represents $(C_3-C_4)$alkynyloxy or the group M;
R³ represents H or halogen;
M is one of the groups $M^A$ and $M^B$ represented below

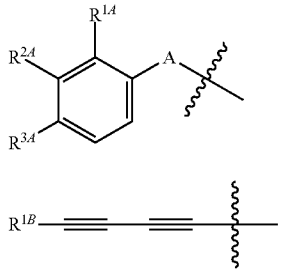

$M^A$

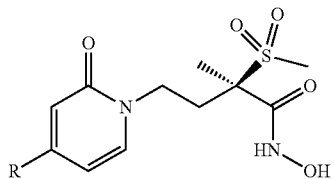

$M^B$ wherein A represents a bond, $CH_2CH_2$, CH=CH or C≡C;
$R^{1A}$ represents H or halogen;
$R^{2A}$ represents H, $(C_1-C_3)$alkoxy or halogen;
$R^{3A}$ represents H, $(C_1-C_3)$alkoxy, hydroxy$(C_1-C_4)$alkoxy, $(C_1-C_3)$thioalkoxy, trifluoromethoxy, amino, hydroxy$(C_1-C_4)$alkyl, 2-hydroxyacetamido, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy$(C_1-C_3)$alkyl)oxetan-3-yl, 3-aminooxetan-3-yl, 3-hydroxythietan-3-yl, morpholin-4-yl$(C_2-C_3)$alkoxy, morpholin-4-yl-$(C_1-C_2)$alkyl, oxazol-2-yl or [1,2,3]triazol-2-yl; and
$R^{1B}$ represents 3-hydroxyoxetan-3-yl, 3-hydroxythietan-3-yl, hydroxy$(C_1-C_3)$alkyl, amino$(C_1-C_3)$alkyl, 1-hydroxymethyl-cycloprop-1-yl or trans-2-hydroxymethyl-cycloprop-1-yl.

Besides, in Montgomery et al., *J. Med. Chem.* (2012), 55(4), 1662-1670, further LpxC inhibitors are disclosed, among others the compounds of general formula (A8)

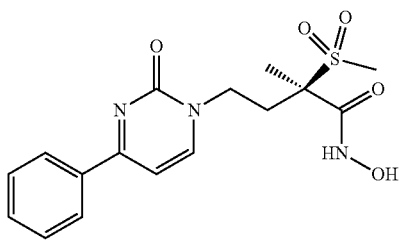

(A8)

wherein R can notably be phenylethynyl or styryl, and the compound of formula (A9)

(A9)

The instant invention provides new antibacterial 1,2-dihydro-3H-pyrrolo[1,2-c]imidazol-3-one derivatives, namely the compounds of formula I described herein.

Various embodiments of the invention are presented hereafter:
1) The invention relates to compounds of formula I

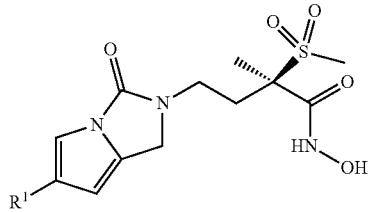

I wherein
R¹ represents the group M;
M is one of the groups $M^A$, $M^B$ and $M^C$ represented below

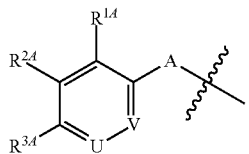

$M^A$

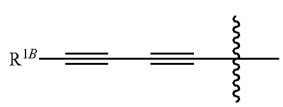

$M^B$

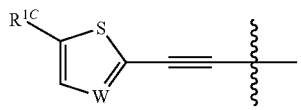

$M^C$ wherein A represents a bond, CH=CH or C≡C;
U represents N or CH;
V represents N or CH;
W represents N or CH;
$R^{1A}$ represents H or halogen;
$R^{2A}$ represents H, $(C_1-C_3)$alkoxy or halogen;
$R^{3A}$ represents H, halogen, $(C_1-C_3)$alkoxy, hydroxy$(C_2-C_4)$alkoxy, dihydroxy$(C_3-C_4)$alkoxy, $(C_1-C_3)$alkoxy$(C_1-C_3)$alkoxy, $(C_1-C_3)$thioalkoxy, trifluoromethoxy, trifluoromethyl, amino, hydroxy$(C_1-C_4)$alkyl, 1,2-dihydroxyethyl, 1-hydroxy-2,2-difluoroethyl, $(C_1-C_3)$alkoxy$(C_1-C_4)$alkyl, 2-hydroxy-1-oxoethyl, [$(C_1-C_4)$alkoxy]carbonyl, methylsulfonamidomethyl, 3-hydroxy-3-methylbut-1-yn-1-yl, 2-hydroxyacetamido, (carbamoyloxy)methyl, 1-aminocyclopropyl, 1-hydroxymethyl-cycloprop-1-yl, 1-(((dimethylglycyl)oxy)methyl)-cycloprop-1-yl, 1-aminomethyl-cycloprop-1-yl, 1-(carbamoyloxy)methyl-cycloprop-1-yl, 1-(morpholin-4-yl)methyl-cycloprop-1-yl, trans-2-hydroxymethyl-cycloprop-1-yl, 1-(hydroxymethyl)-cyclobut-1-yl, 1-(2-hydroxyacetyl)azetidin-3-yl, (1-tert-butyloxycarbonyl)-3-hydroxyazetidin-3-yl, 3-hydroxyoxetan-3-yl, 3-(hydroxy$(C_1-C_3)$alkyl)oxetan-3-yl, 3-aminooxetan-3-yl, 3-hydroxythietan-3-yl, 4-aminopiperidin-1-yl, morpholin-4-yl$(C_2-C_3)$alkoxy, [4-N—$(C_1-C_3)$alkylpiperazin-1-yl]$(C_1-C_3)$alkyl, morpholin-4-yl-$(C_1-C_2)$alkyl, [1,2,3]triazol-2-yl, 3-[hydroxy$(C_2-C_3)$alkyl]-2-oxo-imidazolidin-1-yl, (1s,3r)-(1-hydroxy-3-(hydroxymethyl)cyclobutyl)methyl, (4-hydroxypiperidinyl)methyl or (4-aminopiperidinyl)methyl;

$R^{1B}$ represents 3-hydroxyoxetan-3-yl, 3-hydroxythietan-3-yl, 3-(hydroxy($C_1$-$C_3$)alkyl)oxetan-3-yl, hydroxy($C_1$-$C_3$)alkyl, 1,2-dihydroxyethyl, amino($C_1$-$C_3$)alkyl, (dimethylamino)methyl, methylsulfonamidomethyl, 1-aminocyclopropyl, 1-hydroxymethyl-cycloprop-1-yl, 1-(carbamoyloxy)methyl-cycloprop-1-yl, 1-(((dimethylglycyl)oxy)methyl)-cycloprop-1-yl, 1-((phosphonooxy)methyl)-cycloprop-1-yl, 1-((((phosphonooxy)methoxy)carbonyl)oxymethyl)-cycloprop-1-yl, 1-((((phosphonooxy)methoxy)carbonyl)amino)-cycloprop-1-yl, trans-2-hydroxymethyl-cycloprop-1-yl, 1-fluoro-2-hydroxymethyl-cycloprop-1-yl, 2-fluoro-2-hydroxymethyl-cycloprop-1-yl, 1-methyl-2-hydroxymethyl-cycloprop-1-yl, 2-hydroxymethyl-2-methylcycloprop-1-yl, (1R*,2S*,3s*)-1,2-bis-(hydroxymethyl)-cycloprop-3-yl, 1-(hydroxymethyl)cyclobut-1-yl, 3-amino-oxetan-3-yl, 3-(hydroxy($C_1$-$C_3$)alkyl)oxetan-3-yl, 1-(2-hydroxyacetyl)-azetidin-3-yl, trans-(cis-3,4-dihydroxy)-cyclopent-1-yl, 3-hydroxymethyl-bicyclo[1,1,1]pentan-1-yl, 4-hydroxy-tetrahydro-2H-pyran-4-yl, 5-amino-tetrahydro-2H-pyran-2-yl, 3-hydroxyoxetan-3-ylmethyl, 1-cyclobutyl-2-hydroxyethyl or 1-(oxetan-3-yl)-azetidin-3-yl; and $R^{1C}$ represents 1-aminocyclopropyl or hydroxy($C_1$-$C_3$)alkyl;

and to salts (in particular pharmaceutically acceptable salts) of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a straight or branched chain alkyl group containing from one to four carbon atoms. The term "($C_x$-$C_y$)alkyl" (x and y each being an integer) refers to a straight or branched chain alkyl group containing x to y carbon atoms. For example, a ($C_1$-$C_3$)alkyl group contains from one to three carbon atoms. Representative examples of alkyl groups include methyl, ethyl, propyl, iso-propyl, n-butyl, iso-butyl, sec-butyl and tert-butyl. Preferred are methyl and ethyl. Most preferred is methyl.

The term "hydroxyalkyl", used alone or in combination, refers to an alkyl group as defined before wherein one hydrogen atom has been replaced by a hydroxy group. The term "hydroxy($C_x$-$C_y$)alkyl" (x and y each being an integer) refers to a hydroxyalkyl group as defined which contains x to y carbon atoms. For example, a hydroxy($C_1$-$C_4$)alkyl group is a hydroxyalkyl group as defined before which contains from one to four carbon atoms. Representative examples of hydroxyalkyl groups include hydroxymethyl, 2-hydroxyethyl, 2-hydroxypropyl and 3-hydroxypropyl. Preferred are hydroxymethyl and 2-hydroxyethyl. Most preferred is hydroxymethyl.

The term "aminoalkyl", used alone or in combination, refers to an alkyl group as defined before wherein one hydrogen atom has been replaced by an amino group. The term "amino($C_x$-$C_y$)alkyl" (x and y each being an integer) refers to an aminoalkyl group as defined which contains x to y carbon atoms. For example, an amino($C_1$-$C_4$)alkyl group is an aminoalkyl group as defined before which contains from one to four carbon atoms. Representative examples of aminoalkyl groups include aminomethyl, 2-aminoethyl, 2-aminopropyl, 2-amino-prop-2-yl and 3-aminopropyl. Preferred are aminomethyl, 2-aminoethyl and 2-aminopropyl. Most preferred is 2-aminoprop-2-yl.

The term "alkoxy", used alone or in combination, refers to a straight or branched chain alkoxy group containing from one to four carbon atoms. The term "($C_x$-$C_y$)alkoxy" (x and y each being an integer) refers to an alkoxy group as defined before containing x to y carbon atoms. For example, a ($C_1$-$C_3$)alkoxy group contains from one to three carbon atoms. Representative examples of alkoxy groups include methoxy, ethoxy, n-propoxy and iso-propoxy. Preferred are methoxy and ethoxy. Most preferred is methoxy.

The term "hydroxyalkoxy", used alone or in combination, refers to a straight or branched chain alkoxy group containing from one to four carbon atoms wherein one of the carbon atoms bears a hydroxy group. The term "hydroxy($C_x$-$C_y$)alkoxy" (x and y each being an integer) refers to a hydroxyalkoxy group as defined before containing x to y carbon atoms. For example, a hydroxy($C_2$-$C_4$)alkoxy group contains from two to four carbon atoms. Representative examples of hydroxyalkoxy groups include 2-hydroxyethoxy, 2-hydroxypropoxy, 3-hydroxypropoxy and 4-hydroxybutoxy. Preferred are 2-hydroxyethoxy and 3-hydroxypropoxy. Most preferred is 2-hydroxyethoxy.

The term "dihydroxyalkoxy", used alone or in combination, refers to an alkoxy group containing from three to four carbon atoms wherein two hydrogen atoms on two different carbon atoms have each been replaced by a hydroxy group. For example "dihydroxy($C_3$-$C_4$)alkoxy" refers to an alkoxy group containing from three to four carbon atoms wherein two hydrogen atoms on two different carbon atoms have each been replaced by a hydroxy group. A preferred dihydroxy($C_3$-$C_4$)alkoxy group is 2,3-dihydroxypropoxy.

The term "thioalkoxy", used alone or in combination, refers to a straight or branched chain alkoxy group containing from one to four carbon atoms wherein the oxygen atom has been replaced by a sulphur atom. The term "($C_x$-$C_y$)thioalkoxy" (x and y each being an integer) refers to a thioalkoxy group as defined before containing x to y carbon atoms. For example, a ($C_1$-$C_3$)thioalkoxy group contains from one to three carbon atoms. Representative examples of thioalkoxy groups include methylthio, ethylthio, n-propylthio and iso-propylthio. Preferred are methylthio and ethylthio. Most preferred is methylthio.

The term "3-(hydroxy($C_1$-$C_3$)alkyl)oxetan-3-yl" refers to an oxetan-3-yl group wherein the hydrogen on the carbon at position 3 of the oxetane ring has been replaced by a hydroxy($C_1$-$C_3$)alkyl group as defined before. Examples of 3-(hydroxy($C_1$-$C_3$)alkyl)oxetan-3-yl groups are 3-hydroxymethyl-oxetan-3-yl and 3-(2-hydroxyethyl)-oxetan-3-yl. The most preferred 3-(hydroxy($C_1$-$C_3$)alkyl)oxetan-3-yl group is 3-hydroxymethyl-oxetan-3-yl.

The term "morpholin-4-yl-($C_1$-$C_2$)alkyl" refers to a ($C_1$-$C_2$)alkyl group as defined before wherein one of the hydrogen atoms has been replaced by a morpholin-4-yl group. Examples of morpholin-4-yl-($C_1$-$C_2$)alkyl groups are morpholin-4-ylmethyl and 2-morpholin-4-yl-ethyl. The most preferred morpholino($C_1$-$C_2$)alkyl group is morpholin-4-ylmethyl.

The term "halogen" refers to fluorine, chlorine, bromine or iodine, and preferably to fluorine or chlorine, and most preferably to fluorine.

The term "quinolone-resistant", when used in this text, refers to a bacterial strain against which ciprofloxacin has a Minimal Inhibitory Concentration of at least 16 mg/l (said Minimal Inhibitory Concentration being measured with the standard method described in "*Methods for Dilution Antimicrobial Susceptibility Tests for Bacteria that Grow Aerobically*", Approved standard, 7th ed., a Clinical and Laboratory Standards Institute (CLSI) Document M7-A7, Wayne, Pa., USA (2006)).

The term "multi-drug resistant", when used in this text, refers to a bacterial strain against which at least three antibiotic compounds selected from three distinct antibiotic categories have Minimal Inhibitory Concentrations (MICs) over their respective clinical breakpoints, whereby said three distinct antibiotic categories are chosen among penicillins, combinations of penicillins with beta-lactamase inhibitors, cephalosporins, carbapenems, monobactams, fluoro-quinolones, aminoglycosides, phosphonic acids, tetracyclins and polymixins. Clinical breakpoints are defined according to the latest available list published by Clinical and Laboratory Standards Institute (Wayne, Pa., USA). Accordingly, clinical breakpoints are the levels of MIC at which, at a given time, a bacterium is deemed either susceptible or resistant to treatment by the corresponding antibiotic or antibiotic combination.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example '*Handbook of Pharmaceutical Salts. Properties, Selection and Use.*', P. Heinrich Stahl, Camille G. Wermuth (Eds.), Wiley-VCH (2008) and '*Pharmaceutical Salts and Co-crystals*', Johan Wouters and Luc Quéré (Eds.), RSC Publishing (2012).

In this text, a bond interrupted by a wavy line shows a point of attachment of the radical drawn to the rest of the molecule. For example, the radical drawn below

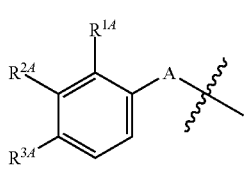

wherein A represents a bond, and each of $R^{1A}$, $R^{2A}$ and $R^{3A}$ represents H is the phenyl group.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

2) The invention notably relates to compounds of formula I according to embodiment 1) which are also compounds of formula $I_P$

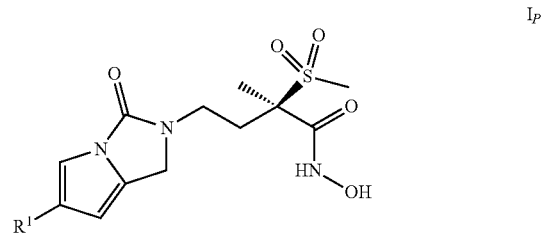

wherein
R¹ represents the group M;
M is one of the groups $M^A$ and $M^B$ represented below

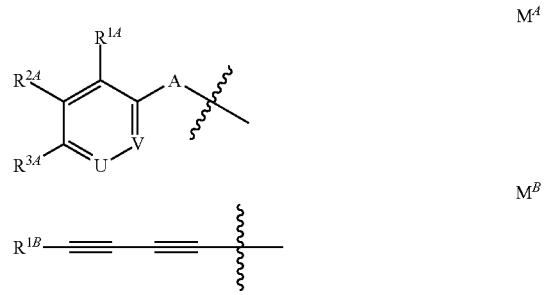

wherein A represents a bond, CH=CH or C≡C;
U represents N or CH;
V represents N or CH;
$R^{1A}$ represents H or halogen;
$R^{2A}$ represents H, ($C_1$-$C_3$)alkoxy or halogen;
$R^{3A}$ represents H, ($C_1$-$C_3$)alkoxy, hydroxy($C_2$-$C_4$)alkoxy, ($C_1$-$C_3$)alkoxy($C_1$-$C_3$)alkoxy, ($C_1$-$C_3$)thioalkoxy, trifluoromethoxy, amino, hydroxy($C_1$-$C_4$)alkyl, ($C_1$-$C_3$)alkoxy($C_1$-$C_4$)alkyl, 3-hydroxy-3-methylbut-1-yn-1-yl, 2-hydroxyacetamido, (carbamoyloxy)methyl, 1-hydroxymethyl-cycloprop-1-yl, 1-aminomethyl-cycloprop-1-yl, 1-(carbamoyloxy)methyl-cycloprop-1-yl, 1-(morpholin-4-yl)methylcycloprop-1-yl, trans-2-hydroxymethyl-cycloprop-1-yl, 1,2-dihydroxyethyl, 3-hydroxyoxetan-3-yl, 3-(hydroxy($C_1$-$C_3$)alkyl)oxetan-3-yl, 3-aminooxetan-3-yl, 3-hydroxythietan-3-yl, morpholin-4-yl($C_2$-$C_3$)alkoxy, [4-N—($C_1$-$C_3$)alkylpiperazin-1-yl]($C_1$-$C_3$)alkyl, morpholin-4-yl-($C_1$-$C_2$)alkyl, [1,2,3]triazol-2-yl or 3-[hydroxy($C_2$-$C_3$)alkyl]-2-oxo-imidazolidin-1-yl; and $R^{1B}$ represents 3-hydroxyoxetan-3-yl, 3-hydroxythietan-3-yl, 3-(hydroxy($C_1$-$C_3$)alkyl)oxetan-3-yl, hydroxy($C_1$-$C_3$)alkyl, 1,2-dihydroxyethyl, amino($C_1$-$C_3$)alkyl, 1-hydroxymethyl-cycloprop-1-yl, trans-2-hydroxymethyl-cycloprop-1-yl, trans-(cis-3,4-dihydroxy)-cyclopent-1-yl or 3-hydroxymethylbicyclo[1,1,1]pentan-1-yl;

and to salts (in particular pharmaceutically acceptable salts) of compounds of formula $I_P$.

3) The invention in particular relates to compounds of formula I according to embodiment 1) which are also compounds of formula $I_{CE}$

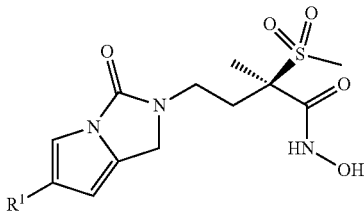

$I_{CE}$ wherein
R¹ represents the group M;
M is one of the groups $M^A$, $M^B$ and $M^C$ represented below

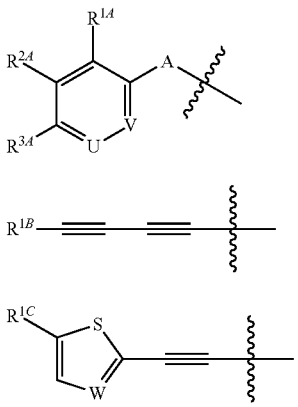

$M^A$ $M^B$ $M^C$ wherein A represents a bond, CH=CH or C≡C;
U represents CH or N;
V represents CH or N;
W represents CH or N;
$R^{1A}$ represents H or halogen;
$R^{2A}$ represents H, $(C_1\text{-}C_3)$alkoxy or halogen;
$R^{3A}$ represents H, halogen, $(C_1\text{-}C_3)$alkoxy, hydroxy$(C_2\text{-}C_4)$alkoxy, dihydroxy$(C_3\text{-}C_4)$alkoxy, $(C_1\text{-}C_3)$alkoxy$(C_1\text{-}C_3)$ alkoxy, trifluoromethyl, hydroxy$(C_1\text{-}C_4)$alkyl, 1,2-dihydroxyethyl, 1-hydroxy-2,2-difluoroethyl, $(C_1\text{-}C_3)$alkoxy $(C_1\text{-}C_4)$alkyl, 2-hydroxy-1-oxoethyl, $[(C_1\text{-}C_4)\text{alkoxy}]$ carbonyl, methylsulfonamidomethyl, 3-hydroxy-3-methylbut-1-yn-1-yl, 2-hydroxyacetamido, (carbamoyloxy) methyl, 1-aminocyclopropyl, 1-hydroxymethyl-cycloprop-1-yl, 1-(((dimethylglycyl)oxy)methyl)cyclopropyl, 1-aminomethyl-cycloprop-1-yl, 1-(carbamoyloxy)methyl-cycloprop-1-yl, 1-(morpholin-4-yl)methylcycloprop-1-yl, trans-2-hydroxymethyl-cycloprop-1-yl, 1-(hydroxymethyl)-cyclobut-1-yl, 1-(2-hydroxyacetyl)azetidin-3-yl, (1-tert-butyloxycarbonyl)-3-hydroxyazetidin-3-yl, 3-hydroxyoxetan-3-yl, 3-(hydroxy$(C_1\text{-}C_3)$alkyl)oxetan-3-yl, 3-aminooxetan-3-yl, 4-aminopiperidin-1-yl, [4-N—$(C_1\text{-}C_3)$alkylpiperazin-1-yl]$(C_1\text{-}C_3)$alkyl, morpholin-4-yl-$(C_1\text{-}C_2)$alkyl, 3-[hydroxy$(C_2\text{-}C_3)$alkyl]-2-oxo-imidazolidin-1-yl, (1s,3r)-(1-hydroxy-3-(hydroxymethyl)cyclobutyl)methyl, (4-hydroxypiperidinyl)methyl or (4-aminopiperidinyl)methyl;
$R^{1B}$ represents 3-hydroxyoxetan-3-yl, hydroxy$(C_1\text{-}C_3)$ alkyl, 1,2-dihydroxyethyl, amino$(C_1\text{-}C_3)$alkyl, (dimethylamino)methyl, methylsulfonamidomethyl, 1-aminocyclopropyl, 1-hydroxymethyl-cycloprop-1-yl, 1-(carbamoyloxy) methyl-cycloprop-1-yl, 1-(((dimethylglycyl)oxy)methyl)-cycloprop-1-yl, 1-((phosphono oxy)methyl)-cycloprop-1-yl, 1-((((phosphonooxy)methoxy)carbonyl)oxymethyl)-cycloprop-1-yl, 1-((((phosphonooxy)methoxy)carbonyl)amino)-cycloprop-1-yl, trans-2-hydroxymethyl-cycloprop-1-yl, 1-fluoro-2-hydroxymethyl-cycloprop-1-yl, 2-fluoro-2-hydroxymethyl-cycloprop-1-yl, 1-methyl-2-hydroxymethyl-cycloprop-1-yl, 2-hydroxymethyl-2-methylcycloprop-1-yl, (1R*,2S*,3s*)-1,2-bis-(hydroxymethyl)-cycloprop-3-yl, 1-(hydroxymethyl)cyclobut-1-yl, 3-amino-oxetan-3-yl, 3-(hydroxy$(C_1\text{-}C_3)$alkyl)oxetan-3-yl, 1-(2-hydroxyacetyl)-azetidin-3-yl, trans-(cis-3,4-dihydroxy)-cyclopent-1-yl, 3-hydroxymethylbicyclo[1,1,1]pentan-1-yl, 4-hydroxy-tetrahydro-2H-pyran-4-yl, 5-amino-tetrahydro-2H-pyran-2-yl, 3-hydroxyoxetan-3-ylmethyl, 1-cyclobutyl-2-hydroxyethyl or 1-(oxetan-3-yl)-azetidin-3-yl; and
$R^{1C}$ represents 1-aminocyclopropyl or hydroxy$(C_1\text{-}C_3)$ alkyl;

and to salts (in particular pharmaceutically acceptable salts) of compounds of formula $I_{CE}$.

4) The invention thus notably relates to compounds of formula I according to embodiment 3) which are also compounds of formula $I_{CEP}$

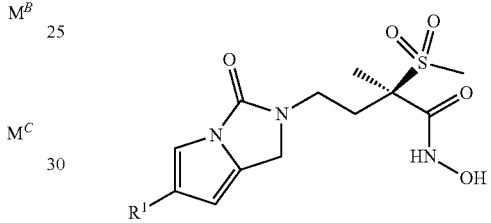

$I_{CEP}$ wherein
R¹ represents the group M;
M is one of the groups $M^A$ and $M^B$ represented below

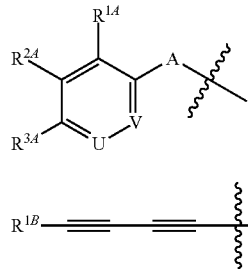

$M^A$ $M^B$ wherein A represents a bond, CH=CH or C≡C;
U represents CH or N;
V represents CH or N;
$R^{1A}$ represents H or halogen;
$R^{2A}$ represents H, $(C_1\text{-}C_3)$alkoxy or halogen;
$R^{3A}$ represents H, $(C_1\text{-}C_3)$alkoxy, hydroxy$(C_2\text{-}C_4)$alkoxy, $(C_1\text{-}C_3)$alkoxy$(C_1\text{-}C_3)$alkoxy, hydroxy$(C_1\text{-}C_4)$alkyl, $(C_1\text{-}C_3)$alkoxy$(C_1\text{-}C_4)$alkyl, 3-hydroxy-3-methylbut-1-yn-1-yl, 2-hydroxyacetamido, (carbamoyloxy)methyl, 1-hydroxymethyl-cycloprop-1-yl, 1-aminomethyl-cycloprop-1-yl, 1-(carbamoyloxy)methyl-cycloprop-1-yl, 1-(morpholin-4-yl)methylcycloprop-1-yl, trans-2-hydroxymethyl-cycloprop-1-yl, 1,2-dihydroxyethyl, 3-hydroxyoxetan-3-yl, [4-N—$(C_1\text{-}C_3)$alkylpiperazin-1-yl]$(C_1\text{-}C_3)$alkyl, morpholin-4-yl-$(C_1\text{-}C_2)$alkyl or 3-[hydroxy$(C_2\text{-}C_3)$alkyl]-2-oxo-imidazolidin-1-yl; and $R^{1B}$ represents 3-hydroxyoxetan-3-yl, hydroxy($C_1$-$C_3$) alkyl, 1,2-dihydroxyethyl, amino($C_1$-$C_3$)alkyl, 1-hydroxymethyl-cycloprop-1-yl, trans-2-hydroxymethyl-cycloprop-1-yl, trans-(cis-3,4-dihydroxy)-cyclopent-1-yl or 3-hydroxymethylbicyclo[1,1,1]pentan-1-yl;

and to salts (in particular pharmaceutically acceptable salts) of compounds of formula $I_{CEP}$.

5) In particular, the compounds of formula $I_{CE}$ according to embodiment 3) or 4) will be such that $R^1$ represents the group M and M represents the group $M^A$ or $M^B$

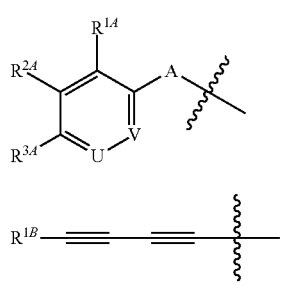

wherein A represents a bond, CH=CH or C≡C;
U represents CH or N;
V represents CH;
$R^{1A}$ represents H or fluorine;
$R^{2A}$ represents H, methoxy or fluorine;
$R^{3A}$ represents H, ($C_1$-$C_3$)alkoxy, hydroxy($C_2$-$C_4$)alkoxy, ($C_1$-$C_3$)alkoxy($C_1$-$C_3$)alkoxy, hydroxy($C_1$-$C_4$)alkyl, ($C_1$-$C_3$)alkoxy($C_1$-$C_4$)alkyl, 3-hydroxy-3-methylbut-1-yn-1-yl, 2-hydroxyacetamido, (carbamoyloxy)methyl, 1-hydroxymethyl-cycloprop-1-yl, 1-aminomethyl-cycloprop-1-yl, 1-(carbamoyloxy)methyl-cycloprop-1-yl, 1-(morpholin-4-yl)methylcycloprop-1-yl, trans-2-hydroxymethyl-cycloprop-1-yl, 1,2-dihydroxyethyl, 3-hydroxyoxetan-3-yl, [4-N—($C_1$-$C_3$)alkylpiperazin-1-yl]($C_1$-$C_3$)alkyl, morpholin-4-yl-($C_1$-$C_2$)alkyl or 3-[hydroxy($C_2$-$C_3$)alkyl]-2-oxo-imidazolidin-1-yl; and $R^{1B}$ represents 3-hydroxyoxetan-3-yl, hydroxy($C_1$-$C_3$)alkyl, 1,2-dihydroxyethyl, amino($C_1$-$C_3$)alkyl, 1-hydroxymethyl-cycloprop-1-yl, trans-2-hydroxymethyl-cycloprop-1-yl, trans-(cis-3,4-dihydroxy)-cyclopent-1-yl or 3-hydroxymethylbicyclo[1,1,1]pentan-1-yl;

6) According to one main embodiment of this invention, the compounds of formula I as defined in one of embodiments 1) to 5) will be such that $R^1$ represents the group $M^A$.

7) One sub-embodiment of embodiment 6) relates to the compounds of formula I as defined in embodiment 6) wherein A represents a bond.

8) Preferably, the compounds of formula I according to embodiment 7) will be such that U represents CH, V represents CH, $R^{1A}$ represents H or halogen, $R^{2A}$ represents H or ($C_1$-$C_3$)alkoxy and $R^{3A}$ represents H, halogen, ($C_1$-$C_3$)alkoxy or 3-hydroxy-3-methylbut-1-yn-1-yl (and in particular such that U represents CH, V represents CH, $R^{1A}$ represents H or halogen, $R^{2A}$ represents H or ($C_1$-$C_3$)alkoxy and $R^{3A}$ represents H, ($C_1$-$C_3$)alkoxy or 3-hydroxy-3-methylbut-1-yn-1-yl).

9) More preferably, the compounds of formula I according to embodiment 7) will be such that U represents CH, V represents CH, $R^{1A}$ represents H, chlorine or fluorine, $R^{2A}$ represents H or methoxy and $R^{3A}$ represents H, chlorine, fluorine, methoxy or 3-hydroxy-3-methylbut-1-yn-1-yl (and in particular such that U represents CH, V represents CH, $R^{1A}$ represents H or fluorine, $R^{2A}$ represents H or methoxy and $R^{3A}$ represents H, methoxy or 3-hydroxy-3-methylbut-1-yn-1-yl).

10) Another sub-embodiment of embodiment 6) relates to the compounds of formula I as defined in embodiment 6) wherein A represents CC.

11) Preferably, the compounds of formula I according to embodiment 10) will be such that U represents CH or N, V represents CH, $R^{1A}$ represents H or halogen, $R^{2A}$ represents H or halogen and $R^{3A}$ represents hydroxy($C_2$-$C_4$)alkoxy, hydroxy($C_1$-$C_4$)alkyl, 1,2-dihydroxyethyl, 1-hydroxy-2,2-difluoroethyl, methylsulfonamidomethyl, 3-hydroxy-3-methylbut-1-yn-1-yl, 2-hydroxyacetamido, (carbamoyloxy)methyl, 1-aminocyclopropyl, 1-hydroxymethyl-cycloprop-1-yl, 1-aminomethyl-cycloprop-1-yl, 1-(carbamoyloxy)methyl-cycloprop-1-yl, 1-(morpholin-4-yl)methylcycloprop-1-yl, trans-2-hydroxymethyl-cycloprop-1-yl, 1-(hydroxymethyl)-cyclobut-1-yl, 3-hydroxyoxetan-3-yl, 3-(hydroxy($C_1$-$C_3$)alkyl)oxetan-3-yl, 3-aminooxetan-3-yl, 4-aminopiperidin-1-yl, [4-N—($C_1$-$C_3$)alkylpiperazin-1-yl]($C_1$-$C_3$)alkyl, morpholin-4-yl-($C_1$-$C_2$)alkyl, 3-[hydroxy($C_2$-$C_3$)alkyl]-2-oxo-imidazolidin-1-yl or (4-hydroxypiperidinyl)methyl (and in particular such that U represents CH or N, V represents CH, $R^{1A}$ represents H or halogen, $R^{2A}$ represents H or halogen and $R^{3A}$ represents hydroxy($C_2$-$C_4$)alkoxy, hydroxy($C_1$-$C_4$)alkyl, 3-hydroxy-3-methylbut-1-yn-1-yl, 2-hydroxyacetamido, (carbamoyloxy)methyl, 1-hydroxymethyl-cycloprop-1-yl, 1-aminomethyl-cycloprop-1-yl, 1-(carbamoyloxy)methyl-cycloprop-1-yl, 1-(morpholin-4-yl)methylcycloprop-1-yl, trans-2-hydroxymethyl-cycloprop-1-yl, 1,2-dihydroxyethyl, 3-hydroxyoxetan-3-yl, [4-N—($C_1$-$C_3$)alkylpiperazin-1-yl]($C_1$-$C_3$)alkyl, morpholin-4-yl-($C_1$-$C_2$)alkyl or 3-[hydroxy($C_2$-$C_3$)alkyl]-2-oxo-imidazolidin-1-yl).

12) More preferably, the compounds of formula I according to embodiment 10) will be such that U represents CH, V represents CH, $R^{1A}$ represents H or fluorine, $R^{2A}$ represents H or fluorine and $R^{3A}$ represents hydroxy($C_2$-$C_4$)alkoxy, hydroxy($C_1$-$C_4$)alkyl, 1,2-dihydroxyethyl, 1-hydroxy-2,2-difluoroethyl, methylsulfonamidomethyl, 2-hydroxyacetamido, (carbamoyloxy)methyl, 1-aminocyclopropyl, 1-hydroxymethyl-cycloprop-1-yl, 1-(carbamoyloxy)methyl-cycloprop-1-yl, trans-2-hydroxymethyl-cycloprop-1-yl, 1-(hydroxymethyl)-cyclobut-1-yl, 3-hydroxyoxetan-3-yl, morpholin-4-ylmethyl or (4-hydroxypiperidinyl)methyl (and in particular such that U represents CH, V represents CH, $R^{1A}$ represents H or fluorine, $R^{2A}$ represents H or fluorine and $R^{3A}$ represents hydroxy($C_2$-$C_4$)alkoxy, hydroxy ($C_1$-$C_4$)alkyl, 2-hydroxyacetamido, (carbamoyloxy)methyl, 1-hydroxymethyl-cycloprop-1-yl, 1-(carbamoyloxy)methyl-cycloprop-1-yl, trans-2-hydroxymethyl-cycloprop-1-yl, 1,2-dihydroxyethyl, 3-hydroxyoxetan-3-yl or morpholin-4-ylmethyl).

13) Even more preferably, the compounds of formula I according to embodiment 10) will be such that U represents CH, V represents CH, $R^{1A}$ represents H or fluorine, $R^{2A}$ represents H or fluorine and $R^{3A}$ represents hydroxy($C_2$-$C_4$) alkoxy, hydroxy($C_1$-$C_4$)alkyl, 1,2-dihydroxyethyl, 2-hydroxyacetamido, (carbamoyloxy)methyl, 1-aminocyclopropyl, 1-hydroxymethyl-cycloprop-1-yl, 1-(carbamoyloxy)methyl-cycloprop-1-yl, trans-2-hydroxymethyl-cycloprop-1-yl or 3-hydroxyoxetan-3-yl (and in particular such that U represents CH, V represents CH, $R^{1A}$ represents H or fluorine, $R^{2A}$ represents H or fluorine and $R^{3A}$ represents hydroxy($C_2$-$C_4$)alkoxy, hydroxy($C_1$-$C_4$)alkyl, 2-hydroxyacetamido, (carbamoyloxy)methyl, 1-hydroxymethyl-cycloprop-1-yl, 1-(carbamoyloxy)methyl-cycloprop-1-yl, trans-2-hydroxymethyl-cycloprop-1-yl, 1,2-dihydroxyethyl or 3-hydroxyoxetan-3-yl).

14) Yet another sub-embodiment of embodiment 6) relates to the compounds of formula I as defined in embodiment 6) wherein A represents CH═CH.

15) Preferably, the compounds of formula I according to embodiment 14) will be such that U represents CH, V represents CH, $R^{1A}$ represents H, $R^{2A}$ represents H and $R^{3A}$ represents hydroxy($C_1$-$C_4$)alkyl (in particular hydroxymethyl).

16) According to another main embodiment of this invention, the compounds of formula I as defined in one of embodiments 1) to 5) will be such that $R^1$ represents the group $M^B$.

17) Preferably, the compounds of formula I according to embodiment 16) will be such that $R^{1B}$ represents 3-hydroxyoxetan-3-yl, hydroxy($C_1$-$C_3$)alkyl, amino($C_1$-$C_3$)alkyl, 1-aminocyclopropyl, 1-hydroxymethyl-cycloprop-1-yl, 1-(carbamoyloxy)methyl-cycloprop-1-yl, 1-((((phosphonooxy)methoxy)carbonyl)oxymethyl)-cycloprop-1-yl, trans-2-hydroxymethyl-cycloprop-1-yl, 1-fluoro-2-hydroxymethyl-cycloprop-1-yl, 2-fluoro-2-hydroxymethyl-cycloprop-1-yl, 1-methyl-2-hydroxymethyl-cycloprop-1-yl, 2-hydroxymethyl-2-methylcycloprop-1-yl, 1-(hydroxymethyl)cyclobut-1-yl, 1-(2-hydroxyacetyl)-azetidin-3-yl, trans-(cis-3,4-dihydroxy)-cyclopent-1-yl, 3-hydroxymethylbicyclo[1,1,1]pentan-1-yl, 5-amino-tetrahydro-2H-pyran-2-yl or 1-(oxetan-3-yl)-azetidin-3-yl (and in particular such that $R^{1B}$ represents 3-hydroxyoxetan-3-yl, hydroxy($C_1$-$C_3$)alkyl, amino($C_1$-$C_3$)alkyl, 1-hydroxymethyl-cycloprop-1-yl, trans-2-hydroxymethyl-cycloprop-1-yl, trans-(cis-3,4-dihydroxy)-cyclopent-1-yl or 3-hydroxymethylbicyclo[1,1,1]pentan-1-yl).

18) More preferably, the compounds of formula I according to embodiment 16) will be such that $R^{1B}$ represents amino($C_1$-$C_3$)alkyl, 1-aminocyclopropyl, 1-hydroxymethyl-cycloprop-1-yl, trans-2-hydroxymethyl-cycloprop-1-yl, 1-fluoro-2-hydroxymethyl-cycloprop-1-yl, 2-fluoro-2-hydroxymethyl-cycloprop-1-yl, 1-methyl-2-hydroxymethyl-cycloprop-1-yl, 2-hydroxymethyl-2-methylcycloprop-1-yl, 1-(2-hydroxyacetyl)-azetidin-3-yl, trans-(cis-3,4-dihydroxy)-cyclopent-1-yl, 3-hydroxymethylbicyclo[1,1,1]pentan-1-yl, 5-amino-tetrahydro-2H-pyran-2-yl or 1-(oxetan-3-yl)-azetidin-3-yl (and in particular such that $R^{1B}$ represents amino($C_1$-$C_3$)alkyl, 1-hydroxymethyl-cycloprop-1-yl, trans-2-hydroxymethyl-cycloprop-1-yl, trans-(cis-3,4-dihydroxy)-cyclopent-1-yl or 3-hydroxymethylbicyclo[1,1,1]pentan-1-yl).

19) Even more preferably, the compounds of formula I according to embodiment 16) will be such that $R^{1B}$ represents trans-2-hydroxymethyl-cycloprop-1-yl, 1-fluoro-2-hydroxymethyl-cycloprop-1-yl, 2-fluoro-2-hydroxymethyl-cycloprop-1-yl, 1-methyl-2-hydroxymethyl-cycloprop-1-yl, 2-hydroxymethyl-2-methylcycloprop-1-yl, trans-(cis-3,4-dihydroxy)-cyclopent-1-yl or 3-hydroxymethylbicyclo[1,1,1]pentan-1-yl (and in particular such that $R^{1B}$ represents trans-2-hydroxymethyl-cycloprop-1-yl, trans-(cis-3,4-dihydroxy)-cyclopent-1-yl or 3-hydroxymethylbicyclo[1,1,1]pentan-1-yl).

20) According to yet another main embodiment of this invention, the compounds of formula I as defined in embodiment 1) or 3) will be such that $R^1$ represents the group $M^C$.

21) According to one variant of embodiment 20), the compounds of formula I as defined in embodiment 1) or 3) will be such that W represents CH.

22) Preferably, the compounds of formula I according to embodiment 21) will be such that $R^{1C}$ represents 1-aminocyclopropyl.

23) According to the other variant of embodiment 20), the compounds of formula I as defined in embodiment 1) or 3) will be such that W represents N.

24) Preferably, the compounds of formula I according to embodiment 23) will be such that $R^{1C}$ represents hydroxy($C_1$-$C_3$)alkyl (and in particular 2-hydroxypropan-2-yl).

25) In a preferred embodiment, the compounds of formula I according to embodiment 1) or 3) will be such that $R^1$ represents the group M and M is the one of the groups $M^A$, $M^B$ and $M^C$ represented below

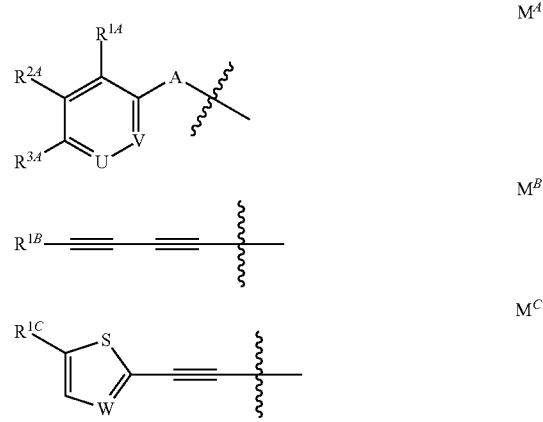

wherein A represents a bond, CH═CH or C≡C;
U represents CH or N;
V represents CH;
W represents CH or N;
$R^{1A}$ represents H or halogen;
$R^{2A}$ represents H, ($C_1$-$C_3$)alkoxy or halogen;
$R^{3A}$ represents H, halogen, ($C_1$-$C_3$)alkoxy, hydroxy($C_2$-$C_4$)alkoxy, hydroxy($C_1$-$C_4$)alkyl, 1,2-dihydroxyethyl, 1-hydroxy-2,2-difluoroethyl, methylsulfonamidomethyl, 3-hydroxy-3-methylbut-1-yn-1-yl, 2-hydroxyacetamido, (carbamoyloxy)methyl, 1-aminocyclopropyl, 1-hydroxymethyl-cycloprop-1-yl, 1-aminomethyl-cycloprop-1-yl, 1-(carbamoyloxy)methyl-cycloprop-1-yl, 1-(morpholin-4-yl)methylcycloprop-1-yl, trans-2-hydroxymethyl-cycloprop-1-yl, 1-(hydroxymethyl)-cyclobut-1-yl, 3-hydroxyoxetan-3-yl, 3-(hydroxy($C_1$-$C_3$)alkyl)oxetan-3-yl, 3-aminooxetan-3-yl, 4-aminopiperidin-1-yl, [4-N—($C_1$-$C_3$)alkylpiperazin-1-yl]($C_1$-$C_3$)alkyl, morpholin-4-yl-($C_1$-$C_2$)alkyl, 3-[hydroxy($C_2$-$C_3$)alkyl]-2-oxo-imidazolidin-1-yl or (4-hydroxypiperidinyl)methyl;
$R^{1B}$ represents 3-hydroxyoxetan-3-yl, hydroxy($C_1$-$C_3$)alkyl, amino($C_1$-$C_3$)alkyl, 1-aminocyclopropyl, 1-hydroxymethyl-cycloprop-1-yl, 1-(carbamoyloxy)methyl-cycloprop-1-yl, 1-((((phosphonooxy)methoxy)carbonyl)oxymethyl)-cycloprop-1-yl, trans-2-hydroxymethyl-cycloprop-1-yl, 1-fluoro-2-hydroxymethyl-cycloprop-1-yl, 2-fluoro-2-hydroxymethyl-cycloprop-1-yl, 1-methyl-2-hydroxymethyl-cycloprop-1-yl, 2-hydroxymethyl-2-methylcycloprop-1-yl, 1-(hydroxymethyl)cyclobut-1-yl, 1-(2-hydroxyacetyl)-azetidin-3-yl, trans-(cis-3,4-dihydroxy)-cyclopent-1-yl, 3-hydroxymethylbicyclo[1,1,1]pentan-1-yl, 5-amino-tetrahydro-2H-pyran-2-yl or 1-(oxetan-3-yl)-azetidin-3-yl; and $R^{1C}$ represents 1-aminocyclopropyl or hydroxy($C_1$-$C_3$)alkyl.

26) In a more preferred embodiment, the compounds of formula I according to embodiment 1) or 3) will be such that $R^1$ represents the group M and M is the one of the groups $M^A$, $M^B$ and $M^C$ represented below

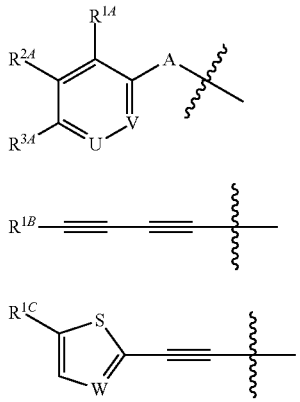

wherein A represents a bond or C≡C;
U represents CH;
V represents CH;
W represents CH;
$R^{1A}$ represents H or fluorine;
$R^{2A}$ represents H, methoxy or fluorine;
$R^{3A}$ represents H, chlorine, fluorine, ($C_1$-$C_3$)alkoxy, hydroxy($C_2$-$C_4$)alkoxy, hydroxy($C_1$-$C_4$)alkyl, 1,2-dihydroxyethyl, 1-hydroxy-2,2-difluoroethyl, methylsulfonamidomethyl, 2-hydroxyacetamido, (carbamoyloxy)methyl, 1-aminocyclopropyl, 1-hydroxymethyl-cycloprop-1-yl, 1-(carbamoyloxy)methyl-cycloprop-1-yl, trans-2-hydroxymethyl-cycloprop-1-yl, 1-(hydroxymethyl)-cyclobut-1-yl, 3-hydroxyoxetan-3-yl, morpholin-4-yl-($C_1$-$C_2$)alkyl or (4-hydroxypiperidinyl)methyl;

$R^{1B}$ represents amino($C_1$-$C_3$)alkyl, 1-aminocyclopropyl, 1-hydroxymethyl-cycloprop-1-yl, trans-2-hydroxymethyl-cycloprop-1-yl, 1-fluoro-2-hydroxymethyl-cycloprop-1-yl, 2-fluoro-2-hydroxymethyl-cycloprop-1-yl, 1-methyl-2-hydroxymethyl-cycloprop-1-yl, 2-hydroxymethyl-2-methylcycloprop-1-yl, 1-(hydroxymethyl)cyclobut-1-yl, 1-(2-hydroxyacetyl)-azetidin-3-yl, trans-(cis-3,4-dihydroxy)-cyclopent-1-yl, 3-hydroxymethylbicyclo[1,1,1]pentan-1-yl, 5-amino-tetrahydro-2H-pyran-2-yl or 1-(oxetan-3-yl)-azetidin-3-yl; and $R^{1C}$ represents 1-aminocyclopropyl.

27) In an even more preferred embodiment, the compounds of formula I according to embodiment 1) or 3) will be such that $R^1$ represents the group M and M is the one of the groups $M^A$ and $M^B$ represented below

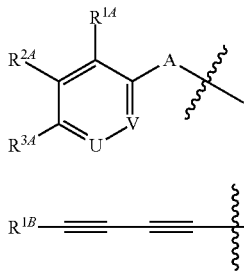

wherein A represents C≡C;
U represents CH;
V represents CH;
$R^{1A}$ represents H;
$R^{2A}$ represents H;
$R^{3A}$ represents hydroxy($C_1$-$C_4$)alkyl, (carbamoyloxy)methyl, 1-aminocyclopropyl, 1-hydroxymethyl-cycloprop-1-yl, 1-(carbamoyloxy)methyl-cycloprop-1-yl or trans-2-hydroxymethyl-cycloprop-1-yl; and $R^{1B}$ represents trans-2-hydroxymethyl-cycloprop-1-yl, 1-fluoro-2-hydroxymethyl-cycloprop-1-yl, 2-fluoro-2-hydroxymethyl-cycloprop-1-yl, 1-methyl-2-hydroxymethyl-cycloprop-1-yl, 2-hydroxymethyl-2-methylcycloprop-1-yl, trans-(cis-3,4-dihydroxy)-cyclopent-1-yl or 3-hydroxymethylbicyclo[1,1,1]pentan-1-yl.

28) According to one variant of embodiment 27), the compounds of formula I according to embodiment 27) will be such that M is the group $M^A$.

29) According to the other variant of embodiment 27), the compounds of formula I according to embodiment 27) will be such that M is the group $M^B$.

30) Besides, the compounds of formula I according to embodiment 2) or 4) will preferably be such that $R^1$ represents the group M and M is the one of the groups $M^A$ and $M^B$ represented below

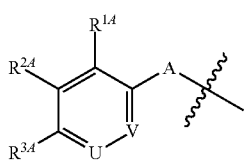

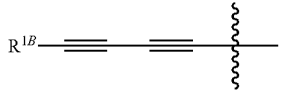

wherein A represents a bond, CH=CH or C≡C;
U represents CH or N;
V represents CH;
$R^{1A}$ represents H or halogen;
$R^{2A}$ represents H, ($C_1$-$C_3$)alkoxy or halogen;
$R^{3A}$ represents H, ($C_1$-$C_3$)alkoxy, hydroxy($C_2$-$C_4$)alkoxy, hydroxy($C_1$-$C_4$)alkyl, 3-hydroxy-3-methylbut-1-yn-1-yl, 2-hydroxyacetamido, (carbamoyloxy)methyl, 1-hydroxymethyl-cycloprop-1-yl, 1-aminomethyl-cycloprop-1-yl, 1-(carbamoyloxy)methyl-cycloprop-1-yl, 1-(morpholin-4-yl)methylcycloprop-1-yl, trans-2-hydroxymethyl-cycloprop-1-yl, 1,2-dihydroxyethyl, 3-hydroxyoxetan-3-yl, [4-N—($C_1$-$C_3$)alkylpiperazin-1-yl]($C_1$-$C_3$)alkyl, morpholin-4-yl-($C_1$-$C_2$)alkyl or 3-[hydroxy($C_2$-$C_3$)alkyl]-2-oxoimidazolidin-1-yl; and $R^{1B}$ represents 3-hydroxyoxetan-3-yl, hydroxy($C_1$-$C_3$)alkyl, amino($C_1$-$C_3$)alkyl, 1-hydroxymethyl-cycloprop-1-yl, trans-2-hydroxymethyl-cycloprop-1-yl, trans-(cis-3,4-dihydroxy)-cyclopent-1-yl or 3-hydroxymethylbicyclo[1,1,1]pentan-1-yl.

31) The compounds of formula I according to embodiment 2) or 4) will more preferably be such that $R^1$ represents the group M and M is the one of the groups $M^A$ and $M^B$ represented below

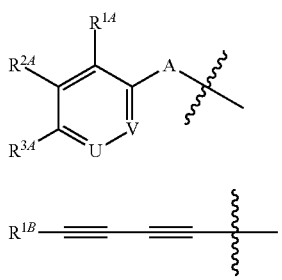

wherein A represents a bond or C≡C;
U represents CH;
V represents CH;
$R^{1A}$ represents H or fluorine;
$R^{2A}$ represents H, methoxy or fluorine;
$R^{3A}$ represents H, ($C_1$-$C_3$)alkoxy, hydroxy($C_2$-$C_4$)alkoxy, hydroxy($C_1$-$C_4$)alkyl, 2-hydroxyacetamido, (carbamoyloxy)methyl, 1-hydroxymethyl-cycloprop-1-yl, 1-(carbamoyloxy)methyl-cycloprop-1-yl, trans-2-hydroxymethyl-cycloprop-1-yl, 1,2-dihydroxyethyl, 3-hydroxyoxetan-3-yl or morpholin-4-yl-($C_1$-$C_2$)alkyl; and
$R^{1B}$ represents amino($C_1$-$C_3$)alkyl, 1-hydroxymethyl-cycloprop-1-yl, trans-2-hydroxymethyl-cycloprop-1-yl, trans-(cis-3,4-dihydroxy)-cyclopent-1-yl or 3-hydroxymethylbicyclo[1,1,1]pentan-1-yl.

32) Even more preferably, the compounds of formula I according to embodiment 2) or 4) will be such that $R^1$ represents the group M and M is the one of the groups $M^A$ and $M^B$ represented below

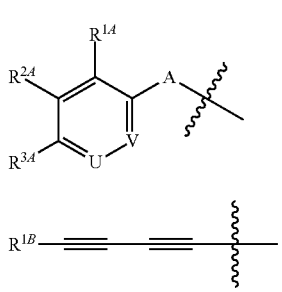

wherein A represents C≡C;
U represents CH;
V represents CH;
$R^{1A}$ represents H;
$R^{2A}$ represents H;
$R^{3A}$ represents hydroxy($C_1$-$C_4$)alkyl, (carbamoyloxy)methyl, 1-hydroxymethyl-cycloprop-1-yl, 1-(carbamoyloxy)methyl-cycloprop-1-yl or trans-2-hydroxymethyl-cycloprop-1-yl; and
$R^{1B}$ represents trans-2-hydroxymethyl-cycloprop-1-yl, trans-(cis-3,4-dihydroxy)-cyclopent-1-yl or 3-hydroxymethylbicyclo[1,1,1]pentan-1-yl.

33) According to one variant of embodiment 32), the compounds of formula I according to embodiment 32) will be such that M is the group $M^A$.

34) According to the other variant of embodiment 32), the compounds of formula I according to embodiment 32) will be such that M is the group $M^B$.

35) Another embodiment of this invention relates to compounds of formula I as defined in one of embodiments 1) to 34) as well as to isotopically labelled, especially $^2$H (deuterium) labelled compounds of formula I as defined in one of embodiments 1) to 34), which compounds are identical to the compounds of formula I as defined in one of embodiments 1) to 34) except that one or more atoms has or have each been replaced by an atom having the same atomic number but an atomic mass different from the atomic mass usually found in nature. Isotopically labelled, especially $^2$H (deuterium) labelled compounds of formula I and salts (in particular pharmaceutically acceptable salts) thereof are thus within the scope of the present invention. Substitution of hydrogen with the heavier isotope $^2$H (deuterium) may lead to greater metabolic stability, resulting e.g. in an increased in-vivo half-life, reduced dosage requirements, or an improved safety profile. In one variant of the invention, the compounds of formula I are not isotopically labelled, or they are labelled only with one or more deuterium atoms. Isotopically labelled compounds of formula I may be prepared in analogy to the methods described hereinafter, but using the appropriate isotopic variation of suitable reagents or starting materials.

36) Particularly preferred are the following compounds of formula I as defined in embodiment 1) or 2):

(R)-4-(6-(2-fluoro-4-methoxyphenyl)-3-oxo-1H-pyrrolo[1,2-c]imidazol-2(3H)-yl)-N-hydroxy-2-methyl-2-(methylsulfonyl)butanamide;

(R)-N-hydroxy-4-(6-((4-(3-hydroxyoxetan-3-yl)phenyl)ethynyl)-3-oxo-1H-pyrrolo[1,2-c]imidazol-2(3H)-yl)-2-methyl-2-(methylsulfonyl)butanamide;

(R)-N-hydroxy-4-(6-((4-(hydroxymethyl)phenyl)ethynyl)-3-oxo-1H-pyrrolo[1,2-c]imidazol-2(3H)-yl)-2-methyl-2-(methylsulfonyl)butanamide;

(R)-N-hydroxy-4-(6-((3-hydroxyoxetan-3-yl)buta-1,3-diyn-1-yl)-3-oxo-1H-pyrrolo[1,2-c]imidazol-2(3H)-yl)-2-methyl-2-(methylsulfonyl)butanamide;

(R)-N-hydroxy-4-(6-((4-((1R,2R)-2-(hydroxymethyl)cyclopropyl)phenyl)ethynyl)-3-oxo-1H-pyrrolo[1,2-c]imidazol-2(3H)-yl)-2-methyl-2-(methylsulfonyl)butanamide;

(R)-N-hydroxy-4-(6-((4-((1S,2S)-2-(hydroxymethyl)cyclopropyl)phenyl)ethynyl)-3-oxo-1H-pyrrolo[1,2-c]imidazol-2(3H)-yl)-2-methyl-2-(methylsulfonyl)butanamide;

(R)-N-hydroxy-4-(6-((4-(1-(hydroxymethyl)cyclopropyl)phenyl)ethynyl)-3-oxo-1H-pyrrolo[1,2-c]imidazol-2(3H)-yl)-2-methyl-2-(methylsulfonyl)butanamide;

(R)-4-(6-((4-(1-(aminomethyl)cyclopropyl)phenyl)ethynyl)-3-oxo-1H-pyrrolo[1,2-c]imidazol-2(3H)-yl)-N-hydroxy-2-methyl-2-(methylsulfonyl)butanamide;

(R)-N-hydroxy-4-(6-((4-(1-hydroxy-2-methylpropan-2-yl)phenyl)ethynyl)-3-oxo-1H-pyrrolo[1,2-c]imidazol-2(3H)-yl)-2-methyl-2-(methylsulfonyl)butanamide;

(R)-N-hydroxy-4-(6-((4-(2-hydroxypropan-2-yl)phenyl)ethynyl)-3-oxo-1H-pyrrolo[1,2-c]imidazol-2(3H)-yl)-2-methyl-2-(methylsulfonyl)butanamide;

(R)-4-(6-((S)-5,6-dihydroxyhexa-1,3-diyn-1-yl)-3-oxo-1H-pyrrolo[1,2-c]imidazol-2(3H)-yl)-N-hydroxy-2-methyl-2-(methylsulfonyl)butanamide;

(R)-N-hydroxy-4-(6-(5-((1S,2S)-2-(hydroxymethyl)cyclopropyl)penta-1,3-diyn-1-yl)-3-oxo-1H-pyrrolo[1,2-c]imidazol-2(3H)-yl)-2-methyl-2-(methylsulfonyl)butanamide;

(R)-N-hydroxy-4-(6-((4-((R)-1-hydroxyethyl)phenyl)ethynyl)-3-oxo-1H-pyrrolo[1,2-c]imidazol-2(3H)-yl)-2-methyl-2-(methylsulfonyl)butanamide;

(R)-N-hydroxy-4-(6-((4-((S)-1-hydroxyethyl)phenyl)ethynyl)-3-oxo-1H-pyrrolo[1,2-c]imidazol-2(3H)-yl)-2-methyl-2-(methylsulfonyl)butanamide;

(R)-N-hydroxy-4-(6-((1-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)butanamide;

(R)-N-hydroxy-4-(6-((4-(2-hydroxyethyl)phenyl)ethynyl)-3-oxo-1H-pyrrolo[1,2-c]imidazol-2(3H)-yl)-2-methyl-2-(methylsulfonyl)butanamide;

(R)-4-(6-((4-((R)-1,2-dihydroxyethyl)phenyl)ethynyl)-3-oxo-1H-pyrrolo[1,2-c]imidazol-2(3H)-yl)-N-hydroxy-2-methyl-2-(methylsulfonyl)butanamide;

(R)-4-(6-((4-((S)-1,2-dihydroxyethyl)phenyl)ethynyl)-3-oxo-1H-pyrrolo[1,2-c]imidazol-2(3H)-yl)-N-hydroxy-2-methyl-2-(methylsulfonyl)butanamide;

(R)-4-(6-((2-fluoro-4-(1-(hydroxymethyl)cyclopropyl)phenyl)ethynyl)-3-oxo-1H-pyrrolo[1,2-c]imidazol-2(3H)-yl)-N-hydroxy-2-methyl-2-(methylsulfonyl)butanamide;

(R)-N-hydroxy-4-(6-((4-(3-(2-hydroxyethyl)-2-oxoimidazolidin-1-yl)phenyl)ethynyl)-3-oxo-1H-pyrrolo[1,2-c]imidazol-2(3H)-yl)-2-methyl-2-(methylsulfonyl)butanamide;

(R)-4-(6-((3-fluoro-4-(2-hydroxyacetamido)phenyl)ethynyl)-3-oxo-1H-pyrrolo[1,2-c]imidazol-2(3H)-yl)-N-hydroxy-2-methyl-2-(methylsulfonyl)butanamide;

(R)-N-hydroxy-4-(6-((4-(2-hydroxyethoxy)phenyl)ethynyl)-3-oxo-1H-pyrrolo[1,2-c]imidazol-2(3H)-yl)-2-methyl-2-(methylsulfonyl)butanamide;

(R)-N-hydroxy-4-(6-((6-(1-(hydroxymethyl)cyclopropyl)pyridin-3-yl)ethynyl)-3-oxo-1H-pyrrolo[1,2-c]imidazol-2(3H)-yl)-2-methyl-2-(methylsulfonyl)butanamide;

(R)-N-hydroxy-4-(6-((5-(1-(hydroxymethyl)cyclopropyl)pyridin-2-yl)ethynyl)-3-oxo-1H-pyrrolo[1,2-c]imidazol-2(3H)-yl)-2-methyl-2-(methylsulfonyl)butanamide;

(R)-N-hydroxy-2-methyl-2-(methylsulfonyl)-4-(6-((4-(morpholinomethyl)phenyl)ethynyl)-3-oxo-1H-pyrrolo[1,2-c]imidazol-2(3H)-yl)butanamide;

(R)-N-hydroxy-2-methyl-2-(methylsulfonyl)-4-(6-((4-(1-(morpholinomethyl)cyclopropyl)phenyl)ethynyl)-3-oxo-1H-pyrrolo[1,2-c]imidazol-2(3H)-yl)butanamide;

(R)-N-hydroxy-4-(6-(((1R,2R)-2-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)butanamide;

(R)-4-(6-(2-fluoro-3-methoxyphenyl)-3-oxo-1H-pyrrolo[1,2-c]imidazol-2(3H)-yl)-N-hydroxy-2-methyl-2-(methylsulfonyl)butanamide;

(R)-(E)-N-hydroxy-4-(6-(4-(hydroxymethyl)styryl)-3-oxo-1H-pyrrolo[1,2-c]imidazol-2(3H)-yl)-2-methyl-2-(methylsulfonyl)butanamide;

(R)-N-hydroxy-4-(6-(4-(3-(hydroxymethyl)bicyclo[1.1.1]pentan-1-yl)cyclobuta-1,3-dien-1-yl)-3-oxo-1H-pyrrolo[1,2-c]imidazol-2(3H)-yl)-2-methyl-2-(methylsulfonyl)butanamide;

(R)-4-(6-(5-amino-5-methylhexa-1,3-diyn-1-yl)-3-oxo-1H-pyrrolo[1,2-c]imidazol-2(3H)-yl)-N-hydroxy-2-methyl-2-(methylsulfonyl)butanamide;

(R)-4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl carbamate;

(R)-4-(6-(((1S,3R,4S)-3,4-dihydroxycyclopentyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-(1-(4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)phenyl)cyclopropyl)methyl carbamate;

as well as the salts (in particular the pharmaceutically acceptable salts) thereof.

37) Also particularly preferred are the following compounds of formula I as defined in embodiment 1):

(R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl carbamate;

(R)-N-hydroxy-4-(6-(((1R,2R)-2-(hydroxymethyl)-1-methylcyclopropyl)buta-1,3-diyn-1-yl)-3-oxo-1H-pyrrolo[1,2-c]imidazol-2(3H)-yl)-2-methyl-2-(methylsulfonyl)butanamide;

(R)-(1-(4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)phenyl)cyclopropyl)methyl dimethylglycinate;

(R)-4-(6-((1-aminocyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-4-(6-((3-aminooxetan-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-N-hydroxy-4-(6-((4-(1-(hydroxymethyl)cyclobutyl)phenyl)ethynyl)-3-oxo-1H-pyrrolo[1,2-c]imidazol-2(3H)-yl)-2-methyl-2-(methylsulfonyl)butanamide;

(R)-4-(6-(2-fluoro-4-(2-hydroxyethoxy)phenyl)-3-oxo-1H-pyrrolo[1,2-c]imidazol-2(3H)-yl)-N-hydroxy-2-methyl-2-(methylsulfonyl)butanamide;

(R)-4-((4(2R,3S)-2,3-bis(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-4-(6-(4-((R)-2,3-dihydroxypropoxy)-2-fluorophenyl)-3-oxo-1H-pyrrolo[1,2-c]imidazol-2(3H)-yl)-N-hydroxy-2-methyl-2-(methylsulfonyl)butanamide;

(R)-4-(6-((4-(1,1-difluoro-2-hydroxyethyl)phenyl)ethynyl)-3-oxo-1H-pyrrolo[1,2-c]imidazol-2(3H)-yl)-N-hydroxy-2-methyl-2-(methylsulfonyl)butanamide;

(R)-N-hydroxy-4-(6-((4-(2-hydroxyacetyl)phenyl)ethynyl)-3-oxo-1H-pyrrolo[1,2-c]imidazol-2(3H)-yl)-2-methyl-2-(methylsulfonyl)butanamide;

(R)-4-(6-(5-(dimethylamino)penta-1,3-diyn-1-yl)-3-oxo-1H-pyrrolo[1,2-c]imidazol-2(3H)-yl)-N-hydroxy-2-methyl-2-(methylsulfonyl)butanamide;

methyl (R)-3-fluoro-4-(2-(4-(hydroxyamino)-3-methyl-3-(methylsulfonyl)-4-oxobutyl)-3-oxo-2,3-dihydro-1H-pyrrolo[1,2-c]imidazol-6-yl)benzoate;

(R)-4-(6-(4-chloro-2-fluorophenyl)-3-oxo-1H-pyrrolo[1,2-c]imidazol-2(3H)-yl)-N-hydroxy-2-methyl-2-(methylsulfonyl)butanamide;

(R)-4-(6-(2-chloro-4-ethoxyphenyl)-3-oxo-1H-pyrrolo[1,2-c]imidazol-2(3H)-yl)-N-hydroxy-2-methyl-2-(methylsulfonyl)butanamide;

(R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl dimethylglycinate;

(R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl dihydrogen phosphate;

(R)-4-(6-(2-chloro-4-methoxyphenyl)-3-oxo-1H-pyrrolo[1,2-c]imidazol-2(3H)-yl)-N-hydroxy-2-methyl-2-(methylsulfonyl)butanamide;

(R)-4-(6-(2-fluoro-4-(trifluoromethyl)phenyl)-3-oxo-1H-pyrrolo[1,2-c]imidazol-2(3H)-yl)-N-hydroxy-2-methyl-2-(methylsulfonyl)butanamide;

(R)-N-hydroxy-2-methyl-2-(methylsulfonyl)-4-(3-oxo-6-(2,3,4-trifluorophenyl)-1H-pyrrolo[1,2-c]imidazol-2(3H)-yl)butanamide;

(R)-4-(6-(2,3-difluoro-4-methoxyphenyl)-3-oxo-1H-pyrrolo[1,2-c]imidazol-2(3H)-yl)-N-hydroxy-2-methyl-2-(methylsulfonyl)butanamide;

(R)-N-hydroxy-4-(6-((1-(hydroxymethyl)cyclobutyl)buta-1,3-diyn-1-yl)-3-oxo-1H-pyrrolo[1,2-c]imidazol-2(3H)-yl)-2-methyl-2-(methylsulfonyl)butanamide;

((R)-N-hydroxy-4-(6-((3-(hydroxymethyl)oxetan-3-yl)buta-1,3-diyn-1-yl)-3-oxo-1H-pyrrolo[1,2-c]imidazol-2(3H)-yl)-2-methyl-2-(methylsulfonyl)butanamide;

(R)-N-hydroxy-2-methyl-4-(6-(5-(methylsulfonamido)penta-1,3-diyn-1-yl)-3-oxo-1H-pyrrolo[1,2-c]imidazol-2(3H)-yl)-2-(methylsulfonyl)butanamide;

tert-butyl (R)-3-hydroxy-3-(4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)phenyl)azetidine-1-carboxylate;

(2R)-4-(6-(5-cyclobutyl-6-hydroxyhexa-1,3-diyn-1-yl)-3-oxo-1H-pyrrolo[1,2-c]imidazol-2(3H)-yl)-N-hydroxy-2-methyl-2-(methylsulfonyl)butanamide;

(R)-N-hydroxy-4-(6-(((1R,2S)-2-(hydroxymethyl)-2-methylcyclopropyl)buta-1,3-diyn-1-yl)-3-oxo-1H-pyrrolo[1,2-c]imidazol-2(3H)-yl)-2-methyl-2-(methylsulfonyl)butanamide;

(R)-N-hydroxy-4-(6-((1-(2-hydroxyacetyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;

(R)-N-hydroxy-4-(6-(5-(3-hydroxyoxetan-3-yl)penta-1,3-diyn-1-yl)-3-oxo-1H-pyrrolo[1,2-c]imidazol-2(3H)-yl)-2-methyl-2-(methylsulfonyl)butanamide;

(R)-N-hydroxy-4-(6-((4-hydroxytetrahydro-2H-pyran-4-yl)buta-1,3-diyn-1-yl)-3-oxo-1H-pyrrolo[1,2-c]imidazol-2(3H)-yl)-2-methyl-2-(methylsulfonyl)butanamide;

(R)-4-(6-(((2S,5R)-5-aminotetrahydro-2H-pyran-2-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-4-(6-(((1R,2R)-1-fluoro-2-(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-4-(6-(((1S,2S)-1-fluoro-2-(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-4-(6-((5-(1-aminocyclopropyl)thiophen-2-yl)ethynyl)-3-oxo-1H-pyrrolo[1,2-c]imidazol-2(3H)-yl)-N-hydroxy-2-methyl-2-(methylsulfonyl)butanamide;

(R)-4-(6-((4-(3-aminooxetan-3-yl)phenyl)ethynyl)-3-oxo-1H-pyrrolo[1,2-c]imidazol-2(3H)-yl)-N-hydroxy-2-methyl-2-(methylsulfonyl)butanamide;

(R)-N-hydroxy-4-(6-((4-(3-(hydroxymethyl)oxetan-3-yl)phenyl)ethynyl)-3-oxo-1H-pyrrolo[1,2-c]imidazol-2(3H)-yl)-2-methyl-2-(methylsulfonyl)butanamide;

(R)-N-hydroxy-4-(6-((4-(2-hydroxyacetamido)phenyl)ethynyl)-3-oxo-1H-pyrrolo[1,2-c]imidazol-2(3H)-yl)-2-methyl-2-(methylsulfonyl)butanamide;

(R)-4-(6-((4-(1-aminocyclopropyl)phenyl)ethynyl)-3-oxo-1H-pyrrolo[1,2-c]imidazol-2(3H)-yl)-N-hydroxy-2-methyl-2-(methylsulfonyl)butanamide;

(R)-N-hydroxy-4-(6-(5-((1s,3R)-1-hydroxy-3-(hydroxymethyl)cyclobutyl)penta-1,3-diyn-1-yl)-3-oxo-1H-pyrrolo[1,2-c]imidazol-2(3H)-yl)-2-methyl-2-(methylsulfonyl)butanamide;

(phosphonooxy)methyl (R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)carbamate;

(R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl ((phosphonooxy)methyl)carbonate;

(R)-N-hydroxy-4-(6-((2-(2-hydroxypropan-2-yl)thiazol-5-yl)ethynyl)-3-oxo-1H-pyrrolo[1,2-c]imidazol-2(3H)-yl)-2-methyl-2-(methylsulfonyl)butanamide;

(R)-4-(6-((4-((4-aminopiperidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide;

(R)-4-(6-(((1R,2R)-2-fluoro-2-(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-4-(6-(((1S,2S)-2-fluoro-2-(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-N-hydroxy-4-(6-((4-((4-hydroxypiperidin-1-yl)methyl)phenyl)ethynyl)-3-oxo-1H-pyrrolo[1,2-c]imidazol-2(3H)-yl)-2-methyl-2-(methylsulfonyl)butanamide;

(R)-4-(6-((4-(4-aminopiperidin-1-yl)phenyl)ethynyl)-3-oxo-1H-pyrrolo[1,2-c]imidazol-2(3H)-yl)-N-hydroxy-2-methyl-2-(methylsulfonyl)butanamide;

(R)-N-hydroxy-2-methyl-4-(6-((4-(methylsulfonamidomethyl)phenyl)ethynyl)-3-oxo-1H-pyrrolo[1,2-c]imidazol-2(3H)-yl)-2-(methylsulfonyl)butanamide;

(R)-N-hydroxy-2-methyl-2-(methylsulfonyl)-4-(6-((1-(oxetan-3-yl)azetidin-3-yl)buta-1,3-diyn-1-yl)-3-oxo-1H-pyrrolo[1,2-c]imidazol-2(3H)-yl)butanamide;

as well as the salts (in particular the pharmaceutically acceptable salts) thereof.

38) Further preferred are the following compounds of formula I as defined in embodiment 1) or 2):

(R)-N-hydroxy-4-(6-(4-(3-hydroxyoxetan-3-yl)phenyl)-3-oxo-1H-pyrrolo[1,2-c]imidazol-2(3H)-yl)-2-methyl-2-(methylsulfonyl)butanamide;

(R)-4-(6-((4-(2-ethoxypropan-2-yl)phenyl)ethynyl)-3-oxo-1H-pyrrolo[1,2-c]imidazol-2(3H)-yl)-N-hydroxy-2-methyl-2-(methylsulfonyl)butanamide;

(R)-4-(6-((2-fluoro-4-(hydroxymethyl)phenyl)ethynyl)-3-oxo-1H-pyrrolo[1,2-c]imidazol-2(3H)-yl)-N-hydroxy-2-methyl-2-(methylsulfonyl)butanamide;

(R)-N-hydroxy-4-(6-(4-(3-hydroxy-3-methylbut-1-yn-1-yl)phenyl)-3-oxo-1H-pyrrolo[1,2-c]imidazol-2(3H)-yl)-2-methyl-2-(methylsulfonyl)butanamide;

(R)-N-hydroxy-4-(6-(5-hydroxy-5-methylhexa-1,3-diyn-1-yl)-3-oxo-1H-pyrrolo[1,2-c]imidazol-2(3H)-yl)-2-methyl-2-(methylsulfonyl)butanamide;

(R)-N-hydroxy-2-methyl-4-(6-((4-((4-methylpiperazin-1-yl)methyl)phenyl)ethynyl)-3-oxo-1H-pyrrolo[1,2-c]imidazol-2(3H)-yl)-2-(methylsulfonyl)butanamide;

(R)-N-hydroxy-4-(6-(4-(2-hydroxyethoxy)phenyl)-3-oxo-1H-pyrrolo[1,2-c]imidazol-2(3H)-yl)-2-methyl-2-(methylsulfonyl)butanamide;

(R)-N-hydroxy-4-(6-(4-(2-methoxyethoxy)phenyl)-3-oxo-1H-pyrrolo[1,2-c]imidazol-2(3H)-yl)-2-methyl-2-(methylsulfonyl)butanamide;

as well as the salts (in particular the pharmaceutically acceptable salts) thereof.

39) Also further preferred are the following compounds of formula I as defined in embodiment 1):

(R)-4-(6-(2-fluoro-4-methylphenyl)-3-oxo-1H-pyrrolo[1,2-c]imidazol-2(3H)-yl)-N-hydroxy-2-methyl-2-(methylsulfonyl)butanamide;

(R)-4-(6-(3-fluoro-4-isopropoxyphenyl)-3-oxo-1H-pyrrolo[1,2-c]imidazol-2(3H)-yl)-N-hydroxy-2-methyl-2-(methylsulfonyl)butanamide;

as well as the salts (in particular the pharmaceutically acceptable salts) thereof.

40) The invention further relates to the compounds of formula I as defined in embodiment 1) or 3) which are selected from the group consisting of the compounds listed in embodiment 36), the compounds listed in embodiment 37), the compounds listed in embodiment 38) and the compounds listed in embodiment 39). In particular, it also relates to the groups of compounds of formula I selected from the group consisting of the compounds listed in embodiment 36), the compounds listed in embodiment 37), the compounds listed in embodiment 38) and the compounds listed in embodiment 39), which groups of compounds furthermore correspond to one of embodiments 2) to 34), as well as to the salts (in particular the pharmaceutically acceptable salts) of such compounds. The invention moreover relates to any individual compound of formula I selected from the group consisting of the compounds listed in embodiment 36), the compounds listed in embodiment 37), the compounds listed in embodiment 38) and the compounds listed in embodiment 39), and to the salts (in particular the pharmaceutically acceptable salts) of such individual compound.

The compounds of formula I according to this invention, i.e. according to one of embodiments 1) to 40) above, exhibit antibacterial activity, especially against Gram-negative organisms and are therefore suitable to treat bacterial infections in mammals, especially humans. Said compounds may also be used for veterinary applications, such as treating infections in livestock and companion animals. They may further constitute substances for preserving inorganic and organic materials in particular all types of organic materials for example polymers, lubricants, paints, fibres, leather, paper and wood.

They may therefore be used for the treatment or prevention of infectious disorders caused by fermentative or non-fermentative gram negative bacteria, especially those caused by susceptible and multi-drug resistant Gram-negative bacteria. Examples of such Gram-negative bacteria include *Acinetobacter* spp. such as *Acinetobacter baumannii* or *Acinetobacter haemolyticus*, *Actinobacillus actinomycetemcomitans*, *Achromobacter* spp. such as *Achromobacter xylosoxidans* or *Achromobacter faecalis*, *Aeromonas* spp. such as *Aeromonas hydrophila*, *Bacteroides* spp. such as *Bacteroides fragilis*, *Bacteroides theataioatamicron*, *Bacteroides distasonis*, *Bacteroides ovatus* or *Bacteroides vulgatus*, *Bartonella hensenae*, *Bordetella* spp. such as *Bordetella pertussis*, *Borrelia* spp. such as *Borrelia Burgdorferi*, *Brucella* spp. such as *Brucella melitensis*, *Burkholderia* spp. such as *Burkholderia cepacia*, *Burkholderia pseudomallei* or *Burkholderia mallei*, *Campylobacter* spp. such as *Campylobacter jejuni*, *Campylobacter fetus* or *Campylobacter coli*, *Cedecea*, *Chlamydia* spp. such as *Chlamydia pneumoniae*, *Chlamydia trachomatis*, *Citrobacter* spp. such as *Citrobacter diversus* (*koseri*) or *Citrobacter freundii*, *Coxiella burnetii*, *Edwardsiella* spp. such as *Edwarsiella tarda*, *Ehrlichia chafeensis*, *Eikenella corrodens*, *Enterobacter* spp. such as *Enterobacter cloacae*, *Enterobacter aerogenes*, *Enterobacter agglomerans*, *Escherichia coli*, *Francisella tularensis*, *Fusobacterium* spp., *Haemophilus* spp. such as *Haemophilus influenzae* (beta-lactamase positive and negative) or *Haemophilus ducreyi*, *Helicobacter pylori*, *Kingella kingae*, *Klebsiella* spp. such as *Klebsiella oxytoca*, *Klebsiella pneumoniae* (including those encoding extended-spectrum beta-lactamases (hereinafter "ESBLs"), carbapenemases (KPCs), cefotaximase-Munich (CTX-M), metallo-beta-lactamases, and AmpC-type beta-lactamases that confer resistance to currently available cephalosporins, cephamycins, carbapenems, beta-lactams, and beta-lactam/beta-lactamase inhibitor combinations), *Klebsiella rhinoscleromatis* or *Klebsiella ozaenae*, *Legionella pneumophila*, *Mannheimia haemolyticus*, *Moraxella catarrhalis* (beta-lactamase positive and negative), *Morganella morganii*, *Neisseria* spp. such as *Neisseria gonorrhoeae* or *Neisseria meningitidis*, *Pasteurella* spp. such as *Pasteurella multocida*, *Plesiomonas shigelloides*, *Porphyromonas* spp. such as *Porphyromonas asaccharolytica*, *Prevotella* spp. such as *Prevotella corporis*, *Prevotella intermedia* or *Prevotella endodontalis*, *Proteus* spp. such as *Proteus mirabilis*, *Proteus vulgaris*, *Proteus penneri* or *Proteus myxofaciens*, *Porphyromonas asaccharolytica*, *Plesiomonas shigelloides*, *Providencia* spp. such as *Providencia stuartii*, *Providencia rettgeri* or *Providencia alcalifaciens*, *Pseudomonas* spp. such as *Pseudomonas aeruginosa* (including ceftazidime-, cefpirome- and cefepime-resistant *P. aeruginosa*, carbapenem-resistant *P. aeruginosa* or quinolone-resistant *P. aeruginosa*) or *Pseudomonas fluorescens*, *Ricketsia prowazekii*, *Salmonella* spp. such as *Salmonella typhi* or *Salmonella paratyphi*, *Serratia marcescens*, *Shigella* spp. such as *Shigella flexneri*, *Shigella boydii*, *Shigella sonnei* or *Shigella dysenteriae*, *Streptobacillus moniliformis*, *Stenotrophomonas maltophilia*, *Treponema* spp., *Vibrio* spp. such as *Vibrio cholerae*, *Vibrio parahaemolyticus*, *Vibrio vulnificus*, *Vibrio alginolyticus*, *Yersinia* spp. such as *Yersinia enterocolitica*, *Yersinia pestis* or *Yersinia pseudotuberculosis*.

The compounds of formula I according to this invention are thus useful for treating a variety of infections caused by fermentative or non-fermentative Gram-negative bacteria, especially infections such as: nosocomial pneumonia (related to infection by *Legionella pneumophila*, *Haemophilus influenzae*, or *Chlamydia* pneumonia); urinary tract infections; systemic infections (bacteraemia and sepsis); skin and soft tissue infections (including burn patients); surgical infections; intraabdominal infections; lung infections (including those in patients with cystic fibrosis); *Helicobacter pylori* (and relief of associated gastric complications such as peptic ulcer disease, gastric carcinogenesis, etc.); endocarditis; diabetic foot infections; osteomyelitis; otitis media, sinusitus, bronchitis, tonsillitis, and mastoiditis related to infection by *Haemophilus influenzae* or *Moraxella catarrhalis*; pharyngitis, rheumatic fever, and glomerulonephritis related to infection by *Actinobacillus haemolyticum*; sexually transmitted diseases related to infection by *Chlamydia trachormatis*, *Haemophilus ducreyi*, *Treponema pallidum*, *Ureaplasma urealyticum*, or *Neisseria gonorrheae*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis*, *Neisseria gonorrhoeae* or *H. influenzae*; gastroenteritis related to infection by *Campylobacter jejuni*; persistent cough related to infection by *Bordetella pertussis* and gas gangrene related to infection by *Bacteroides* spp. Other bacterial infections and disorders related to such infections that may be treated or prevented in accord with the method of the present invention are referred to in J. P. Sanford et al., "*The Sanford Guide to Antimicrobial Therapy*", 26th Edition, (Antimicrobial Therapy, Inc., 1996).

The preceding lists of infections and pathogens are to be interpreted merely as examples and in no way as limiting.

The compounds of formula I according to this invention, or the pharmaceutically acceptable salts thereof, may therefore be used for the preparation of a medicament, and are suitable, for the prevention or treatment of a bacterial infection, in particular for the prevention or treatment of a bacterial infection caused by Gram-negative bacteria, especially by multi-drug resistant Gram-negative bacteria.

The compounds of formula I according to this invention, or the pharmaceutically acceptable salts thereof, may thus especially be used for the preparation of a medicament, and are suitable, for the prevention or treatment of a bacterial infection caused by Gram-negative bacteria selected from the group consisting of *Acinetobacter baumannii, Burkholderia* spp. (e.g. *Burkholderia cepacia*), *Citrobacter* spp., *Enterobacter aerogenes, Enterobacter cloacae, Escherichia coli, Klebsiella oxytoca, Klebsiella pneumoniae, Serratia marcescens, Stenotrophomonas maltophilia* and *Pseudomonas aeruginosa* (notably for the prevention or treatment of a bacterial infection caused by *Acinetobacter baumannii* bacteria, *Escherichia coli* bacteria, *Klebsiella pneumoniae* bacteria or *Pseudomonas aeruginosa* bacteria, and in particular for the prevention or treatment of a bacterial infection mediated by quinolone-resistant *Acinetobacter baumannii* bacteria or quinolone-resistant *Klebsiella pneumoniae* bacteria).

The compounds of formula I according to this invention, or the pharmaceutically acceptable salts thereof, may more especially be used for the preparation of a medicament, and are suitable, for the prevention or treatment of a bacterial infection caused by Gram-negative bacteria selected from the group consisting of *Citrobacter* spp., *Enterobacter aerogenes, Enterobacter cloacae, Escherichia coli, Klebsiella oxytoca, Klebsiella pneumoniae, Serratia marcescens, Stenotrophomonas maltophilia* and *Pseudomonas aeruginosa* bacteria (notably of a bacterial infection caused by Gram-negative bacteria selected from the group consisting of *Klebsiella pneumoniae* and *Pseudomonas aeruginosa* bacteria, and in particular of a bacterial infection caused by *Pseudomonas aeruginosa* bacteria).

The compounds of formula I according to this invention, or the pharmaceutically acceptable salts thereof, may thus especially be used for the preparation of a medicament, and are suitable, for the prevention or treatment of a bacterial infection selected from urinary tract infections, systemic infections (such as bacteraemia and sepsis), skin and soft tissue infections (including burn patients), surgical infections; intraabdominal infections and lung infections (including those in patients with cystic fibrosis).

The compounds of formula I according to this invention, or the pharmaceutically acceptable salts thereof, may more especially be used for the preparation of a medicament, and are suitable, for the prevention or treatment of a bacterial infection selected from urinary tract infections, intraabdominal infections and lung infections (including those in patients with cystic fibrosis), and in particular for the prevention or treatment of a bacterial infection selected from urinary tract infections and intraabdominal infections.

Besides, the compounds of formula I according to this invention display intrinsic antibacterial properties and have the ability to improve permeability of the outer membrane of Gram-negative bacteria to other antibacterial agents. Their use in combination with another antibacterial agent might offer some further advantages such as lowered side-effects of drugs due to lower doses used or shorter time of treatment, more rapid cure of infection shortening hospital stays, increasing spectrum of pathogens controlled, and decreasing incidence of development of resistance to antibiotics. The antibacterial agent for use in combination with a compound of formula I according to this invention will be selected from the group consisting of a penicillin antibiotic (such as ampicillin, piperacillin, penicillin G, amoxicillin, or ticarcillin), a cephalosporin antibiotic (such as ceftriaxone, ceftazidime, cefepime, cefotaxime) a carbapenem antibiotic (such as imipenem, or meropenem), a monobactam antibiotic (such as aztreonam), a fluoroquinolone antibiotic (such as ciprofloxacin, moxifloxacin or levofloxacin), a macrolide antibiotic (such as erythromycin or azithromycin), an aminoglycoside antibiotic (such as amikacin, gentamycin or tobramycin), a glycopeptide antibiotic (such as vancomycin or teicoplanin), a tetracycline antibiotic (such as tetracycline, oxytetracycline, doxycycline, minocycline or tigecycline), and linezolid, clindamycin, telavancin, daptomycin, novobiocin, rifampicin and polymyxin. Preferably, the antibacterial agent for use in combination with a compound of formula I according to this invention will be selected from the group consisting of vancomycin, tigecycline and rifampicin.

The compounds of formula I according to this invention, or the pharmaceutically acceptable salt thereof, may moreover be used for the preparation of a medicament, and are suitable, for the prevention or treatment (and especially the treatment) of infections caused by biothreat Gram negative bacterial pathogens as listed by the US Center for Disease Control (the list of such biothreat bacterial pathogens can be found at the web page http://www.selectagents.gov/Select%20Agents%20and%20Toxins%20List.html), and in particular by Gram negative pathogens selected from the group consisting of *Yersinia pestis, Francisella tularensis* (tularemia), *Burkholderia pseudomallei* and *Burkholderia mallei*.

One aspect of this invention therefore relates to the use of a compound of formula I according to one of embodiments 1) to 40), or of a pharmaceutically acceptable salt thereof, for the manufacture of a medicament for the prevention or treatment of a bacterial infection (in particular one of the previously mentioned infections caused by Gram-negative bacteria, especially by multi-drug resistant Gram-negative bacteria). Another aspect of this invention relates to a compound of formula I according to one of embodiments 1) to 40), or a pharmaceutically acceptable salt thereof, for the prevention or treatment of a bacterial infection (in particular for the prevention or treatment of one of the previously mentioned infections caused by Gram-negative bacteria, especially by multi-drug resistant Gram-negative bacteria). Yet another aspect of this invention relates to a compound of formula I according to one of embodiments 1) to 40), or a pharmaceutically acceptable salt thereof, as a medicament. Yet a further aspect of this invention relates to a pharmaceutical composition containing, as active ingredient, a compound of formula I according to one of embodiments 1) to 40), or a pharmaceutically acceptable salt thereof, and at least one therapeutically inert excipient.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I, $I_P$, $I_{CE}$ or $I_{CEP}$.

Any reference to a compound of formula I, $I_P$, $I_{CE}$ or $I_{CEP}$ in this text is to be understood as referring also to the salts (and especially the pharmaceutically acceptable salts) of such compounds, as appropriate and expedient.

A pharmaceutical composition according to the present invention contains at least one compound of formula I (or a pharmaceutically acceptable salt thereof) as the active ingredient and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a Gram-negative bacterial infection in a patient, comprising the administration to said patient of a pharmaceutically active amount of a compound of formula I according to one of embodiments 1) to 40) or a pharmaceutically acceptable salt thereof. Accordingly, the invention provides a method for the prevention or the treatment of a bacterial infection caused by Gram-negative bacteria (notably for the prevention or treatment of a bacterial infection caused by *Acinetobacter baumannii* bacteria, *Escherichia coli* bacteria, *Klebsiella pneumoniae* bacteria or *Pseudomonas aeruginosa* bacteria, and in particular for the prevention or treatment of a bacterial infection caused by quinolone-resistant *Acinetobacter baumannii* quinolone-resistant bacteria or *Klebsiella pneumoniae* quinolone-resistant bacteria) in a patient, comprising the administration to said patient of a pharmaceutically active amount of a compound of formula I according to one of embodiments 1) to 40) or a pharmaceutically acceptable salt thereof.

Moreover, the compounds of formula I according to this invention may also be used for cleaning purposes, e.g. to remove pathogenic microbes and bacteria from surgical instruments, catheters and artificial implants or to make a room or an area aseptic. For such purposes, the compounds of formula I could be contained in a solution or in a spray formulation.

This invention, thus, relates to the compounds of formula I as defined in embodiment 1), or further limited under consideration of their respective dependencies by the characteristics of any one of embodiments 2) to 40), and to pharmaceutically acceptable salts thereof. It relates furthermore to the use of such compounds as medicaments, especially for the prevention or treatment of a bacterial infection, in particular for the prevention or treatment of a bacterial infection caused by Gram-negative bacteria (notably for the prevention or treatment of a bacterial infection caused by *Acinetobacter baumannii* bacteria, *Escherichia coli* bacteria, *Klebsiella pneumoniae* bacteria or *Pseudomonas aeruginosa* bacteria, and in particular for the prevention or treatment of a bacterial infection caused by quinolone-resistant *Acinetobacter baumannii* quinolone-resistant bacteria or *Klebsiella pneumoniae* quinolone-resistant bacteria). The following embodiments relating to the compounds of formula I according to embodiment 1) are thus possible and intended and herewith specifically disclosed in individualised form:

1, 2+1, 3+1, 4+3+1, 5+3+1, 5+4+3+1, 6+1, 6+2+1, 6+3+1, 6+4+3+1, 6+5+3+1, 6+5+4+3+1, 7+6+1, 7+6+2+1, 7+6+3+1, 7+6+4+3+1, 7+6+5+3+1, 7+6+5+4+3+1, 8+7+6+1, 8+7+6+2+1, 8+7+6+3+1, 8+7+6+4+3+1, 8+7+6+5+3+1, 8+7+6+5+4+3+1, 9+7+6+1, 9+7+6+2+1, 9+7+6+3+1, 9+7+6+4+3+1, 9+7+6+5+3+1, 9+7+6+5+4+3+1, 10+6+1, 10+6+2+1, 10+6+3+1, 10+6+4+3+1, 10+6+5+3+1, 10+6+5+4+3+1, 11+10+6+1, 11+10+6+2+1, 11+10+6+3+1, 11+10+6+4+3+1, 11+10+6+5+3+1, 11+10+6+5+4+3+1, 12+10+6+1, 12+10+6+2+1, 12+10+6+3+1, 12+10+6+4+3+1, 12+10+6+5+3+1, 12+10+6+5+4+3+1, 13+10+6+1, 13+10+6+2+1, 13+10+6+3+1, 13+10+6+4+3+1, 13+10+6+5+3+1, 13+10+6+5+4+3+1, 14+6+1, 14+6+2+1, 14+6+3+1, 14+6+4+3+1, 14+6+5+3+1, 14+6+5+4+3+1, 15+14+6+1, 15+14+6+2+1, 15+14+6+3+1, 15+14+6+4+3+1, 15+14+6+5+3+1, 15+14+6+5+4+3+1, 16+1, 16+2+1, 16+3+1, 16+4+3+1, 16+5+3+1, 16+5+4+3+1, 17+16+1, 17+16+2+1, 17+16+3+1, 17+16+4+3+1, 17+16+5+3+1, 17+16+5+4+3+1, 18+16+1, 18+16+2+1, 18+16+3+1, 18+16+4+3+1, 18+16+5+3+1, 18+16+5+4+3+1, 19+16+1, 19+16+2+1, 19+16+3+1, 19+16+4+3+1, 19+16+5+3+1, 19+16+5+4+3+1, 20+1, 20+3+1, 21+20+1, 21+20+3+1, 22+21+20+1, 22+21+20+3+1, 23+20+1, 23+20+3+1, 24+23+20+1, 24+23+20+3+1, 25+1, 25+3+1, 26+1, 26+3+1, 27+1, 27+3+1, 28+27+1, 28+27+3+1, 29+27+1, 29+27+3+1, 30+2+1, 30+4+3+1, 31+2+1, 31+4+3+1, 32+2+1, 32+4+3+1, 33+32+2+1, 33+32+4+3+1, 34+32+2+1, 34+32+4+3+1, 35+1, 35+2+1, 35+3+1, 35+4+3+1, 35+5+3+1, 35+5+4+3+1, 35+6+1, 35+6+2+1, 35+6+3+1, 35+6+4+3+1, 35+6+5+3+1, 35+6+5+4+3+1, 35+7+6+1, 35+7+6+2+1, 35+7+6+3+1, 35+7+6+4+3+1, 35+7+6+5+3+1, 35+7+6+5+4+3+1, 35+8+7+6+1, 35+8+7+6+2+1, 35+8+7+6+3+1, 35+8+7+6+4+3+1, 35+8+7+6+5+3+1, 35+8+7+6+5+4+3+1, 35+9+7+6+1, 35+9+7+6+2+1, 35+9+7+6+3+1, 35+9+7+6+4+3+1, 35+9+7+6+5+3+1, 35+9+7+6+5+4+3+1, 35+10+6+1, 35+10+6+2+1, 35+10+6+3+1, 35+10+6+4+3+1, 35+10+6+5+3+1, 35+10+6+5+4+3+1, 35+11+10+6+1, 35+11+10+6+2+1, 35+11+10+6+3+1, 35+11+10+6+4+3+1, 35+11+10+6+5+3+1, 35+11+10+6+5+4+3+1, 35+12+10+6+1, 35+12+10+6+2+1, 35+12+10+6+3+1, 35+12+10+6+4+3+1, 35+12+10+6+5+3+1, 35+12+10+6+5+4+3+1, 35+13+10+6+1, 35+13+10+6+2+1, 35+13+10+6+3+1, 35+13+10+6+4+3+1, 35+13+10+6+5+3+1, 35+13+10+6+5+4+3+1, 35+14+6+1, 35+14+6+2+1, 35+14+6+3+1, 35+14+6+4+3+1, 35+14+6+5+3+1, 35+14+6+5+4+3+1, 35+15+14+6+1, 35+15+14+6+2+1, 35+15+14+6+3+1, 35+15+14+6+4+3+1, 35+15+14+6+5+3+1, 35+15+14+6+5+4+3+1, 35+16+1, 35+16+2+1, 35+16+3+1, 35+16+4+3+1, 35+16+5+3+1, 35+16+5+4+3+1, 35+17+16+1, 35+17+16+2+1, 35+17+16+3+1, 35+17+16+4+3+1, 35+17+16+5+3+1, 35+17+16+5+4+3+1, 35+18+16+1, 35+18+16+2+1, 35+18+16+3+1, 35+18+16+4+3+1, 35+18+16+5+3+1, 35+18+16+5+4+3+1, 35+19+16+1, 35+19+16+2+1, 35+19+16+3+1, 35+19+16+4+3+1, 35+19+16+5+3+1, 35+19+16+5+4+3+1, 35+20+1, 35+20+3+1, 35+21+20+1, 35+21+20+3+1, 35+22+21+20+1, 35+22+21+20+3+1, 35+23+20+1, 35+23+20+3+1, 35+24+23+20+1, 35+24+23+20+3+1, 35+25+1, 35+25+3+1, 35+26+1, 35+26+3+1, 35+27+1, 35+27+3+1, 35+28+27+1, 35+28+27+3+1, 35+29+27+1, 35+29+27+3+1, 35+30+2+1, 35+30+4+3+1, 35+31+2+1, 35+31+4+3+1, 35+32+2+1, 35+32+4+3+1, 35+33+32+2+1, 35+33+32+4+3+1, 35+34+

32+2+1, 35+34+32+4+3+1, 36+1, 36+2+1, 36+3+1, 36+4+ 3+1, 36+5+3+1, 36+5+4+3+1, 36+6+1, 36+6+2+1, 36+6+ 3+1, 36+6+4+3+1, 36+6+5+3+1, 36+6+5+4+3+1, 36+7+6+ 1, 36+7+6+2+1, 36+7+6+3+1, 36+7+6+4+3+1, 36+7+6+5+ 3+1, 36+7+6+5+4+3+1, 36+8+7+6+1, 36+8+7+6+2+1, 36+8+7+6+3+1, 36+8+7+6+4+3+1, 36+8+7+6+5+3+1, 36+8+7+6+5+4+3+1, 36+9+7+6+1, 36+9+7+6+2+1, 36+9+ 7+6+3+1, 36+9+7+6+4+3+1, 36+9+7+6+5+3+1, 36+9+7+ 6+5+4+3+1, 36+10+6+1, 36+10+6+2+1, 36+10+6+3+1, 36+10+6+4+3+1, 36+10+6+5+3+1, 36+10+6+5+4+3+1, 36+11+10+6+1, 36+11+10+6+2+1, 36+11+10+6+3+1, 36+11+10+6+4+3+1, 36+11+10+6+5+3+1, 36+11+10+6+ 5+4+3+1, 36+12+10+6+1, 36+12+10+6+2+1, 36+12+10+ 6+3+1, 36+12+10+6+4+3+1, 36+12+10+6+5+3+1, 36+12+ 10+6+5+4+3+1, 36+13+10+6+1, 36+13+10+6+2+1, 36+13+10+6+3+1, 36+13+10+6+4+3+1, 36+13+10+6+5+ 3+1, 36+13+10+6+5+4+3+1, 36+14+6+1, 36+14+6+2+1, 36+14+6+3+1, 36+14+6+4+3+1, 36+14+6+5+3+1, 36+14+ 6+5+4+3+1, 36+15+14+6+1, 36+15+14+6+2+1, 36+15+ 14+6+3+1, 36+15+14+6+4+3+1, 36+15+14+6+5+3+1, 36+15+14+6+5+4+3+1, 36+16+1, 36+16+2+1, 36+16+3+1, 36+16+4+3+1, 36+16+5+3+1, 36+16+5+4+3+1, 36+17+ 16+1, 36+17+16+2+1, 36+17+16+3+1, 36+17+16+4+3+1, 36+17+16+5+3+1, 36+17+16+5+4+3+1, 36+18+16+1, 36+18+16+2+1, 36+18+16+3+1, 36+18+16+4+3+1, 36+18+16+5+3+1, 36+18+16+5+4+3+1, 36+19+16+1, 36+19+16+2+1, 36+19+16+3+1, 36+19+16+4+3+1, 36+19+16+5+3+1, 36+19+16+5+4+3+1, 36+20+1, 36+20+ 3+1, 36+21+20+1, 36+21+20+3+1, 36+22+21+20+1, 36+22+21+20+3+1, 36+23+20+1, 36+23+20+3+1, 36+24+ 23+20+1, 36+24+23+20+3+1, 36+25+1, 36+25+3+1, 36+26+1, 36+26+3+1, 36+27+1, 36+27+3+1, 36+28+27+1, 36+28+27+3+1, 36+29+27+1, 36+29+27+3+1, 36+30+2+1, 36+30+4+3+1, 36+31+2+1, 36+31+4+3+1, 36+32+2+1, 36+32+4+3+1, 36+33+32+2+1, 36+33+32+4+3+1, 36+34+ 32+2+1, 36+34+32+4+3+1, 37+1, 37+2+1, 37+3+1, 37+4+ 3+1, 37+5+3+1, 37+5+4+3+1, 37+6+1, 37+6+2+1, 37+6+ 3+1, 37+6+4+3+1, 37+6+5+3+1, 37+6+5+4+3+1, 37+7+6+ 1, 37+7+6+2+1, 37+7+6+3+1, 37+7+6+4+3+1, 37+7+6+5+ 3+1, 37+7+6+5+4+3+1, 37+8+7+6+1, 37+8+7+6+2+1, 37+8+7+6+3+1, 37+8+7+6+4+3+1, 37+8+7+6+5+3+1, 37+8+7+6+5+4+3+1, 37+9+7+6+1, 37+9+7+6+2+1, 37+9+ 7+6+3+1, 37+9+7+6+4+3+1, 37+9+7+6+5+3+1, 37+9+7+ 6+5+4+3+1, 37+10+6+1, 37+10+6+2+1, 37+10+6+3+1, 37+10+6+4+3+1, 37+10+6+5+3+1, 37+10+6+5+4+3+1, 37+11+10+6+1, 37+11+10+6+2+1, 37+11+10+6+3+1, 37+11+10+6+4+3+1, 37+11+10+6+5+3+1, 37+11+10+6+ 5+4+3+1, 37+12+10+6+1, 37+12+10+6+2+1, 37+12+10+ 6+3+1, 37+12+10+6+4+3+1, 37+12+10+6+5+3+1, 37+12+ 10+6+5+4+3+1, 37+13+10+6+1, 37+13+10+6+2+1, 37+13+10+6+3+1, 37+13+10+6+4+3+1, 37+13+10+6+5+ 3+1, 37+13+10+6+5+4+3+1, 37+14+6+1, 37+14+6+2+1, 37+14+6+3+1, 37+14+6+4+3+1, 37+14+6+5+3+1, 37+14+ 6+5+4+3+1, 37+15+14+6+1, 37+15+14+6+2+1, 37+15+ 14+6+3+1, 37+15+14+6+4+3+1, 37+15+14+6+5+3+1, 37+15+14+6+5+4+3+1, 37+16+1, 37+16+2+1, 37+16+3+1, 37+16+4+3+1, 37+16+5+3+1, 37+16+5+4+3+1, 37+17+ 16+1, 37+17+16+2+1, 37+17+16+3+1, 37+17+16+4+3+1, 37+17+16+5+3+1, 37+17+16+5+4+3+1, 37+18+16+1, 37+18+16+2+1, 37+18+16+3+1, 37+18+16+4+3+1, 37+18+16+5+3+1, 37+18+16+5+4+3+1, 37+19+16+1, 37+19+16+2+1, 37+19+16+3+1, 37+19+16+4+3+1, 37+19+16+5+3+1, 37+19+16+5+4+3+1, 37+20+1, 37+20+ 3+1, 37+21+20+1, 37+21+20+3+1, 37+22+21+20+1, 37+22+21+20+3+1, 37+23+20+1, 37+23+20+3+1, 37+24+ 23+20+1, 37+24+23+20+3+1, 37+25+1, 37+25+3+1, 37+26+1, 37+26+3+1, 37+27+1, 37+27+3+1, 37+28+27+1, 37+28+27+3+1, 37+29+27+1, 37+29+27+3+1, 37+30+2+1, 37+30+4+3+1, 37+31+2+1, 37+31+4+3+1, 37+32+2+1, 37+32+4+3+1, 37+33+32+2+1, 37+33+32+4+3+1, 37+34+ 32+2+1, 37+34+32+4+3+1, 38+1, 38+2+1, 38+3+1, 38+4+ 3+1, 38+5+3+1, 38+5+4+3+1, 38+6+1, 38+6+2+1, 38+6+ 3+1, 38+6+4+3+1, 38+6+5+3+1, 38+6+5+4+3+1, 38+7+6+ 1, 38+7+6+2+1, 38+7+6+3+1, 38+7+6+4+3+1, 38+7+6+5+ 3+1, 38+7+6+5+4+3+1, 38+8+7+6+1, 38+8+7+6+2+1, 38+8+7+6+3+1, 38+8+7+6+4+3+1, 38+8+7+6+5+3+1, 38+8+7+6+5+4+3+1, 38+9+7+6+1, 38+9+7+6+2+1, 38+9+ 7+6+3+1, 38+9+7+6+4+3+1, 38+9+7+6+5+3+1, 38+9+7+ 6+5+4+3+1, 38+10+6+1, 38+10+6+2+1, 38+10+6+3+1, 38+10+6+4+3+1, 38+10+6+5+3+1, 38+10+6+5+4+3+1, 38+11+10+6+1, 38+11+10+6+2+1, 38+11+10+6+3+1, 38+11+10+6+4+3+1, 38+11+10+6+5+3+1, 38+11+10+6+ 5+4+3+1, 38+12+10+6+1, 38+12+10+6+2+1, 38+12+10+ 6+3+1, 38+12+10+6+4+3+1, 38+12+10+6+5+3+1, 38+12+ 10+6+5+4+3+1, 38+13+10+6+1, 38+13+10+6+2+1, 38+13+10+6+3+1, 38+13+10+6+4+3+1, 38+13+10+6+5+ 3+1, 38+13+10+6+5+4+3+1, 38+14+6+1, 38+14+6+2+1, 38+14+6+3+1, 38+14+6+4+3+1, 38+14+6+5+3+1, 38+14+ 6+5+4+3+1, 38+15+14+6+1, 38+15+14+6+2+1, 38+15+ 14+6+3+1, 38+15+14+6+4+3+1, 38+15+14+6+5+3+1, 38+15+14+6+5+4+3+1, 38+16+1, 38+16+2+1, 38+16+3+1, 38+16+4+3+1, 38+16+5+3+1, 38+16+5+4+3+1, 38+17+ 16+1, 38+17+16+2+1, 38+17+16+3+1, 38+17+16+4+3+1, 38+17+16+5+3+1, 38+17+16+5+4+3+1, 38+18+16+1, 38+18+16+2+1, 38+18+16+3+1, 38+18+16+4+3+1, 38+18+16+5+3+1, 38+18+16+5+4+3+1, 38+19+16+1, 38+19+16+2+1, 38+19+16+3+1, 38+19+16+4+3+1, 38+19+16+5+3+1, 38+19+16+5+4+3+1, 38+20+1, 38+20+ 3+1, 38+21+20+1, 38+21+20+3+1, 38+22+21+20+1, 38+22+21+20+3+1, 38+23+20+1, 38+23+20+3+1, 38+24+ 23+20+1, 38+24+23+20+3+1, 38+25+1, 38+25+3+1, 38+26+1, 38+26+3+1, 38+27+1, 38+27+3+1, 38+28+27+1, 38+28+27+3+1, 38+29+27+1, 38+29+27+3+1, 38+30+2+1, 38+30+4+3+1, 38+31+2+1, 38+31+4+3+1, 38+32+2+1, 38+32+4+3+1, 38+33+32+2+1, 38+33+32+4+3+1, 38+34+ 32+2+1, 38+34+32+4+3+1, 39+1, 39+2+1, 39+3+1, 39+4+ 3+1, 39+5+3+1, 39+5+4+3+1, 39+6+1, 39+6+2+1, 39+6+ 3+1, 39+6+4+3+1, 39+6+5+3+1, 39+6+5+4+3+1, 39+7+6+ 1, 39+7+6+2+1, 39+7+6+3+1, 39+7+6+4+3+1, 39+7+6+5+ 3+1, 39+7+6+5+4+3+1, 39+8+7+6+1, 39+8+7+6+2+1, 39+8+7+6+3+1, 39+8+7+6+4+3+1, 39+8+7+6+5+3+1, 39+8+7+6+5+4+3+1, 39+9+7+6+1, 39+9+7+6+2+1, 39+9+ 7+6+3+1, 39+9+7+6+4+3+1, 39+9+7+6+5+3+1, 39+9+7+ 6+5+4+3+1, 39+10+6+1, 39+10+6+2+1, 39+10+6+3+1, 39+10+6+4+3+1, 39+10+6+5+3+1, 39+10+6+5+4+3+1, 39+11+10+6+1, 39+11+10+6+2+1, 39+11+10+6+3+1, 39+11+10+6+4+3+1, 39+11+10+6+5+3+1, 39+11+10+6+ 5+4+3+1, 39+12+10+6+1, 39+12+10+6+2+1, 39+12+10+ 6+3+1, 39+12+10+6+4+3+1, 39+12+10+6+5+3+1, 39+12+ 10+6+5+4+3+1, 39+13+10+6+1, 39+13+10+6+2+1, 39+13+10+6+3+1, 39+13+10+6+4+3+1, 39+13+10+6+5+ 3+1, 39+13+10+6+5+4+3+1, 39+14+6+1, 39+14+6+2+1, 39+14+6+3+1, 39+14+6+4+3+1, 39+14+6+5+3+1, 39+14+ 6+5+4+3+1, 39+15+14+6+1, 39+15+14+6+2+1, 39+15+ 14+6+3+1, 39+15+14+6+4+3+1, 39+15+14+6+5+3+1, 39+15+14+6+5+4+3+1, 39+16+1, 39+16+2+1, 39+16+3+1, 39+16+4+3+1, 39+16+5+3+1, 39+16+5+4+3+1, 39+17+ 16+1, 39+17+16+2+1, 39+17+16+3+1, 39+17+16+4+3+1, 39+17+16+5+3+1, 39+17+16+5+4+3+1, 39+18+16+1, 39+18+16+2+1, 39+18+16+3+1, 39+18+16+4+3+1, 39+18+16+5+3+1, 39+18+16+5+4+3+1, 39+19+16+1, 39+19+16+2+1, 39+19+16+3+1, 39+19+16+4+3+1, 39+19+16+5+3+1, 39+19+16+5+4+3+1, 39+20+1, 39+20+ 3+1, 39+21+20+1, 39+21+20+3+1, 39+22+21+20+1,

39+22+21+20+3+1, 39+23+20+1, 39+23+20+3+1, 39+24+ 23+20+1, 39+24+23+20+3+1, 39+25+1, 39+25+3+1, 39+26+1, 39+26+3+1, 39+27+1, 39+27+3+1, 39+28+27+1, 39+28+27+3+1, 39+29+27+1, 39+29+27+3+1, 39+30+2+1, 39+30+4+3+1, 39+31+2+1, 39+31+4+3+1, 39+32+2+1, 39+32+4+3+1, 39+33+32+2+1, 39+33+32+4+3+1, 39+34+ 32+2+1, 39+34+32+4+3+1, 40+1, 40+2+1, 40+3+1, 40+4+ 3+1, 40+5+3+1, 40+5+4+3+1, 40+6+1, 40+6+2+1, 40+6+ 3+1, 40+6+4+3+1, 40+6+5+3+1, 40+6+5+4+3+1, 40+7+6+ 1, 40+7+6+2+1, 40+7+6+3+1, 40+7+6+4+3+1, 40+7+6+5+ 3+1, 40+7+6+5+4+3+1, 40+8+7+6+1, 40+8+7+6+2+1, 40+8+7+6+3+1, 40+8+7+6+4+3+1, 40+8+7+6+5+3+1, 40+8+7+6+5+4+3+1, 40+9+7+6+1, 40+9+7+6+2+1, 40+9+ 7+6+3+1, 40+9+7+6+4+3+1, 40+9+7+6+5+3+1, 40+9+7+ 6+5+4+3+1, 40+10+6+1, 40+10+6+2+1, 40+10+6+3+1, 40+10+6+4+3+1, 40+10+6+5+3+1, 40+10+6+5+4+3+1, 40+11+10+6+1, 40+11+10+6+2+1, 40+11+10+6+3+1, 40+11+10+6+4+3+1, 40+11+10+6+5+3+1, 40+11+10+6+ 5+4+3+1, 40+12+10+6+1, 40+12+10+6+2+1, 40+12+10+ 6+3+1, 40+12+10+6+4+3+1, 40+12+10+6+5+3+1, 40+12+ 10+6+5+4+3+1, 40+13+10+6+1, 40+13+10+6+2+1, 40+13+10+6+3+1, 40+13+10+6+4+3+1, 40+13+10+6+5+ 3+1, 40+13+10+6+5+4+3+1, 40+14+6+1, 40+14+6+2+1, 40+14+6+3+1, 40+14+6+4+3+1, 40+14+6+5+3+1, 40+14+ 6+5+4+3+1, 40+15+14+6+1, 40+15+14+6+2+1, 40+15+ 14+6+3+1, 40+15+14+6+4+3+1, 40+15+14+6+5+3+1, 40+15+14+6+5+4+3+1, 40+16+1, 40+16+2+1, 40+16+3+1, 40+16+4+3+1, 40+16+5+3+1, 40+16+5+4+3+1, 40+17+ 16+1, 40+17+16+2+1, 40+17+16+3+1, 40+17+16+4+3+1, 40+17+16+5+3+1, 40+17+16+5+4+3+1, 40+18+16+1, 40+18+16+2+1, 40+18+16+3+1, 40+18+16+4+3+1, 40+18+16+5+3+1, 40+18+16+5+4+3+1, 40+19+16+1, 40+19+16+2+1, 40+19+16+3+1, 40+19+16+4+3+1, 40+19+16+5+3+1, 40+19+16+5+4+3+1, 40+20+1, 40+20+ 3+1, 40+21+20+1, 40+21+20+3+1, 40+22+21+20+1, 40+22+21+20+3+1, 40+23+20+1, 40+23+20+3+1, 40+24+ 23+20+1, 40+24+23+20+3+1, 40+25+1, 40+25+3+1, 40+26+1, 40+26+3+1, 40+27+1, 40+27+3+1, 40+28+27+1, 40+28+27+3+1, 40+29+27+1, 40+29+27+3+1, 40+30+2+1, 40+30+4+3+1, 40+31+2+1, 40+31+4+3+1, 40+32+2+1, 40+32+4+3+1, 40+33+32+2+1, 40+33+32+4+3+1, 40+34+ 32+2+1 and 40+34+32+4+3+1.

In the list above, the numbers refer to the embodiments according to their numbering provided hereinabove whereas "+" indicates the dependency from another embodiment. The different individualised embodiments are separated by commas. In other words, "4+3+1" for example refers to embodiment 4) depending on embodiment 3), depending on embodiment 1), i.e. embodiment "4+3+1" corresponds to embodiment 1) further limited by the features of embodiments 3) and 4). Likewise, "13+10+6+1" refers to embodiment 13) depending mutatis mutandis on embodiments 10) and 6), depending on embodiment 1), i.e. embodiment "13+10+6+1" corresponds to embodiment 1) further limited by the features of embodiments 6) and 10), further limited by the features of embodiment 13).

The compounds of formula I can be manufactured in accordance with the present invention using the procedures described hereafter.

Preparation of the Compounds of Formula I
Abbreviations:

The following abbreviations are used throughout the specification and the examples:

Ac acetyl
AcOH acetic acid
aq. aqueous
Boc tert-butoxycarbonyl
BuLi n-butyl lithium
CC column chromatography over silica gel
CDI 1,1'-carbonyldiimidazole
Cipro ciprofloxacin
conc. concentrated
Cy cyclohexyl
DAD diode array detection
dba dibenzylideneacetone
DCC dicyclohexylcarbodiimide
DCE 1,2-dichloroethane
DCM dichloromethane
DIBAH diisobutylaluminum hydride
DME 1,2-dimethoxyethane
DMF N,N-dimethylformamide
DMAP 4-dimethylaminopyridine
DMSO dimethylsulfoxide
dppf 1,1'-bis(diphenylphosphino)ferrocene
EA ethyl acetate
EDC    N-(3-dimethylaminopropyl)-N'-ethylcarbodiimide hydrochloride
ELSD evaporative light scattering detector
ESI electron spray ionisation
eq. equivalent
Et ethyl
Et$_2$O diethyl ether
EtOH ethanol
HATU   O-(7-azabenzotriazol-1-yl)-N,N,N',N'-tetramethyluronium hexafluorophosphate
Hept heptane
Hex hexane
HOBT hydroxybenzotriazole
HPLC high pressure liquid chromatography
iPr iso-propyl
IT internal temperature
LC liquid chromatography
Me methyl
MeCN acetonitrile
MeOH methanol
MS mass spectroscopy
Ms methylsulfonyl (mesyl)
nBu n-butyl
NBS N-bromosuccinimide
Nf nonafluorobutanesulfonyl
NMR Nuclear Magnetic Resonance
Ns 4-nitrobenzenesulfonyl (nosylate)
org. organic
Pd/C palladium on carbon
PEPPSI™-IPr   [1,3-bis(2,6-diisopropylphenyl)imidazol-2-ylidene](3-chloropyridyl)palladium(II) dichloride
PE petroleum ether
Ph phenyl
PPTS para-toluenesulfonic acid pyridinium salt
prep-HPLC preparative HPLC
Pyr pyridine
quant. quantitative
Q-phos   1,2,3,4,5-pentaphenyl-1'-(di-tert-butylphosphino)ferrocene
rt room temperature
sat. saturated
SK-CC01-A 2'-(dimethylamino)-2-biphenylyl-palladium(II) chloride dinorbornylphosphine complex
S-Phos 2-dicyclohexylphosphino-2',6'-dimethoxybiphenyl
TBAF tetra-n-butylammonium fluoride
TBDPS tert-butyldiphenylsilyl
TBDMS tert-butyldimethylsilyl
TBME tert-butylmethyl ether
tBu tert-butyl TEA triethylamine
TFA trifluoroacetic acid
THF tetrahydrofuran
THP tetrahydropyranyl
TLC thin layer chromatography
TMS trimethylsilyl
TMSE 2-(trimethylsilyl)ethyl
$t_R$ retention time
General Reaction Techniques:
General Reaction Technique 1 (Hydroxamic Acid Protecting Group Removal):

The protecting groups R of the hydroxamic acid ester derivatives (CONHOR) are removed as follows:

When R is THP, (2-methylpropoxy)ethyl, methoxymethyl, tBu, COOtBu or COtBu: by acidic treatment with e.g. TFA or HCl in an org. solvent such as DCM, dioxane, $Et_2O$ or MeOH between 0° C. and rt or by treatment with pyridinium para-toluenesulfonate in EtOH between rt and 80° C.;

When R is trityl: by treatment with diluted acid such as citric acid or HCl in an org. solvent such as MeOH or DCM;

When R is benzyl: by hydrogenation using general reaction technique 5;

When R is TMSE: by using fluoride anion sources such as $BF_3$.etherate complex in MeCN at 0° C., TBAF in THF between 0° C. and +40° C. or HF in MeCN or water between 0° C. and +40° C., or using acidic conditions such as AcOH in THF/MeOH or HCl in MeOH;

When R is allyl: by treatment with $Pd(PPh_3)_4$ in a solvent such as MeOH in presence of $K_2CO_3$ or a scavenger such as dimedone, morpholine or tributyltin hydride;

Further general methods to remove hydroxamic acid protecting groups have been described in T. W. Greene & P. G. M. Wuts, *Protecting Groups in Organic Synthesis*, $3^{rd}$ Ed (1999), 23-147 (Publisher: John Wiley and Sons, Inc., New York, N.Y.).

General Reaction Technique 2 (Amide Coupling);

The carboxylic acid is reacted with the hydroxylamine derivative in the presence of an activating agent such as DCC, EDC, HOBT, n-propylphosphonic cyclic anhydride, HATU or di-(N-succinimidyl)-carbonate, in a dry aprotic solvent such as DCM, MeCN or DMF between −20° C. and 60° C. (see G. Benz in *Comprehensive Organic Synthesis*, B. M. Trost, I. Fleming, Eds; Pergamon Press: New York (1991), vol. 6, p. 381). Alternatively, the carboxylic acid can be activated by conversion into its corresponding acid chloride by reaction with oxalyl chloride or thionyl chloride neat or in a solvent like DCM between −20° and 60° C. Further activating agents can be found in R. C. Larock, *Comprehensive Organic Transformations. A guide to Functional Group Preparations*, $2^{nd}$ Edition (1999), section nitriles, carboxylic acids and derivatives, p. 1941-1949 (Wiley-VC; New York, Chichester, Weinheim, Brisbane, Singapore, Toronto).

General Reaction Technique 3 (Suzuki Coupling):

The aromatic halide (typically a bromide) is reacted with the required boronic acid derivative or its boronate ester equivalent (e.g. pinacol ester) in the presence of a palladium catalyst and a base such as $K_2CO_3$, $Cs_2CO_3$, $K_3PO_4$, tBuONa or tBuOK between 20 and 120° C. in a solvent such as toluene, THF, dioxane, DME or DMF, usually in the presence of water (20 to 50%). Examples of typical palladium catalysts are triarylphosphine palladium complexes such as $Pd(PPh_3)_4$. These catalysts can also be prepared in situ from a common palladium source such as $Pd(OAc)_2$ or $Pd_2(dba)_3$ and a ligand such as trialkylphosphines (e.g. $PCy_3$ or $P(tBu)_3$), dialkylphosphinobiphenyls (e.g. S-Phos) or ferrocenylphosphines (e.g. Q-phos). Alternatively, one can use a commercially available precatalyst based on palladacycle (e.g. SK-CC01-A) or N-heterocyclic carbene complexes (e.g. PEPPSI™-IPr). The reaction can also be performed by using the corresponding aromatic triflate. Further variations of the reaction are described in Miyaura and Suzuki, *Chem. Rev.* (1995), 95, 2457-2483, Bellina et al., *Synthesis* (2004), 2419-2440, Mauger and Mignani, *Aldrichimica Acta* (2006), 39, 17-24, Kantchev et al., *Aldrichimica Acta* (2006), 39, 97-111, Fu, *Acc. Chem. Res.* (2008), 41, 1555-1564, and references cited therein.

General Reaction Technique 4 (Alkyne-Alkyne Cross Coupling, Haloaryl-Alkyne or Alkyne-Haloalkyne Cross Coupling):

An alkyne derivative is coupled with a second alkyne or a haloalkyne derivative, using a catalytic amount of a palladium salt, an org. base such as TEA and a catalytic amount of a copper derivative (usually copper iodide) in a solvent such as DMF at a temperature from 20 to 100° C. (see Sonogashira, K. in *Metal-Catalyzed Reactions*, Diederich, F., Stang, P. J., Eds.; Wiley-VCH: New York (1998)). Alternatively, the alkyne-haloalkyne cross coupling reaction can be performed using only a catalytic amount of copper derivative in presence of aqueous hydroxylamine and a base such as piperidine or pyrrolidine (see Chodkiewicz and Cadiot, *C. R. Hebd. Seances Acad. Sci.* (1955), 241, 1055-1057).

General Reaction Technique 5 (Hydrogenation of a Double Bond):

The unsaturated derivative dissolved in a solvent such as MeOH, EA or THF is hydrogenated over a noble metal catalyst such as Pd/C or $PtO_2$, or over Raney Ni. At the end of the reaction the catalyst is filtered off and the filtrate is evaporated under reduced pressure. Alternatively the reduction can be performed by catalytic transfer hydrogenation using Pd/C and ammonium formate as hydrogen source.

General Reaction Technique 6 (Transformation of an Ester into an Acid):

When the ester side chain is a linear alkyl, the hydrolysis is usually performed by treatment with an alkali hydroxide such as LiOH, KOH or NaOH in a water-dioxan or water-THF mixture between 0° C. and 80° C. When the ester side chain is tBu, the release of the corresponding acid can also be performed in neat TFA or diluted TFA or HCl in an org. solvent such as ether or THF. When the ester side chain is the allyl group, the reaction is performed in the presence of tetrakis(triphenylphosphine)palladium(0) in the presence of an allyl cation scavenger such as morpholine, dimedone or tributyltin hydride between 0° C. and 50° C. in a solvent such as THF. When the ester side chain is benzyl, the reaction is performed under hydrogen in the presence of a noble metal catalyst such as Pd/C in a solvent such as MeOH, THF or EA. Further strategies to introduce other acid protecting groups and general methods to remove them have been described in T. W. Greene & P. G. M. Wuts, *Protecting Groups in Organic Synthesis*, $3^{rd}$ Ed. (1999), 369-441 (Publisher: John Wiley and Sons, Inc., New York, N.Y.).

General Preparation Methods:

Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

The sections hereafter describe general methods for preparing compounds of formula I. If not indicated otherwise, the generic groups $R^1$, M, $M^A$, $M^B$, A, U, V, W, $R^{1A}$, $R^{2A}$, $R^{3A}$, $R^{1B}$ and $R^{1C}$ are as defined for formula I. General synthetic methods used repeatedly throughout the text below are referenced to and described in the above section entitled "General reaction techniques". In some instances certain generic groups might be incompatible with the assembly illustrated in the procedures and schemes below and so will require the use of protecting groups. The use of protecting groups is well known in the art (see for example T. W. Greene, P. G. M. Wuts, *Protective Groups in Organic Synthesis*, 3$^{rd}$ Ed (1999), Wiley-Interscience).

The compounds of formula I can be obtained by deprotecting a compound of formula II

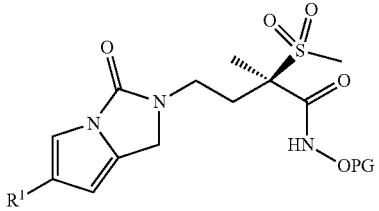

II wherein $R^1$ has the same meaning as in formula I and PG represents THP, TMSE, benzyl, trityl, (2-methylpropoxy) ethyl, methoxymethyl, allyl, tBu, COOtBu or COtBu using general reaction technique 1. The reaction can also be performed with racemic material and the (R) enantiomer can be obtained by chiral HPLC separation.

If desired, the compounds of formula I thus obtained may be converted into their salts, and notably into their pharmaceutically acceptable salts using standard methods.

Besides, whenever the compounds of formula I are obtained in the form of mixtures of enantiomers, the enantiomers can be separated using methods known to one skilled in the art, e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in the presence or absence of an amine such as TEA or diethylamine) and eluent B (Hex), at a flow rate of 0.8 to 150 mL/min.

Preparation of the Compounds of Formula II:
The compounds of formula II can be obtained by:
a) reacting a compound of formula III

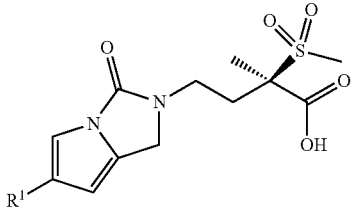

III wherein $R^1$ is as defined in formula I with a compound of formula IV $H_2N-OPG$ IV wherein PG has the same meaning as in formula II using general reaction technique 2 (this reaction can also be performed with racemic compound of formula III and the (R)-enantiomer can then be obtained by chiral HPLC separation of the reaction product), whereby functional groups (e g amino or hydroxy) present on $R^1$ that would be incompatible with the coupling conditions mentioned in general reaction technique 2 can be protected (as carbamates or THP/silyl ethers respectively) before performing said reaction and deprotected after performing said reaction; or b) reacting a boron derivative of formula V

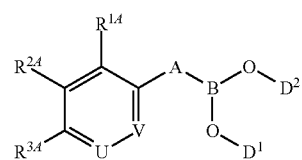

V wherein U, V, $R^{1A}$, $R^{2A}$ and $R^{3A}$ have the same respective meanings as in formula I, A represents a bond or CH=CH and $D^1$ and $D^2$ represent H, methyl or ethyl or $D^1$ and $D^2$ together represent $CH_2C(Me)_2CH_2$ or $C(Me)_2C(Me)_2$ with a compound of formula VI

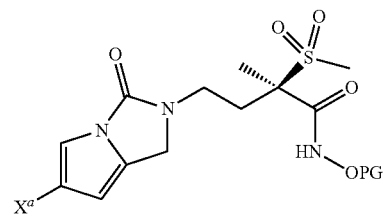

VI wherein $X^a$ represents a halogen such as bromine or iodine and PG has the same meaning as in formula II, using general reaction technique 3 (this reaction can also be performed with racemic compound of formula VI and the (R)-enantiomer can then be obtained by chiral HPLC separation of the reaction product); or c) reacting a compound of formula VII

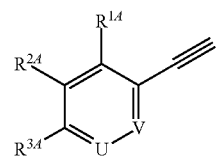

VII wherein U, V, $R^{1A}$, $R^{2A}$ and $R^{3A}$ have the same respective meanings as in formula I, with a compound of formula VI as defined in section b) above wherein $X^a$ represents iodine, using general reaction technique 4 (this reaction can also be performed with racemic compound of formula VI and the (R)-enantiomer can then be obtained by chiral HPLC separation of the reaction product); or d) reacting a compound of formula VIII

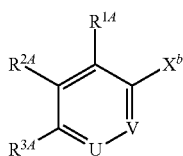

wherein U, V, $R^{1A}$, $R^{2A}$ and $R^{3A}$ have the same respective meanings as in formula I and $X^b$ represents iodine or bromine (and preferably iodine), with a compound of formula VIa

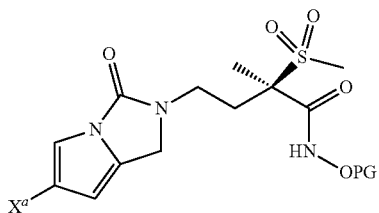

wherein $X^a$ represents ethynyl and PG has the same meaning as in formula II, using general reaction technique 4 (this reaction can also be performed with racemic compound of formula VIa and the (R)-enantiomer can then be obtained by chiral HPLC separation of the reaction product); or e) reacting a compound of formula IX

wherein $R^{1B}$ has the same meaning as in formula I and $X^c$ represents iodine or bromine, with a compound of formula VIa as defined in section d) above, using general reaction technique 4 (this reaction can also be performed with racemic compound of formula VIa and the (R)-enantiomer can then be obtained by chiral HPLC separation of the reaction product); or f) reacting a compound of formula X

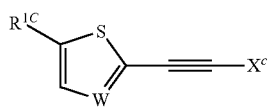

wherein $R^{1C}$ has the same meaning as in formula I and $X^c$ represents iodine or bromine, with a compound of formula VIa as defined in section d) above, using general reaction technique 4 (this reaction can also be performed with racemic compound of formula VIa and the (R)-enantiomer can then be obtained by chiral HPLC separation of the reaction product).

Preparation of the Synthesis Intermediates of Formulae III, IV, V, VI, VIa, VII, VIII, IX and X:

Compounds of Formula III:

The compounds of formula III can be prepared as summarised in Scheme 1 hereafter.

Scheme 1

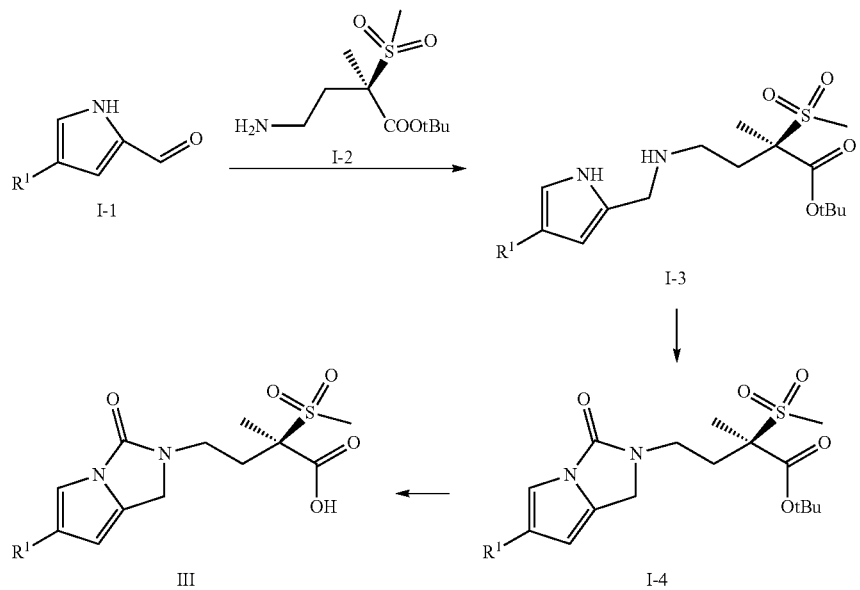

In Scheme 1, $R^1$ has the same meaning as in formula I. The reactions can also be performed with racemic material and the (R)-enantiomer can be obtained by chiral HPLC separation at any step when suitable.

The derivatives of formula I-3 can be obtained (Scheme 1) by reaction of the pyrrole aldehydes of formula I-1 with the amine of formula I-2 using general reaction technique 5. Alternatively, the derivatives of formula I-3 can be obtained by reacting the derivatives of formula I-1 with the derivative of formula I-2 in a solvent such as MeOH, DCM or DCE (or a mixture of such solvents) in the presence of a reducing agent such as $NaBH_4$ or $NaBH(OAc)_3$; the reductive amination reaction is well known in the art (see for example Abdel-Magid et al., *J. Org. Chem.* (1996), 61, 3849-3862). The derivatives of formula I-4 can be obtained from the derivatives of formula I-3 by treatment with CDI in a solvent such as THF in the presence of a base such as NaH; this reaction can be performed at a temperature ranging from 0 to 50° C., and ideally at rt. The compounds of formula I-4 can be transformed into the compounds of formula III using general reaction technique 6.

The compounds of formula III can also be prepared as summarised in Scheme 1a hereafter.

Compounds of Formula V:

The compounds of formula V wherein A is a bond and $D^1$ and $D^2$ each represent H or ($C_1$-$C_2$)alkyl are commercially available or can be prepared according to Sleveland et al., *Organic Process Research & Development* (2012), 16, 1121-1130 starting from tri(($C_1$-$C_2$)alkyl)borate and the corresponding commercially available bromo derivatives (optionally followed by acidic hydrolysis). The compounds of formula V wherein A represents a bond and $D^1$ and $D^2$ together represent $CH_2C(Me)_2CH_2$ or $C(Me)_2C(Me)_2$ are commercially available or can be prepared according to WO Scheme 1a

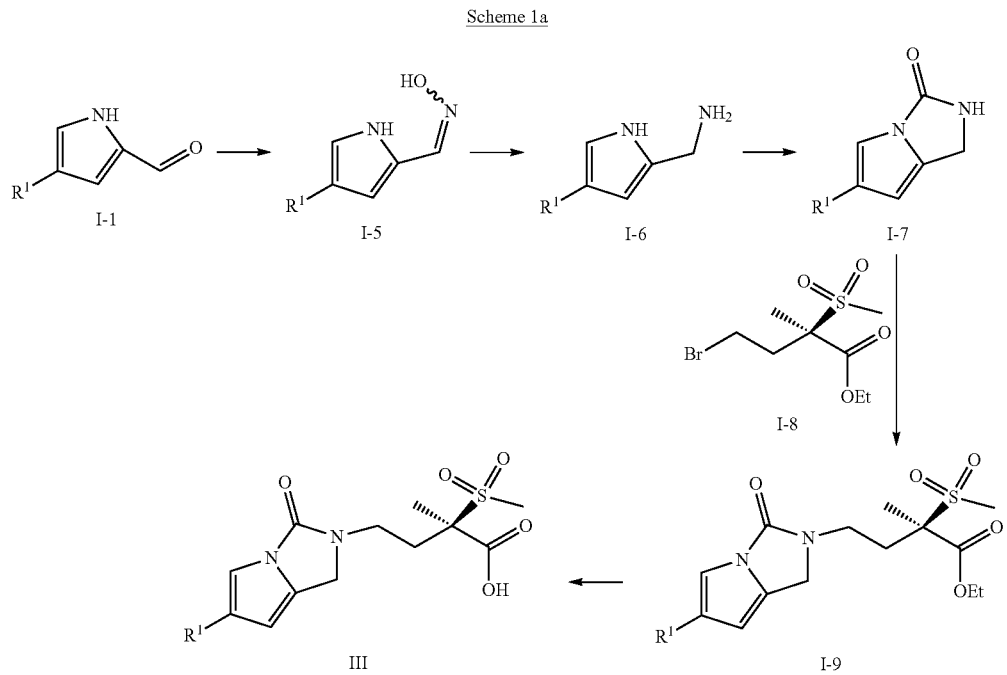

In Scheme 1a, $R^1$ has the same meaning as in formula I. The reactions can also be performed with racemic material and the (R)-enantiomer can be obtained by chiral HPLC separation at any step when suitable.

The oxime derivatives of formula I-5 can be obtained (Scheme 1a) by reaction of the pyrrole aldehydes of formula I-1 with hydroxylamine in acetic acid in presence of NaOAc. The oxime derivatives of formula I-5 can be reduced into the amine derivatives of formula I-6 by treatment with Zn in a solvent such as AcOH. The derivatives of formula I-7 can be obtained from the derivatives of formula I-6 by treatment with CDI in a solvent such as THF in the presence of a base such as NaH. This reaction can be performed at a temperature ranging from 0 to 50° C., and ideally at rt. The compounds of formula I-7 can be transformed into the compounds of formula I-9 by treatment with the bromide of formula I-8 in the presence of a base such as NaH and in a solvent such as THF or DMF. The compounds of formula I-9 can then be transformed into the compounds of formula III using general reaction technique 6.

Compounds of Formula IV:

The compounds of formula IV are commercially available (PG=THP, tBu, COOtBu or allyl) or can be prepared according to WO 2010/060785 (PG=(2-methylpropoxy)ethyl) or Marmer and Maerker, *J. Org. Chem.* (1972), 37, 3520-3523 (PG=COtBu).

2012/093809, starting from bis(pinacolato)diborane or 5,5-dimethyl-1,3,2-dioxaborinane (both commercially available) with the corresponding commercially available bromo derivatives of formula VIII. The compounds of formula V wherein A is CH═CH and $D^1$ and $D^2$ each represent H are commercially available or can be prepared according to Perner et al., *Biorg. Med. Chem. Lett.* (2005), 15, 2803-2807 by reaction of catechol borane on the appropriate alkyne derivatives followed by acidic hydrolysis.

Compounds of Formulae VI and VIa:

The compounds of formulae VI and VIa can be prepared as summarised in Scheme 2 hereafter.

Scheme 2

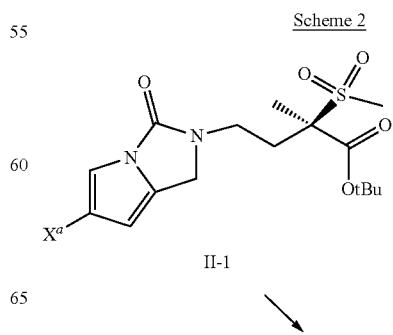

-continued

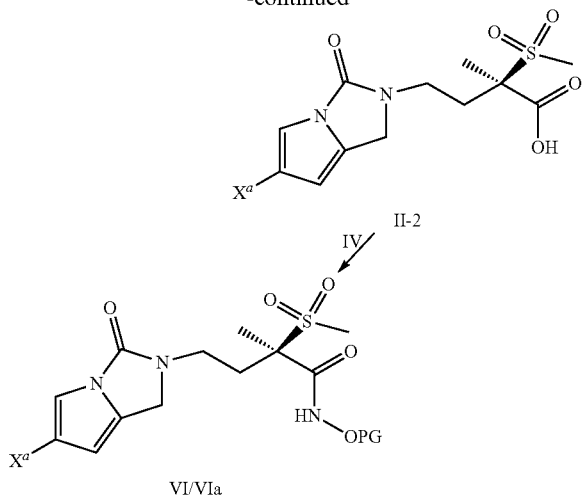

In Scheme 2, $X^a$ represents a halogen (such as iodine or bromine) or ethynyl and PG has the same meaning as in formula II. The reactions can also be performed with racemic material and the (R)-enantiomer can be obtained by chiral HPLC separation at any step when suitable.

The derivatives of formula II-1 can be transformed (Scheme 2) into the carboxylic acid derivatives of formula II-2 using general reaction technique 6 and further reacted with the compounds of formula IV using general reaction technique 2, thus affording the compounds of formula VI ($X^a$=halogen) or VIa ($X^a$=ethynyl).

Alternatively, the compounds of formula II-2 can be prepared as summarised in Scheme 2a hereafter.

Scheme 2a

In Scheme 2a, $X^a$ represents a halogen (such as iodine or bromine) or ethynyl. The reactions can also be performed with racemic material and the (R)-enantiomer can be obtained by chiral HPLC separation at any step when suitable.

The derivatives of formula II-3 can be transformed (Scheme 2a) into the carboxylic acid derivatives of formula II-2 using general reaction technique 6.

Compounds of Formula VII:

The compounds of formula VII are commercially available or can be prepared as summarised in Scheme 3 hereafter.

Scheme 3

In Scheme 3, U, V, $R^{1A}$, $R^{2A}$ and $R^{3A}$ have the same respective meanings as in formula I.

The compounds of formula VIII wherein $X^b$ represents iodine can be reacted (Scheme 3) with trimethylsilylacetylene (III-1) using general reaction technique 4 followed by treatment with TBAF in THF, affording the derivatives of formula VII.

Compounds of Formula VIII:

The compounds of formula VIII wherein $X^b$ represents bromine are commercially available or can be prepared by standard methods known to one skilled in the art. The compounds of formula VIII wherein $X^b$ represents iodine can be obtained from the corresponding bromine derivatives by reaction with NaI in the presence of a copper (I) salt and a ligand such as trans-N,N'-dimethylcyclohexa-1,2-diamine in a solvent such as dioxane at a temperature ranging between rt and 100° C., or in a microwave oven at 150° C.

Compounds of Formula IX:

The compounds of formula IX wherein $X^c$ represents iodine can be prepared by iodination of the corresponding compounds wherein $X^c$ would be H with iodine in the presence of an inorganic base such as KOH. The compounds of formula IX wherein $X^c$ represents bromine can be prepared from the corresponding compounds wherein $X^c$ would be H by treatment with NBS in the presence of $AgNO_3$ in a solvent such as acetone or MeCN.

Compounds of Formula X:

The compounds of formula X can be prepared as summarised in Scheme 3a hereafter

Scheme 3a

In Scheme 3a, $X^d$ represents iodine or bromine and W and $R^{1C}$ have the same respective meanings as in formula X.

The compounds of formula X-1 can be reacted (Scheme 3a) with trimethylsilylacetylene (III-1) using general reaction technique 4 followed by treatment with TBAF in THF, affording the derivatives of formula X-2. The compounds of formula X wherein $X^c$ represents iodine can be prepared from the compounds of formula X-2 by treatment with iodine in the presence of an inorganic base such as KOH. The compounds of formula X wherein $X^c$ represents bromine can be prepared from the compounds of formula X-2 by treatment with NBS in the presence of $AgNO_3$ in a solvent such as acetone or MeCN.

Other Synthesis Intermediates and Starting Materials:

The compounds of formula I-1 are commercially available or can be prepared by standard methods known to one skilled in the art.

The compound of formula I-2 can be prepared in analogy to the methods described in the section entitled "EXAMPLES" hereafter (see Preparations A and B), or by standard methods known to one skilled in the art.

The compounds of formula II-1 wherein $X^a$ represents bromine, iodine or ethynyl can be prepared as summarised in Scheme 4 hereafter.

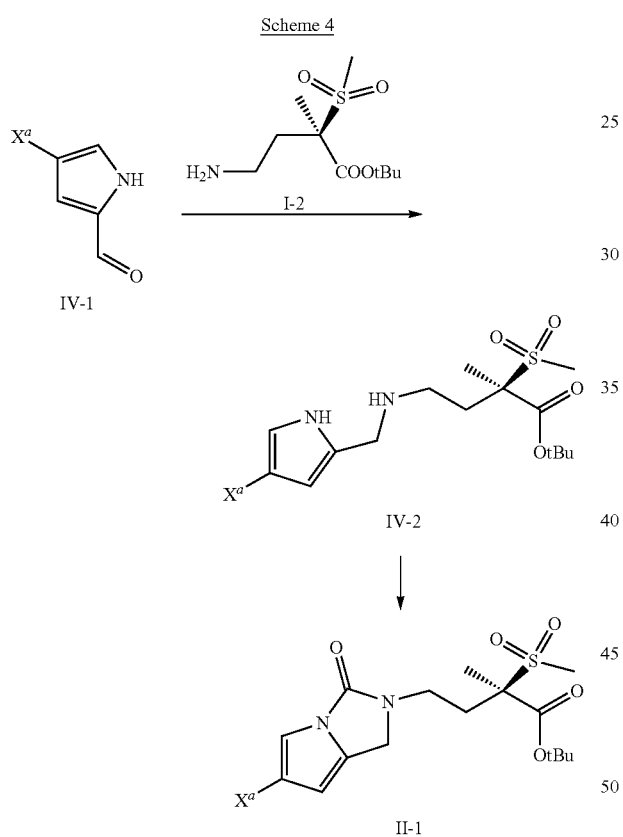

In Scheme 4, $X^a$ represents a halogen (such as iodine or bromine) or ethynyl. The reactions can also be performed with racemic material and the (R)-enantiomer can be obtained by chiral HPLC separation at any step when suitable.

The derivatives of formula IV-2 can be obtained (Scheme 4) by reaction of the pyrrole aldehydes of formula IV-1 with the amine of formula I-2 using general reaction technique 5. The derivatives of formula II-1 can then be obtained from the derivatives of formula IV-2 by treatment with CDI in the presence of a base such as NaH in a solvent such as THF; this reaction can be performed at a temperature ranging from 0° C. to 50° C., and ideally at rt. The compounds of formula IV-3 wherein $X^a$ is iodine can be transformed to the derivatives of formula II-1 wherein $X^a$ is ethynyl using the protocol described for the formation of the compounds of formula VII.

Moreover the compounds of formula II-1 wherein $X^a$ is ethynyl can be obtained from the compounds of formula II-3 wherein $X^a$ is iodine using the protocol described for the formation of the compounds of formula VII.

The compounds of formula II-3 wherein $X^a$ represents bromine, iodine or ethynyl can be prepared as summarised in Scheme 4a hereafter.

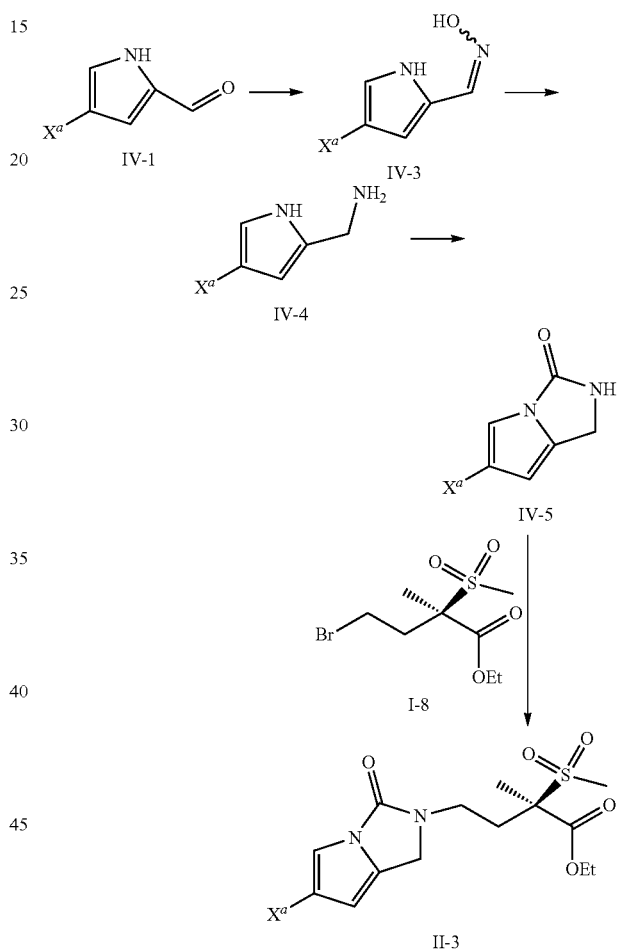

In Scheme 4a, $X^a$ represents a halogen (such as iodine or bromine) or ethynyl. The reactions can also be performed with racemic material and the (R)-enantiomer can be obtained by chiral HPLC separation at any step when suitable.

The oxime derivatives of formula IV-3 can be obtained (Scheme 4a) by reaction of the pyrrole aldehydes of formula IV-1 with hydroxylamine in AcOH in the presence of NaOAc. The oxime derivatives of formula IV-3 can be reduced to the amine derivatives of formula IV-4 by treatment with Zn in a solvent such as AcOH. The derivatives of formula IV-5 can be obtained from the derivatives of formula IV-4 by treatment with CDI in a solvent such as THF in the presence of a base such as NaH. This reaction can be performed at a temperature ranging from 0 to 50° C., and ideally at rt. The compounds of formula IV-5 can then be transformed into the compounds of formula II-3 by treatment with the bromide of formula I-8 in the presence of a base such as NaH and in a solvent such as THF or DMF.

The compounds of formula IV-1 are commercially available or can be prepared by standard methods known to one skilled in the art.

The compounds of formula X-1 are commercially available or can be prepared by standard methods known to one skilled in the art.

Particular embodiments of the invention are described in the following Examples, which serve to illustrate the invention in more detail without limiting its scope in any way.

EXAMPLES

All temperatures are stated in ° C. Unless otherwise indicated, the reactions take place at rt.

Analytical TLC characterisations were performed with 0.2 mm plates: Merck, Silica gel 60 $F_{254}$. Elution is performed with EA, Hept, DCM, MeOH or mixtures thereof. Detection was done with UV or with a solution of $KMnO_4$ (3 g), $K_2CO_3$ (20 g), 5% NaOH (3 mL) and $H_2O$ (300 mL) with subsequent heating.

CCs were performed using Brunschwig 60A silica gel (0.032-0.63 mm) or using an ISCO CombiFlash system and prepacked $SiO_2$ cartridges, elution being carried out with either Hept-EA or DCM-MeOH mixtures with an appropriate gradient. When the compounds contained an acid function, 1% of AcOH was added to the eluent(s). When the compounds contained a basic function, 25% aq. $NH_4OH$ was added to the eluents.

The compounds were characterized by $^1$H-NMR (300 MHz, Varian Oxford; 400 MHz, Bruker Avance 400 or 500 MHz, Bruker Avance 500 Cryoprobe). Chemical shifts δ are given in ppm relative to the solvent used; multiplicities: s=singlet, d=doublet, t=triplet, q=quartet, p=pentet, hex=hexet, hep=heptet, m=multiplet, br.=broad; coupling constants J are given in Hz. Alternatively compounds were characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC plates from Merck, Silica gel 60 $F_{254}$); or by melting point.

The analytical LC-MS data have been obtained using the following respective conditions:
    Column: Zorbax SB-Aq, 30.5 µm, 4.6×50 mm;
    Injection volume: 1 µL;
    Column oven temperature: 40° C.;
    Detection: UV 210 nm, ELSD and MS;
    MS ionization mode: ESI-F;
    Eluents: A: $H_2O$+0.04% TFA; and B: MeCN;
    Flow rate: 40.5 mL/min;
    Gradient: 5% B to 95% B (0.0 min-1.0 min), 95% B (1.0 min-1.45 min).

The number of decimals given for the corresponding [M+H$^+$] peak(s) of each tested compound depends upon the accuracy of the LC-MS device actually used.

The prep-HPLC purifications were performed on a Gilson HPLC system, equipped with a Gilson 215 autosampler, Gilson 333/334 pumps, Dionex MSQ Plus detector system, and a Dionex UVD340U (or Dionex DAD-3000) UV detector, using the following respective conditions:
    Method 1:
        Column: Waters XBridge C18, 10 µm, 30×75 mm;
        Flow rate: 75 mL/min;
        Eluents: A: $H_2O$+0.5% HCOOH; B: MeCN;
        Gradient: 90% A to 5% A (0.0 min-4.0 min), 5% A (4.0 min-6.0 min)
    Method 2:
        Column: Waters Atlantis T3 OBD, 10 µm, 30×75 mm;
        Flow rate: 75 mL/min;
        Eluents: A: $H_2O$+0.1% HCOOH; B: MeCN+0.1% HCOOH;
        Gradient: 90% A to 5% A (0.0 min-4.0 min), 5% A (4.0 min-6.0 min)
    Method 3:
        Column: Waters XBridge C18, 10 µm, 30×75 mm;
        Flow rate: 75 mL/min;
        Eluents: A: $H_2O$+0.5% $NH_4OH$ solution (25%); B: MeCN;
        Gradient: 90% A to 5% A (0.0 min-4.0 min), 5% A (4.0 min-6.0 min).

Besides, semi-preparative chiral HPLCs were performed using the conditions hereafter.

Semi-Preparative Chiral HPLC Method A:

The semi-preparative chiral HPLC is performed on a Daicel ChiralPak ASV column (250×110 mm, 20 µM) using the eluent mixture, flow rate and detection conditions indicated between brackets in the corresponding experimental protocol. The retention times are obtained by elution of analytical samples on a Daicel ChiralPak AS-H column (250×4.6 mm, 5 µM) using the same eluent mixture with the flow rate indicated between brackets in the corresponding experimental protocol.

Semi-Preparative Chiral HPLC Method B:

The semi-preparative chiral HPLC is performed on a Daicel ChiralPak IA column (20×250 mm; 5 µM) using the eluent mixture, flow rate and detection conditions indicated between brackets in the corresponding experimental protocol. The retention times are obtained by elution of analytical samples on a Daicel ChiralPak IA column (4.6×250 mm; 5 µM) using the same eluent mixture with the flow rate indicated between brackets in the corresponding experimental protocol.

Semi-Preparative Chiral HPLC Method C:

The semi-preparative chiral HPLC is performed on a Daicel ChiralPak AY-H column (20×250 mm, 5 µM) using the eluent mixture, flow rate and detection conditions indicated between brackets in the corresponding experimental protocol. The retention times are obtained by elution of analytical samples on a Daicel ChiralPak AY-H column (4.6×250 mm, 5 µM) using the same eluent mixture with the flow rate indicated between brackets in the corresponding experimental protocol.

Semi-Preparative Chiral HPLC Method D:

The semi-preparative chiral HPLC is performed on a Daicel ChiralCel OD-H column (20×250 mm; 5 µM) using the eluent mixture, flow rate and detection conditions indicated between brackets in the corresponding experimental protocol. The retention times are obtained by elution of analytical samples on a Daicel ChiralCel OD-H column (4.6×250 mm; 5 µM) using the same eluent mixture with the flow rate indicated between brackets in the corresponding experimental protocol.

Procedures:

Procedure A:

A mixture of the bromo derivative (1.63 mmol), the phenylboronic acid or boronate ester derivative (1.8 mmol), $K_2CO_3$ (0.34 g; 2.4 mmol) and Pd(PPh$_3$)$_4$ (0.19 g; 0.16 mmol) is flushed with nitrogen for 15 min. Dioxane (6 mL) and water (1.5 mL) are added and the mixture is refluxed for 1 h. After cooling, water (15 mL) and EA (20 mL) are added and the two layers are separated. The aq. layer is extracted with EA (2×20 mL) and the combined org. layers are washed with brine, dried over MgSO$_4$ and concentrated to dryness. The residue is then purified by CC (Hept-EA).

Procedure B:

To a solution of the THP-protected hydroxamic acid derivative (0.84 mmol) in dioxane (3.6 mL) and water (0.8 mL) is added PPTS (0.12 g; 0.48 mmol). The reaction mixture is stirred at 70° C. for 2 h. The reaction is cooled to rt and concentrated to dryness. The residue is then purified by CC (DCM-MeOH).

Procedure C:

CuI (0.218 g; 1.14 mmol), PdCl$_2$(PPh$_3$)$_2$ (0.401 g; 0.57 mmol), (trimethylsilyl)ethynyl acetylene (5.71 mmol) and the iodo derivative (5.71 mmol) are introduced in a two-necked round flask. The atmosphere is flushed with nitrogen during 30 min, then degassed THF (50 mL) and degassed TEA (2 mL; 14.3 mmol) are added. The suspension is stirred under nitrogen atmosphere at 50° C. for 45 min. After concentration to dryness, the residue is then purified by CC (Hept-EA).

Procedure D:

To the THP-protected hydroxamic acid derivative (0.02 mmol) in EtOH (3 mL) is added PPTS (0.025 g; 0.03 mmol). The mixture is stirred at 80° C. for 2 h, cooled to rt and directly purified by CC (DCM-MeOH) or by prep-HPLC using a suitable method.

Procedure E:

CuI (0.2 mmol), PdCl$_2$(PPh$_3$)$_2$ (0.1 mmol), the terminal alkyne derivative (1 mmol) and the iodo derivative (1.5 mmol) are introduced in a two-necked round flask. The atmosphere is flushed with nitrogen during 30 min, then degassed THF (5 mL) and degassed TEA (2.5 mmol) are added. The suspension is stirred under nitrogen atmosphere at 50° C. for 45 min. After concentration to dryness, the residue is then purified by CC (Hept-EA).

Procedure F:

CuI (0.2 mmol), PdCl$_2$(PPh$_3$)$_2$ (0.1 mmol), the iodo derivative (1 mmol) and the terminal alkyne derivative (1.5 mmol) are introduced in a two-necked round flask. The atmosphere is flushed with nitrogen during 30 min, then degassed THF (5 mL) and degassed TEA (2.5 mmol) are added. The suspension is stirred under nitrogen atmosphere at 50° C. for 45 min. After concentration to dryness, the residue is then purified by CC (Hept-EA).

Procedure G:

CuI (0.2 mmol), PdCl$_2$(PPh$_3$)$_2$ (0.1 mmol), the terminal alkyne derivative (1 mmol) and the halo-alkyne derivative (1.5 mmol) are introduced in a two-necked round flask. The atmosphere is flushed with nitrogen during 30 min, then degassed THF (5 mL) and degassed TEA (2.5 mmol) are added. The suspension is stirred under nitrogen atmosphere at 50° C. for 45 min. After concentration to dryness, the residue is then purified by CC (Hept-EA).

Procedure H:

To the THP-protected hydroxamic acid derivative (0.070 g, 0.119 mmol) in H$_2$O (0.745 mL, 41.4 mmol) was added TFA (0.357 mL, 4.62 mmol). After one hour stirring at rt, the mixture was directly purified by prep-HPLC using a suitable method.

Procedure I:

A solution of the THP-protected hydroxamic acid derivative (0.070 g, 0.119 mmol) in 4M HCl in dioxane (1 mL) was stirred 10 min at rt. The mixture was directly purified by prep-HPLC using a suitable method.

Preparations:

Preparation A: (RS)-tert-butyl 4-amino-2-methyl-2-(methylsulfonyl)butanoate

A.i. (RS)-tert-butyl 2-(methylsulfonyl)propanoate

To a suspension of sodium methanesulfinate (100 g; 929 mmol) in tBuOH (350 mL) was added tert-butyl-2-bromo-propionate (150 mL; 877 mmol). The reaction mixture was stirred at 90° C. for 24 h under nitrogen atmosphere, then cooled to rt and concentrated to dryness. The residue was partitioned between water (750 mL) and EA (600 mL). The aq. layer was extracted with EA (2×500 mL) and the combined org. layers were washed with brine (350 mL), dried over MgSO$_4$, filtered and concentrated to dryness to afford the title compound as a white yellow solid (175 g, 96% yield).

$^1$H NMR (d$_6$-DMSO) δ: 4.24 (q, J=7.2 Hz, 1H); 3.11 (s, 3H); 1.45 (s, 9H); 1.40 (d, J=7.2 Hz, 3H).

A.ii. (RS)-tert-butyl 4-bromo-2-methyl-2-(methylsulfonyl)butanoate

To an ice-chilled suspension of intermediate A.i (130 g; 626 mmol) in DMF (750 mL) was added portionwise NaH (60% in mineral oil; 32.1 g; 802 mmol) for 1.5 h, keeping the temperature below 7° C. The mixture was stirred at 0° C. for 1.5 h, allowed to reach rt and stirred at rt for 0.5 h. The mixture was cooled down to 12° C. with an ice bath and 1,2-dibromoethane (166 mL; 1.9 mol) was then added dropwise, keeping the temperature below 22° C. The reaction mixture was stirred at rt for 2 h. The mixture was poured into cold water (1 L) and Et$_2$O (1 L) and the aq. layer was extracted with Et$_2$O (2×750 mL). The org. layer was washed with cold water (2×500 mL). The combined org. layers were washed with brine (750 mL), dried over MgSO$_4$, filtered and concentrated to dryness. The residue was purified by CC (Hept-EA) to afford the title compound as a pale yellowish oil (116.8 g; 59% yield).

$^1$H NMR (d$_6$-DMSO) δ: 3.63-3.71 (m, 1H); 3.37-3.45 (m, 1H); 3.12 (s, 3H); 2.62-2.72 (m, 1H); 2.33-2.43 (m, 1H); 1.49 (s, 3H); 1.46 (s, 9H).

A.iii. (RS)-tert-butyl 4-azido-2-methyl-2-(methylsulfonyl)butanoate

To a solution of intermediate A.ii (70.3 g; 223 mmol) in DMF (400 mL) was added sodium azide (54.6 g; 831 mmol). The reaction was stirred at 80° C. overnight. The mixture was cooled to rt and water (500 mL) and EA (500 mL) were added. The aq. layer was extracted with EA (2×500 mL) and the org. layer was washed with water (2×500 mL). The combined org. layers were washed with brine (600 mL), dried over MgSO$_4$, filtered and concentrated to dryness. The residue was triturated in Hept, filtered and washed with Hept to afford the title compound as a white solid (59.6 g; 96% yield).

$^1$H NMR (d$_6$-DMSO) δ: 3.60-3.66 (m, 1H); 3.29-3.35 (overlapped m, 1H); 3.11 (s, 3H); 2.43-2.49 (m, 1H); 1.96-2.04 (m, 1H); 1.46 (s, 9H); 1.44 (s, 3H).

MS (ESI, m/z): 278.95 [M+H$^+$] for C$_{10}$H$_{19}$N$_3$O$_4$S; t$_R$=0.80 min.

A.iv. (RS)-tert-butyl 4-amino-2-methyl-2-(methylsulfonyl)butanoate

A solution of intermediate A.iii (45 g; 162 mmol) in a mixture of tBuOH/EA (1/1, 900 mL) was treated with 10%

Pd/C (2.3 g). The suspension was stirred at rt under hydrogen for 4 h. Then 10% Pd/C (0.5 g) was added to the suspension and the reaction was stirred under hydrogen for 2 days. The catalyst was filtered off and the filtrate concentrated to dryness to afford the crude material which crystallized on standing (grey solid; 40.6 g; 99% yield).

$^1$H NMR (d$_6$-DMSO) δ: 3.06 (s, 3H); 2.63-2.75 (m, 1H); 2.40-2.53 (overlapped m, 1H); 2.16-2.28 (m, 1H); 1.74-1.85 (m, 1H); 1.44 (s, 9H); 1.40 (s, 3H).

MS (ESI, m/z): 252.03 [M+H$^+$] for C$_{10}$H$_{21}$NO$_4$S; t$_R$=0.45 min.

Preparation B: (R)-tert-butyl 4-amino-2-methyl-2-(methylsulfonyl)butanoate

B.i. (R)-tert-butyl 4-azido-2-methyl-2-(methylsulfonyl)butanoate

Intermediate A.iii (184 g) was separated by semi-preparative chiral HPLC Method A (Hept-iPrOH 4-1; flow rate: 570 mL/min; UV detection at 235 nM); the respective retention times were 8.3 and 10.7 min. The title (R)-enantiomer, identified as the second eluting compound, was obtained as a light orange oil (90.7 g).

$^1$H NMR (d$_6$-DMSO) δ: 3.60-3.66 (m, 1H); 3.29-3.35 (overlapped m, 1H); 3.11 (s, 3H); 2.43-2.50 (overlapped m, 1H); 1.97-2.04 (m, 1H); 1.46 (s, 9H); 1.44 (s, 3H).

B. ii. (R)-tert-butyl 4-amino-2-methyl-2-(methylsulfonyl)butanoate

Starting from intermediate B.i (45 g; 162 mmol) and proceeding in analogy to Preparation A, step A.iv, the title compound was obtained as grey solid (40.6 g; 99% yield).

$^1$H NMR (d$_6$-DMSO) δ: 3.06 (s, 3H); 2.63-2.75 (m, 11H); 2.40-2.53 (overlapped m, $^1$H); 2.16-2.28 (m, 1H); 1.74-1.85 (m, 1H); 1.44 (s, 9H); 1.40 (s, 3H).

MS (ESI, m/z): 252.03 [M+H$^+$] for C$_{10}$H$_{21}$NO$_4$S; t$_R$=0.45 min.

Preparation C: (2R)-4-(6-bromo-3-oxo-1H-pyrrolo[1,2-c]imidazol-2(3H)-yl)-2-methyl-2-(methylsulfonyl)-N-(((RS)-tetrahydro-2H-pyran-2-yl)oxy)butanamide C.i. (R)-tert-butyl 4-(((4-bromo-1H-pyrrol-2-yl)methyl)amino)-2-methyl-2-(methylsulfonyl)butanoate To a solution of 4-bromo-1H-pyrrole-2-carbaldehyde (4.6 g; 26.3 mmol, commercial) in dry THF (90 mL) were added 3 Å molecular sieves (5.5 g) and the compound of Preparation B (6.9 g; 27.6 mmol). The reaction mixture was stirred at rt for 2.5 h, diluted with dry MeOH (25 mL) and cooled to 0° C. NaBH$_4$ (1.0 g; 26.3 mmol) was added portionwise and the reaction was stirred at 0° C. for 1.5 h. The mixture was quenched with water (50 mL). The volatiles were removed in vacuo and the residue was partitioned between DCM (100 mL) and sat. aq. NaHCO$_3$ (50 mL). The mixture was filtered and the phases were separated. The aq. phase was extracted with DCM (100 mL). The combined org. layers were dried over MgSO$_4$ and filtered. The filtrate was concentrated to dryness. After purification by CC (DCM-EA-MeOH), the title compound was obtained as an orange gum (9.0 g, 84% yield).

$^1$H NMR (d$_6$-DMSO) δ: 10.78-10.95 (br. s, 1H); 6.71-6.74 (m, 1H); 5.91-5.93 (m, 1H); 3.50-3.60 (m, 2H); 3.06 (s, 3H); 2.53-2.59 (m, 1H); 2.35-2.41 (m, 1H); 2.25-2.32 (m, 1H); 1.93-1.98 (br. s, 1H); 1.76-1.84 (m, 1H); 1.40 (s, 9H); 1.38 (s, 3H).

MS (ESI, m/z): 410.89 [M+H$^+$] for C$_{15}$H$_{25}$N$_2$O$_4$BrS; t$_R$=0.63 min.

C.ii. (R)-tert-butyl 4-(6-bromo-3-oxo-1H-pyrrolo[1,2-c]imidazol-2(3H)-yl)-2-methyl-2-(methylsulfonyl)butanoate To a solution of intermediate C.i (9.0 g; 22.1 mmol) in THF (80 mL) was added CDI (4.3 g; 26.5 mmol) and NaH (60% in mineral oil, 0.123 g; 3.1 mmol). The reaction was stirred at rt for 30 min. The reaction was quenched with water (70 mL) and sat. NH$_4$Cl (25 mL). EA (75 mL) was added and the two phases were separated. The aq. phase was extracted with EA (75 mL). The combined org. layers were washed with brine (125 mL), dried over MgSO$_4$ and filtered. The filtrate was concentrated to dryness. The residue was triturated in Et$_2$O, filtered and washed with Et$_2$O to afford the title compound as a light beige solid (5.2 g; 54% yield).

$^1$H NMR (d$_6$-DMSO) δ: 7.37 (s, 1H); 6.24 (d, J=1.0 Hz, 1H); 4.36-4.48 (m, 2H); 3.52-3.61 (m, 1H); 3.41-3.51 (m, 1H); 3.13 (s, 3H); 2.50-2.60 (overlapped m, 1H); 2.00-2.08 (m, 1H); 1.53 (s, 3H); 1.35 (s, 9H).

MS (ESI, m/z): 434.87 [M+H$^+$] for C$_{16}$H$_{23}$N$_2$O$_5$BrS; t$_R$=0.87 min.

C.iii. (R)-4-(6-bromo-3-oxo-1H-pyrrolo[1,2-c]imidazol-2(3H)-yl)-2-methyl-2-(methylsulfonyl)butanoic acid A solution of intermediate C.ii (5.2 g; 11.9 mmol) in dioxane (45 mL) and water (23 mL) was treated dropwise with conc. sulfuric acid (7.4 mL; 135 mmol). The mixture was stirred at 70° C. for 5 h. The reaction mixture was cooled to rt, diluted in cold water (90 mL) and extracted with DCM-MeOH (9-1; 2×130 mL). The combined org. layers were dried over MgSO$_4$ and filtered. The filtrate was concentrated to dryness. The residue was triturated in DCM, filtered and washed with DCM to afford the title compound as a yellow solid (3.4 g, 76% yield).

$^1$H NMR (d$_6$-DMSO) δ: 13.46-14.16 (br. s, 1H); 7.35 (d, J=0.8 Hz, 1H); 6.22 (d, J=0.8 Hz, 1H); 4.35-4.49 (m, 2H); 3.55-3.65 (m, 1H); 3.43-3.53 (m, 1H); 3.13 (s, 3H); 2.51-2.59 (overlapped m, 1H); 2.00-2.10 (m, 1H); 1.54 (s, 3H).

MS (ESI, m/z): 380.82 [M+H$^+$] for C$_{12}$H$_{15}$N$_2$O$_5$BrS; t$_R$=0.67 min.

C.iv. (2R)-4-(6-bromo-3-oxo-1H-pyrrolo[1,2-c]imidazol-2(3H)-yl)-2-methyl-2-(methylsulfonyl)-N-(((RS)-tetrahydro-2H-pyran-2-yl)oxy)butanamide To a solution of intermediate C.iii (3.4 g; 8.1 mmol) in DMF (50 mL) were successively added EDC (3.4 g; 17.8 mmol), HOBT.H$_2$O (2.2 g; 16.1 mmol), TEA (3.39 mL, 24.4 mmol) and NH$_2$—OTHP (1.428 g; 12.2 mmol). The reaction was stirred at 50° C. for 2 h under nitrogen. The mixture was cooled to rt, EA (400 mL) and sat. aq. NaHCO$_3$ (400 mL) were added. The phases were separated and the aq. layer was extracted with EA (400 mL). The combined org. layers were washed successively with sat. aq. NaHCO$_3$ (400 mL), water (400 mL) and brine (400 mL), dried over MgSO$_4$ and filtered. The filtrate was concentrated to dryness. After purification by CC (Hept-EA), the title compound was obtained as a white solid (3.4 g; 89% yield).

¹H NMR (d₆-DMSO) (mixture of stereoisomers) δ: 11.34-11.41 (br. s, 0.5H); 11.29-11.34 (br. s, 0.5H); 7.32 (s, 0.5H); 7.30 (s, 0.5H); 6.19-6.22 (m, 1H); 4.84-4.87 (m, 0.5H); 4.43-4.45 (overlapped m, 0.5H); 4.40-4.43 (overlapped m, 2H); 3.98-4.05 (m, 0.5H); 3.92-3.98 (m, 0.5H); 3.42-3.55 (overlapped m, 3H); 3.06 (s, 1.5H); 3.03 (s, 1.5H); 2.55-2.70 (overlapped m, 1H); 1.92-2.01 (m, 1H); 1.61-1.70 (m, 2H); 1.56 (s, 1.5H); 1.54 (s, 1.5H); 1.43-1.52 (overlapped m, 4H).

MS (ESI, m/z): 477.89 [M+H⁺] for $C_{12}H_{24}N_3O_6SBr$; $t_R$=0.77 min.

Preparation D: (2RS)-4-(6-bromo-3-oxo-1H-pyrrolo[1,2-c]imidazol-2(3H)-yl)-2-methyl-2-(methylsulfonyl)-N-(((RS)-tetrahydro-2H-pyran-2-yl)oxy)butanamide Starting from the compound of Preparation A (3.05 g; 20.1 mmol) and proceeding in analogy to Preparation C, steps C.i to C.iv (yields: reductive amination: 47%; cyclisation: 52%; acid formation: 71%; amide coupling with THPO—NH₂: 53%), the title compound was obtained as a white solid (1.7 g).

¹H NMR (d₆-DMSO) (mixture of stereoisomers) δ: 11.38 (br. s, 0.5H); 11.32 (br. s, 0.5H); 7.32 (s, 0.5H); 7.30 (s, 0.5H); 6.19-6.22 (m, 1H); 4.84-4.87 (m, 0.5H); 4.43-4.45 (overlapped m, 0.5H); 4.40-4.43 (overlapped m, 2H); 3.98-4.05 (m, 0.5H); 3.92-3.98 (m, 0.5H); 3.42-3.55 (overlapped m, 3H); 3.06 (s, 1.5H); 3.03 (s, 1.5H); 2.55-2.70 (overlapped m, 1H); 1.92-2.01 (m, 1H); 1.61-1.70 (m, 2H); 1.56 (s, 1.5H); 1.54 (s, 1.5H); 1.43-1.52 (overlapped m, 4H).

MS (ESI, m/z): 479.85 [M+H⁺] for $C_{12}H_{24}N_3O_6SBr$; $t_R$=0.77 min.

Preparation E: (2R)-4-(6-iodo-3-oxo-1H-pyrrolo[1,2-c]imidazol-2(3H)-yl)-2-methyl-2-(methylsulfonyl)-N-(((RS)-tetrahydro-2H-pyran-2-yl)oxy)butanamide Starting from 4-iodo-1H-pyrrole-2-carbaldehyde (15 g; 67.9 mmol; commercial) and proceeding in analogy to Preparation C, steps C.i to C.iv (yields: reductive amination: 85%; cyclisation: 67%; acid formation: 74%; amide coupling with THPO—NH₂: 51%), the title compound was obtained as a white solid (7.6 g).

¹H NMR (d₆-DMSO) (mixture of stereoisomers) δ: 11.34-11.46 (br. s, 0.5H); 11.28-11.34 (br. s, 0.5H); 7.29 (d, J=0.7 Hz, 0.5H); 7.28 (d, J=0.7 Hz, 0.5H); 6.20-6.23 (m, 1H); 4.83-4.87 (m, 0.5H); 4.35-4.48 (m, 2.5H); 3.99-4.08 (m, 0.5H); 3.90-3.98 (m, 0.5H); 3.38-3.56 (m, 3H); 3.06 (s, 1.5H); 3.03 (s, 1.5H); 2.56-2.72 (m, 1H); 1.92-2.00 (m, 1H); 1.60-1.68 (m, 2H); 1.55 (s, 1.5H); 1.54 (s, 1.5H); 1.41-1.54 (overlapped m, 4H).

MS (ESI, m/z): 525.84 [M+H⁺] for $C_{12}H_{24}N_3O_6IS$; $t_R$=0.78 min.

Preparation F: (2RS)-4-(6-iodo-3-oxo-1H-pyrrolo[1,2-c]imidazol-2(3H)-yl)-2-methyl-2-(methylsulfonyl)-N-(((RS)-tetrahydro-2H-pyran-2-yl)oxy)butanamide Starting from 4-iodo-1H-pyrrole-2-carbaldehyde (4.7 g; 21.2 mmol) and the compound of Preparation A (5.6 g; 22.2 mmol) and proceeding in analogy to Preparation C, steps C.i to C.iv (yields: reductive amination: 45%; cyclisation: 81%; acid formation: 78%; amide coupling with THPO—NH₂: 71%), the title compound was obtained as a white foam (2.3 g).

¹H NMR (d₆-DMSO) (mixture of stereoisomers) δ: 11.26 (br. s, 1H); 7.26-7.30 (m, 1H); 6.20-6.23 (m, 1H); 4.83-4.87 (m, 0.5H); 4.38-4.44 (m, 2.5H); 3.88-4.06 (m, 1H); 3.36-3.56 (m, 3H); 3.05 (s, 1.5H); 3.02 (s, 1.5H); 2.54-2.68 (m, 1H); 1.90-2.03 (m, 1H); 1.57-1.69 (m, 2H); 1.56 (s, 1.5H); 1.54 (s, 1.5H); 1.38-1.51 (overlapped m, 4H).

MS (ESI, m/z): 525.90 [M+H⁺] for $C_{17}H_{24}N_3O_6IS$; $t_R$=0.79 min.

Preparation G: (RS)-4-(6-ethynyl-3-oxo-1H-pyrrolo[1,2-c]imidazol-2(3H)-yl)-2-methyl-2-(methylsulfonyl)-N-(((RS)-tetrahydro-2H-pyran-2-yl)oxy)butanamide G.i. (RS)-2-methyl-2-(methylsulfonyl)-4-(3-oxo-6-((trimethylsilyl)ethynyl)-1H-pyrrolo[1,2-c]imidazol-2(3H)-yl)-N-(((RS)-tetrahydro-2H-pyran-2-yl)oxy)butanamide CuI (0.126 g; 0.662 mmol) and PdCl₂(PPh₃)₂ (0.236 g; 0.336 mmol) were introduced in a two-necked round-bottom flask. After flushing with nitrogen for 30 min, a solution of the compound of Preparation F (1.73 g; 3.29 mmol) in degassed THF (3 mL) was added followed with trimethylsilylacetylene (0.516 mL, 3.62 mmol). Degassed TEA (1.15 mL, 0.73 mmol) was added and the reaction proceeded at 50° C. for 2 h. The mixture was concentrated to dryness and the residue was purified by CC (Hept-EA) to afford the title compound as a yellow foam (1.54 g, 94% yield).

¹H NMR (d₆-DMSO) (mixture of stereoisomers) δ: 11.25-11.40 (m, 1H); 7.29-7.39 (m, 1H); 6.12-6.21 (m, 1H); 4.80-4.91 (m, 0.5H); 4.45-4.53 (m, 0.5H); 4.32-4.44 (m, 2H); 3.96-4.05 (m, 1H); 3.34-3.51 (m, 3H); 3.06 (s, 1.5H); 3.03 (s, 1.5H); 2.53-2.72 (m, 1H); 1.88-2.04 (m, 1H); 1.60-1.68 (overlapped m, 2H); 1.56 (s, 1.5H); 1.54 (s, 1.5H); 1.44-1.54 (overlapped m, 4H); 0.17 (s, 9H).

MS (ESI, m/z): 496.01 [M+H⁺] for $C_{22}H_{33}N_3O_6SSi$; $t_R$=0.90 min.

G.ii. (RS)-4-(6-ethynyl-3-oxo-1H-pyrrolo[1,2-c]imidazol-2(3H)-yl)-2-methyl-2-(methylsulfonyl)-N-(((RS)-tetrahydro-2H-pyran-2-yl)oxy)butanamide To a solution of intermediate G.i (1.53 g; 3.09 mmol) in MeOH (10 mL) was added K₂CO₃ (0.77 g; 5.56 mmol). The mixture was stirred at rt for 1 h. The reaction was diluted with DCM-MeOH 9-1 (100 mL) and water (50 mL). The aq. layer was extracted three times with DCM-MeOH 9-1 (3×75 mL). The combined org. layers were dried over MgSO₄, filtered and the filtrate concentrated to dryness. The residue was purified by CC (DCM-MeOH) to afford the title compound as a yellow foam (1.09 g; 83% yield).

¹H NMR (d₆-DMSO) (mixture of stereoisomers) δ: 11.32-11.36 (br. s, 0.5H); 11.28-11.32 (br. s, 0.5H); 7.35-7.40 (m, 1H); 6.16-6.20 (m, 1H); 4.83-4.88 (m, 0.5H); 4.46-4.52 (m, 0.5H) 4.38-4.44 (m, 2H); 3.89-4.08 (overlapped m, 1H); 3.94 (s, 1H); 3.38-3.54 (m, 3H); 3.05 (s, 1.5H); 3.03 (s, 1.5H); 2.40-2.50 (overlapped m, 1H); 1.86-2.04 (m, 1H); 1.61-1.69 (m, 2H); 1.56 (s, 1.5H); 1.54 (s, 1.5H); 1.42-1.52 (overlapped m, 4H).

MS (ESI, m/z): 423.98 [M+H⁺] for $C_{19}H_{25}N_3O_6S$; $t_R$=0.74 min.

Preparation H: (R)-4-(6-ethynyl-3-oxo-1H-pyrrolo[1,2-c]imidazol-2(3H)-yl)-2-methyl-2-(methylsulfonyl)-N-(((RS)-tetrahydro-2H-pyran-2-yl)oxy)butanamide

H.i. (R)-2-methyl-2-(methylsulfonyl)-4-(3-oxo-6-((trimethylsilyl) ethynyl)-1H-pyrrolo[1,2-c]imidazol-2(3H)-yl)-N-(((RS)-tetrahydro-2H-pyran-2-yl)oxy)butanamide Starting from the compound of Preparation E (3.0 g; 5.7 mmol) and proceeding in analogy to Preparation G, step G.i, the title compound was obtained as a brown foam (2.52 g; 89% yield).

$^1$H NMR (d$_6$-DMSO) (mixture of stereoisomers) δ: 11.36-11.38 (br. s, 0.5H); 11.31-11.34 (br. s, 0.5H); 7.38 (s, 0.5H); 7.37 (s, 0.5H); 6.17-6.22 (m, 1H); 4.84-4.88 (m, 0.5H); 4.44-4.48 (m, 0.5H); 4.37-4.44 (m, 2H); 4.01-4.06 (m, 0.5H); 3.93-4.00 (m, 0.5H); 3.36-3.55 (m, 3H); 3.06 (s, 1.5H); 3.03 (s, 1.5H); 2.55-2.68 (m, 1H); 1.94-2.00 (m, 1H); 1.60-1.67 (m, 2H); 1.55 (s, 1.5H); 1.54 (s, 1.5H); 1.45-1.52 (overlapped m, 4H); 0.20 (s, 9H).

MS (ESI, m/z): 496.01 [M+H$^+$] for C$_{24}$H$_{34}$N$_2$O$_5$SSi; t$_R$=0.90 min.

H.ii. (R)-4-(6-ethynyl-3-oxo-1H-pyrrolo[1,2-c]imidazol-2(3H)-yl)-2-methyl-2-(methylsulfonyl)-N-(((RS)-tetrahydro-2H-pyran-2-yl)oxy)butanamide To a solution of intermediate H.i (2.5 g; 5.4 mmol) in THF (11 mL) was added TBAF (1M in THF; 5.2 mL). The mixture was stirred at rt for 20 min. The mixture was concentrated to dryness and the residue was purified by CC (DCM-MeOH) to afford the title compound as a pale brown foam (2.02 g; 94% yield).

$^1$H NMR (d$_6$-DMSO) (mixture of stereoisomers) δ: 11.35-11.40 (br. s, 0.5H); 11.29-11.34 (br. s, 0.5H); 7.39 (d, J=0.5 Hz, 0.5H); 7.38 (d, J=0.5 Hz, 0.5H); 6.16-6.21 (m, 1H); 4.84-4.87 (m, 0.5H); 4.45-4.48 (m, 0.5H); 4.38-4.43 (m, 2H); 4.00-4.06 (overlapped m, 0.5H); 3.97 (s, 1H); 3.91-3.97 (overlapped m, 0.5H); 3.45-3.55 (m, 1.5H); 3.38-3.45 (m, 1.5H); 3.06 (s, 1.5H); 3.03 (s, 1.5H); 2.54-2.69 (m, 1H); 1.92-2.01 (m, 1H); 1.59-1.68 (m, 2H); 1.55 (s, 1.5H); 1.54 (s, 1.5H); 1.42-1.54 (overlapped m, 4H).

MS (ESI, m/z): 423.98 [M+H$^+$] for C$_{19}$H$_{25}$N$_3$O$_6$S; t$_R$=0.73 min.

Preparation I: (4-(3-hydroxy-3-methylbut-1-yn-1-yl)phenyl)boronic acid

A mixture of 4-iodophenylboronic acid (2.48 g; 10 mmol; commercial), Pd(PPh$_3$)$_4$ (0.17 g; 0.15 mmol) in pyrrolidine (10 mL) was flushed with nitrogen for 15 min. The mixture was cooled to 0° C. and 2-methyl-3-butyn-2-ol (1.68 g; 20 mmol; commercial) was added. The reaction was stirred at rt overnight and then concentrated to dryness. The residue was diluted in 2N NaOH (20 mL) and washed twice with DCM (2×20 mL). The filtrate was cooled to 0° C. and acidified with 2N HCl. The precipitate was collected by filtration, washed with water and purified by CC (DCM-MeOH) to afford the title compound as a white solid (1.4 g; 68% yield).

$^1$H NMR (d$_6$-DMSO) δ: 8.04-8.14 (br. s, 2H); 7.76 (d, J=8.0 Hz, 2H); 7.34 (d, J=8.0 Hz, 2H); 5.35-5.51 (br. s, 1H); 1.46 (s, 9H).

Preparation J: 3-(4-iodophenyl)oxetan-3-ol

A solution of 1,4-diiodobenzene (0.800 g; 2.43 mmol) in THF (8 mL) was treated at −78° C. with BuLi (1.68M in Hex; 2.23 mL). After stirring at this temperature for 30 min, the solution was treated with a suspension of 3-oxetanone (0.24 g; 3.34 mmol, commercial) in THF (3 mL). The reaction mixture was allowed to reach rt and was further stirred overnight. The reaction mixture was treated with 10% aq. NaHSO$_4$ solution (4 mL) and diluted water (20 mL) and EA (30 mL). The aq. layer was extracted with EA (30 mL). The combined org. layers were washed with brine (50 mL), dried over MgSO$_4$, filtered and concentrated to dryness. The residue was purified by CC (Hept-EA) to afford the title compound as a white solid (0.2 g; 55% yield).

$^1$H NMR (d$_6$-DMSO) δ: 7.73 (d, J=8.5 Hz, 2H); 7.39 (d, J=8.5 Hz, 2H); 6.39 (s, 1H); 4.73 (d, J=6.8 Hz, 2H); 4.60 (d, J=6.8 Hz, 2H).

Preparation K: 3-(iodoethynyl)oxetan-3-ol

To a solution of 3-ethynyloxetan-3-ol (1.097 g; 11.2 mmol; commercial) in MeOH (50 mL) and 1M aq. KOH (28 mL) was added iodine (3.549 g; 14 mmol). The reaction mixture was stirred for 2 h at rt. Water (150 mL) and DCM (500 mL) were added. The aq. layer was extracted with EA (500 mL). The org. layer was washed with brine, dried over MgSO$_4$, filtered and concentrated down to afford the desired compound as a light yellow solid (2.21 g; 88% yield).

$^1$H NMR (d$_6$-DMSO) δ: 4.60 (d, J=6.5 Hz, 2H); 4.45 (d, J=6.5 Hz, 2H).

Preparation L: ((1R,2R)-2-(4-iodophenyl)cyclopropyl)methanol and ((1S,2S)-2-(4-iodophenyl)cyclopropyl)methanol Rac-(trans-2-(4-iodophenyl)cyclopropyl)methanol (0.956 g; prepared as described in WO 2005/103032) was separated by semi-preparative chiral HPLC Method B (Hept-EtOH 3-1; flow rate: 16 mL/min, UV detection at 210 nM); the respective retention times (flow rate: 0.8 mL/min) were 5.7 and 7.1 min. The title enantiomers were obtained as white solids (0.45 g each).

First-Eluting Enantiomer, (1R,2R)-Configurated:
$^1$H NMR (d$_6$-DMSO) δ: 7.56 (d, J=8.2 Hz, 2H); 6.89 (d, J=8.2 Hz, 2H); 4.53-4.69 (m, 1H); 3.40-3.51 (m, 1H); 3.31-3.39 (overlapped m, 1H); 1.71-1.81 (m, 1H); 1.18-1.31 (m, 1H); 0.76-0.94 (m, 2H).

[α]$_D$=−61° (c=1.04; MeOH).

Second-Eluting Enantiomer, (1S,2S)-Configurated:
$^1$H NMR (d$_6$-DMSO) δ: 7.56 (d, J=8.2 Hz, 2H); 6.89 (d, J=8.2 Hz, 2H); 4.55-4.63 (m, 1H); 3.39-3.51 (m, 1H); 3.27-3.38 (overlapped m, 1H); 1.71-1.80 (m, 1H); 1.18-1.31 (m, 1H); 0.77-0.93 (m, 2H).

[α]$_D$=+62° (c=1.04; MeOH).

The respective absolute configurations of these compounds have been determined though transformation of the second-eluting enantiomer into the corresponding (S) and (R) α-methoxy-α-trifluoromethylphenylacetyl esters and the subsequent analysis of their NMR spectra as described by Tsuda et al. in *Chem. Pharm. Bull.* (2003), 51, 448-451.

Preparation M: (1-(4-ethynylphenyl)cyclopropyl)methanol

Starting from (1-(4-iodophenyl)cyclopropyl)methanol (0.660 g; 2.4 mmol; commercial) and TMS-acetylene (0.51 mL; 1.5 eq.), and proceeding in analogy to Preparation G, steps G.i and G.ii (yields: Sonogashira coupling: 96%; say' cleavage: 39% yield), the title compound was obtained, after purification by CC (Hept-EA), as a yellow solid (0.167 g).

$^1$H NMR (d$_6$-DMSO) δ: 7.37 (d, J=8.2 Hz, 2H); 7.29 (d, J=8.2 Hz, 2H); 4.68 (t, J=5.7 Hz, 1H); 4.08 (s, 1H); 3.53 (d, J=5.6 Hz, 2H); 0.81-0.92 (m, 2H); 0.67-0.79 (m, 2H).

Preparation N:
(1-(4-ethynylphenyl)cyclopropyl)methanamine

In a 7 ml flask, [1-(4-bromophenyl)cyclopropyl]methanamine (0.108 g; 0.479 mmol; commercial), bis(tri-tert-butylphosphine)palladium (0.021 g; 0.04 mmol), cesium fluoride (0.145 g; 0.96 mmol), degassed dioxane (1.8 mL) and ethynyltri-n-butyltin (0.21 mL; 0.71 mmol) were introduced successively. The solution was stirred at 80° C. for 30 min. The mixture was concentrated to dryness and purified by CC (DCM-MeOH) to afford the title compound (still contaminated by unknown impurities) as a brown foam (0.1 g).

$^1$H NMR (d$_6$-DMSO) δ: 7.40 (d, J=8.4 Hz, 2H); 7.31 (d, J=8.4 Hz, 2H); 4.13 (s, 1H); 2.82 (s, 2H); 0.84-0.90 (m, 2H); 0.74-0.77 (m, 2H).

Preparation O:
2-(4-ethynylphenyl)-2-methylpropan-1-ol

Starting from 2-(4-bromophenyl)-2-methylpropan-1-ol (0.742 g; 3.2 mmol; commercial) and proceeding in analogy to Preparation N, the title compound was obtained, after purification by CC (Hept-EA), as an ochre solid (0.54 g; 96% yield).

$^1$H NMR (d$_6$-DMSO): 7.33-7.42 (m, 4H); 4.69 (t, J=5.4 Hz, 1H); 4.09 (s, 1H); 3.40 (d, J=5.4 Hz, 2H); 1.20 (s, 6H).

Preparation P: ((1S,2S)-2-(bromoethynyl)cyclopropyl)methyl acetate AND ((1R,2R)-2-(bromoethynyl)cyclopropyl)methyl acetate P.i.
((1S*,2S*)-2-(2,2-dibromovinyl)cyclopropyl)methyl acetate To a solution of CBr$_4$ (30.0 g; 88.9 mmol) in DCM (60 mL) cooled at −20° C., was added dropwise over 45 min a solution of PPh$_3$ (45.8 g, 175 mmol) in DCM (100 mL). The mixture was kept stirred at this temperature for 30 min and then cooled to −78° C. A solution of ((1S*,2S*)-2-formylcyclopropyl)methyl acetate (6.18 g, 43.5 mmol, prepared as described in WO 2012/154204) in DCM (80 mL) was added dropwise over 45 min, keeping the internal temperature below −70° C. The mixture was stirred at this temperature for 30 min and allowed to warm to rt over 1 h. The solvent was removed in vacuo and the residue was purified by CC (EA-Hept) to afford the title acetate as a clear oil (4.84 g; 37% yield).

$^1$H NMR (CDCl$_3$) δ: 5.84 (d, J=9.0 Hz, 1H); 3.97 (m, 2H); 2.07 (s, 3H); 1.61 (m, 1H); 1.33 (m, 1H); 0.78-0.92 (m, 2H).

MS (ESI, m/z): 295.0 [M+H$^+$] for C$_8$H$_{10}$O$_2$Br$_2$; t$_R$=0.87 min.

P.ii. ((1S,2S)-2-(bromoethynyl)cyclopropyl)methyl acetate and ((1R,2R)-2-(bromoethynyl)cyclopropyl)methyl acetate To a solution of intermediate P.i (3.94 g; 13.2 mmol) in THF (75 mL) was added TBAF trihydrate (23.2 g; 72.8 mmol). The reaction mixture was heated at 60° C. for 4 h. The reaction mixture was cooled to rt and diluted with diethyl ether (150 mL). The org. phase was washed with water (60 mL) and brine (60 mL), dried over MgSO$_4$ and concentrated to dryness. The residue was purified by CC (EA-Hept) to afford the title compound as a yellow oil (1.76 g, 61% yield). The racemic product was separated by semi-preparative chiral HPLC Method B (Hept-EtOH 9-1; flow rate: 20 mL/min, UV detection at 223 nm), the respective retention times (flow rate: 0.8 mL/min) were 5.9 and 8.7 min. The title enantiomers were obtained as clear oils (0.64 g each).

First-Eluting Enantiomer, (1S,2S)-Configurated:
$^1$H NMR (CDCl$_3$) δ: 3.97 (dd, J=6.5, 11.7 Hz, 1H); 3.84 (dd, J=7.5, 11.7 Hz, 1H); 2.06 (s, 3H); 1.50 (m, 1H); 1.25 (m, 1H); 0.97 (m, 1H); 0.76 (m, 1H).

[α]$_D$=+96° (c=1.03; MeOH).

Second-Eluting Enantiomer, (1R,2R)-Configurated:
$^1$H NMR (CDCl$_3$) δ: 3.97 (dd, J=6.5, 11.7 Hz, 1H); 3.84 (dd, J=7.5, 11.7 Hz, 1H); 2.06 (s, 3H); 1.50 (m, 1H); 1.25 (m, 1H); 0.97 (m, 1H); 0.76 (m, 1H).

[α]$_D$=−94° (c=1.01; MeOH).

The respective absolute configurations of these compounds have been determined though transformation of the second-eluting enantiomer into the corresponding (S) and (R) α-methoxy-α-trifluoromethylphenylacetyl esters and the subsequent analysis of their NMR spectra as described by Tsuda et al. in *Chem. Pharm. Bull.* (2003), 51, 448-451.

Preparation Q: ((1-(bromoethynyl)cyclopropyl)methoxy)(tert-butyl)diphenylsilane

To a mixture of (dibromomethyl)triphenylphosphonium bromide (8.527 g; 16.6 mmol) and THF (40 mL) was added a solution of tBuOK (1M in THF; 16.6 mL; 16.6 mmol). The resulting dark brown solution was stirred for 3 min at rt, then cooled to 0° C. A solution of 1-(((tert-butyldiphenylsilyl)oxy)methyl)cyclopropanecarbaldehyde (2.2 g; 6.62 mmol; prepared as described in WO 2010/135536) in THF (23 mL) was added drop wise. The reaction was stirred at 0° C. for 40 min. The reaction mixture was cooled to −78° C. and tBuOK (1M in THF; 29.1 mL; 29.1 mmol) was added rapidly and stirred at −78° C. for 30 min. The reaction mixture was quenched with brine (150 mL). The aq. layer was separated and extracted with diethyl ether (3×150 mL). The combined org. phases were washed with brine, dried over MgSO$_4$, filtered, and concentrated to dryness. The residue was purified by CC (Hept-EA) to afford the title compound as a colourless oil (2.052 g; 75% yield).

$^1$H NMR (d$_6$-DMSO) δ: 7.59-7.70 (m, 4H); 7.37-7.53 (m, 6H); 3.56 (s, 2H); 1.01 (s, 9H); 0.82-0.89 (m, 2H); 0.71-0.76 (m, 2H).

Preparation R:
(1-(3-fluoro-4-iodophenyl)cyclopropyl)methanol

R.i. Methyl 1-(4-bromo-3-fluorophenyl)cyclopropanecarboxylate

To an ice-chilled mixture of 1-(4-bromo-3-fluorophenyl)cyclopropanecarboxylic acid (1.188 g; 4.59 mmol; commercial) in MeOH (9 mL), was added dropwise thionyl chloride (0.7 mL; 9.6 mmol). The mixture was stirred at 0° C. for 1 h and then at rt for 17 h. The mixture was concentrated to dryness and the residue was partitioned between sat. aq. NaHCO$_3$ (30 mL) and EA (30 mL). The two layers were separated. The aq. phase was extracted with EA (30 mL). The combined org. layers were washed with brine (45 mL), dried over MgSO$_4$, filtered and concentrated to dryness. The residue was purified by CC (Hept-EA) to afford the title compound as a yellow oil (0.501 g; 40% yield).

¹H NMR (d₆-DMSO) δ: 7.63 (t, J=8.3 Hz, 1H); 7.39 (dd, J=1.9, 10.1 Hz, 1H); 7.15 (dd, J=1.9, 8.3 Hz, 1H); 3.56 (s, 3H); 1.46-1.51 (m, 2H); 1.22-1.28 (m, 2H).

R.ii.
(1-(4-bromo-3-fluorophenyl)cyclopropyl)methanol

To a solution of intermediate R.i (0.491 g; 1.792 mmol) in DCM (9 mL) cooled to −78° C. was added dropwise DIBAH (1M in DCM; 5.6 mL; 5.6 mmol). The solution was stirred at −78° C. for 20 min. The reaction was allowed to warm to 0° C. Water (0.224 mL), 15% NaOH (0.224 mL), water (0.56 mL) were added carefully. The mixture was stirred for 15 min at this temperature and MgSO₄ was added. The mixture was filtered and washed with DCM and EA. The filtrate was concentrated to dryness to give the title compound as a yellow oil (0.424 g; 97% yield).
¹H NMR (d₆-DMSO) δ: 7.57 (t, J=8.0 Hz, 1H); 7.26 (dd, J=1.9, 10.7 Hz, 1H); 7.08 (dd, J=1.9, 8.0 Hz, 1H); 4.77 (t, J=5.8 Hz, 1H); 3.51 (d, J=5.5 Hz, 2H); 0.82-0.89 (m, 2H); 0.76-0.82 (m, 2H).

R.iii.
(1-(3-fluoro-4-iodophenyl)cyclopropyl)methanol

To a solution of intermediate R.ii (0.405 g; 1.65 mmol) in 1,4-dioxane (2.2 mL) in a vial was added NaI (0.496 g; 3.31 mmol) and then CuI (0.063 g; 0.331 mmol). The reaction mixture was degassed and trans-N,N'-dimethylcyclohexane-1,2-diamine (0.104 mL, 0.661 mmol) was added. The mixture was degassed and stirred at 125° C. for 17 h. The suspension was cooled down to rt. The residue was filtered and washed with EA (10 mL). The filtrate was washed with water (10 mL). The aq. layer was extracted with EA (2×10 mL). The combined org. layers were washed with brine (20 mL), dried over MgSO₄ and filtered before being concentrated to dryness. The residue was purified by CC (Hept-EA) to afford the title product as a yellow oil (0.352 g; 73% yield).
¹H NMR (d₆-DMSO) δ: 7.70 (dd, J=7.0, 8.1 Hz, 1H); 7.16 (dd, J=2.0, 10.0 Hz, 1H); 6.93 (dd, J=2.0, 8.1 Hz, 1H); 4.75 (t, J=5.7 Hz, 1H); 3.51 (d, J=5.7 Hz, 2H); 0.84-0.87 (m, 2H); 0.76-0.79 (m, 2H).

Preparation S: 1-(2-hydroxyethyl)-3-(4-iodophenyl) imidazolidin-2-one

S.i. 1-(4-bromophenyl)-3-(2-hydroxyethyl)imidazolidin-2-one AND 1-(2-hydroxyethyl)-3-(4-iodophenyl)imidazolidin-2-one CuI (0.0762 g; 0.4 mmol), (1R,2R)-1,2-diaminocyclohexane (0.137 g; 1.2 mmol) and K₂CO₃ (1.11 g; 8 mmol) were added to degassed 1,4-dioxane (15 mL). The reaction mixture was degassed and 1-(2-hydroxyethyl)-imidazolidinone (0.521 g; 4 mmol) and 1-bromo-4-iodobenzene (1.132 g; 4 mmol) were added. The resulting mixture was heated to reflux at 110° C. for 15 h. The reaction mixture was cooled to rt, filtered through a Celite and the Celite bed was washed with chloroform. The filtrate was dried over Na₂SO₄ and filtered before being concentrated to dryness. The residue was purified by CC (Hept-EA) to afford a 4-1 unseparable mixture of 1-(4-bromophenyl)-3-(2-hydroxyethyl)imidazolidin-2-one and 1-(2-hydroxyethyl)-3-(4-iodophenyl)imidazolidin-2-one as a white solid (0.445 g; 39% yield).
MS (ESI, m/z): 285.04 [M+H⁺] for C₁₁H₁₃N₂O₂Br; t_R=0.69 min.
MS (ESI, m/z): 332.93 [M+H⁺] for C₁₁H₁₃N₂O₂I; t_R=0.71 min.

S.ii. 1-(2-hydroxyethyl)-3-(4-iodophenyl)imidazolidin-2-one

Starting from intermediate S.i (0.06 g; 0.119 mmol) and proceeding in analogy to Preparation R, step R.iii, the title compound was obtained as a yellow solid (0.345 g; 53% yield).
¹H NMR (CDCl₃) δ: 7.61 (d, J=8.9 Hz, 2H); 7.32 (d, J=8.9 Hz, 2H); 3.77-3.86 (m, 4H); 3.56-3.64 (m, 2H); 3.41-3.48 (m, 2H); 2.64-2.77 (m, 1H).
MS (ESI, m/z): 332.93 [M+H⁺] for C₁₁H₁₃N₂O₂I; t_R=0.71 min.

Preparation T:
N-(2-fluoro-4-iodophenyl)-2-hydroxyacetamide

To a solution of 2-((4-bromo-2-fluorophenyl)amino)-2-oxoethyl acetate (1.0 g; 3.45 mmol; commercial) in 1,4-dioxane (2.3 mL) were added trans-N,N'-dimethylcyclohexane-1,2-diamine (0.06 mL; 0.38 mmol), NaI (1.03 g; 6.9 mmol) and CuI (0.066 g; 0.35 mmol). The reaction mixture was irradiated in a microwave oven at 170° C. for 30 min and then at 180° C. for 30 min. Water (20 mL) and EA (50 mL) were added. The aq. layer was extracted with EA (45 mL). The combined org. layers were washed with brine, dried over MgSO₄, filtered and concentrated to dryness. The residue was dissolved in MeOH (20 mL) and K₂CO₃ (2.5 g; 17.2 mmol) was added. The reaction was stirred at rt for 10 min. EA (100 mL) and water (60 mL) were added. The aq. phase was extracted with EA (100 mL). The combined org. phases were washed with brine, dried over MgSO₄ and filtered. After concentration to dryness of the filtrate, the title compound was obtained as a brown solid (0.8 g; 79% yield).
¹H NMR (d₆-DMSO) δ: 7.66-7.78 (m, 2H); 7.51-7.57 (m, 1H); 5.85 (t, J=5.9 Hz, 1H); 4.02 (d, J=5.9 Hz, 2H).

Preparation U:
(1-(5-iodopyridin-2-yl)cyclopropyl)methanol

Starting from (1-(5-bromopyridin-2-yl)cyclopropyl) methanol (0.98 g; 4.28 mmol; commercial) and proceeding in analogy to Preparation R, step R.iii, the title compound was obtained, after purification by CC (Hept-EA), as a white solid (0.97 g; 82% yield).
¹H NMR (d₆-DMSO) δ: 8.63 (d, J=2.0 Hz, 1H); 8.03 (dd, J=2.0, 8.4 Hz, 1H); 7.37 (d, J=8.4 Hz, 1H); 4.78 (t, J=5.5 Hz, 1H); 3.70 (d, J=5.5 Hz, 2H); 1.04-1.10 (m, 2H); 0.87-0.93 (m, 2H).
MS (ESI, m/z): 275.77 [M+H⁺] for C₉H₁₀NOI; t_R=0.55 min.

Preparation V:
(1-(6-iodopyridin-3-yl)cyclopropyl)methanol

Starting from (1-(6-bromopyridin-3-yl)cyclopropyl) methanol (0.42 g; 2.29 mmol; commercial) and proceeding in analogy to Preparation R, step R.iii, the title compound was obtained, after purification by CC (Hept-EA), as a colourless oil (0.35 g; 55% yield).
¹H NMR (d₆-DMSO) δ: 8.30 (dd, J=0.6, 2.6 Hz, 1H); 7.72 (dd, J=0.6, 8.1 Hz, 1H); 7.40 (dd, J=2.6, 8.1 Hz, 1H); 4.80 (t, J=5.7 Hz, 1H); 3.48 (d, J=5.7 Hz, 2H); 0.83-0.87 (m, 2H); 0.77-0.80 (m, 2H).

MS (ESI, m/z): 275.78 [M+H$^+$] for C$_9$H$_{10}$NOI; t$_R$=0.63 min.

Preparation W:
4-((1-(4-iodophenyl)cyclopropyl)methyl)morpholine

W.i.
4-((1-(4-bromophenyl)cyclopropyl)methyl)morpholine

To a solution of 1-(4-bromophenyl)cyclopropanecarbaldehyde (0.405 g; 1.8 mmol, commercial) in MeOH (5.8 mL) was added 3 Å molecular sieves (0.05 g) and morpholine (0.174 mL; 1.98 mmol). The reaction was stirred at rt overnight under nitrogen. Morpholine (0.2 mL; 2.27 mmol) was added and the mixture was stirred at 70° C. for 20 h. The reaction mixture was cooled to 0° C. and DCE (5.8 mL) was added followed by sodium triacetoxyborohydride (1.144 g; 5.4 mmol). The reaction mixture was stirred at this temperature for 10 min, then at rt for 30 min. Sat. aq. NaHCO$_3$ (20 mL) and DCM (25 mL) were added. The mixture was filtered and the phases were separated. The aq. layer was extracted with DCM-MeOH (9-1, 3×20 mL). The combined org. layers were dried over MgSO$_4$, filtered and concentrated to dryness. The residue was purified by CC (Hept-EA) to afford the title compound as a colourless oil (0.413 g; 78% yield).

$^1$H NMR (d$_6$-DMSO) δ: 7.42 (d, J=8.5 Hz, 2H); 7.27 (d, J=8.5 Hz, 2H); 3.43-3.47 (m, 4H); 2.48 (s, 2H); 2.32-2.40 (m, 4H); 0.79-0.82 (m, 2H); 0.70-0.74 (m, 2H).

MS (ESI, m/z): 295.92 [M+H$^+$] for C$_{14}$H$_{18}$NOBr; t$_R$=0.58 min.

W.ii.
4-((1-(4-iodophenyl)cyclopropyl)methyl)morpholine

Starting from intermediate W.i (0.41 g; 1.39 mmol) and proceeding in analogy to Preparation R, step R.iii, the title compound was obtained, after purification by CC (Hept-EA), as a yellow oil (0.29 g; 61% yield).

$^1$H NMR (d$_6$-DMSO) δ: 7.59 (d, J=8.3 Hz, 2H); 7.13 (d, J=8.3 Hz, 2H); 3.46 (t, J=4.5 Hz, 4H); 2.48 (s, 2H); 2.30-2.40 (m, 4H); 0.78-0.82 (m, 2H); 0.68-0.74 (m, 2H).

MS (ESI, m/z): 343.87 [M+H$^+$] for C$_{14}$H$_{18}$NOI; t$_R$=0.55 min.

Preparation X: (E)-tert-butyldimethyl((4-(2-(4,4,5,5-tetramethyl-1,3,2-dioxaborolan-2-yl)vinyl)benzyl)oxy)silane To a solution of tert-butyl((4-ethynylbenzyl)oxy)dimethylsilane (6.836 g; 27.7 mmol; prepared as described in Allen et al., J. Am. Chem. Soc. (2009), 131(35), 12560-12561) was dissolved in DCM (130 mL) and 4,4,5,5-tetramethyl-1,3,2-dioxaborolane (12 mL; 82.7 mmol) was added. The solution was degassed and tris(triphenylphosphine)rhodium(I) chloride (0.292 g; 0.281 mmol) was added. The mixture was stirred at rt overnight under argon. Tris(triphenylphosphine)rhodium(I) chloride (0.302 g; 0.291 mmol) and 4,4,5,5-tetramethyl-1,3,2-dioxaborolane (6 mL; 41.4 mmol) were added to the mixture which was degassed and stirred at rt for 1 h under argon. The reaction was carefully quenched with sat. NH$_4$Cl (150 mL). The phases were separated and the aq. phase was extracted with EA (2×150 mL). The combined org. layers were dried over MgSO$_4$ and filtered. After concentration of the filtrate to dryness, the residue was purified by CC (Hept-EA) to afford the title compound as an orange oil (5.7 g; 55% yield).

$^1$H NMR (d$_6$-DMSO) δ: 7.55 (d, J=8.2 Hz, 2H); 7.30 (d, J=8.2 Hz, 2H); 6.11 (d, J=18.5 Hz, 1H); 4.63-4.73 (m, 3H); 1.24 (s, 12H), 0.90 (s, 9H), 0.07 (s, 6H).

Preparation Y: 03-(bromoethynyl)bicyclo[1.1.1]pentan-1-yl)methoxy)(tert-butyl)diphenylsilane Y.i. Bicyclo[1.1.1]pentane-1,3-diyldimethanol To a solution of dimethyl bicyclo[1.1.1]pentane-1,3-dicarboxylate (1.74 g; 9.45 mmol; commercial) in THF (12 mL), cooled at 0° C. was added dropwise LiAlH$_4$ (2.4M in THF; 5.29 mL; 12.7 mmol) over 45 min, keeping IT below 15° C. The suspension was stirred at rt for 3 h. The crude mixture was cooled to 0° C. and carefully quenched by water (0.48 mL), 15% aq. NaOH (0.48 mL) and water (1.44 mL). The mixture was stirred at rt for 35 min then THF (17 mL) and MgSO$_4$ were added. The mixture was stirred at rt for 10 min. The mixture was filtered and concentrated to dryness. The residue was purified by CC (Hept-EA) to afford the title compound as a colourless oil (1.2 g; 99% yield).

$^1$H NMR (d$_6$-DMSO) δ: 4.40 (t, J=5.5 Hz, 2H); 3.35 (d, J=5.6 Hz, 4H); 1.46 (s, 6H).

Y.ii. (3-(((tert-butyldiphenylsilyl)oxy)methyl)bicyclo[1.1.1]pentan-1-yl)methanol To a suspension of NaH (60% in mineral oil; 0.23 g; 5.67 mmol) in THF (4.5 mL) was added slowly at rt a solution of intermediate Y.i (0.66 g; 5.16 mmol) in THF (3.3 mL), keeping IT below 27° C. After 1 h stirring, a solution of TBDPS-Cl (1.36 mL; 5.16 mmol) in THF (2.8 mL) was added drop wise over 15 min. The solution was stirred for 4 h, then diluted in Et$_2$O (20 mL). The org. phase was washed with brine (2×20 mL), dried over Na$_2$SO$_4$, filtered and concentrated to dryness. The residue was purified by CC (Hept-EA) to afford the title compound as a colourless oil (0.49 g; 26% yield).

$^1$H NMR (d$_6$-DMSO) δ: 7.56-7.64 (m, 4H); 7.39-7.50 (m, 6H); 4.43 (t, J=5.6 Hz, 1H); 3.64 (s, 2H); 3.36 (d, J=5.5 Hz, 2H); 1.49 (s, 6H); 1.01 (s, 9H).

Y.iii. 3-(((tert-butyldiphenylsilyl)oxy)methyl)bicyclo[1.1.1]pentane-1-carbaldehyde To a solution of intermediate Y.ii (1.09 g; 2.98 mmol) in DCM (6.9 mL) cooled to −10° C., was added DIPEA (1.59 mL; 9.31 mmol) over 15 min. A solution of Pyr.SO$_3$ complex (45%; 1.44 g; 4.07 mmol) in DMSO (4.03 mL) was then dropwise added over 10 min. The reaction mixture was stirred for 1.5 h at 0° C. and 1 h at rt. The reaction mixture was partitioned between water (35 mL) and DCM (20 mL). The aq. layer was extracted with DCM (15 mL). The combined org. layers were dried over Na$_2$SO$_4$, filtered and concentrated to dryness. The residue was co-evaporated with toluene (2×10 mL) and then purified by CC (Hept-EA) to afford the title compound as a colourless oil (0.94 g; 87% yield).

$^1$H NMR (d$_6$-DMSO) δ: 9.53 (s, 1H); 7.57-7.62 (m, 4H); 7.41-7.49 (m, 6H); 3.68 (s, 2H); 1.86 (s, 6H); 1.01 (s, 9H).

Y.iv. Tert-butyl((3-(2,2-dibromovinyl)bicyclo[1.1.1]pentan-1-yl)methoxy)diphenylsilane To a solution of carbon tetrabromide (1.76 g; 5.25 mmol) in DCM (3.8 mL) cooled at −20° C., was added dropwise over 20 min a solution of triphenylphosphine (2.81 g; 10.3 mmol) in DCM (6.2 mL). The yellow suspension was allowed to warm slowly (over 8 min) to −5° C. and was then cooled to −78° C. A solution of intermediate Y.iii (0.94 g; 2.58 mmol) in DCM (4.9 mL) was added dropwise over 50 min at −78° C. The mixture was stirred at this temperature for 30 min. The mixture was allowed to slowly warm to rt (over 1 h). The mixture was diluted in $Et_2O$ (60 mL), filtered and washed with $Et_2O$. The filtrate was concentrated to dryness and slurried in $Et_2O$ (50 mL). The mixture was vigorously stirred at rt for 30 min. The mixture was filtered, washed with $Et_2O$ and the filtrate concentrated to dryness. The residue was then purified by CC (Hept-EA) to afford the title compound as a yellow oil (1.2 g; 89% yield).

$^1$H NMR ($d_6$-DMSO) δ: 7.57-7.61 (m, 4H); 7.41-7.49 (m, 6H); 6.74 (s, 1H); 3.64 (s, 2H); 1.90 (s, 6H); 1.01 (s, 9H).

Y.v. ((3-(bromoethynyl)bicyclo[1.1.1]pentan-1-yl) methoxy)(tert-butyl)diphenylsilane A solution of intermediate Y.iv (0.45 g; 0.86 mmol) in THF (2 mL) cooled at −78° C. was treated with a solution of tBuOK (1M, 3.8 mL). The reaction mixture was stirred for 30 min at −78° C. then was diluted with brine (8 mL) and was allowed to reach rt. $Et_2O$ (15 mL) was added. The two layers were separated and the aq. phase was extracted with $Et_2O$ (15 mL). The combined org. layers were washed with brine (10 mL), dried over $Na_2SO_4$, filtered and concentrated to dryness to afford the title compound as a yellow oil (0.37 g; 97% yield).

$^1$H NMR ($d_6$-DMSO) δ: 7.55-7.60 (m, 4H); 7.41-7.49 (m, 6H); 3.60 (s, 2H); 1.91 (s, 6H); 1.00 (s, 9H).

Preparation Z: 4-iodo-2-methylbut-3-yn-2-amine

Starting from 2-methylbut-3-yn-2-amine (0.5 g; 6 mmol; commercial) and proceeding in analogy to Preparation K, the title compound was obtained as a yellow solid (0.98 g; 78% yield).

$^1$H NMR ($d_6$-DMSO) δ: 2.01 (s, 2H); 1.24 (s, 6H).
MS (ESI, m/z): 210.01 [M+H$^+$] for $C_5H_8NI$; $t_R$=0.33 min.

Preparation AA: 4-iodobenzyl carbamate

AA.i. 4-iodobenzyl (2,2,2-trichloroacetyl)carbamate

To a solution of iodobenzylalcool (1 g; 4.27 mmol) in DCM (20 mL) was added at 0° C. trichloroacetylisocyanate (0.56 mL; 4.7 mmol; commercial). The mixture was stirred at 0° C. for 1 h, allowed to reach rt and stirred at rt for 3 h. Water (20 mL) was added. The aq. layer was extracted with DCM (20 mL). The combined org. phases were dried over $MgSO_4$ and filtered. The filtrate was concentrated to dryness to afford the title compound as a beige solid (1.85 g; quant.).

$^1$H NMR ($d_6$-DMSO) δ: 12.02 (s, 1H); 7.76-7.82 (m, 2H); 7.24-7.31 (m, 2H); 5.21 (s, 2H).

AA.ii. 4-iodobenzyl carbamate

Intermediate AA.i (1.85 g; 4.38 mmol) was dissolved in MeOH (8 mL). $K_2CO_3$ (1.816 g; 13.1 mmol) was added and the mixture was stirred at rt for 4 h. EA (100 mL) was added. The aq. phase was extracted with EA (100 mL). The combined org. layers were washed with brine, dried over $MgSO_4$, filtered and the filtrate concentrated to dryness. The residue was taken in $Et_2O$ (5 mL). The mixture was stirred for 20 min and filtered to afford the title compound as a white solid (1.05 g; 87% yield).

$^1$H NMR ($d_6$-DMSO) δ: 7.70-7.78 (m, 1H); 7.13-7.20 (m, 1H); 6.39-6.87 (m, 1H); 4.93 (s, 1H).

Preparation AB: (3aR,5S,6aS)-5-(bromoethynyl)-2,2-dimethyltetrahydro-4H-cyclopenta[d][1,3]dioxole Starting from (3aR,5S,6aS)-5-(2,2-dibromovinyl)-2,2-dimethyltetrahydro-4H-cyclopenta[d][1,3]dioxole (2.06 g; 6.32 mmol; prepared as described in WO 2013/170030) and proceeding in analogy to Preparation N, step N.v, the title compound was obtained as a yellow oil (1.37 g; 88% yield).

$^1$H NMR (CDCl$_3$) δ: 4.60-4.63 (m, 2H); 2.85-2.93 (m, 1H); 2.12-2.17 (m, 2H); 1.51-1.60 (overlapped m, 2H); 1.41 (s, 3H); 1.26 (s, 3H).

Preparation AC: (1-(4-iodophenyl)cyclopropyl)methyl carbamate

Starting from (1-(4-iodophenyl)cyclopropyl)methanol (0.887 g, 3.24 mmol), and proceeding as described in Preparation AA, steps AA.i and AA.ii, the title carbamate was obtained as a white solid (0.63 g; 59% yield over the two steps).

$^1$H NMR ($d_6$-DMSO) δ: 7.63 (m, 2H); 7.08-7.13 (m, 2H); 6.31-6.64 (m, 2H); 4.05 (s, 2H); 0.92-0.98 (m, 2H); 0.83-0.89 (m, 2H).

Preparation AD: 1-(bromoethynyl)cyclopropyl)methyl carbamate

AD.i. (1-(bromoethynyl)cyclopropyl)methanol

To a solution of the compound of Preparation Q (0.5 g; 1.21 mmol) in THF (2 mL) was added TBAF (1M in THF; 2.42 mL; 2.42 mmol). The mixture was stirred at rt for 1 h. Sat. aq. $NH_4Cl$ (5 mL) was added and the mixture was extracted with EA (2×5 mL). The org. layer was washed with brine, dried over $MgSO_4$ and filtered. The filtrate was concentrated to dryness. The residue was purified by CC (Hept-EA) to afford the title compound as a colourless oil (0.175 g; 83% yield).

$^1$H NMR ($d_6$-DMSO) δ: 4.90 (t, J=6.0 Hz, 1H); 3.32 (d, J=6.0 Hz, 2H); 0.76-0.80 (m, 2H); 0.72-0.76 (m, 2H).

AD.ii. (1-(bromoethynyl)cyclopropyl)methyl carbamate

Starting from intermediate AD.i (0.175 g; 1 mmol) and proceeding successively in analogy to Preparation AA, steps AA.i (94% yield) and AA.ii (64% yield), the title compound was obtained, after purification by CC (Hept-EA), as a white solid (0.13 g).

$^1$H NMR ($d_6$-DMSO) δ: 6.11-7.10 (m, 2H); 3.82 (s, 2H); 0.85-0.89 (m, 2H).

Preparation AE: (((1R,2R)-2-(bromoethynyl)-2-methylcyclopropyl)methoxy)(tert-butyl)diphenylsilane AE.i. ((1R,2R)-2-(hydroxymethyl)-1-methylcyclopropyl)methyl acetate To a solution of ((1R,2R)-2-formyl-1-methylcyclopropyl) methyl acetate (0.925 g; 5.92 mmol; prepared as described in WO 2012/154204) in MeOH (10 mL) was added NaBH$_4$ (0.297 g; 7.7 mmol) portion-wise at 0° C. The reaction was stirred for 80 min at 0° C. then for 30 min at rt. Water (10 mL) and DCM (40 mL) were added and the phases were separated. The aq. layer was extracted with DCM-MeOH 9-1 (2×15 mL) and the combined org. layers were dried over Na$_2$SO$_4$ and filtered. The filtrate was evaporated under reduced pressure to give the title compound as a colourless oil (0.968 g; quant.).

$^1$H NMR (CDCl$_3$) δ: 3.89 (d, J=11.3 Hz, 1H); 3.82 (d, J=11.3 Hz, 1H); 3.74-3.80 (m, 1H); 3.49-3.56 (m, 1H); 2.08 (s, 3H); 1.19 (s, 3H); 1.09-1.15 (m, 1H); 0.70-0.76 (m, 1H); 0.27-0.31 (m, 1H).

AE.ii. ((1R,2R)-2-(((tert-butyldiphenylsilyl)oxy) methyl)-1-methylcyclopropyl)methyl acetate To a solution of intermediate AE.i (0.94 g; 5.92 mmol) in DCM (12 mL) was added imidazole (0.819 g; 11.9 mmol). The solution was cooled to 0° C. and TBDPSCl (1.6 mL; 6.03 mmol) was added dropwise. The reaction mixture was stirred at 0° C. for 20 min then at rt for 2.5 h. Aq. NaHSO$_4$ (15%, 20 mL) was added. The aq. phase was extracted with DCM (10 mL). The combined org. layers were dried over MgSO$_4$, filtered and the filtrate concentrated to dryness. The residue was purified by CC (Hept-EA) to afford the title compound as a colourless oil (2.29 g; 97% yield).

$^1$H NMR (CDCl$_3$) δ: 7.66-7.70 (m, 4H); 7.35-7.45 (m, 6H); 3.84 (s, 2H); 3.82-3.88 (overlapped m, 1H); 3.46-3.55 (m, 1H); 2.07 (s, 3H); 1.14 (s, 3H); 1.05 (s, 9H), 1.03-1.11 (overlapped m, 1H); 0.59-0.65 (m, 1H); 0.14-0.19 (m, 1H).

MS (ESI, m/z): 397.01 [M+H$^+$] for C$_{24}$H$_{32}$O$_3$Si; t$_R$=1.13 min.

AE.iii. ((1R,2R)-2-(((tert-butyldiphenylsilyl)oxy) methyl)-1-methylcyclopropyl)methanol To a solution of intermediate AE.ii (2.29 g; 5.77 mmol) in MeOH (50 mL) was added K$_2$CO$_3$ (1.59 g; 11.5 mmol). The suspension was stirred at rt for 4 h. The reaction mixture was filtered and the solid was washed with DCM. The filtrate was evaporated under reduced pressure. The residue was partitioned between water (30 mL) and DCM (40 mL). The aq. layer was extracted with DCM-MeOH 9-1 (40 mL) and EA-MeOH 9-1 (40 mL). The combined org. layers were dried over MgSO$_4$, filtered and evaporated under reduced pressure. The residue was purified by CC (Hept-EA) to afford the title compound as a colourless oil (1.59 g; 78% yield).

$^1$H NMR (CDCl$_3$) δ: 7.66-7.72 (m, 4H); 7.36-7.45 (m, 6H); 3.86 (dd, J=5.8, 11.1 Hz, 1H); 3.49 (dd, J=8.7, 11.1 Hz, 1H); 3.38 (d, J=11.0 Hz, 1H); 3.30 (d, J=11.0 Hz, 1H); 1.16 (s, 3H); 1.05 (s, 9H); 0.95-1.02 (m, 1H); 0.55 (dd, J=4.8, 9.0 Hz, 1H); 0.12-0.16 (m, 1H).

AE.iv. (((1R,2R)-2-(bromoethynyl)-2-methylcyclopropyl)methoxy)(tert-butyl)diphenylsilane Starting from intermediate AE.iii (1.59 g; 4.5 mmol) and proceeding successively in analogy to Preparation Y, step Y.iii (92% yield), Preparation P, step P.i (85% yield) and Preparation Y, step Y.v (98% yield), the title compound was obtained as a yellow oil (1.48 g).

$^1$H NMR (CDCl$_3$) δ: 7.65-7.72 (m, 4H); 7.36-7.46 (m, 6H); 3.79 (dd, J=5.6, 11.5 Hz, 1H); 3.49 (dd, J=8.4, 11.5 Hz, 1H); 1.43-1.51 (m, 1H); 1.25 (s, 3H); 1.05 (s, 9H); 1.02 (dd, J=4.7, 9.1 Hz, 1H); 0.37 (dd, J=4.7, 6.4 Hz, 1H).

Preparation AF: (1-(4-ethynylphenyl)cyclopropyl)methyl dimethylglycinate

To a solution of the compound of Preparation M (0.20 g; 1.18 mmol) in DCM (13 mL) were added N,N-dimethylglycine (0.13 g; 1.18 mmol), EDC.HCl (0.31 g; 1.6 mmol) and DMAP (0.19 g; 1.53 mmol). The reaction was stirred at rt for 27 h. 5% aq. NaHCO$_3$ (5 mL) was added to the reaction mixture and. the aq. layer was extracted with DCM (2×20 mL). The combined org. layers were dried over MgSO$_4$, filtered and concentrated to dryness. The residue was purified by CC (DCM-MeOH) to afford the title compound as a yellow oil (0.23 g, 76% yield).

$^1$H NMR (d$_6$-DMSO) δ: 7.37-7.41 (m, 2H); 7.26-7.30 (m, 2H); 4.21 (s, 2H); 4.13 (s, 1H); 3.10 (s, 2H); 2.17 (s, 6H); 0.97-1.01 (m, 2H); 0.90-0.94 (m, 2H).

MS (ESI, m/z): 258.07 [M+H$^+$] for C$_{16}$H$_{19}$NO$_2$; t$_R$=0.63 min.

Preparation AG: 1-(iodoethynyl)cyclopropan-1-amine hydrochloride

AG.i. Tert-butyl (1-(iodoethynyl)cyclopropyl)carbamate

Starting from tert-butyl 1-ethynylcyclopropylcarbamate (0.855 g; 4.88 mmol; commercial) and proceeding in analogy to Preparation K (91% yield), the title compound was obtained as a yellow solid (1.36 g).

$^1$H NMR (CDCl$_3$) δ: 4.85-5.16 (br. s, 1H); 1.49 (s, 9H); 1.18-1.24 (m, 2H); 1.05-1.11 (m, 2H).

AG.ii. 1-(iodoethynyl)cyclopropan-1-amine hydrochloride

A solution of intermediate AG.i (0.6 g; 1.95 mmol) in HCl (4N in dioxane; 4 mL; 16 mmol) was stirred at rt for 2 h. The mixture was concentrated to the dryness and the residue was triturated in Et$_2$O, filtered, and washed with Et$_2$O to afford the title compound as a beige solid (0.354 g, 75% yield).

$^1$H NMR (d$_6$-DMSO) δ: 8.74-8.81 (br. s, 3H); 1.24-1.29 (m, 2H); 1.16-1.20 (m, 2H).

Preparation AH: tert-butyl (3-(iodoethynyl)oxetan-3-yl)carbamate

AH.i. Tert-butyl (3-((trimethylsilyl)ethynyl)oxetan-3-yl)carbamate

To a solution of 3-((trimethylsilyl)ethynyl)oxetan-3-amine hydrochloride (1.39 g; 6.75 mmol; commercial) in DCM (34 mL) were added TEA (2.2 mL; 15.8 mmol) and Boc$_2$O (3.09 g; 14.2 mmol). The reaction mixture was stirred at rt overnight. Boc$_2$O (1.3 g; 6.31 mmol) was added again and the reaction was stirred for 6 h. The reaction mixture was diluted with DCM (5 mL) and sat. aq. NaHCO$_3$ (5 mL) was added. The phases were separated and the aq. layer was extracted twice with DCM (2×5 mL). The combined org. layers were washed with brine (5 mL), dried over MgSO$_4$, filtered and the filtrate concentrated to dryness to afford the title compound, slightly contaminated by Boc$_2$O, as a yellow oil (3.34 g).

$^1$H NMR (CDCl$_3$) δ: 4.72-4.81 (m, 4H); 3.05 (br. s, 1H); 1.47 (s, 9H); 0.18 (s, 9H).

AH.ii. Tert-butyl (3-(iodoethynyl)oxetan-3-yl)carbamate

Starting from intermediate AH.i (crude; 1.8 g; 6.75 mmol) and proceeding successively in analogy to Preparation G, step G.ii (quant. yield) and Preparation K (92% yield), the title compound was obtained as a beige solid (1.61 g).

$^1$H NMR (CDCl$_3$) δ: 4.94-5.10 (br. s, 1H); 4.81-4.85 (m, 2H); 4.70-4.75 (m, 2H); 1.47 (s, 9H).

Preparation AI: (1-(4-iodophenyl)cyclobutyl)methanol

Starting from (1-(4-bromophenyl)cyclobutyl)methanol (0.64 g; 2.66 mmol, commercial) and proceeding in analogy to Preparation R, step R.iii (93% yield), the title compound was obtained, after purification by CC (Hept-EA), as a colourless oil (0.71 g).

$^1$H NMR (CDCl$_3$) δ: 7.64-7.67 (m, 2H); 6.89-6.92 (m, 2H); 3.73 (d, J=5.3 Hz, 2H); 2.26-2.32 (m, 2H); 2.19-2.27 (m, 2H); 2.03-2.13 (m, 1H); 1.84-1.93 (m, 1H).

Preparation AJ: 2-(3-fluoro-4-(4,4,5,5-tetramethyl-1,3,2-dioxaborolan-2-yl)phenoxy)ethan-1-ol

AJ.i. Ethyl 2-(3-fluoro-4-(4,4,5,5-tetramethyl-1,3,2-dioxaborolan-2-yl)phenoxy)acetate A mixture of bis(pinacolato)diboron (0.97 g; 3.8 mmol), Pd(dppf)Cl$_2$ (0.21 g; 0.26 mmol) and KOAc (1.07 g; 10.9 mmol) was flushed with nitrogen for 15 min and treated with a solution of 2-(4-bromo-3-fluorophenoxy)acetate (1 g; 3.61 mmol; commercial) in dioxane (14.5 mL). The reaction mixture was heated to reflux overnight. After cooling, the reaction mixture was filtered and the filtrate concentrated to dryness. The residue was purified by CC (Hept-EA) to afford the desired compound as a yellow oil (0.82 g; 70% yield).

$^1$H NMR (d$_6$-DMSO) δ: 7.53-7.57 (m, 1H); 6.75-6.81 (m, 2H); 4.86 (s, 2H); 4.17 (q, J=7.1 Hz, 2H); 1.28 (s, 12H); 1.21 (t, J=7.1 Hz, 3H).

MS (ESI, m/z): 324.9 [M+H$^+$] for C$_{16}$H$_{22}$NO$_5$BF; $t_R$=0.93 min.

AJ.ii. 2-(3-fluoro-4-(4,4,5,5-tetramethyl-1,3,2-dioxaborolan-2-yl)phenoxy)ethan-1-ol NaBH$_4$ (0.14 g; 3.76 mmol) was added portion-wise to an ice chilled ethanol (4.5 mL) solution of intermediate AJ.i (0.81 g; 2.5 mmol). The mixture was stirred for 2 h in the ice bath melting. Acetone (0.37 mL), EA (5 mL) and water (10 mL) were added sequentially at rt. Solvents were distilled off under reduced pressure. EA (20 mL) was added to the resulting residue. The org. phase was washed with water (10 mL) and brine (10 mL), dried over Na$_2$SO$_4$, filtered. The filtrate was concentrated to dryness and the residue was purified by CC (DCM-MeOH) to afford the title compound as a colourless oil (0.48 g; 68% yield).

$^1$H NMR (d$_6$-DMSO) δ: 7.52-7.57 (m, 1H); 6.79 (dd, J=2.3, 8.4 Hz, 1H); 6.74 (dd, J=2.2, 11.5 Hz, 1H); 4.90 (t, J=5.5 Hz, 1H); 4.00-4.05 (m, 2H); 3.68-3.73 (m, 2H); 1.28 (s, 12H).

Preparation AK: ((1R,2S,3s)-3-(iodoethynyl)cyclopropane-1,2-diyl)dimethanol

Starting from ((1R,2S,3s)-3-ethynylcyclopropane-1,2-diyl)dimethanol (0.168 g; 0.85 mmol; prepared as described in WO 2013/170030) and proceeding in analogy to Preparation K (28% yield), the title compound was obtained, after purification by CC (Hept-EA), as a yellow oil (0.06 g).

$^1$H NMR (d$_6$-DMSO) δ: 4.60 (t, J=5.6 Hz, 1H); 4.55 (t, J=5.3 Hz, 1H); 3.40-3.45 (m, 3H); 3.14-3.20 (m, 1H); 1.47 (dd, J=4.8, 8.2 Hz, 1H); 1.07-1.13 (m, 1H); 0.98-1.03 (m, 1H).

Preparation AL: (4-ethynyl-3-fluorophenyl)methanol

Starting from (3-fluoro-4-iodophenyl)methanol (0.510 g; 2.0 mmol; commercial) and proceeding in analogy to Procedure C (96% yield) and Preparation G, step G.ii (79% yield), the title compound was obtained as a colourless oil (0.23 g).

$^1$H NMR δ (d$_6$-DMSO) δ: 7.51 (t, J=7.7 Hz, 1H); 7.18-7.24 (m, 1H); 7.12-7.17 (m, 1H); 5.42 (t, J=5.8 Hz, 1H); 4.53 (d, J=5.8 Hz, 2H); 4.45 (s, 1H).

Preparation AM: (S)-2-(4-((2,2-dimethyl-1,3-dioxolan-4-yl)methoxy)-2-fluorophenyl)-4,4,5,5-tetramethyl-1,3,2-dioxaborolane A suspension of 3-fluoro-4-(4,4,5,5-tetramethyl-1,3,2-dioxaborolan-2-yl)phenol (0.5 g; 2.1 mmol; commercial), (R)-(2,2-dimethyl-1,3-dioxolan-4-yl)methyl 4-methylbenzenesulfonate (0.6 g; 2.1 mmol; commercial) and K$_2$CO$_3$ (0.58 g; 4.2 mmol) in DMF (4 mL) was stirred at 100° C. overnight. The mixture was cooled to rt and diluted with water (40 mL). The mixture was extracted with EA (3×20 mL). The combined org. layers were washed with brine (15 mL), dried over Na$_2$SO$_4$, filtered and concentrated to dryness. The residue was purified by CC (Hept-EA) to afford the title compound as a yellow oil which crystallized on standing (0.38 g; 51% yield).

$^1$H NMR δ (d$_6$-DMSO) δ: 7.55 (m, 1H); 6.75-6.83 (m, 2H); 4.40 (m, 1H); 4.06-4.11 (m, 2H); 4.01 (m, 1H); 3.74 (dd, J=6.4, 8.4 Hz, 1H); 1.35 (s, 3H); 1.31 (s, 3H); 1.28 (s, 12H).

Preparation AN: 2,2-difluoro-2-(4-iodophenyl)ethan-1-ol

AN.i. 2-(4-bromophenyl)-2,2-difluoroethan-1-ol

NaBH$_4$ (0.312 g, 8.24 mmol) was added portion-wise to a solution of ethyl 2-(4-bromophenyl)-2,2-difluoroacetate (1.52 g, 5.45 mmol, commercial) in EtOH (50 mL). The mixture was stirred for 2 h at rt. 1N HCl (0.5 mL) was added and the resulting mixture was extracted with DCM (2×70 mL). The org. layer was washed with brine (70 mL), dried over Na$_2$SO$_4$, filtered and concentrated to dryness to give the title compound as a white solid (1.21 g, 94% yield).

$^1$H NMR (d$_6$-DMSO) δ: 7.70 (d, J=8.6 Hz, 2H); 7.47 (d, J=8.6 Hz, 2H); 5.65 (t, J=6.4 Hz, 1H); 3.80-3.88 (m, 2H).

MS (ESI, m/z): 242.13 [M+H$^+$] for C$_8$H$_7$OBrF$_2$; $t_R$=0.75 min.

AN.ii. 2,2-difluoro-2-(4-iodophenyl)ethan-1-ol

Starting from intermediate AN.i (0.5 g; 2.11 mmol) and proceeding in analogy to Preparation R, step R.iii, the title compound was obtained as a white solid (0.26 g; 43% yield).

$^1$H NMR (d6-DMSO) δ: 7.86 (d, J=8.5 Hz, 2H); 7.31 (d, J=8.5 Hz, 2H); 5.63 (t, J=6.4 Hz, 1H); 3.79-3.86 (m, 2H).

Preparation AO:
3-iodo-N,N-dimethylprop-2-yn-1-amine

Starting from N,N-dimethylprop-2-yn-1-amine (1 g; 12 mmol; commercial) and proceeding in analogy to Preparation K (56% yield), the title compound was obtained as a yellow solid (0.746 g).
$^1$H NMR (CDCl$_3$) δ: 3.45 (s, 2H); 2.33 (s, 6H).

Preparation AP:
(1-(bromoethynyl)cyclopropyl)methyl dimethylglycinate

AP.i. (1-(bromoethynyl)cyclopropyl)methanol

To a solution of the compound of Preparation Q (2.4 g; 5.8 mmol) in THF (5.5 mL) was added TBAF (1M in THF; 14.5 mL). The resulting solution was stirred at rt for 1 h. The reaction mixture was concentrated in vacuo and the residue purified by CC (Hept-EA) to afford the title compound as a colourless oil (1.01 g; quant.).
$^1$H NMR (d6-DMSO) δ: 4.90 (t, J=6.0 Hz, 1H); 3.32 (d, J=6.0 Hz, 2H); 0.77-0.80 (m, 2H); 0.72-0.76 (m, 2H).

AP.ii. (1-(bromoethynyl)cyclopropyl)methyl dimethylglycinate

Starting from intermediate AP.i (1.01 g, 5.8 mmol) and proceeding in analogy to Preparation AF (coupling: 70% yield), the title product was obtained as a colourless oil (1.07 g).
$^1$H NMR (d6-DMSO) δ: 3.98 (s, 2H); 3.22 (s, 2H); 2.27 (s, 6H); 0.93-0.98 (m, 2H); 0.88-0. m, 2H).
MS (ESI, m/z): 260.0 [M+H$^+$] for C$_{10}$H$_{14}$NO$_2$Br; t$_R$=0.53 min.

Preparation AQ:
(1-(bromoethynyl)cyclopropyl)methyl di-tert-butyl phosphate

AQ.i. Di-tert-butyl ((1-(((tert-butyldiphenylsilyl)oxy)methyl)cyclopropyl)methyl)phosphate To a solution of (1-(((tert-butyldiphenylsilyl)oxy)methyl)cyclopropyl)methanol (13.1 g, 38.5 mmol, prepared as described in WO 2010/135536) in THF (140 mL) at rt was added tetrazole (0.45M in MeCN; 170 mL) and di-tert-butyl diisopropylphosphoramidite (17.2 mL; 51.8 mmol). The reaction mixture was stirred at 40° C. overnight. 35% H$_2$O$_2$ (330 mL) and was added slowly at 0° C. over 75 min, keeping the internal temperature below 10° C. After stirring 1 h at 10° C., water (400 mL) was added. The aq. layer was extracted with EA (3×100 mL). The combined org. layers were collected, washed with 10% aq. NaHSO$_3$ (5×100 mL) and brine (100 mL), dried over MgSO$_4$, filtered and concentrated to dryness. The residue was purified by CC (Hept-EA) to afford a colourless oil (7.16 g; 35% yield).
$^1$H NMR (CDCl$_3$) δ: 7.62-7.68 (m, 4H); 7.35-7.45 (m, 6H); 3.97 (d, J=5.5 Hz, 2H); 3.60 (s, 2H); 1.46 (s, 18H); 1.05 (s, 9H); 0.50-0.53 (m, 2H); 0.40-0.44 (m, 2H).
MS (ESI, m/z): 533.10 [M+H$^+$] for C$_{29}$H$_{45}$O$_5$PSi; t$_R$=1.15 min.

AQ.ii. Di-tert-butyl ((1-formylcyclopropyl)methyl)phosphate

Starting from intermediate AQ.i (7.16 g, 13.4 mmol) and proceeding successively in analogy to Preparation AD, step AD.i (94% yield) and Preparation Y, step Y.iii (85% yield), the title compound was obtained as a colourless oil (3.12 g).
$^1$H NMR (CDCl$_3$) δ: 9.08 (s, 1H); 4.20 (d, J=6.7 Hz, 2H); 1.48 (s, 18H); 1.20-1.30 (m, 4H).
MS (ESI, m/z): 293.00 [M+H$^+$] for C$_{13}$H$_{25}$O$_5$P; t$_R$=0.77 min.

AQ.iii. Di-tert-butyl ((1-ethynylcyclopropyl)methyl)phosphate

A suspension of intermediate AQ.ii (1 g; 3.44 mmol) and K$_2$CO$_3$ (0.947 g; 6.85 mmol) in MeOH (30 mL) was treated dropwise with dimethyl(1-diazo-2-oxo-propyl)phosphate (0.992 g, 5.16 mmol). The reaction mixture was stirred at rt overnight. The solvent was evaporated and the residue was dissolved in DCM (30 mL) and water (30 mL). The aq. layer was extracted with EA (20 mL). The combined org. layer were dried over MgSO$_4$, filtered and concentrated to dryness to afford the title compound as a yellow oil (0.93 g, 94% yield).
$^1$H NMR (CDCl$_3$) δ: 3.87 (d, J=6.4 Hz, 2H); 1.90 (s, 1H); 1.49 (s, 18H); 0.98-1.01 (m, 2H); 0.88-0.91 (m, 2H).
MS (ESI, m/z): 289.01 [M+H$^+$] for C$_{14}$H$_{25}$O$_4$P; t$_R$=0.85 min.

AQ.iv. (1-(bromoethynyl)cyclopropyl)methyl di-ten-butyl phosphate

To a solution of intermediate AQ.iii (0.93 g, 3.22 mmol) and NBS (0.691 g, 3.88 mmol) in acetone (13 mL) was added AgNO$_3$ (0.0586 g, 0.345 mmol). The mixture was stirred at rt for 2.25 h. The reaction mixture was filtered through Celite and the filtrate was concentrated to dryness. The residue was purified by CC (Hept-EA) to give the title compound as a colourless oil (1.07 g, 91% yield).
$^1$H NMR (CDCl$_3$) δ: 3.84 (d, J=6.3 Hz, 2H); 1.49 (s, 18H); 0.98-1.01 (m, 2H); 0.86-0.88 (m, 2H)
MS (ESI, m/z): 368.80 [M+H$^+$] for C$_{14}$H$_{24}$O$_4$BrP; t$_R$=0.92 min.

Preparation AR: tert-butyl((1-((3-fluoro-4-(4,4,5,5-tetramethyl-1,3,2-dioxaborolan-2-yl)phenyl)ethynyl)cyclopropyl)methoxy)diphenylsilane To a solution of 2-(2-fluoro-4-iodophenyl)-4,4,5,5-tetramethyl-1,3,2-dioxaborolane (0.62 g; 1.52 mmol; commercial) in THF (10 mL) were added tert-butyl((1-ethynylcyclopropyl)methoxy)diphenylsilane (0.507 g; 1.52 mmol; prepared as described in WO 2010/135536), TEA (0.707 mL) and CuI (0.077 g). The mixture was flushed with argon and PdCl$_2$(PPh$_3$)$_2$ (0.212 g) was added. The reaction mixture stirred at rt for 2 h. The solvent was removed in vacuo and the residue was purified by CC (Hept-EA) to afford the title compound as a white solid (0.36 g; 43% yield).
$^1$H NMR (CDCl$_3$) δ: 7.70-7.73 (m, 4H); 7.64 (dd, J=6.5, 7.5 Hz, 1H); 7.37-7.46 (m, 6H); 7.14 (dd, J=1.2, 7.7 Hz, 1H); 7.02 (dd, J=1.1, 10.0 Hz, 1H); 3.74 (s, 2H); 1.38 (s, 12H); 1.09 (s, 9H); 0.99-1.02 (m, 2H); 0.92-0.94 (m, 2H).

Preparation AS: ((1-(bromoethynyl)cyclobutyl)methoxy)(tert-butyl)diphenylsilane

Starting from cyclobutane-1,1-diyldimethanol (3.03 g; 24.8 mmol; commercial) and proceeding successively in analogy to Preparation Y, steps Y.ii (98% yield), Y.iii (86% yield), Y.iv (93% yield) and Y.v (quant.), the title compound was obtained as a colourless oil (4.79 g).

¹H NMR (CDCl₃) δ: 7.70-7.74 (m 4H); 7.40-7.48 (m, 6H); 3.67 (s, 2H); 2.18-2.29 (m, 4H); 2.00-2.08 (m, 1H); 1.86-1.95 (m, 1H); 1.11 (s, 9H).

Preparation AT: ((3-(bromoethynyl)oxetan-3-yl) methoxy)(tert-butyl)diphenylsilane AT.i. 3-(((tert-butyldiphenylsilyl)oxy)methyl)oxetane-3-carbaldehyde Starting from oxetane-3,3-diyldimethanol (5 g; 42.3 mmol; commercial) and proceeding successively in analogy to Preparation Y, steps Y.ii (95% yield) and Y.iii (90% yield), the title compound was obtained, after purification by CC (Hept-EA), as a colourless oil (12.87 g).
¹H NMR (d₆-DMSO) δ: 9.82 (s, 1H); 7.59-7.62 (m, 4H); 7.44-7.50 (m, 6H); 4.66 (d, J=6.3 Hz, 2H); 4.43 (d, J=6.3 Hz, 2H); 4.15 (s, 2H); 0.98 (s, 9H).

AT.ii. ((3-(bromoethynyl)oxetan-3-yl)methoxy)(tert-butyl)diphenylsilane

Starting from intermediate AT.i (2 g; 5.64 mmol) and proceeding successively in analogy to Preparation AQ, steps AQ.iii (87% yield) and AQ.iv (98% yield), the title compound was obtained, after purification by CC (Hept-EA), as a colourless oil (0.24 g).
¹H NMR (d₆-DMSO) δ: 7.64-7.72 (m, 4H); 7.42-7.54 (m, 6H); 4.60 (d, J=5.9 Hz, 2H); 4.48 (d, J=5.9 Hz, 2H); 3.92 (s, 2H); 1.03 (s, 9H).

Preparation AU: (((1R*,2R*)-2-(bromoethynyl)-2-fluorocyclopropyl)methoxy)(tert-butyl)diphenylsilane AU.i. ((1R*,2R*)-2-(((tert-butyldiphenylsilyl)oxy) methyl)-1-fluorocyclopropyl)methanol To a solution of ethyl (1R*,2R*)-2-(((tert-butyldiphenylsilyl)oxy)methyl)-1-fluorocyclopropane-1-carboxylate (0.5 g; 1.25 mmol; prepared as described in Sakagami et al., *Bioorg. Med. Chem.* (2008), 16(8), 4359-4366) in THF (9 mL), cooled to −78° C., was added dropwise LiBH₄ (2M in THF; 2.2 mL; 4.4 mmol). The reaction mixture was allowed to reach rt and stirred at rt for 24 h. MeOH (2 mL) was carefully added, the reaction mixture was stirred for 20 min, concentrated to dryness and partitioned between water (10 mL) and DCM (15 mL). The aq. layer was extracted with DCM (2×10 mL). The combined org. layers were dried over Na₂SO₄ and filtered. After concentration of the filtrate to dryness, the title compound was obtained as a colourless oil (0.429 g; 96% yield).
¹H NMR (CDCl₃) δ: 7.66-7.72 (m, 4H); 7.36-7.45 (m, 6H); 3.89 (ddd, J=1.6, 6.0, 11.0 Hz, 1H); 3.80-3.83 (m, 1H); 3.70-3.78 (m, 2H); 1.74 (t, J=6.4 Hz, 1H); 1.24-1.33 (m, 1H); 1.05 (s, 9H); 0.79-0.88 (m, 2H).
MS (ESI, m/z): 358.95 [M+H⁺] for C₂₁H₂₇O₂FSi; t_R=1.01 min.

AU.ii. (((1R*,2R*)-2-(bromoethynyl)-2-fluorocyclopropyl)methoxy)(tert-butyl)diphenylsilane Starting from intermediate AU.i (2.04 g; 5.7 mmol) and proceeding successively in analogy to Preparation Y, steps Y.iii (83% yield), Y.iv (17% yield) and Y.v (99% yield), the title compound was obtained as a brown oil (0.351 g).

¹H NMR (CDCl₃) δ: 7.66-7.70 (m 4H); 7.36-7.45 (m, 6H); 3.84 (ddd, J=1.6, 5.8, 11.3 Hz, 1H); 3.71 (ddd, J=1.1, 8.0, 11.3 Hz, 1H); 1.56-1.64 (m, 1H); 1.14-1.20 (m, 1H); 1.06 (s, 9H); 0.98-1.04 (m, 1H).

Preparation AV: (((1R*,2R*)-2-(bromoethynyl)-1-fluorocyclopropyl)methoxy)(tert-butyl)diphenylsilane AV.i. ((1R*,2R*)-2-(((tert-butyldiphenylsilyl)oxy) methyl)-1-fluorocyclopropyl)methyl acetate To a solution of intermediate AU.i (1.5 g, 4.19 mmol) in THF (25 mL) was added TEA (1.6 mL, 11.5 mmol). AcCl (0.62 mL, 8.51 mmol) was added dropwise over 5 min at 0° C. The reaction mixture was stirred at 0° C. for 1 h. The reaction mixture was poured onto water (40 mL) and the aq. layer was extracted with EA (3×40 mL). The combined org. layers were dried over MgSO₄ and the solvent was removed under reduce pressure to give the crude product as a yellow oil (2.18 g).
¹H NMR (CDCl₃) δ: 7.66-7.71 (m, 4H); 7.36-7.45 (m, 6H); 4.27-4.35 (m, 2H); 3.90 (ddd, J=1.6, 5.8, 11.0 Hz, 1H); 3.69 (ddd, J=1.2, 8.3, 11.0 Hz, 1H); 2.11 (s, 3H); 1.31-1.40 (m, 1H); 1.06 (s, 9H); 0.80-0.94 (m, 2H).
MS (ESI, m/z): 400.98 [M+H⁺] for C₁₂H₁₈NO₂; t_R=1.09 min.

AV.ii. ((1R*,2R*)-1-fluoro-2-(hydroxymethyl)cyclopropyl)methyl acetate

To a solution of intermediate AV.i (2.16 g; 5.39 mmol) in THF (10 mL) was added TBAF (1M in THF; 7 mL). The reaction mixture was stirred at rt for 1 h. The reaction mixture was concentrated in vacuo and purified by CC (DCM-MeOH) to afford the title alcohol as a yellow oil (0.726 g; 83% yield).
¹H NMR (CDCl₃) δ: 4.27-4.41 (m, 2H); 3.94 (m, 1H); 3.64 (m, 1H); 2.13 (s, 3H); 1.51 (m, 1H); 1.41 (m, 1H); 0.98-1.06 (m, 2H).

AV.iii. ((1R*,2R*)-2-ethynyl-1-fluorocyclopropyl)methanol

Starting from intermediate AV.ii (0.62 g; 3.8 mmol) and proceeding successively in analogy to Preparation Y, step Y.iii (100% yield) and Preparation AQ, step AQ.iii (100% yield), the title compound was obtained as a colourless oil (0.25 g).
¹H NMR (CDCl₃) δ: 3.86 (d, J=2.5 Hz, 1H); 3.82 (d, J=2.8 Hz, 1H); 2.00 (d, J=2.2 Hz, 1H); 1.61 (ddt, J=2.1, 7.1, 10.2 Hz, 1H); 1.37 (ddt, J=0.7, 7.0, 19.4 Hz, 1H); 1.21 (ddd, J=6.9, 10.2, 11.3 Hz, 1H).

AV.iv. Tert-butyl(((1R,2R)-2-ethynyl-1-fluorocyclopropyl)methoxy)diphenylsilane

To a solution of intermediate AV.iii (0.232 g, 2.0 mmol) in DCM (4.1 mL) was added imidazole (0.28 g; 4.1 mmol). The solution was cooled to 0° C. and TBDPSCl (0.55 mL; 2.1 mmol) was added dropwise. The reaction mixture was stirred at rt for 2 h. 10% aq. NaHSO₄ (6 mL) was added and the phases were separated. The aq. layer was extracted with DCM (10 mL). The combined org. layers were dried over MgSO₄, filtered and evaporated under reduced pressure. The residue was purified by CC (Hept-EA) to afford the title product as a colourless oil (0.45 g; 63% yield).

¹H NMR (500 MHz, CDCl₃) δ: 7.63-7.67 (m, 4H); 7.37-7.47 (m, 6H); 3.91 (m, 2H); 1.97 (d, J=2.2 Hz, 1H); 1.58 (m, 1H); 1.29 (m, 1H); 1.18 (m, 1H); 1.05 (s, 9H).

AV.v. (((1R*,2R*)-2-(bromoethynyl)-1-fluorocyclopropyl)methoxy)(tert-butyl)diphenylsilane Starting from intermediate AV.iv (0.45 g; 1.28 mmol) and proceeding in analogy to Preparation AQ, step AQ.iv, the title compound was obtained as a colourless oil (0.32 g; 58% yield).

¹H NMR (CDCl₃) δ: 7.62-7.67 (m, 4H); 7.37-7.48 (m, 6H); 3.89 (dd, J=1.0, 14.3 Hz, 2H); 1.57 (m, 1H); 1.27 (m, 1H); 1.16 (m, 1H); 1.05 (s, 9H).

Preparation AW: (RS)-((4-bromo-2-cyclobutylbut-3-yn-1-yl)oxy)(tert-butyl)dimethylsilane

AW.i. (RS)-2-cyclobutyl-3-hydroxypropyl acetate

To a solution of 2-cyclobutylpropane-1,3-diol (4.170 g; 32 mmol) and camphor-10-sulfonic acid (0.149 g; 0.641 mmol) in DCM (60 mL) was added trimethylorthoacetate (16.3 mL, 128 mmol). The mixture was stirred for 2 h at rt. The solvent was evaporated and 50% aq. AcOH (55 mL; 480 mmol) was added. The reaction mixture was stirred at rt for 3 h. The solvent was evaporated and the residue was dissolved in TBME (60 mL), washed with sat. aq. NaHCO₃ (50 mL) and brine (50 mL), dried over MgSO₄ and filtered. After concentration to dryness, the title compound was obtained as a yellowish oil (5.210 g; 94% yield).

¹H NMR (CDCl₃) δ: 4.20 (dd, J=4.0, 11.3 Hz, 1H); 4.06 (dd, J=6.8, 11.3 Hz, 1H); 3.59 (dd, J=3.8, 11.3 Hz, 1H); 3.45 (dd, J=6.5, 11.3 Hz, 1H); 2.23-2.35 (m, 1H); 2.02-2.13 (m, 2H, overlapped); 2.09 (s, 3H); 1.86-1.97 (m, 1H); 1.73-1.85 (m, 4H).

AW.ii. (RS)-3-((tert-butyldimethylsilyl)oxy)-2-cyclobutylpropyl acetate

To a solution of intermediate AW.i (5.210 g; 30.3 mmol) in DCM (50 mL) was added imidazole (4.119 g; 60.5 mmol) and TBDMS-Cl (5.280 g; 33.3 mmol). After stirring for 3 h, water (40 mL) was added. The two phases were separated and the aq. layer was extracted with DCM (2×50 mL). The combined org. layers were dried over MgSO₄, filtered and concentrated to dryness. The residue was purified by CC (Hept-EA) to afford the title compound as a colourless oil (7.417 g; 86% yield).

¹H NMR (CDCl₃) δ: 4.01-4.08 (m, 2H); 3.59 (dd, J=4.0, 10.0 Hz, 1H); 3.49 (dd, J=6.0, 10.0 Hz, 1H); 2.26-2.36 (m, 1H); 1.99-2.08 (m, 2H, overlapped); 2.05 (m, 3H); 1.83-1.93 (m, 1H); 1.71-1.83 (m, 4H); 0.87-0.92 (m, 9H); 0.02-0.05 (m, 6H).

MS (ESI, m/z): 287.09 [M+H⁺] for C₁₅H₃₀O₃Si; $t_R$=1.10 min.

AW.iii. (RS)-((4-bromo-2-cyclobutylbut-3-yn-1-yl)oxy)(tert-butyl)dimethylsilane Starting from intermediate AW.ii (7.4 g; 25.9 mmol), and proceeding successively in analogy to Preparation AE, step AE.iii (91% yield) and Preparation Y, steps Y.iii to Y.v (85% yield over the 3 steps), the title compound was obtained as a colourless oil (3.23 g).

¹H NMR (CDCl₃) δ: 3.59 (dd, J=6.0, 9.7 Hz, 1H); 3.52 (dd, J=6.6, 9.7 Hz, 1H); 2.54-2.60 (m, 1H); 2.46-2.54 (m, 1H); 1.97-2.05 (m, 2H); 1.77-1.96 (m, 4H); 0.90-0.94 (m, 9H); 0.06-0.10 (m, 6H).

Preparation AX: ((1S,2S)-2-(bromoethynyl)-1-methylcyclopropyl)methyl acetate

AX.i. (R,E)-3-(2,2-dimethyl-1,3-dioxolan-4-yl)-2-methylallyl acetate

To a solution of (R,E)-3-(2,2-dimethyl-1,3-dioxolan-4-yl)-2-methylprop-2-en-1-ol (1.4 g; 8.1 mmol; prepared as reported in Smith III et al., *Tetrahedron* (2009), 65(33), 6470-6488) in THF (48 mL) was added TEA (2.8 mL; 20.1 mmol). Then AcCl (1.2 mL; 16.5 mmol) was added dropwise over 10 min at 0° C. The reaction mixture was stirred at 0° C. for 2 h. The reaction mixture was poured into water (80 mL) and extracted with EA (3×50 mL). The combined org. layers were dried over MgSO₄, filtered and the filtrate removed under reduce pressure. The crude product was purified by CC (PE-EA) to afford the title compound as a colourless oil (1.64 g; 94% yield).

¹H NMR (CDCl₃) δ: 5.48-5.51 (m, 1H); 4.79-4.84 (m, 1H); 4.44-4.52 (m, 2H); 4.07-4.11 (m, 1H); 3.55 (t, J=8.0 Hz, 1H); 2.09 (s, 3H); 1.75 (d, J=1.3 Hz, 3H); 1.43 (s, 3H); 1.40 (s, 3H).

AX.ii. ((1S,2S)-2-((R)-2,2-dimethyl-1,3-dioxolan-4-yl)-1-methylcyclopropyl)methyl acetate To a mechanically stirred solution of intermediate AX.i (1.64 g; 7.65 mmol) in toluene (102 mL), cooled to −25° C., was added dropwise ZnEt₂ (15% in toluene; 34.5 mL; 38.3 mmol) over 20 min, keeping IT below −20° C. Then diiodomethane (6.5 mL; 79.9 mmol) was added dropwise over 10 min, keeping IT below −20° C. The reaction mixture was stirred at −20° C. for 2 h, then allowed to slowly warm up to rt and stirred overnight. The reaction mixture was quenched with sat. aq. NH₄Cl (33 mL) and extracted with Et₂O (4×30 mL). The combined org. layers were washed with sat. aq. Na₂S₂O₃ (30 mL), water (30 mL) and brine (30 mL), then dried over MgSO₄ and filtered. After evaporation of the filtrate under reduced pressure, a yellow oil (22.4 g) was obtained. The crude product was purified by CC (PE-EA) to afford the title compound as a colourless oil (1.4 g; 80% yield).

¹H NMR (CDCl₃) δ: 4.09 (dd, J=5.9, 7.9 Hz, 1H); 3.89 (d, J=11.3 Hz, 1H); 3.77 (d, J=11.3 Hz, 1H); 3.70-3.76 (overlapped m, 1H); 3.61-3.66 (m, 1H); 2.07 (s, 3H); 1.45 (s, 3H); 1.36 (s, 3H); 1.13 (s, 3H); 0.85-0.95 (m, 2H); 0.56 (t, J=5.0 Hz, 1H).

AX.iii. ((1S,2S)-2-((R)-1,2-dihydroxyethyl)-1-methylcyclopropyl)methyl acetate A mixture of intermediate AX.ii (1.4 g; 6.1 mmol) in AcOH (80%; 14 mL) was stirred at rt for 23 h. The mixture was added to sat. aq. NaHCO₃ (100 mL; pH 6-7) and the aq. layer was extracted with DCM (3×60 mL). The combined org. layers were washed with water (10 mL) and brine (20 mL), dried over MgSO₄, filtered and concentrated to dryness. The residue was co-evaporated with cyclohexane. The crude was purified by CC (DCM-MeOH) to afford the title compound as a colourless oil (1 g; 87% yield).

¹H NMR (CDCl₃) δ: 3.89 (d, J=11.3 Hz, 1H); 3.74 (d, J=11.3 Hz, 1H); 3.68 (dd, J=3.4, 11.2 Hz, 1H); 3.57 (dd,

J=7.4, 11.2 Hz, 1H); 3.33-3.39 (m, 1H); 2.07 (s, 3H); 1.16 (s, 3H); 0.89 (td, J=5.7, 9.0 Hz, 1H); 0.80 (dd, J=4.9, 8.8 Hz, 1H); 0.48 (t, J=5.3 Hz, 1H).

AX.iv. ((1S,2S)-2-formyl-1-methylcyclopropyl)methyl acetate

To a solution of intermediate AX.iii (1 g; 5.3 mmol) in THF (16.5 mL), water (3.4 mL) and sat. aq. NaHCO$_3$ (1.6 mL), cooled to 0° C., was added NaIO$_4$ (1.48 g; 6.9 mmol). The reaction mixture was stirred at 0° C. for 30 min, then filtered and washed with Et$_2$O. The aq. layer was extracted with Et$_2$O (3×40 mL). The combined org. layers were dried over MgSO$_4$, filtered and concentrated to dryness. The title compound was obtained as a colourless oil (0.81 g; 98% yield).

$^1$H NMR (CDCl$_3$) δ: 9.47 (d, J=4.7 Hz, 1H); 4.00 (d, J=11.4 Hz, 1H); 3.85 (d, J=11.4 Hz, 1H); 2.09 (s, 3H); 1.92-1.97 (m, 1H); 1.39 (t, J=5.3 Hz, 1H); 1.32 (s, 3H); 1.21 (dd, J=5.0, 8.3 Hz, 1H).

AX.v. ((1S,2S)-2-(bromoethynyl)-1-methylcyclopropyl)methyl acetate

Starting from intermediate AX.iv (0.81 g; 5.19 mmol) and proceeding successively in analogy to Preparation P, steps P.i (81% yield) and P.ii (62% yield), the title compound was obtained, after purification by CC (PE/TBME), as a colourless oil (0.6 g).

$^1$H NMR (CDCl$_3$) δ: 3.89 (d, J=11.4 Hz, 1H); 3.80 (d, J=11.4 Hz, 1H); 2.07 (s, 3H); 1.39 (dd, J=5.5, 8.9 Hz, 1H); 1.27 (s, 3H); 0.94 (dd, J=4.8, 8.9 Hz, 1H); 0.65 (t, J=5.1 Hz, 1H).

Preparation AY: 1-(3-(bromoethynyl)azetidin-1-yl)-2-hydroxyethan-1-one

AY.i. Tert-butyl 3-(bromoethynyl)azetidine-1-carboxylate

Starting from tert-butyl 3-ethynylazetidine-1-carboxylate (0.5 g; 2.76 mmol; prepared as described in WO 2014/165075), and proceeding in analogy to Preparation AQ, step AQ.iv, the title compound was obtained, after purification by CC (Hex-TBME), as a colourless oil (0.673 g, 94% yield).

$^1$H NMR (CDCl$_3$) δ: 4.14 (m, 2H), 3.96 (dd, J=6.3 Hz, 8.4 Hz, 2H), 3.34 (m, 1H), 1.46 (s, 9H).

AY.ii. 3-(bromoethynyl)azetidine hydrochloride

Starting from the intermediate AY.i (0.670 g, 2.7 mmol) and proceeding in analogy to Preparation AG, step AG.ii, the title compound was obtained, after trituration in Et$_2$O, as an off-white solid (0.49 g; 97% yield).

$^1$H NMR (CDCl$_3$) δ: 9.10-9.44 (m, 2H), 4.06-4.15 (m, 2H), 3.87-3.96 (m, 2H), 3.74 (m, 1H).

MS (ESI, m/z): 162.0 [M+H$^+$] for C$_5$H$_6$NBr; t$_R$=0.23 min.

AY.iii. 1-(3-(bromoethynyl)azetidin-1-yl)-2-hydroxyethan-1-one

To a solution of intermediate AY.ii (0.49 g; 2.48 mmol) in DMF (5 mL) were added successively HOBT (0.7 g; 5.05 mmol), TEA (1.21 mL; 8.69 mmol), glycolic acid (0.2 g; 2.63 mmol) and EDC (0.85 g; 4.38 mmol). The reaction mixture was diluted with DMF (4 mL) and the reaction mixture was stirred at 60° C. for 90 min. The solvent was removed in vacuo and the residue was partitioned between brine (20 mL) and EA-MeOH (9-1; 30 mL). The aq. layer was extracted with EA-MeOH (9-1; 4×20 mL). The org. layer was dried over Na$_2$SO$_4$, filtered and concentrated to dryness. The residue was purified by CC (Hept-EA) to afford a the title compound (0.32 g, 60% yield) as an off-white solid.

$^1$H NMR (d6-DMSO) δ: 4.97 (t, J=6.1 Hz, 1H); 4.40 (t, J=8.7 Hz, 1H); 4.11 (m, 2H), 3.89 (d, J=6.0 Hz, 2H); 3.77 (dd, J=6.2, 9.0 Hz, 1H); 3.55 (m, 1H).

MS (ESI, m/z): 220.1 [M+H$^+$] for C$_7$H$_8$NO$_2$Br; t$_R$=0.48 min.

Preparation AZ: 3-(3-iodoprop-2-yn-1-yl)oxetan-3-ol

A flask charged with ZnBr$_2$ (1.08 g, 4.80 mmol) and Mg turnings (5.85 g) was heated with stirring under vacuum at 150° C. for 2 h and then cooled to rt. Et$_2$O (90 mL) and a few drops of 1,2-dibromoethane were added. Propargyl bromide (9 mL; 118.78 mmol) in Et$_2$O (70 mL) was then added dropwise. The mixture was stirred at the same temperature for 1 h. In a separate flask were introduced 3-oxetanone (3.15 g; 43.71 mmol) and THF (420 mL). The Grignard reagent solution (127 mL; 65.56 mmol), cannulated in a graduated addition funnel, was added dropwise. The solution was stirred at the same temperature for 1 h and diluted with sat. aq. NH$_4$Cl and Hex (100 mL). The two layers were separated and the aq. layer was extracted with Hex (100 mL). The combined org. layers were dried over MgSO$_4$, filtered and concentrated under reduced pressure. Starting from the crude intermediate thus obtained (4.33 g; 38.63 mmol) and proceeding in analogy to Preparation K, the title compound was obtained as a yellow solid (3.01 g; 33% yield).

$^1$H NMR (CDCl$_3$) δ: 4.51 (d, J=7.4 Hz, 2H); 4.66 (d, J=7.1 Hz, 2H); 2.98 (s, 2H); 2.55 (s, 1H).

Preparation BA: 4-(iodoethynyl)tetrahydro-2H-pyran-4-ol

Starting from 4-ethynyltetrahydro-2H-pyran-4-ol (1.17 g; 9.33 mmol; commercial) and proceeding in analogy to Preparation K, the title iodide was obtained, after purification by CC (Hept-EA), as a yellowish solid (1.57 g, 67% yield).

$^1$H NMR (d6-DMSO) δ: 5.64 (s, 1H); 3.64-3.74 (m, 2H); 3.40-3.51 (m, 2H); 1.68-1.79 (m, 2H); 1.51-1.62 (m, 2H).

Preparation BB: (3R,6S)-6-(bromoethynyl)tetrahydro-2H-pyran-3-amine hydrochloride Starting from tert-butyl ((3R,6S)-6-formyltetrahydro-2H-pyran-3-yl)carbamate (3.1 g; 13.6 mmol, prepared as described in Surivet et al., J. Med. Chem. (2013), 56, 7396-7415) and proceeding successively in analogy to Preparation P, step P.i (68% yield), Preparation Y, step Y.v (97% yield) and Preparation AG, step AG.ii (89% yield), the title compound was obtained, after final trituration in diethyl ether, as a white solid (0.353 g).

$^1$H NMR (d$_6$-DMSO) δ: 8.21-8.38 (m, 3H); 4.41 (dd, J=3.2, 7.4 Hz, 1H); 3.97 (dd, J=3.2, 11.6 Hz, 1H); 3.45 (dd, J=7.4, 11.6 Hz, 1H); 3.17 (m, 1H); 1.98-2.08 (m, 2H); 1.55-1.72 (m, 2H).

Preparation BC: 1-(5-ethynylthiophen-2-yl)cyclopropan-1-amine

Starting from 1-(5-bromothiophen-2-yl)cyclopropan-1-amine hydrochloride (0.299 g; 1.17 mmol; commercial) and proceeding in analogy to Procedure C (84% yield) and Preparation H, step H.ii (74% yield), the title compound was obtained, after purification by CC (DCM-MeOH containing 1% aq. $NH_4OH$), as a yellowish oil (0.118 g).

$^1$H NMR (d6-DMSO) δ: 7.13 (d, J=3.7 Hz, 1H); 6.64 (d, J=3.7 Hz, 1H); 4.42 (s, 1H); 2.58 (s, 2H); 1.05-1.08 (m, 2H); 0.94-0.97 (m, 2H).

Preparation BD: 3-(4-iodophenyl)oxetan-3-amine hydrochloride

BD.i. N-(3-(4-iodophenyl)oxetan-3-yl)-2-methylpropane-2-sulfinamide

BuLi (1.1M in hexanes; 11.4 mL) was added dropwise to a solution of 1,4-iodobenzene (4.36 g) in THF (50 mL) at −78° C. After stirring for 1 h, a solution of 2-methyl-N-oxetan-3-ylidenepropane-2-sulfinamide (1.64 g; commercial) in THF (10 mL) was added dropwise over the course of 30 min at −78° C. The reaction mixture was gradually warmed to rt. After 1 h, sat. aq. $NH_4Cl$ was added and the aq. layer was extracted with EA. The combined org. layer was washed with sat. aq. $NaHCO_3$ and brine, dried over $Na_2SO_4$, filtered and concentrated to dryness. The residue was purified by CC (EA-Hept) to give the title compound as a colourless oil (0.751 g; 21% yield).

$^1$H NMR (d6-DMSO) δ: 7.77 (d, J=8.4 Hz, 2H); 7.30 (d, J=8.4 Hz, 2H); 6.35 (s, 1H); 4.98 (d, J=6.3 Hz, 1H); 4.90-4.94 (m, 1H); 4.85-4.88 (m, 1H); 4.67 (d, J=6.3 Hz, 1H); 1.11 (s, 9H).

MS (ESI, m/z): 379.97 [M+H$^+$] for $C_{13}H_{18}NO_2IS$; $t_R$=0.78 min.

BD.ii. 3-(4-iodophenyl)oxetan-3-amine hydrochloride

To a solution of intermediate BD.i (0.751 g; 1.98 mmol) in DCM (20 mL) was added a 4M solution of HCl in dioxane (1.06 mL). After stirring for 30 min at rt, the solids were filtered off and washed with Hex (3 mL) to afford the title compound as a white solid (0.624 g; 100% yield)

$^1$H NMR (d6-DMSO) δ: 9.14-9.30 (m, 3H); 7.82-7.90 (m, 2H); 7.34-7.40 (d, J=8.5 Hz, 2H); 4.80-5.00 (m, 4H).

MS (ESI, m/z): 299.89 [M+Na$^+$] for $C_9H_{10}NOI$; $t_R$=0.50 min.

Preparation BE: (3-(4-iodophenyl)oxetan-3-yl)methanol

Starting from (3-(4-bromophenyl)oxetan-3-yl)methanol (0.24 g; 0.98 mmol; commercial) and proceeding in analogy to Preparation R, step R.iii, the title iodide was obtained, after purification by CC (Hept-EA), as an off-white solid (0.27 g, 94% yield).

$^1$H NMR (d6-DMSO) δ: 7.69 (d, J=7.1 Hz, 2H); 6.96 (d, J=7.1 Hz, 2H); 5.10 (t, J=5.6 Hz, 1H); 4.60-4.73 (m, 4H); 3.69 (d, J=5.3 Hz, 2H).

Preparation BF: 1-(4-iodophenyl)cyclopropan-1-amine hydrochloride

BF.i. Tert-butyl (1-(4-iodophenyl)cyclopropyl)carbamate

Starting from tert-butyl (1-(4-bromophenyl)cyclopropyl)carbamate (0.502 g; 1.61 mmol; commercial) and proceeding in analogy to Preparation R, step R.iii, the title iodide was obtained as a brown solid (0.53 g, 92% yield).

$^1$H NMR (d6-DMSO) δ: 7.71 (s, 1H); 7.61 (d, J=8.4 Hz, 2H); 6.93 (d, J=8.4 Hz, 2H); 1.37 (s, 9H); 1.11 (s, 2H); 1.09 (s, 2H).

MS (ESI, m/z): 360.0 [M+H$^+$] for $C_{14}H_{18}NO_2I$; $t_R$=0.94 min.

BF.ii. 1-(4-iodophenyl)cyclopropan-1-amine hydrochloride

Intermediate BF.i (0.347 g; 0.966 mmol) was stirred at rt for 3 h in a HCl solution (4M in dioxane; 3 mL). $Et_2O$ was added (5 mL) and the precipitate was filtered, washed with ether (2 mL) and dried to afford the title compound as a brown solid (0.231 g; 81% yield).

$^1$H NMR (d6-DMSO) δ: 8.93 (s, 2H); 7.78 (d, J=8.4 Hz, 2H); 7.23 (d, J=8.4 Hz, 2H); 1.37-1.44 (m, 2H); 1.16-1.23 (m, 2H).

Preparation BG: cis-3-(hydroxymethyl)-1-(3-iodoprop-2-yn-1-yl)cyclobutan-1-ol

BG.i. Cis-3-(((tert-butyldiphenylsilyl)oxy)methyl)-1-(3-(trimethylsilyl)prop-2-yn-1-yl)cyclobutan-1-ol To a solution of 3-(((tert-butyldiphenylsilyl)oxy)methyl)cyclobutan-1-one (2 g; 3.54 mmol; prepared as described in WO 2006/063281) in dry THF (5.9 mL) at rt under nitrogen atmosphere, was added a solution of trimethyl(3-(4,4,5,5-tetramethyl-1,3,2-dioxaborolan-2-yl)prop-1-yn-1-yl)silane (1.27 g; 5.32 mmol; commercial) in dry THF (5.9 mL) followed by $ZnEt_2$ (15% in toluene; 0.73 mL; 1.06 mmol). The reaction mixture was stirred at rt for 4 h. Water (10 mL) was added carefully followed by aq. HCl (6M; 0.3 mL) and the reaction was stirred for 15 min. The mixture was extracted with EA (3×15 mL). The combined org. layers were washed with brine (15 mL), dried over $Na_2SO_4$, filtered and the filtrate concentrated under reduced pressure. The residue was purified by CC (Hept-EA) to afford the desired product as a colourless oil (2 g; quant.).

$^1$H NMR (d6-DMSO) δ: 7.59-7.63 (m, 4H); 7.41-7.49 (m, 6H); 5.09 (s, 1H); 3.62 (d, J=6.8 Hz, 2H); 2.31 (s, 2H); 1.88-1.99 (m, 3H); 1.22-1.31 (m, 2H); 1.00 (s, 9H); 0.07 (s, 9H).

MS (ESI, m/z): 451.0 [M+H$^+$] for $C_{27}H_{38}O_2Si_2$; $t_R$=1.14 min.

BG.ii. Cis-3-(hydroxymethyl)-1-(3-iodoprop-2-yn-1-yl)cyclobutan-1-ol

Starting from intermediate BG.i (crude; 2 g; 1.77 mmol) and proceeding successively in analogy to Preparation AD, step AD.ii (72% yield) and Preparation K (48% yield), the title compound was obtained, after purification by CC (Hept-EA), as a yellow oil (0.4 g) which crystallized.

$^1$H NMR (d6-DMSO) δ: 5.06 (s, 1H); 4.45 (t, J=5.4 Hz, 1H); 3.32-3.36 (overlapped m, 2H); 2.48-2.52 (overlapped m, 1H); 1.98-2.04 (m, 2H); 1.88 (m, 1H); 1.64-1.70 (m, 2H).

MS (ESI, m/z): 266.95 [M+H$^+$] for $C_8H_{11}O_2I$; $t_R$=0.52 min.

Preparation BH: ((di-tert-butoxyphosphoryl)oxy) methyl (1-(iodoethynyl)cyclopropyl)carbamate BH.i. Chloromethyl (1-(iodoethynyl)cyclopropyl)carbamate To a solution of the compound of Preparation AG (0.134 g; 0.48 mmol) and 1,8-bis(dimethylamino)naphthalene (0.321 g; 1.5 mmol) in DCM (9.5 mL) was added chloromethyl chloroformate (0.05 mL; 0.56 mmol). The mixture was stirred at rt for 1 h. Water (10 mL) was added, the phases were separated and the aq. layer was extracted with DCM (10 mL). The combined org. layers were washed with water (5 mL) and brine (10 mL), dried over MgSO$_4$ and concentrated under reduced pressure. The residue was purified by CC (Hept-EA) to afford the title compound as a yellowish oil (0.111 g; 77% yield).
$^1$H NMR (CDCl$_3$) δ: 5.68-5.81 (m, 2H); 5.41 (m, 1H); 1.28-1.31 (m, 2H); 1.16-1.20 (m, 2H).

BH.ii. ((Di-tert-butoxyphosphoryl)oxy)methyl (1-(iodoethynyl)cyclopropyl)carbamate To a solution of intermediate BH.i (0.111 g; 0.37 mmol) in DME (5.5 mL) was added tetra-n-butylammonium di-tert-butylphosphate (0.237 g; 0.53 mmol). The reaction mixture was heated at 80° C. for 2.5 h. Water (10 mL) was added and the mixture was extracted with EA (10 mL). The combined org. layers were washed with water (2×5 mL) and brine (5 mL), dried over MgSO$_4$ and concentrated to dryness to afford the title compound as a brown gum (0.133 g; 76% yield).
$^1$H NMR (CDCl$_3$) δ: 3.54 (s, 1H); 3.40 (s, 2H); 1.49 (s, 18H); 1.24-1.30 (m, 2H); 1.12-1.16 (m, 2H).
MS (ESI, m/z): 473.9 [M+H$^+$] for $C_{15}H_{25}NO_6IP$; $t_R$=0.85 min.

Preparation BI: 2-(5-ethynylthiazol-2-yl)propan-2-ol

Starting from 2-(5-bromothiazol-2-yl)propan-2-ol (0.429 g, 1.87 mmol; commercial) and proceeding in analogy to Procedure C (Sonogashira coupling, 76% yield) and Preparation H. step H.ii (TMS cleavage, 68% yield), the title compound was obtained, after purification by CC (Hept-EtOAc), as an yellowish solid (0.118 g).
$^1$H NMR (d6-DMSO) δ: 7.91 (s, 1H); 6.15 (s, 1H); 4.68 (s, 1H); 1.48 (s, 6H).
MS (ESI, m/z): 168.00 [M+H$^+$] for $C_8H_9NOS$; $t_R$=0.62 min.

Preparation BJ: ((1R,2R)-2-(bromoethynyl)-1-fluorocyclopropyl)methyl benzoate and ((1S,2S)-2-(bromoethynyl)-1-fluorocyclopropyl)methyl benzoate BJ.i. ((1R*,2R*)-2-(((tert-butyldiphenylsilyl)oxy) methyl)-1-fluorocyclopropyl)methyl benzoate To a solution of intermediate AU.i (5.51 g, 15.4 mmol) in THF (93 mL) was added TEA (6 mL; 43.1 mmol). Benzoyl chloride (3.6 mL; 30.7 mmol) was added dropwise over 2 min at 0° C. The reaction mixture was stirred at 0° C. for 5 h before being poured onto water (75 mL). The aq. layer was extracted with EA (3×50 mL). The combined org. layers were dried over MgSO$_4$ and concentrated to dryness. The residue was purified by CC (Hept-EA) to afford the title compound as a colourless oil (6.49 g; 91% yield).
$^1$H NMR (500 MHz, CDCl$_3$) δ: 8.09-8.12 (m, 2H); 7.67-7.70 (m, 4H); 7.56 (m, 1H); 7.40-7.44 (m, 4H); 7.35-7.38 (m, 4H); 4.62 (m, 1H); 4.51 (ddd, J=1.1, 13.0, 23.8 Hz, 1H); 3.93 (ddd, J=1.5, 5.6, 11.0 Hz, 1H); 3.70 (ddd, J=1.1, 8.4, 10.9 Hz, 1H); 1.46 (m, 1H); 1.30 (m, 1H); 1.02 (s, 7H); 0.97 (m, 1H); 0.84-0.91 (m, 2H).
MS (ESI, m/z): 463.07 [M+H$^+$] for $C_{28}H_{31}O_3FSi$; $t_R$=1.14 min.

BJ.ii. ((1R,2R)-2-(2,2-dibromovinyl)-1-fluorocyclopropyl)methyl benzoate and ((1S,2S)-2-(2,2-dibromovinyl)-1-fluorocyclopropyl)methyl benzoate Starting from intermediate BJ.i (6.49 g; 14 mmol) and proceeding successively in analogy to Preparation AP, step AP.i (89% yield), Preparation Y, step Y.iii (84% yield) and Y.iv (adding 2 eq. TEA, 96% yield), a mixture of enantiomers (2.71 g) was obtained. After separation by chiral prep-HPLC (Method C) (Hept-EtOH 3-7; flow rate: 16 mL/min, UV detection at 224 nM), the title enantiomers (the absolute stereochemistries of which have not been assigned) were obtained as white solids (1.25 g each); their respective retention times (measured under same conditions as analytical LC-MS except that the flow rate is 0.8 mL/min) were 5.3 and 7.0 min.
$^1$H NMR (d6-DMSO) δ: 7.99-8.01 (m, 2H); 7.69 (m, 1H); 7.54-7.58 (m, 2H); 6.38 (dd, J=1.4, 8.9 Hz, 1H); 4.57-4.75 (m, 2H); 2.09 (m, 1H); 1.48-1.55 (m, 2H).

Preparation BK: tert-butyl 3-hydroxy-3-(4-iodophenyl)azetidine-1-carboxylate

Starting from tert-butyl 3-oxoazetidine-1-carboxylate (1 g; 5.84 mmol; commercial) and proceeding in analogy to Preparation BD, step BD.i, the title compound was obtained, after purification by CC (Hept-EA), as a white solid (1.29 g; 69% yield).
$^1$H NMR (d6-DMSO) δ: 7.74 (d, J=8.5 Hz, 2H); 7.31 (d, J=8.5 Hz, 2H); 6.42 (s, 1H); 3.94-4.08 (m, 4H); 1.41 (s, 9H).

Preparation BL: 3-(4-iodophenyl)azetidin-3-ol trifluoroacetate

To a solution of the compound of Preparation BK (0.1 g, 0.26 mmol) in DCM (5 mL) at 0° C. was added TFA (1.2 mL). After stirring at rt for 15 min., the mixture was concentrated to dryness and the residue was triturated in a DCM-Et$_2$O mixture. After drying, the title compound was obtained as a white solid (0.108 g; quant.).
$^1$H NMR (d6-DMSO) δ: 7.81 (d, J=8.5 Hz, 2H); 7.37 (d, J=8.5 Hz, 2H); 6.76 (br. s, 1H); 4.31 (d, J=11.4 Hz, 2H); 4.06 (d, J=11.4 Hz, 2H).
MS (ESI, m/z): 275.88 [M+H$^+$] for $C_9H_{10}NOI$; $t_R$=0.48 min.

Preparation BM: 4-(4-iodophenyl)piperidin-4-ol

Starting from tert-butyl 3-oxopiperidine-1-carboxylate (0.226 g; 11 mmol; commercial) and proceeding in analogy to Preparation BD, step BD.i (77% yield) and Preparation BL (54% yield), the title compound was obtained, after basic work-up and purification by CC (DCM-MeOH containing 1% aq. NH$_4$OH), as a yellowish solid (0.127 g).
$^1$H NMR (d6-DMSO) δ: 7.74 (d, J=8.5 Hz, 2H); 7.31 (d, J=8.5 Hz, 2H); 6.42 (s, 1H); 3.94-4.08 (m, 4H); 1.41 (s, 9H).

MS (ESI, m/z): 375.8 [M+H$^+$] for C$_{14}$H$_{18}$NO$_3$I; t$_R$=0.87 min.

Preparation BN:
N-(3-bromoprop-2-yn-1-yl)methanesulfonamide

Starting from N-(prop-2-yn-1-yl)methanesulfonamide (1.52 g; 11.4 mmol) and proceeding in analogy to Preparation G, step G.iv (71% yield), the title compound was obtained after purification by CC (DCM-TBME), as a yellowish solid (1.71 g).

$^1$H NMR (d6-DMSO): 7.58 (t, J=6.0 Hz, 1H); 3.87 (d, J=6.1 Hz, 2H); 2.95 (s, 3H).

REFERENCE EXAMPLES

Reference Example 1: (RS)—N-hydroxy-4-(6-(4-(3-hydroxyoxetan-3-yl)phenyl)-3-oxo-1H-pyrrolo[1,2-c]imidazol-2(3H)-yl)-2-methyl-2-(methylsulfonyl)butanamide RE1.i. (RS)-4-(6-(4-(3-hydroxyoxetan-3-yl)phenyl)-3-oxo-1H-pyrrolo[1,2-c]imidazol-2(3H)-yl)-2-methyl-2-(methylsulfonyl)-N-(((RS)-tetrahydro-2H-pyran-2-yl)oxy)butanamide Starting from the compound of Preparation D (0.06 g; 0.119 mmol) and 3-(4-(4,4,5,5-tetramethyl-1,3,2-dioxaborolan-2-yl)phenyl)oxetan-3-ol (0.05 g; 0.179 mmol), and proceeding in analogy to Procedure A, the title compound, slightly contaminated with OPPh$_3$, was obtained as a colourless oil (0.037 g; 57% yield).

MS (ESI, m/z): 548.07 [M+H$^+$] for C$_{26}$H$_{33}$N$_3$O$_8$S; t$_R$=0.70 min.

RE1.ii. (RS)—N-hydroxy-4-(6-(4-(3-hydroxyoxetan-3-yl)phenyl)-3-oxo-1H-pyrrolo[1,2-c]imidazol-2(3H)-yl)-2-methyl-2-(methylsulfonyl)butanamide Starting from intermediate RE1.i (0.037 g; 0.02 mmol) and using Procedure D, the title compound was obtained as a yellowish foam (0.008 g; 25% yield).

$^1$H NMR (d$_6$-DMSO) δ: 7.63-7.73 (m, 2H); 7.51-7.63 (m, 3H); 6.55 (s, 1H); 6.28 (s, 1H); 4.76 (d, J=6.45 Hz, 2H); 4.69 (d, J=6.45 Hz, 2H); 4.48 (s, 2H); 3.45-3.58 (m, 1H); 3.34-3.44 (m, 1H); 3.07 (s, 3H); 2.56-2.66 (m, 1H); 1.93-2.04 (m, 1H); 1.54 (s, 3H).

MS (ESI, m/z): 464.0 [M+H$^+$] for C$_{21}$H$_{25}$N$_3$O$_7$S; t$_R$=0.80 min.

Reference Example 2: (RS)-4-(6-((4-(2-ethoxypropan-2-yl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation G (0.13 g; 0.31 mmol) and 2-(4-iodophenyl)propan-2-ol (0.121 g; 0.46 mmol; prepared as described in JP 2008001635 A) and proceeding successively in analogy to Procedure E (51% yield) and Procedure D (42% yield), the title compound was obtained, after purification by prep-HPLC (Method 1), as a white solid (0.033 g).

$^1$H NMR (d$_6$-DMSO) δ: 10.83-11.07 (br. s, 1H); 9.03-9.33 (br. s, 1H); 7.30-7.57 (m, 5H); 6.24-6.29 (m, 1H); 4.46 (s, 2H); 3.33-3.56 (m, 2H); 3.15 (q, J=6.9 Hz, 2H); 3.07 (s, 3H); 2.55-2.65 (m, 1H); 1.90-2.04 (m, 1H); 1.54 (s, 3H); 1.44 (s, 6H); 1.08 (t, J=6.9 Hz, 3H).

MS (ESI, m/z): 501.90 [M+H$^+$] for C$_{25}$H$_{31}$N$_3$O$_6$S; t$_R$=0.79 min.

Reference Example 3: (RS)-4-(6-((2-fluoro-4-(hydroxymethyl)phenyl)ethynyl)-3-oxo-1H-pyrrolo[1,2-c]imidazol-2(3H)-yl)-N-hydroxy-2-methyl-2-(methylsulfonyl)butanamide Starting from (4-ethynylphenyl)-2-fluoro-methanol (0.054 g; 0.36 mmol; prepared according to WO 2011/021209) and the compound of Preparation F (0.16 g; 0.3 mmol) and proceeding successively in analogy to Procedure F (80% yield) and Procedure B (60% yield), the title compound was obtained, after precipitation in water and trituration in DCM, as a white solid (0.066 g).

$^1$H NMR (d$_6$-DMSO) δ: 10.89-10.98 (br. s, 1H); 9.12-9.21 (br. s, 1H); 7.45-7.57 (m, 2H); 7.14-7.27 (m, 2H); 6.27-6.31 (m, 1H); 5.38 (t, J=5.8 Hz, 1H); 4.53 (d, J=5.8 Hz, 2H); 4.46 (s, 2H); 3.35-3.58 (m, 2H); 3.07 (s, 3H); 2.54-2.69 (m, 1H); 1.91-2.06 (m, 1H); 1.54 (s, 3H).

MS (ESI, m/z): 463.97 [M+H$^+$] for C$_{21}$H$_{22}$N$_3$O$_6$FS; t$_R$=0.68 min.

Reference Example 4: (RS)—N-hydroxy-4-(6-(4-(3-hydroxy-3-methylbut-1-yn-1-yl)phenyl)-3-oxo-1H-pyrrolo[1,2-c]imidazol-2(3H)-yl)-2-methyl-2-(methylsulfonyl)butanamide RE4.i. (RS)-4-(6-(4-(3-hydroxy-3-methylbut-1-yn-1-yl)phenyl)-3-oxo-1H-pyrrolo[1,2-c]imidazol-2(3H)-yl)-2-methyl-2-(methylsulfonyl)-N-(((RS)-tetrahydro-2H-pyran-2-yl)oxy)butanamide A mixture of Pd$_2$(dba)$_3$ (0.055 g; 0.06 mmol) and PCy$_3$ (0.04 g; 0.144 mmol) in degassed dioxane (4 mL) was premixed at 90° C. for 5 min. To the mixture were added the compound of Preparation F (0.315 g; 0.6 mmol), the compound of Preparation I (0.122 g; 0.6 mmol) and a degassed 1M K$_3$PO$_4$ solution (0.9 mL). The mixture was degassed and heated at 90° C. for 1.5 h. After cooling, the reaction was concentrated to dryness and the residue was purified by CC (DCM-EA) to afford the title compound as a yellow oil (0.039 g; 12% yield).

MS (ESI, m/z): 557.9 [M+H$^+$] for C$_{28}$H$_{35}$N$_3$O$_7$S; t$_R$=0.81 min

RE4.ii. (RS)—N-hydroxy-4-(6-(4-(3-hydroxy-3-methylbut-1-yn-1-yl)phenyl)-3-oxo-1H-pyrrolo[1,2-c]imidazol-2(3H)-yl)-2-methyl-2-(methylsulfonyl)butanamide Starting from intermediate RE4.i (0.038 g; 0.068 mmol) and proceeding in analogy to Procedure B, the title compound was obtained, after purification by CC (DCM-MeOH), as a white solid (0.005 g; 15% yield).

$^1$H NMR (d$_6$-DMSO) δ: 10.84-11.05 (br. s, 1H); 9.07-9.27 (br. s, 1H); 7.59-7.69 (m, 3H); 7.34 (d, J=7.9 Hz, 2H); 6.52-6.59 (m, 1H); 5.41-5.45 (br. s, 1H); 4.48 (s, 2H); 3.35-3.58 (m, 2H); 3.07 (s, 3H); 2.55-2.68 (m, 1H); 1.91-2.07 (m, 1H); 1.54 (s, 3H); 1.47 (s, 6H).

MS (ESI, m/z): 473.96 [M+H$^+$] for C$_{23}$H$_{27}$N$_3$O$_6$S; t$_R$=0.70 min.

Reference Example 5: (RS)—N-hydroxy-4-(6-(5-hydroxy-5-methylhexa-1,3-diyn-1-yl)-3-oxo-1H-pyrrolo[1,2-c]imidazol-2(3H)-yl)-2-methyl-2-(methylsulfonyl)butanamide Starting from the compound of Preparation G (0.2 g; 0.472 mmol) and 4-iodo-2-methylbut-3-yn-2-ol (0.119 g;

0.567 mmol; prepared as described in Rajender Reddy et al., *Tetrahedron Lett.* (2010), 51, 2170-2173), and proceeding successively in analogy to Procedure E (100% yield) and Procedure B (21% yield), the title compound was obtained, after purification by prep-HPLC (Method 1), as a beige solid (0.041 g).

$^1$H NMR (d$_6$-DMSO) δ: 10.87-10.98 (br. s, 1H); 9.17 (br. s, 1H); 7.57 (s, 1H); 6.26 (s, 1H); 5.60 (s, 1H); 4.42 (s, 2H); 3.44-3.52 (m, 1H); 3.34-3.42 (m, 1H); 3.06 (s, 3H); 2.54-2.65 (m, 1H); 1.91-1.99 (m, 1H); 1.52 (s, 3H); 1.41 (s, 6H).

MS (ESI, m/z): 421.93 [M+H$^+$] for $C_{19}H_{23}N_3O_6S$; $t_R$=0.66 min.

Reference Example 6: (RS)—N-hydroxy-2-methyl-4-(6-((4-((4-methylpiperazin-1-yl)methyl)phenyl)ethynyl)-3-oxo-1H-pyrrolo[1,2-c]imidazol-2(3H)-yl)-2-(methylsulfonyl)butanamide Starting from the compound of Preparation G (0.2 g; 0.472 mmol) and 1-(4-iodobenzyl)-4-methylpiperazine (0.179 g; 0.567 mmol; prepared as described in Chai et al., *Chemistry—A European Journal* (2011), 17, 10820-10824), and proceeding successively in analogy to Procedure E (84% yield) and Procedure B (44% yield), the title compound was obtained as a yellow solid (0.093 g).

$^1$H NMR (d$_6$-DMSO) δ: 10.75-11.10 (br. s, 1H); 9.06-9.35 (br. s, 1H); 7.45 (d, J=8.1 Hz, 2H); 7.42 (s, 1H); 7.31 (d, J=8.1 Hz, 2H); 6.26 (s, 1H); 4.46 (s, 2H); 3.47-3.53 (overlapped m, 1H); 3.46 (overlapped s, 2H); 3.34-3.42 (overlapped m, 1H); 3.06 (s, 3H); 2.50-2.62 (m, 1H); 2.24-2.43 (m, 8H); 2.14 (s, 3H); 1.93-2.01 (m, 1H); 1.53 (s, 3H).

MS (ESI, m/z): 527.97 [M+H$^+$] for $C_{26}H_{33}N_5O_5S$; $t_R$=0.52 min.

Reference Example 7: (RS)—N-hydroxy-4-(6-(4-(2-hydroxyethoxy)phenyl)-3-oxo-1H-pyrrolo[1,2-c]imidazol-2(3H)-yl)-2-methyl-2-(methylsulfonyl)butanamide Starting from the compound of Preparation D (0.3 g; 0.636 mmol) and (RS)-4,4,5,5-tetramethyl-2-(4-(2-((tetrahydro-2H-pyran-2-yl)oxy)ethoxy)phenyl)-1,3,2-dioxaborolane (0.233 g; 0.668 mmol; prepared according to EP 2418203 A1), and proceeding successively in analogy to Procedure A (19% yield) and Procedure B (46% yield), the title compound was obtained, after purification by prep-HPLC (Method 1), as a white solid (0.0247 g).

$^1$H NMR (d$_6$-DMSO) δ: 10.77-11.05 (br. s, 1H); 9.05-9.22 (br. s, 1H); 7.55 (d, J=8.7 Hz, 2H); 7.48 (s, 1H); 6.91 (d, J=8.7 Hz, 2H); 6.47 (s, 1H); 4.86 (t, J=5.2 Hz, 1H); 4.46 (s, 2H); 3.98 (t, J=5.2 Hz, 2H); 3.71 (q, J=5.2 Hz, 2H); 3.46-3.54 (m, 1H); 3.30-3.40 (overlapped m, 1H); 3.07 (s, 3H); 2.50-2.60 (overlapped m, 1H); 1.93-2.00 (m, 1H); 1.53 (s, 3H).

MS (ESI, m/z): 451.92 [M+H$^+$] for $C_{20}H_{25}N_3O_7S$; $t_R$=0.60 min.

Reference Example 8: (RS)—N-hydroxy-4-(6-(4-(2-methoxyethoxy)phenyl)-3-oxo-1H-pyrrolo[1,2-c]imidazol-2(3H)-yl)-2-methyl-2-(methylsulfonyl)butanamide Starting from the compound of Preparation D (0.2 g; 0.418 mmol) and 2-(4-(2-methoxyethoxy)phenyl)-4,4,5,5-tetramethyl-1,3,2-dioxaborolane (0.14 g; 0.502 mmol; prepared according to US 2007/287708 A1), and proceeding successively in analogy to Procedure A (38% yield) and Procedure B (27% yield), the title compound was obtained, after purification by prep-HPLC (Method 1), as a white solid (0.019 g).

$^1$H NMR (d$_6$-DMSO) δ: 10.90-11.06 (br. s, 1H); 9.14-9.29 (br. s, 1H); 7.56 (d, J=8.6 Hz, 2H); 7.49 (s, 1H); 6.92 (d, J=8.7 Hz, 2H); 6.48 (s, 1H); 4.47 (s, 2H); 4.08-4.12 (m, 2H); 3.63-3.69 (m, 2H); 3.47-3.56 (m, 1H); 3.36-3.43 (m, 1H); 3.32 (s, 3H); 3.08 (s, 3H); 2.56-2.66 (m, 1H); 1.94-2.03 (m, 1H); 1.54 (s, 3H).

MS (ESI, m/z): 465.85 [M+H$^+$] for $C_{21}H_{27}N_3O_7S$; $t_R$=0.69 min.

Reference Example 9: (RS)-4-(6-(2-fluoro-4-methylphenyl)-3-oxo-1H-pyrrolo[1,2-c]imidazol-2(3H)-yl)-N-hydroxy-2-methyl-2-(methylsulfonyl)butanamide Starting from the compound of Preparation D (0.2 g; 0.418 mmol) and (2-fluoro-4-methylphenyl)boronic acid (0.064 g; 0.42 mmol; commercial), and proceeding successively in analogy to Procedure A (51% yield) and Procedure B (32% yield), the title compound was obtained, after purification by CC (Hept-EA), as a white solid (0.027 g).

$^1$H NMR (d6-DMSO) δ: 10.95 (s, 1H); 9.19 (s, 1H); 7.61 (t, J=8.2 Hz, 1H); 7.42 (s, 1H); 7.07 (d, J=12.6 Hz, 1H); 7.03 (dd, J=0.7, 7.9 Hz, 1H); 6.54 (s, 1H); 4.48 (s, 2H); 3.48-3.55 (m, 1H); 3.36-3.43 (m, 1H); 3.07 (s, 3H); 2.58-2.65 (m, 1H); 2.31 (s, 3H); 1.95-2.02 (m, 1H); 1.54 (s, 3H).

MS (ESI, m/z): 423.95 [M+H$^+$] for $C_{19}H_{22}N_3O_5FS$; $t_R$=0.75 min.

Reference Example 10: (RS)-4-(6-(3-fluoro-4-isopropoxyphenyl)-3-oxo-1H-pyrrolo[1,2-c]imidazol-2(3H)-yl)-N-hydroxy-2-methyl-2-(methylsulfonyl)butanamide Starting from the compound of Preparation D (0.2 g; 0.418 mmol) and (3-fluoro-4-isopropoxyphenyl)boronic acid (0.084 g; 0.42 mmol; commercial), and proceeding successively in analogy to Procedure A (29% yield) and Procedure B (43% yield), the title compound was obtained, after purification by CC (Hept-EA), as a white solid (0.025 g).

$^1$H NMR (d6-DMSO) δ: 10.95 (s, 1H); 9.19 (s, 1H); 7.59 (s, 1H); 7.51 (d, J=12.9 Hz, 1H); 7.38 (d, J=8.5 Hz, 1H); 7.13 (m, 1H); 6.51 (s, 1H); 4.57-4.63 (m, 1H); 4.46 (s, 2H); 3.46-3.53 (m, 1H); 3.34-3.41 (m, 1H); 3.07 (s, 3H); 1.94-2.01 (m, 1H); 1.53 (s, 3H); 1.28 (m, 6H).

MS (ESI, m/z): 467.98 [M+H$^+$] for $C_{21}H_{26}N_3O_6FS$; $t_R$=0.78 min.

EXAMPLES OF COMPOUNDS ACCORDING TO THE INVENTION

Example 1: (R)-4-(6-(2-fluoro-4-methoxyphenyl)-3-oxo-1H-pyrrolo[1,2-c]imidazol-2(3H)-yl)-N-hydroxy-2-methyl-2-(methylsulfonyl)butanamide 1.i. (R)-4-(6-(2-fluoro-4-methoxyphenyl)-3-oxo-1H-pyrrolo[1,2-c]imidazol-2(3H)-yl)-2-methyl-2-(methylsulfonyl)-N-(((RS)-tetrahydro-2H-pyran-2-yl)oxy)butanamide Starting from the compound of Preparation C (0.78 g; 1.63 mmol) and 2-fluoro-4-methoxyphenylboronic acid (0.3 g; 1.8 mmol) and proceeding in analogy to Procedure A, the title compound as a yellowish foam (0.4 g, 48% yield).

¹H NMR (d₆-DMSO) (mixture of stereoisomers) δ: 11.39 (overlapped br. s, 0.5H); 11.34 (overlapped br. s, 0.5H); 7.62 (t, J=8.4 Hz, 1H); 7.36 (d, J=6.7 Hz, 1H); 6.88 (dd, J=2.4, 13.3 Hz, 1H); 6.81 (dd, J=2.4, 8.4 Hz, 1H); 6.50 (s, 1H); 4.85-4.88 (m, 0.5H); 4.39-4.52 (m, 2.5H); 3.99-4.05 (m, 0.5H); 3.88-3.97 (m, 0.5H); 3.78 (s, 3H); 3.36-3.58 (m, 3H); 3.07 (s, 1.5H); 3.04 (s, 1.5H); 2.54-2.71 (m, 1H); 1.92-2.03 (m, 1H); 1.60-1.68 (m, 2H); 1.58 (s, 1.5H); 1.56 (s, 1.5H); 1.33-1.54 (m, 4H).

MS (ESI, m/z): 523.97 [M+H⁺] for $C_{24}H_{30}N_3O_7FS$; $t_R$=0.85 min.

1.ii. (R)-4-(6-(2-fluoro-4-methoxyphenyl)-3-oxo-1H-pyrrolo[1,2-c]imidazol-2(3H)-yl)-N-hydroxy-2-methyl-2-(methylsulfonyl)butanamide Starting from intermediate 1.i (0.44 g; 0.84 mmol) and using Procedure B, the title compound was obtained, after purification by CC (DCM-MeOH), as a white solid (0.23 g; 63% yield).

¹H NMR (d₆-DMSO) δ: 10.81-11.05 (br. s, 1H); 9.14-9.23 (br. s, 1H); 7.63 (t, J=8.8 Hz, 1H); 7.36-7.39 (m, 1H); 6.88 (dd, J=2.4, 13.3 Hz, 1H); 6.81 (dd, J=2.4, 8.5 Hz, 1H); 6.49-6.51 (m, 1H); 4.48 (s, 2H); 3.78 (s, 3H); 3.47-3.54 (m, 1H); 3.35-3.42 (m, 1H); 3.07 (s, 3H); 2.57-2.62 (m, 1H); 1.94-2.02 (m, 1H); 1.54 (s, 3H).

MS (ESI, m/z): 439.93 [M+H⁺] for $C_{19}H_{22}N_3O_6FS$; $t_R$=0.73 min.

Example 2: (R)-N-hydroxy-4-(6-((4-(3-hydroxyoxetan-3-yl)phenyl)ethynyl)-3-oxo-1H-pyrrolo[1,2-c]imidazol-2(3H)-yl)-2-methyl-2-(methylsulfonyl)butanamide 2.i. (RS)—N-hydroxy-4-(6-((4-(3-hydroxyoxetan-3-yl)phenyl)ethynyl)-3-oxo-1H-pyrrolo[1,2-c]imidazol-2(3H)-yl)-2-methyl-2-(methylsulfonyl)butanamide Starting from the compound of Preparation G (0.13 g; 0.31 mmol) and the compound of Preparation J (0.127 g; 0.46 mmol) and proceeding successively in analogy to Procedure E and Procedure D, the title compound was obtained, after purification by prep-HPLC (Method 1), as a yellow solid (0.038 g; 45% yield).

MS (ESI, m/z): 488.00 [M+H⁺] for $C_{23}H_{25}N_3O_7S$; $t_R$=0.64 min.

2.ii. (R)-N-hydroxy-4-(6-((4-(3-hydroxyoxetan-3-yl)phenyl)ethynyl)-3-oxo-1H-pyrrolo[1,2-c]imidazol-2(3H)-yl)-2-methyl-2-(methylsulfonyl)butanamide Intermediate 2.i (0.032 g) was separated by semi-preparative chiral HPLC Method D (Hept-EtOH-TFA 3-7-0.01; flow rate: 16 mL/min; UV detection at 210 nm); the respective retention times (flow rate: 0.8 mL/min) were 8.14 and 11.41 min. The title (R)-enantiomer, identified as the second eluting compound, was obtained as a yellow solid (0.007 g).

¹H NMR (d₆-DMSO) δ: 10.90-10.96 (br. s, 1H); 9.14-9.20 (br. s, 1H); 7.63 (d, J=8.3 Hz, 2H); 7.52 (d, J=8.3 Hz, 2H); 7.46 (s, 1H); 6.42 (s, 1H); 6.28 (s, 1H); 4.77 (d, J=6.5 Hz, 2H); 4.67 (d, J=6.5 Hz, 2H); 4.46 (s, 2H); 3.37-3.56 (m, 2H); 3.07 (s, 3H); 2.58-2.65 (m, 1H); 1.89-2.04 (m, 1H); 1.54 (s, 3H).

MS (ESI, m/z): 488.00 [M+H⁺] for $C_{23}H_{25}N_3O_7S$; $t_R$=0.64 min.

Example 3: (R)-N-hydroxy-4-(6-((4-(hydroxymethyl)phenyl)ethynyl)-3-oxo-1H-pyrrolo[1,2-c]imidazol-2(3H)-yl)-2-methyl-2-(methylsulfonyl)butanamide 3.i. (RS)—N-hydroxy-4-(6-((4-(hydroxymethyl)phenyl)ethynyl)-3-oxo-1H-pyrrolo[1,2-c]imidazol-2(3H)-yl)-2-methyl-2-(methylsulfonyl)butanamide Starting from the compound of Preparation F (0.2 g; 0.381 mmol) and 4-ethynylbenzyl alcohol (0.06 g; 0.457 mmol), and proceeding successively in analogy to Procedure E (48% yield) and Procedure F (69% yield), the title compound was obtained, after purification by prep-HPLC (Method 1), as a beige solid (0.056 g).

MS (ESI, m/z): 445.98 [M+H⁺] for $C_{21}H_{23}N_3O_6S$; $t_R$=0.65 min.

3.ii. (R)-N-hydroxy-4-(6-((4-(hydroxymethyl)phenyl)ethynyl)-3-oxo-1H-pyrrolo[1,2-c]imidazol-2(3H)-yl)-2-methyl-2-(methylsulfonyl)butanamide Intermediate 3.i (0.05 g) was separated by semi-preparative chiral HPLC Method D (Hept-EtOH-TFA: 1-9-0.01; flow rate: 16 mL/min; UV detection at 287 nm); the respective retention times (flow rate: 0.8 mL/min) were 6.34 and 8.48 min. The title (R)-enantiomer, identified as the second eluting compound, was obtained as a yellow solid (0.01 g).

¹H NMR (d₆-DMSO) δ: 10.73-11.11 (br. s, 1H); 9.05-9.34 (br. s, 1H); 7.41-7.47 (m, 3H); 7.34 (d, J=8.2 Hz, 2H); 6.25-6.28 (m, 1H); 5.25 (t, J=5.8 Hz, 1H); 4.51 (d, J=5.7 Hz, 2H); 4.43-4.48 (m, 2H); 3.37-3.56 (m, 2H); 3.06 (s, 3H); 2.55-2.66 (m, 1H); 1.90-2.04 (m, 1H); 1.53 (s, 3H).

MS (ESI, m/z): 445.98 [M+H⁺] for $C_{21}H_{23}N_3O_6S$; $t_R$=0.65 min.

Example 4: (R)-N-hydroxy-4-(6-((3-hydroxyoxetan-3-yl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation H (0.285 g; 0.586 mmol) and the compound of Preparation K (0.143 g; 0.64 mmol), and proceeding successively in analogy to Procedure G (51% yield) and Procedure B (37% yield), the title compound was obtained, after purification by prep-HPLC (Method 1), as a beige solid (0.048 g).

¹H NMR (d₆-DMSO) δ: 10.87-11.00 (br. s, 1H); 9.12-9.21 (br. s, 1H); 7.61-7.64 (m, 1H); 6.69-6.72 (m, 1H); 6.28-6.31 (m, 1H); 4.69 (d, J=6.4 Hz, 2H); 4.54 (d, J=6.4 Hz, 2H); 4.42-4.46 (m, 2H); 3.33-3.54 (m, 1H); 3.06 (s, 3H); 2.50-2.75 (overlapped m, 1H); 2.32-2.50 (overlapped m, 1H); 1.87-2.04 (m, 1H); 1.52 (s, 3H).

MS (ESI, m/z): 435.86 [M+H⁺] for $C_{19}H_{21}N_3O_7S$; $t_R$=0.60 min.

Example 5: (R)-N-hydroxy-4-(6-((4-((1R,2R)-2-(hydroxymethyl)cyclopropyl)phenyl)ethynyl)-3-oxo-1H-pyrrolo[1,2-c]imidazol-2(3H)-yl)-2-methyl-2-(methylsulfonyl)butanamide Starting from the compound of Preparation H (0.097 g; 0.229 mmol) and the first-eluting enantiomer of Preparation L (0.07 g; 0.255 mmol), and proceeding successively in analogy to Procedure E (93% yield) and Procedure B (22% yield), the title compound was obtained, after purification by prep-HPLC (Method 1), as a beige solid (0.023 g).

¹H NMR (d₆-DMSO) δ: 10.77-11.06 (br. s, 1H); 9.08-9.28 (br. s, 1H); 7.43 (s, 1H); 7.35 (d, J=7.9 Hz, 2H); 7.08 (d, J=7.9 Hz, 2H); 6.25 (s, 1H); 4.63 (t, J=5.6 Hz, 1H); 4.45 (s, 2H); 3.42-3.53 (m, 2H); 3.30-3.42 (overlapped m, 2H); 3.07 (s, 3H); 2.54-2.65 (m, 1H); 1.93-2.01 (m, 1H); 1.77-1.83 (m, 1H); 1.53 (s, 3H); 1.24-1.35 (m, 1H); 0.83-0.93 (m, 2H).

MS (ESI, m/z): 485.92 [M+H⁺] for $C_{24}H_{27}N_3O_6S$; $t_R$=0.71 min.

Example 6: (R)-N-hydroxy-4-(6-((4-((1S,2S)-2-(hydroxymethyl)cyclopropyl)phenyl)ethynyl)-3-oxo-1H-pyrrolo[1,2-c]imidazol-2(3H)-yl)-2-methyl-2-(methylsulfonyl)butanamide Starting from the compound of Preparation H (0.118 g; 0.279 mmol) and the second-eluting enantiomer of Preparation L (0.083 g; 0.301 mmol), and proceeding successively in analogy to Procedure E (99% yield) and Procedure B (21% yield), the title compound was obtained, after purification by prep-HPLC (Method 1), as a beige solid (0.027 g).

¹H NMR (d₆-DMSO) δ: 10.60-11.21 (br. s, 1H); 9.00-9.36 (br. s, 1H); 7.43 (s, 1H); 7.34 (d, J=7.9 Hz, 2H); 7.08 (d, J=7.9 Hz, 2H); 6.25 (s, 1H); 4.60-4.67 (m, 1H); 4.45 (s, 2H); 3.42-3.53 (m, 2H); 3.30-3.42 (overlapped m, 2H); 3.06 (s, 3H); 2.50-2.63 (overlapped m, 1H); 1.92-2.01 (m, 1H); 1.77-1.84 (m, 1H); 1.52 (s, 3H); 1.24-1.35 (m, 1H); 0.83-0.93 (m, 2H).

MS (ESI, m/z): 485.91 [M+H⁺] for $C_{24}H_{27}N_3O_6S$; $t_R$=0.71 min.

Example 7: (R)-N-hydroxy-4-(6-((4-(1-(hydroxymethyl)cyclopropyl)phenyl)ethynyl)-3-oxo-1H-pyrrolo[1,2-c]imidazol-2(3H)-yl)-2-methyl-2-(methylsulfonyl)butanamide Starting from the compound of Preparation E (0.15 g; 0.286 mmol) and the compound of Preparation M (0.054 g; 0.314 mmol), and proceeding successively in analogy to Procedure F (55% yield) and Procedure B (63% yield), the title compound was obtained, after purification by prep-HPLC (Method 1), as a white solid (0.049 g).

¹H NMR (d₆-DMSO) δ: 10.86-11.07 (br. s, 1H); 9.05-9.23 (br. s, 1H); 7.44 (s, 1H); 7.38 (d, J=8.2 Hz, 2H); 7.30 (d, J=8.2 Hz, 2H); 6.25 (s, 1H); 4.71 (t, J=5.6 Hz, 1H); 4.45 (s, 2H); 3.54 (d, J=5.6 Hz, 2H); 3.45-3.52 (overlapped m, 1H); 3.34-3.42 (m, 1H); 3.07 (s, 3H); 2.55-2.62 (m, 1H); 1.93-2.00 (m, 1H); 1.52 (s, 3H); 0.85-0.88 (m, 2H); 0.74-0.78 (m, 2H).

MS (ESI, m/z): 485.94 [M+H⁺] for $C_{24}H_{22}N_3O_6S$; $t_R$=0.72 min.

Example 8: (R)-4-(6-((4-(1-(aminomethyl)cyclopropyl)phenyl)ethynyl)-3-oxo-1H-pyrrolo[1,2-c]imidazol-2(3H)-yl)-N-hydroxy-2-methyl-2-(methylsulfonyl)butanamide formate Starting from the compound of Preparation E (0.15 g; 0.286 mmol) and the compound of Preparation N (0.1 g; 0.58 mmol), and proceeding successively in analogy to Procedure F (45% yield) and Procedure B (36% yield), the title compound was obtained, after purification by prep-HPLC (Method 1), as a white solid (0.023 g).

¹H NMR (d₆-DMSO) δ: 8.73-9.53 (br. s, 1H); 7.41-7.47 (m, 3H); 7.35 (d, J=8.0 Hz, 2H); 6.25 (s, 1H); 4.45 (s, 2H); 3.45-3.54 (m, 1H); 3.30-3.43 (overlapped m, 1H); 3.07 (s, 3H); 2.95 (s, 2H); 2.50-2.62 (m, 1H); 1.93-2.01 (m, 1H); 1.53 (s, 3H); 0.93-0.97 (m, 2H); 0.83-0.87 (m, 2H).

MS (ESI, m/z): 485.00 [M+H⁺] for $C_{24}H_{28}N_4O_5S$; $t_R$=0.59 min.

Example 9: (R)-N-hydroxy-4-(6-((4-(1-hydroxy-2-methylpropan-2-yl)phenyl)ethynyl)-3-oxo-1H-pyrrolo[1,2-c]imidazol-2(3H)-yl)-2-methyl-2-(methylsulfonyl)butanamide Starting from the compound of Preparation E (0.15 g; 0.286 mmol) and the compound of Preparation O (0.055 g; 0.31 mmol), and proceeding successively in analogy to Procedure F (99% yield) and Procedure B (27% yield), the title compound was obtained, after purification by prep-HPLC (Method 1), as a white solid (0.037 g).

¹H NMR (d₆-DMSO) δ: 10.85-11.03 (br. s, 1H); 9.11-9.23 (br. s, 1H); 7.44 (s, 1H); 7.36-7.42 (m, 4H); 6.26 (s, 1H); 4.70 (t, J=5.3 Hz, 1H); 4.45 (s, 2H); 3.46-3.53 (m, 1H); 3.41 (d, J=5.3 Hz, 2H); 3.30-3.41 (overlapped m, 1H); 3.07 (s, 3H); 2.57-2.61 (overlapped m, 1H); 1.93-2.00 (m, 1H); 1.53 (s, 3H); 1.22 (s, 6H).

MS (ESI, m/z): 487.98 [M+H⁺] for $C_{24}H_{29}N_3O_6S$; $t_R$=0.74 min.

Example 10: (R)-N-hydroxy-4-(6-((4-(2-hydroxypropan-2-yl)phenyl)ethynyl)-3-oxo-1H-pyrrolo[1,2-c]imidazol-2(3H)-yl)-2-methyl-2-(methylsulfonyl)butanamide Starting from the compound of Preparation H (0.235 g; 0.556 mmol) and 2-(4-iodophenyl)propan-2-ol (0.16 g; 0.61 mmol, prepared as described in JP 2008001635 A1), and proceeding successively in analogy to Procedure E (47% yield) and Procedure B (61% yield), the title compound was obtained, after purification by prep-HPLC (Method 1), as a beige solid (0.076 g).

¹H NMR (d₆-DMSO) δ: 10.88-11.05 (br. s, 1H); 9.08-9.25 (br. s, 1H); 7.46-7.50 (m, 2H); 7.45 (d, J=1.2 Hz, 1H); 7.40-7.43 (m, 2H); 6.26 (d, J=1.2 Hz, 1H); 5.09 (s, 1H); 4.46 (s, 2H); 3.46-3.53 (m, 1H); 3.35-3.43 (m, 1H); 3.07 (s, 3H); 2.56-2.61 (m, 1H); 1.93-2.00 (m, 1H); 1.52 (s, 3H); 1.42 (s, 6H).

MS (ESI, m/z): 473.99 [M+H⁺] for $C_{23}H_{27}N_3O_6S$; $t_R$=0.70 min.

Example 11: (R)-4-(6-((S)-5,6-dihydroxyhexa-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation H (0.128 g; 0.302 mmol) and (S)-4-iodobut-3-yne-1,2-diol (0.09 g; 0.423 mmol; prepared as described in Wang et al., *J. Org. Chem.* (2001), 66, 2146-2148), and proceeding successively in analogy to Procedure G (27% yield) and Procedure D (30% yield), the title compound was obtained, after purification by prep-HPLC (Method 1), as a beige solid (0.01 g).

¹H NMR (d₆-DMSO) δ: 8.66-9.87 (br. s, 1H); 8.31 (s, 1H); 7.59 (s, 1H); 6.28 (d, J=1.2 Hz, 1H); 5.55-5.81 (br.s, 1H); 4.91-5.17 (br.s, 1H); 4.43 (s, 2H); 4.31 (t, J=6.1 Hz, 1H); 3.45-3.52 (overlapped m, 1H); 3.44 (d, J=6.1 Hz, 2H); 3.40-3.45 (overlapped m, 1H); 3.06 (s, 3H); 2.54-2.62 (overlapped m, 1H); 1.93-1.99 (m, 1H); 1.52 (s, 3H).

MS (ESI, m/z): 423.90 [M+H⁺] for $C_{18}H_{21}N_3O_7S$; $t_R$=0.53 min.

Example 12: (R)-N-hydroxy-4-(6-(5-((1S,2S)-2-(hydroxymethyl)cyclopropyl)penta-1,3-diyn-1-yl)-3-oxo-1H-pyrrolo[1,2-c]imidazol-2(3H)-yl)-2-methyl-2-(methylsulfonyl)butanamide

12.i. ((1 S, 2S)-24(2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl acetate CuCl (0.01 g; 0.1 mmol) was added to a solution of nBuNH$_2$ (30% in water; 0.3 g in 0.7 mL) at rt. NH$_2$OH.HCl (0.099 g; 1.42 mmol) was added. The compound of Preparation H (0.4 g; 0.95 mmol) was added and the solution was immediately ice-chilled. The (1S,2S)-configured compound of Preparation P (0.308 g; 1.42 mmol) in Et$_2$O (0.5 mL) was added in one portion. The reaction proceeded at rt overnight. The reaction mixture was diluted with water (40 mL) and extracted with EA (4×60 mL). The combined org. layers were dried over MgSO$_4$, filtered and evaporated under reduced pressure. The residue was purified by CC (DCM-MeOH) to afford the title compound as a yellow foam (0.252 g; 56% yield).

$^1$H NMR (d$_6$-DMSO) δ: 10.89-10.98 (br. s, 1H); 9.14-9.21 (br. s, 1H); 7.53 (s, 1H); 6.23-6.24 (m, 1H); 4.42 (s, 2H); 3.93-3.99 (m, 1H); 3.78-3.85 (m, 1H); 3.44-3.52 (m, 1H); 3.34-3.42 (m, 1H); 3.05 (s, 3H); 2.54-2.62 (m, 1H); 2.03 (s, 3H); 1.91-2.00 (m, 1H); 1.57-1.63 (m, 1H); 1.53-1.57 (m, 1H); 1.52 (s, 3H); 0.99-1.04 (m, 1H); 0.91-0.97 (m, 1H).

MS (ESI, m/z): 475.99 [M+H$^+$] for C$_{22}$H$_{25}$N$_3$O$_7$S; t$_R$=0.76 min.

12.ii. (R)-N-hydroxy-4-(6-(5-((1S,2S)-2-(hydroxymethyl)cyclopropyl)penta-1,3-diyn-1-yl)-3-oxo-1H-pyrrolo[1,2-c]imidazol-2(3H)-yl)-2-methyl-2-(methylsulfonyl)butanamide To a solution of intermediate 12.i (0.252 g; 0.53 mmol) in MeOH (3 mL) was added K$_2$CO$_3$ (0.146 g; 1.06 mmol). The reaction mixture was stirred at rt for 30 min. Water (1 mL) was added and the reaction mixture was directly purified by prep-HPLC (Method 1) to afford the title compound as a white solid (0.085 g; 37% yield).

$^1$H NMR (d$_6$-DMSO) δ: 10.84-11.05 (br. s, 1H); 9.02-9.20 (br. s, 1H); 7.52 (s, 1H); 6.24 (d, J=1.1 Hz, 1H); 4.69 (t, J=5.8 Hz, 1H); 4.42 (s, 2H); 3.43-3.51 (m, 1H); 3.37-3.43 (m, 2H); 3.21-3.27 (m, 1H); 3.05 (s, 3H); 2.55-2.63 (m, 1H); 1.92-1.99 (m, 1H); 1.51 (s, 3H); 1.35-1.43 (m, 2H); 0.87-0.91 (overlapped m, 1H); 0.81-0.87 (overlapped m, 1H).

MS (ESI, m/z): 433.95 [M+H$^+$] for C$_{20}$H$_{23}$N$_3$O$_6$S; t$_R$=0.66 min.

Example 13: (R)-N-hydroxy-4-(6-((4-((R)-1-hydroxyethyl)phenyl)ethynyl)-3-oxo-1H-pyrrolo[1,2-c]imidazol-2(3H)-yl)-2-methyl-2-(methylsulfonyl)butanamide Starting from the compound of Preparation H (0.203 g; 0.479 mmol) and (R)-1-(4-iodophenyl)ethan-1-ol (0.131 g. 0.527 mmol; commercial), and proceeding successively in analogy to Procedure E (50% yield) and Procedure B (65% yield), the title compound was obtained, after purification by prep-HPLC (Method 1), as a beige solid (0.06 g).

$^1$H NMR (d$_6$-DMSO) δ: 10.72-11.03 (br. s, 1H); 9.07-9.23 (br. s, 1H); 7.44 (d, J=5.4 Hz, 2H); 7.42 (s, 1H); 7.36 (d, J=5.4 Hz, 2H); 6.27 (s, 1H); 5.23 (d, J=4.1 Hz, 1H); 4.73 (q, J=6.4 Hz, 1H); 4.45 (s, 2H); 3.46-3.54 (m, 1H); 3.30-3.36 (overlapped m, 1H); 3.07 (s, 3H); 2.50-2.62 (overlapped m, 1H); 1.93-2.00 (m, 1H); 1.53 (s, 3H); 1.31 (d, J=6.4 Hz, 3H).

MS (ESI, m/z): 459.97 [M+H$^+$] for C$_{22}$H$_{25}$N$_3$O$_6$S; t$_R$=0.68 min.

Example 14: (R)-N-hydroxy-4-(6-((4-(((S)-1-hydroxyethyl)phenyl)ethynyl)-3-oxo-1H-pyrrolo[1,2-c]imidazol-2(3H)-yl)-2-methyl-2-(methylsulfonyl)butanamide Starting from the compound of Preparation H (0.16 g; 0.378 mmol) and (S)-1-(4-iodophenyl)ethan-1-ol (0.103 g; 0.416 mmol; commercial), and proceeding successively in analogy to Procedure E (25% yield) and Procedure B (17% yield), the title compound was obtained, after purification by prep-HPLC (Method 1), as a beige solid (0.006 g).

$^1$H NMR (d$_6$-DMSO) δ: 10.20-11.60 (br. s, 1H); 8.94-9.73 (br. s, 1H); 7.45 (s, 1H); 7.43 (d, J=8.2 Hz, 2H); 7.36 (d, J=8.2 Hz, 2H); 6.26 (d, J=1.0 Hz, 1H); 5.22-5.57 (m, 1H); 4.70-4.76 (m, 1H); 4.46 (s, 2H); 3.46-3.54 (m, 1H); 3.30-3.43 (overlapped m, 1H); 3.07 (s, 3H); 2.57-2.65 (m, 1H); 1.93-2.01 (m, 1H); 1.53 (s, 3H); 1.31 (d, J=6.5 Hz, 3H).

MS (ESI, m/z): 460.00 [M+H$^+$] for C$_{22}$H$_{25}$N$_3$O$_6$S; t$_R$=0.68 min.

Example 15: (R)-N-hydroxy-4-(6-((1-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)butanamide

15.i. (2R)-4-(6-((1-(((tert-butyldiphenylsilyl)oxy)methyl)cyclopropyl)buta-1,3-diyn-1-yl)-3-oxo-1H-pyrrolo[1,2-c]imidazol-2(3H)-yl)-2-methyl-2-(methylsulfonyl)-N-(((RS)-tetrahydro-2H-pyran-2-yl)oxy)butanamide Starting from the compound of Preparation H (0.2 g; 0.472 mmol) and the compound of Preparation Q (0.205 g; 0.495 mmol; commercial), and proceeding in analogy to Example 12, step 12.i, the title compound was obtained, after purification by CC (Hept-EA), as a white foam (0.118 g; 33% yield).

$^1$H NMR (d$_6$-DMSO) (mixture of stereoisomers) δ: 11.34-11.40 (br. s, 0.5H); 11.29-11.34 (br. s, 0.5H); 7.63-7.67 (m, 4H); 7.53-7.55 (m, 1H); 7.42-7.50 (m, 6H); 6.24-6.27 (m, 1H); 4.83-4.86 (m, 0.5H); 4.36-4.47 (m, 2.5H); 3.97-4.05 (m, 0.5H); 3.89-3.96 (m, 0.5H); 3.62 (s, 2H); 3.37-3.57 (m, 3H); 3.07 (s, 1.5H); 3.04 (s, 1.5H); 2.54-2.62 (m, 1H); 1.90-1.99 (m, 1H); 1.59-1.66 (m, 2H); 1.56 (s, 1.5H); 1.54 (s, 1.5H); 1.42-1.52 (overlapped m, 4H); 1.03 (s, 9H); 0.94-0.99 (m, 2H); 0.83-0.88 (m, 2H).

MS (ESI, m/z): 382.99 [M+H$^+$] for C$_{41}$H$_{49}$N$_3$O$_7$SSi; t$_R$=1.11 min.

15.ii. (2R)-4-(6-((1-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)-N-(((RS)-tetrahydro-2H-pyran-2-yl)oxy)butanamide To a solution of intermediate 15.i (0.066 g; 0.0873 mmol) in THF (2 mL) was added TBAF 1M (0.175 mmol). The reaction was stirred at rt for 1 h. DCM (20 mL) and water (20 mL) were added. The aq. phase was extracted with EA (2×20 mL). The combined org. layers were dried over MgSO$_4$, filtered and concentrated to dryness. The residue was purified by CC (Hept-EA) to afford the title compound as a colourless oil (0.035 g; 77% yield).

$^1$H NMR (d$_6$-DMSO) (mixture of stereoisomers) δ: 11.34-11.39 (br. s; 0.5H); 11.29-11.34 (br.s; 0.5H); 7.52 (s, 0.5H); 7.53 (s, 0.5H); 6.22-6.25 (m, 1H); 5.00 (t, J=6.0 Hz, 1H); 4.84-4.87 (m, 0.5H); 4.36-4.49 (m, 2.5H); 3.98-4.07 (m, 0.5H); 3.90-3.97 (m, 0.5H); 3.46-3.56 (m, 1.5H); 3.38-3.45 (overlapped m, 1.5H); 3.37 (d, J=6.0 Hz, 2H); 3.06 (s, 1.5H); 3.03 (s, 1.5H); 2.53-2.64 (m, 1H); 1.93-2.02 (m, 1H); 1.60-1.68 (m, 2H); 1.56 (s, 1.5H); 1.55 (s, 1.5H); 1.43-1.53 (overlapped m, 4H); 0.87-0.91 (m, 2H); 0.81-0.86 (m, 2H).

MS (ESI, m/z): 517.86 [M+H$^+$] for C$_{25}$H$_{31}$N$_3$O$_7$S; t$_R$=0.78 min.

15.iii. (R)-N-hydroxy-4-(6-((1-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl) butanamide Starting from intermediate 15.ii (0.035 g; 0.066 mmol) and proceeding in analogy to Procedure D, the title compound was obtained, after precipitation in water, as a white solid (0.013 g, 46% yield).

$^1$H NMR (d$_6$-DMSO) δ: 10.87-10.97 (br. s, 1H); 9.14-9.20 (br. s, 1H); 7.53 (s, 1H); 6.24 (d, J=1.1 Hz, 1H); 5.00 (t, J=6.1 Hz, 1H); 4.43 (s, 2H); 3.45-3.51 (m, 1H); 3.38 (overlapped d, J=6.1 Hz, 2H); 3.36-3.41 (overlapped m, 1H); 3.06 (s, 3H); 2.54-2.63 (m, 1H); 1.92-2.00 (m, 1H); 1.52 (s, 3H); 0.88-0.91 (m, 2H); 0.83-0.87 (m, 2H).

MS (ESI, m/z): 433.98 [M+H$^+$] for C$_{20}$H$_{23}$N$_3$O$_6$S; t$_R$=0.66 min.

Example 16: (R)-N-hydroxy-4-(6-((4-(2-hydroxyethyl)phenyl)ethynyl)-3-oxo-1H-pyrrolo[1,2-c]imidazol-2(3H)-yl)-2-methyl-2-(methylsulfonyl)butanamide Starting from the compound of Preparation H (0.194 g; 0.457 mmol) and 2-(4-iodophenyl)ethanol (0.125 g; 0.503 mmol; commercial), and proceeding successively in analogy to Procedure E (49% yield) and Procedure B (61% yield), the title compound was obtained, after purification by prep-HPLC (Method 1), as a beige solid (0.063 g).

$^1$H NMR (d$_6$-DMSO) δ: 10.81-11.08 (br. s, 1H); 9.11-9.27 (br. s, 1H); 7.44 (s, 1H); 7.39 (d, J=8.1 Hz, 2H); 7.24 (d, J=8.1 Hz, 2H); 6.26 (s, 1H); 4.66 (t, J=5.2 Hz, 1H); 4.45 (s, 2H); 3.58-3.63 (m, 2H); 3.46-3.53 (m, 1H); 3.36-3.43 (m, 1H); 3.07 (s, 3H); 2.73 (t, J=6.9 Hz, 2H); 2.56-2.62 (m, 1H); 1.93-2.01 (m, 1H); 1.53 (s, 3H).

MS (ESI, m/z): 459.98 [M+H$^+$] for C$_{22}$H$_{25}$N$_3$O$_6$S; t$_R$=0.67 min.

Example 17: (R)-4-(6-((4-((R)-1,2-dihydroxyethyl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation H (0.194 g; 0.457 mmol) and (R)-1-(4-iodophenyl)-1,2-ethanediol (0.133 g; 0.503 mmol; commercial), and proceeding successively in analogy to Procedure E (72% yield) and Procedure B (52% yield), the title compound was obtained, after purification by prep-HPLC (Method 1), as a light brown solid (0.081 g).

$^1$H NMR (d$_6$-DMSO) δ: 10.84-11.04 (br. s, 1H); 9.14-9.23 (br. s, 1H); 7.45 (s, 1H); 7.42 (d, J=8.2 Hz, 2H); 7.36 (d, J=8.2 Hz, 2H); 6.27 (s, 1H); 5.32 (d, J=4.3 Hz, 1H); 4.74 (t, J=5.9 Hz, 1H); 4.52-4.58 (m, 1H); 4.46 (s, 2H); 3.46-3.53 (m, 1H); 3.35-3.46 (m, 3H); 3.07 (s, 3H); 2.56-2.62 (m, 1H); 1.94-2.01 (m, 1H); 1.53 (s, 3H).

MS (ESI, m/z): 475.99 [M+H$^+$] for C$_{22}$H$_{25}$N$_3$O$_7$S; t$_R$=0.58 min.

Example 18: (R)-4-(6-((4-((S)-1,2-dihydroxyethyl)phenyl)ethynyl)-3-oxo-1H-pyrrolo[1,2-c]imidazol-2(3H)-yl)-N-hydroxy-2-methyl-2-(methylsulfonyl) butanamide Starting from the compound of Preparation H (0.194 g; 0.457 mmol) and (S)-1-(4-iodophenyl)-1,2-ethanediol (0.133 g; 0.503 mmol; commercial), and proceeding successively in analogy to Procedure E (69% yield) and Procedure B (50% yield), the title compound was obtained, after purification by prep-HPLC (Method 1), as a light brown solid (0.074 g).

$^1$H NMR (d$_6$-DMSO) δ: 10.93 (br. s, 1H); 9.15-9.22 (br. s, 1H); 7.45 (s, 1H); 7.42 (d, J=8.2 Hz, 2H); 7.36 (d, J=8.2 Hz, 2H); 6.27 (s, 1H); 5.32 (d, J=4.3 Hz, 1H); 4.74 (t, J=5.9 Hz, 1H); 4.53-4.58 (m, 1H); 4.46 (s, 2H); 3.46-3.53 (m, 1H); 3.35-3.46 (m, 3H); 3.07 (s, 3H); 2.56-2.62 (m, 1H); 1.94-2.01 (m, 1H); 1.53 (s, 3H).

MS (ESI, m/z): 475.99 [M+H$^+$] for C$_{22}$H$_{25}$N$_3$O$_7$S; t$_R$=0.58 min.

Example 19: (R)-4-(6-((2-fluoro-4-(1-(hydroxymethyl)cyclopropyl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation H (0.183 g; 0.432 mmol) and the compound of Preparation R (0.139 g; 0.475 mmol), and proceeding successively in analogy to Procedure E (46% yield) and Procedure B (58% yield), the title compound was obtained, after purification by prep-HPLC (Method 1), as a yellow solid (0.058 g).

$^1$H NMR (d$_6$-DMSO) δ: 10.89-10.99 (br. s, 1H); 9.14-9.20 (br. s, 1H); 7.48 (s, 1H); 7.44 (t, J=8.1 Hz, 1H); 7.19 (dd, J=1.7, 11.4 Hz, 1H); 7.12 (dd, J=1.7, 11.4 Hz, 1H); 6.28 (s, 1H); 4.78 (t, J=5.6 Hz, 1H); 4.46 (s, 2H), 3.55 (d, J=5.6 Hz, 2H); 3.45-3.53 (m, 1H); 3.36-3.43 (m, 1H); 3.07 (s, 3H); 2.57-2.64 (m, 1H); 1.93-2.00 (m, 1H); 1.53 (s, 3H); 0.88-0.91 (m, 2H); 0.81-0.84 (m, 2H).

MS (ESI, m/z): 503.99 [M+H$^+$] for C$_{24}$H$_{26}$N$_3$O$_6$FS; t$_R$=0.73 min.

Example 20: (R)-N-hydroxy-4-(6-((4-(3-(2-hydroxyethyl)-2-oxoimidazolidin-1-yl)phenyl)ethynyl)-3-oxo-1H-pyrrolo[1,2-c]imidazol-2(3H)-yl)-2-methyl-2-(methylsulfonyl)butanamide Starting from the compound of Preparation H (0.16 g; 0.378 mmol) and the compound of Preparation S (0.138 g; 0.416 mmol), and proceeding successively in analogy to Procedure E (59% yield) and Procedure B (58% yield), the title compound was obtained, after precipitation in water and EtOH and recrystallisation from DMF/MeCN (6/94), as a beige solid (0.070 g).

$^1$H NMR (d$_6$-DMSO) δ: 10.88-11.05 (br. s, 1H); 9.17-9.22 (br. s, 1H); 7.60 (d, J=8.3 Hz, 2H); 7.40-7.45 (m, 3H); 6.25 (s, 1H); 4.75 (t, J=5.1 Hz, 1H); 4.45 (s, 2H); 3.77-3.83 (m, 2H); 3.45-3.58 (m, 5H); 3.35-3.43 (m, 1H); 3.25 (t, J=5.3 Hz, 2H); 3.07 (s, 3H); 2.56-2.65 (m, 1H); 1.92-2.02 (m, 1H); 1.53 (s, 3H).

MS (ESI, m/z): 544.99 [M+H$^+$] for C$_{25}$H$_{29}$N$_5$O$_7$S; t$_R$=0.65 min.

Example 21: (R)-4-(6-((3-fluoro-4-(2-hydroxyacetamido)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation H (0.1 g; 0.236 mmol) and the compound of Preparation T (0.077 g; 0.26 mmol), and proceeding successively in analogy to Procedure E (39% yield) and Procedure D (68% yield), the title compound was obtained, after precipitation in water and EtOH, as an orange solid (0.032 g).

$^1$H NMR (d$_6$-DMSO) δ: 10.96 (d, J=1.4 Hz, 1H); 9.40-9.43 (br. s, 1H); 9.20 (d, J=1.6 Hz, 1H); 8.05 (t, J=8.4 Hz, 1H); 7.48 (s, 1H); 7.44 (dd, J=1.6, 11.5 Hz, 1H); 7.33 (d, J=8.4 Hz, 1H); 6.28 (d, J=0.9 Hz, 1H); 5.90 (t, J=5.9 Hz, 1H); 4.47 (s, 2H); 4.06 (d, J=5.8 Hz, 2H); 3.46-3.54 (m, 1H); 3.35-3.46 (m, 1H); 3.07 (s, 3H); 2.58-2.65 (m, 1H); 1.93-2.02 (m, 1H); 1.54 (s, 3H).

MS (ESI, m/z): 507.0 [M+H$^+$] for C$_{22}$H$_{23}$N$_4$O$_7$FS; t$_R$=0.64 min.

Example 22: (R)-N-hydroxy-4-(6-((4-(2-hydroxyethoxy)phenyl)ethynyl)-3-oxo-1H-pyrrolo[1,2-c]imidazol-2(3H)-yl)-2-methyl-2-(methylsulfonyl)butanamide Starting from the compound of Preparation H (0.105 g; 0.248 mmol) and 2-(4-iodophenoxy)ethanol (0.072 g; 0.273 mmol; commercial), and proceeding successively in analogy to Procedure E (61% yield) and Procedure D (40% yield), the title compound was obtained, after precipitation in water and EtOH, as a beige solid (0.0282 g).

$^1$H NMR (d$_6$-DMSO) δ: 10.93-10.96 (br. s, 1H); 9.17-9.20 (br. s, 1H); 7.39-7.45 (m, 3H); 6.94-6.99 (m, 2H); 6.25 (d, J=1.1 Hz, 1H); 4.82-4.96 (m, 1H); 4.46 (s, 2H); 4.02 (t, J=4.9 Hz, 2H); 3.72 (t, J=4.9 Hz, 2H); 3.46-3.55 (m, 1H); 3.36-3.46 (overlapped m, 1H); 3.07 (s, 3H); 2.57-2.63 (m, 1H); 1.93-2.03 (m, 1H); 1.53 (s, 3H).

MS (ESI, m/z): 475.97 [M+H$^+$] for C$_{22}$H$_{23}$N$_4$O$_7$FS; t$_R$=0.66 min.

Example 23: (R)-N-hydroxy-4-(6-((6-(1-(hydroxymethyl)cyclopropyl)pyridin-3-yl)ethynyl)-3-oxo-1H-pyrrolo[1,2-c]imidazol-2(3H)-yl)-2-methyl-2-(methylsulfonyl)butanamide Starting from the compound of Preparation H (0.183 g; 0.432 mmol) and the compound of Preparation U (0.131 g; 0.475 mmol), and proceeding successively in analogy to Procedure E (75% yield) and Procedure D (42% yield), the title compound was obtained, after purification by prep-HPLC (Method 1), as a beige solid (0.067 g).

$^1$H NMR (d$_6$-DMSO) δ: 10.93-10.96 (br. s, 1H); 9.17-9.19 (br. s, 1H); 8.53 (d, J=2.3 Hz, 1H); 7.80 (dd, J=2.3, 8.4 Hz, 1H); 7.54 (d, J=8.4 Hz, 1H); 7.48 (s, 1H); 6.28 (d, J=1.1 Hz, 1H); 4.79-4.84 (m, 1H); 4.46 (s, 2H); 3.75 (d, J=3.6 Hz, 2H); 3.46-3.53 (m, 1H); 3.36-3.43 (m, 1H); 3.07 (s, 3H); 2.56-2.65 (m, 1H); 1.93-2.01 (m, 1H); 1.53 (s, 3H); 1.11-1.15 (m, 2H); 0.92-0.96 (m, 2H).

MS (ESI, m/z): 486.97 [M+H$^+$] for C$_{22}$H$_{26}$N$_4$O$_6$S; t$_R$=0.57 min.

Example 24: (R)-N-hydroxy-4-(6-((5-(1-(hydroxymethyl)cyclopropyl)pyridin-2-yl)ethynyl)-3-oxo-1H-pyrrolo[1,2-c]imidazol-2(3H)-yl)-2-methyl-2-(methylsulfonyl)butanamide formate Starting from the compound of Preparation H (0.132 g; 0.311 mmol) and the compound of Preparation V (0.105 g; 0.343 mmol), and proceeding successively in analogy to Procedure E (40% yield) and Procedure D (51% yield), the title compound was obtained, after purification by prep-HPLC (Method 1), as a yellow solid (0.032 g).

$^1$H NMR (d$_6$-DMSO) δ: 12.68-12.85 (br. s, 1H, formic acid); 10.90-10.99 (br. s, 1H); 9.13-9.25 (br. s, 1H); 8.50 (d, J=2.3 Hz, 1H); 8.13 (s, 1H, formic acid); 7.67 (dd, J=2.3, 8.1 Hz, 1H); 7.54 (s, 1H); 7.46 (d, J=8.2 Hz, 1H); 6.30-6.32 (m, 1H); 4.79-4.84 (m, 1H); 4.47 (s, 2H); 3.54 (s, 2H); 3.46-3.52 (overlapped m, 1H); 3.36-3.43 (m, 1H); 3.07 (s, 3H); 2.57-2.65 (m, 1H); 1.93-2.01 (m, 1H); 1.53 (s, 3H); 0.87-0.91 (m, 2H); 0.82-0.86 (m, 2H).

MS (ESI, m/z): 486.99 [M+H$^+$] for C$_{23}$H$_{28}$N$_4$O$_6$S; t$_R$=0.55 min.

Example 25: (R)-N-hydroxy-2-methyl-2-(methylsulfonyl)-4-(6-((4-(morpholinomethyl)phenyl)ethynyl)-3-oxo-1H-pyrrolo[1,2-c]imidazol-2(3H)-yl)butanamide Starting from the compound of Preparation H (0.133 g; 0.315 mmol) and 4-(4-iodobenzyl)morpholine (0.105 g; 0.347 mmol; commercial), and proceeding successively in analogy to Procedure E (84% yield) and Procedure D (24% yield), the title compound was obtained, after purification by prep-HPLC (Method 1) and washing with sat. aq. NaHCO$_3$, as a white solid (0.033 g).

$^1$H NMR (d$_6$-DMSO) δ: 10.90-10.97 (br. s, 1H); 9.15-9.21 (br. s, 1H); 7.45 (s, 1H); 7.44 (d, J=8.1 Hz, 2H); 7.33 (d, J=8.1 Hz, 2H); 6.26 (s, 1H); 4.45 (s, 2H); 3.54-3.60 (m, 4H); 3.47-3.52 (overlapped m, 1H); 3.47 (s, 2H); 3.35-3.43 (m, 1H); 3.07 (s, 3H); 2.53-2.65 (m, 1H); 2.29-2.39 (m, 4H); 1.94-2.02 (m, 1H); 1.53 (s, 3H).

MS (ESI, m/z): 514.95 [M+H$^+$] for C$_{25}$H$_{30}$N$_4$O$_6$S; t$_R$=0.54 min.

Example 26: (R)-N-hydroxy-2-methyl-2-(methylsulfonyl)-4-(6-((4-(1-(morpholinomethyl)cyclopropyl)phenyl)ethynyl)-3-oxo-1H-pyrrolo[1,2-c]imidazol-2(3H)-yl)butanamide Starting from the compound of Preparation H (0.13 g; 0.307 mmol) and the compound of Preparation W (0.116 g; 0.338 mmol), and proceeding successively in analogy to Procedure E (39% yield) and Procedure B (40% yield), the title compound was obtained, after washing with sat. aq. NaHCO$_3$ and purification by CC (DCM-MeOH), as a yellow solid (0.027 g).

$^1$H NMR (d$_6$-DMSO) δ: 10.92-10.96 (br. s, 1H); 9.15-9.20 (br. s, 1H); 7.44 (d, J=0.8 Hz, 1H); 7.31-7.38 (m, 4H); 6.25 (d, J=1.2 Hz, 1H); 4.45 (s, 2H); 3.48-3.53 (overlapped m, 1H); 3.44-3.48 (m, 4H); 3.35-3.43 (m, 1H); 3.07 (s, 3H); 2.55-2.62 (m, 1H); 2.52 (s, 2H); 2.34-2.41 (m, 4H); 1.94-2.01 (m, 1H); 1.53 (s, 3H); 0.83-0.87 (m, 2H); 0.73-0.77 (m, 2H).

MS (ESI, m/z): 555.01 [M+H$^+$] for C$_{28}$H$_{34}$N$_4$O$_6$S; t$_R$=0.60 min.

Example 27: (R)-N-hydroxy-4-(6-(((1R,2R)-2-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation H (0.121 g; 0.286 mmol) and the (1R,2R)-configured compound of Preparation P (0.068 g; 0.315 mmol), and proceeding successively in analogy to Example 12, step 12.i (37% yield) and Procedure B (45% yield), the title compound was obtained, after purification by CC (DCM-MeOH) and trituration in Et$_2$O, as a yellow solid (0.018 g).

$^1$H NMR (d$_6$-DMSO) δ: 10.84-11.05 (br. s, 1H); 9.02-9.20 (br. s, 1H); 7.52 (s, 1H); 6.23 (s, 1H); 4.69 (t, J=5.8 Hz, 1H); 4.42 (s, 2H); 3.43-3.51 (m, 1H); 3.30-3.43 (overlapped m, 2H); 3.21-3.27 (m, 1H); 3.05 (s, 3H); 2.50-2.60 (overlapped m, 1H); 1.92-1.99 (m, 1H); 1.51 (s, 3H); 1.35-1.43 (m, 2H); 0.87-0.91 (overlapped m, 1H); 0.81-0.87 (overlapped m, 1H).

MS (ESI, m/z): 433.95 [M+H$^+$] for C$_{20}$H$_{23}$N$_3$O$_6$S; t$_R$=0.66 min.

Example 28: (R)-4-(6-(2-fluoro-3-methoxyphenyl)-3-oxo-1H-pyrrolo[1,2-c]imidazol-2(3H)-yl)-N-hydroxy-2-methyl-2-(methylsulfonyl)butanamide Starting from the compound of Preparation C (0.12 g; 0.251 mmol) and 2-fluoro-3-methoxyphenylboronic acid (0.043 g; 0.251 mmol), and proceeding successively in analogy to Procedure A (68% yield) and Procedure B (55% yield), the title compound was obtained, after purification by prep-HPLC (Method 1), as a white solid (0.041 g).

$^1$H NMR (500 MHz, d$_6$-DMSO) δ: 10.65-11.23 (br. s, 1H); 9.05-9.35 (br. s, 1H); 7.47 (s, 1H); 7.25-7.30 (m, 1H); 7.12 (t, J=8.1 Hz, 1H); 7.03 (td, J=0.9, 8.1 Hz. 1H); 6.54 (s, 1H); 4.49 (s, 2H); 3.85 (s, 3H); 3.48-3.55 (m, 1H); 3.36-3.44 (m, 1H); 3.07 (s, 3H); 2.57-2.65 (m, 1H); 1.95-2.02 (m, 1H); 1.54 (s, 3H).

MS (ESI, m/z): 439.97 [M+H$^+$] for C$_{19}$H$_{22}$N$_3$O$_6$FS; t$_R$=0.72 min.

Example 29: (R)-(E)-N-hydroxy-4-(6-(4-(hydroxymethyl)styryl)-3-oxo-1H-pyrrolo[1,2-c]imidazol-2(3H)-yl)-2-methyl-2-(methylsulfonyl)butanamide Starting from the compound of Preparation C (0.2 g; 0.472 mmol) and the compound of Preparation Q (0.205 g; 0.495 mmol; commercial), and proceeding successively in analogy to Procedure A (51% yield), Example 15, step 15.ii (59% yield), and Procedure B (17% yield), the title compound was obtained, after purification by CC (DCM-MeOH) and prep-HPLC (Method 1), as a yellow solid (0.012 g).

$^1$H NMR (500 MHz, d$_6$-DMSO) δ: 10.80-11.11 (br. s, 1H); 9.11-9.34 (br. s, 1H); 7.44 (d, J=6.6 Hz, 2H); 7.28 (d, J=6.6 Hz, 2H); 7.24 (s, 1H); 7.08 (d, J=16.3 Hz, 1H); 6.92 (d, J=16.3 Hz, 1H); 6.45 (s, 1H); 5.11-5.20 (m, 1H); 4.41-4.52 (m, 4H); 3.44-3.54 (m, 1H); 3.30-3.42 (overlapped m, 1H); 3.08 (s, 3H); 2.50-2.67 (overlapped m, 1H); 1.92-2.02 (m, 1H); 1.54 (s, 3H).

MS (ESI, m/z): 448.01 [M+H$^+$] for C$_{21}$H$_{25}$N$_3$O$_6$S; t$_R$=0.66 min.

Example 30: (R)-N-hydroxy-4-(6-(4-(3-(hydroxymethyl)bicyclo[1.1.1]pentan-1-yl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation H (0.08 g; 0.189 mmol) and the compound of Preparation Y (0.087 g; 0.189 mmol; commercial), and proceeding successively in analogy to Example 12, step 12.i (31% yield), Example 15, step 15.ii (16% yield), and Procedure D (10% yield) the title compound was obtained, after purification by prep-HPLC (Method 1), as a yellow solid (0.003 g).

$^1$H NMR (500 MHz, d$_6$-DMSO) δ: 10.56-11.42 (br. s, 1H); 9.07-9.26 (br. s, 1H); 7.56 (s, 1H); 6.24-6.26 (m, 1H); 4.58 (t, J=5.6 Hz, 1H); 4.43 (s, 2H); 3.45-3.53 (m, 1H); 3.37-3.43 (m, 1H); 3.30-3.35 (overlapped m, 2H); 3.06 (s, 3H); 2.50-2.61 (overlapped m, 1H); 1.91-1.99 (m, 7H); 1.52 (s, 3H).

MS (ESI, m/z): 459.98 [M+H$^+$] for C$_{22}$H$_{25}$N$_3$O$_6$S; t$_R$=0.70 min.

Example 31: (R)-4-(6-(5-amino-5-methylhexa-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation H (0.2 g; 0.472 mmol) and the compound of Preparation Z (0.124 g; 0.592 mmol), and proceeding successively in analogy to Procedure G (48% yield) and Procedure D (15% yield), the title compound was obtained, after washing with sat. aq. NaHCO$_3$ and purification by CC (DCM-MeOH), as a yellow solid (0.01 g).

$^1$H NMR (500 MHz, d$_6$-DMSO) δ: 10.32-11.39 (br. s, 1H); 9.08-9.34 (br. s, 1H); 7.56 (s, 1H); 6.25 (d, J=1.2 Hz, 1H); 4.43 (s, 2H); 3.44-3.56 (m, 1H); 3.35-3.44 (m, 1H); 3.06 (m, 3H); 2.54-2.63 (m, 1H); 1.91-2.04 (m, 1H); 1.53 (s, 3H); 1.35 (s, 6H).

MS (ESI, m/z): 421.82 [M+H$^+$] for C$_{19}$H$_{24}$N$_4$O$_5$S; t$_R$=0.51 min.

Example 32: (R)-4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl) benzyl carbamate Starting from the compound of Preparation H (0.15 g; 0.354 mmol) and the compound of Preparation AA (0.147 g; 0.531 mmol) and proceeding successively in analogy to Procedure E (71% yield) and Procedure H (49% yield), the title compound was obtained, after purification by prep-HPLC (Method 1), as a beige solid (0.06 g).

$^1$H NMR (500 MHz, d$_6$-DMSO) δ: 10.95 (s, 1H); 9.19 (s, 1H); 7.47-7.51 (m, 3H); 7.37 (d, J=8.4 Hz, 2H); 6.52-6.86 (m, 2H); 6.28 (d, J=1.2 Hz, 1H); 5.00 (s, 2H); 4.47 (s, 2H); 3.46-3.56 (m, 1H); 3.36-3.44 (m, 1H); 3.08 (s, 3H); 2.56-2.65 (m, 1H); 1.92-2.04 (m, 1H); 1.49-1.58 (m, 3H).

MS (ESI, m/z): 488.97 for C$_{22}$H$_{24}$N$_4$O$_7$S; t$_R$=0.68 min.

Example 33: (R)-4-(6-(((1S,3R,4S)-3,4-dihydroxycyclopentyl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation H (0.1 g; 0.236 mmol) and the compound of Preparation AB (0.087 g; 0.35 mmol), and proceeding successively in analogy to Example 12, step 12.i (72% yield) and Procedure H (14% yield), the title compound was obtained, after purification by prep-HPLC (Method 1), as a beige solid (0.008 g).

$^1$H NMR (d6-DMSO) δ: 10.83 (br. s, 1H); 8.72 (br. s, 1H); 7.53 (s, 1H); 6.23 (s, 1H); 4.56 (d, J=1.9 Hz, 2H); 4.43 (s, 2H); 4.11 (d, J=4.2 Hz, 1H); 3.95 (s, 2H); 3.43-3.53 (m, 1H);

3.29-3.42 (m, 1H); 3.08-3.15 (m, 1H); 3.05 (s, 3H); 1.83-2.01 (m, 3H); 1.72-1.82 (m, 2H); 1.44 (s, 3H).

MS (ESI, m/z): 463.97 for $C_{21}H_{25}N_3O_7S$; $t_R$=0.60 min.

Example 34: (R)-(1-(4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)phenyl)cyclopropyl)methyl carbamate Starting from the compound of Preparation H (0.15 g; 0.354 mmol) and the compound of Preparation AC (0.168 g; 0.531 mmol) and proceeding successively in analogy to Procedure E (70% yield) and Procedure D (63% yield), the title compound was obtained, after purification by prep-HPLC (Method 1), as a white solid (0.06 g).

$^1$H NMR (d$_6$-DMSO) δ: 10.95 (br. s, 1H); 9.19 (s, 1H); 7.45 (d, J=0.8 Hz, 1H); 7.39-7.43 (m, 2H); 7.27-7.32 (m, 2H); 6.30-6.71 (m, 2H); 6.27 (d, J=1.2 Hz, 1H); 4.43-4.49 (m, 2H); 4.11 (s, 2H); 3.46-3.57 (m, 1H); 3.36-3.45 (m, 1H); 3.08 (s, 3H); 2.58-2.64 (m, 1H); 1.94-2.03 (m, 1H); 1.54 (s, 3H); 0.97-1.02 (m, 2H); 0.89-0.94 (m, 2H).

MS (ESI, m/z): 529.02 for $C_{25}H_{28}N_4O_7S$; $t_R$=0.74 min.

Example 35: (R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl carbamate Starting from the compound of Preparation H (0.18 g; 0.425 mmol) and the compound of Preparation AD (0.13 g; 0.595 mmol) and proceeding successively in analogy to Example 12, step 12.i (80% yield) and Procedure D (71% yield), the title compound was obtained, after purification by prep-HPLC (Method 2), as a yellow solid (0.116 g).

$^1$H NMR (d$_6$-DMSO) δ: 10.78-11.22 (br. s, 1H); 8.99-9.45 (br. s, 1H); 7.56 (s, 1H); 6.36-6.95 (m, 2H); 6.25 (d, J=1.1 Hz, 1H); 4.43 (s, 2H); 3.88 (s, 2H); 3.45-3.54 (m, 1H); 3.34-3.43 (m, 1H); 3.06 (s, 3H); 2.55-2.66 (m, 1H); 1.92-2.02 (m, 1H); 1.53 (s, 3H); 0.96-1.06 (m, 4H).

MS (ESI, m/z): 476.97 for $C_{21}H_{24}N_4O_7S$; $t_R$=0.66 min.

Example 36: (R)-N-hydroxy-4-(6-(((1R,2R)-2-(hydroxymethyl)-1-methylcyclopropyl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation H (0.207 g; 0.49 mmol) and the compound of Preparation AE (0.313 g; 0.73 mmol) and proceeding successively in analogy to Example 12, step 12.i (72% yield), Example 15, step 15.ii (80% yield) and Procedure D (72% yield), the title compound was obtained, after purification by prep-HPLC (Method 2), as a white solid (0.091 g).

$^1$H NMR (d$_6$-DMSO) δ: 10.58-11.23 (br. s, 1H); 9.04-9.44 (br. s, 1H); 7.52 (d, J=1.0 Hz, 1H); 6.23 (d, J=1.0 Hz, 1H); 4.67 (t, J=5.3 Hz, 1H), 4.43 (s, 2H); 3.57-3.65 (m, 1H); 3.35-3.43 (m, 1H); 3.23-3.30 (m, 1H); 3.06 (s, 3H); 2.55-2.64 (m, 1H); 1.91-2.01 (m, 1H); 1.53 (s, 3H); 1.36-1.43 (m, 1H); 1.29 (s, 3H); 1.08 (dd, J=4.4, 9.2 Hz, 1H); 0.61 (dd, J=4.6, 6.6 Hz, 1H).

MS (ESI, m/z): 448.03 for $C_{21}H_{25}N_3O_6S$; $t_R$=0.69 min.

Example 37: (R)-(1-(4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)phenyl)cyclopropyl)methyl dimethylglycinate hydrochloride Starting from the compound of Preparation H (0.2 g; 0.472 mmol) and the compound of Preparation AF (0.217 g; 0.604 mmol) and proceeding successively in analogy to Procedure E (36% yield) and Procedure D (28% yield), the title salt was obtained, after purification by prep-HPLC (Method 2) and lyophilisation in HCl 1M, as a yellow lyophilisate (0.027 g).

$^1$H NMR (d$_6$-DMSO) δ: 10.94-10.96 (br. s, 1H); 9.94-10.08 (br. s, 1H); 9.17-9.21 (br. s, 1H); 7.45 (d, J=0.8 Hz, 1H); 7.41-7.45 (m, 2H); 7.31-7.36 (m, 2H); 6.25-6.28 (m, 1H); 4.45-4.48 (m, 2H), 4.36-4.39 (m, 2H); 4.08-4.22 (m, 2H); 3.47-3.56 (m, 1H); 3.36-3.45 (m, 1H); 3.08 (s, 3H); 2.78 (s, 6H); 2.57-2.64 (m, 1H); 1.94-2.03 (m, 1H); 1.54 (s, 3H); 1.04-1.10 (m, 2H); 0.97-1.01 (m, 2H).

MS (ESI, m/z): 571.01 for $C_{28}H_{35}N_4O_7ClS$; $t_R$=0.63 min.

Example 38: (R)-4-(6-((1-aminocyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide hydrochloride Starting from the compound of Preparation H (0.2 g; 0.472 mmol) and the compound of Preparation AG (0.115 g; 0.472 mmol) and proceeding successively in analogy to Procedure G (49% yield) and Procedure H (22% yield), the title salt was obtained, after purification by prep-HPLC (Method 2) and lyophilisation in 1M HCl, as a pale beige lyophilisate (0.023 g).

$^1$H NMR (d$_6$-DMSO) δ: 10.93-10.95 (br. s, 1H); 9.16-9.19 (br. s, 1H); 8.65-8.99 (m, 3H); 7.66 (s, 1H); 6.30 (d, J=1.2 Hz, 1H); 4.44 (s, 2H); 3.45-3.54 (m, 1H); 3.36-3.45 (m, 1H); 3.06 (s, 3H); 2.54-2.62 (m, 1H); 1.92-2.02 (m, 1H); 1.53 (s, 3H); 1.32-1.43 (m, 4H).

MS (ESI, m/z): 419.09 for $C_{19}H_{23}N_4O_5ClS$; $t_R$=0.49 min.

Example 39: (R)-4-(6-((3-aminooxetan-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide hydrochloride Starting from the compound of Preparation H (0.15 g; 0.354 mmol) and the compound of Preparation AH (0.148 g; 0.46 mmol) and proceeding successively in analogy to Procedure G (53% yield) and Procedure H (40% yield), the title salt was obtained, after purification by prep-HPLC (Method 2) and lyophilisation in 1M HCl, as a pale beige lyophilisate (0.036 g).

$^1$H NMR (d$_6$-DMSO) δ: 10.93-10.96 (br. s, 1H); 9.16-9.19 (br. s, 1H); 8.97-9.15 (m, 3H); 7.71 (s, 1H); 6.33 (s, 1H); 4.74-4.82 (m, 4H); 4.52 (s, 2H); 3.45-3.53 (m, 1H); 3.36-3.44 (m, 1H); 3.06 (s, 3H); 2.56-2.62 (m, 1H); 1.93-2.01 (m, 1H); 1.52 (s, 3H).

MS (ESI, m/z+MeCN): 476.04 for $C_{19}H_{23}N_4O_6ClS$; $t_R$=0.47 min.

Example 40: (R)-N-hydroxy-4-(6-((4-(1-(hydroxymethyl)cyclobutyl)phenyl)ethynyl)-3-oxo-1H-pyrrolo[1,2-c]imidazol-2(3H)-yl)-2-methyl-2-(methylsulfonyl)butanamide Starting from the compound of Preparation H (0.062 g; 0.146 mmol) and the compound of Preparation AI (0.063 g; 0.22 mmol) and proceeding successively in analogy to Procedure E (67% yield) and Procedure B (40% yield), the title compound was obtained, after purification by CC (DCM-MeOH), as an off-white solid (0.018 g).

$^1$H NMR (d$_6$-DMSO) δ: 10.92-10.98 (br. s, 1H); 9.17-9.22 (br. s, 1H); 7.44 (s, 1H); 7.40 (d, J=8.2 Hz, 2H); 7.13 (d, J=8.2 Hz, 2H); 6.26 (d, J=1.0 Hz, 1H); 4.78 (t, J=5.5 Hz,

1H); 4.45 (s, 2H); 3.46-3.54 (overlapped m, 1H); 3.51 (overlapped d, J=5.5 Hz, 2H); 3.35-3.43 (m, 1H); 3.07 (s, 3H); 2.57-2.63 (m, 1H); 2.12-2.25 (m, 4H); 1.94-2.02 (m, 2H); 1.72-1.81 (m, 1H); 1.53 (s, 3H).

MS (ESI, m/z): 500.03 for $C_{25}H_{29}N_3O_6S$; $t_R$=0.68 min.

Example 41: (R)-4-(6-(2-fluoro-4-(2-hydroxy-ethoxy)phenyl)-3-oxo-1H-pyrrolo[1,2-c]imidazol-2(3H)-yl)-N-hydroxy-2-methyl-2-(methylsulfonyl)butanamide Starting from the compound of Preparation C (0.198 g; 0.414 mmol) and the compound of Preparation AJ (0.134 g; 0.474 mmol) and proceeding successively in analogy to Procedure A (43% yield) and Procedure B (17% yield), the title compound was obtained, after purification by prep-HPLC (Method 1), as a yellow solid (0.014 g).

$^1$H NMR ($d_6$-DMSO) δ: 10.95 (br. s, 1H); 9.19 (br. s, 1H); 7.62 (t, J=9.0 Hz, 1H); 7.37 (s, 1H); 6.88 (dd, J=2.5, 13.4 Hz, 1H); 6.81 (dd, J=2.4, 8.7 Hz, 1H); 6.50 (s, 1H); 4.89 (t, J=5.5 Hz, 1H); 4.48 (s, 2H); 4.01 (t, J=4.8 Hz, 2H); 3.71 (q, J=5.2 Hz, 2H); 3.51 (m, 1H); 3.39 (m, 1H); 3.07 (s, 3H); 2.60 (m, 1H); 1.98 (m, 1H); 1.54 (s, 3H).

MS (ESI, m/z): 469.98 [M+H$^+$] for $C_{26}H_{24}N_3O_2FS$; $t_R$=0.62 min.

Example 42: (R)-4-(6-(((2R,3S)-2,3-bis(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation H (0.1 g; 0.236 mmol) and the compound of Preparation AK (0.089 g; 0.354 mmol) and proceeding successively in analogy to Procedure G (82% yield) and Procedure D (14% yield), the title compound was obtained, after purification by prep-HPLC (Method 1) and CC (DCM-MeOH), as a yellow solid (0.011 g).

$^1$H NMR ($d_6$-DMSO) δ: 10.94 (s, 1H); 9.19 (s, 1H); 7.54 (s, 1H); 6.23-6.26 (m, 1H); 4.64-4.69 (m, 2H); 4.43 (s, 2H); 3.35-3.56 (m, 5H); 3.23-3.28 (m, 1H); 3.06 (s, 3H); 2.55 (m, 1H); 1.96 (m, 1H); 1.60 (dd, J=4.8, 8.1 Hz, 1H); 1.52 (s, 3H); 1.28 (m, 1H); 1.18 (m, 1H).

MS (ESI, m/z): 463.97 [M+H$^+$] for $C_{21}H_{25}N_3O_7S$; $t_R$=0.57 min.

Example 43: (R)-4-(6-(4-((R)-2,3-dihydroxypropoxy)-2-fluorophenyl)-3-oxo-1H-pyrrolo[1,2-c]imidazol-2(3H)-yl)-N-hydroxy-2-methyl-2-(methylsulfonyl)butanamide Starting from the compound of Preparation C (0.11 g; 0.234 mmol) and the compound of Preparation AM (0.082 g; 0.232 mmol) and proceeding successively in analogy to Procedure A (36% yield) and Procedure B (17% yield), the title compound was obtained, after purification by prep-HPLC (Method 1), as a white solid (0.007 g).

$^1$H NMR ($d_6$-DMSO) δ: 10.97 (br. s, 1H); 9.19 (br s, 1H); 7.62 (t, J=9.0 Hz, 1H); 7.37 (s, 1H); 6.87 (dd, J=2.4, 13.4 Hz, 1H); 6.81 (dd, J=2.4, 8.7 Hz, 1H); 6.50 (s, 1H); 4.98 (d, J=5.1 Hz, 1H); 4.69 (t, J=5.7 Hz, 1H); 4.48 (s, 2H); 4.03 (dd, J=4.0, 10.1 Hz, 1H); 3.89 (dd, J=6.2, 10.1 Hz, 1H); 3.79 (m, 1H); 3.52 (m, 1H); 3.44 (t, J=5.7 Hz, 2H); 3.39 (m, 1H); 3.07 (s, 3H); 2.60 (m, 1H); 1.99 (m, 1H); 1.52 (s, 3H).

MS (ESI, m/z): 499.98 [M+H$^+$] for $C_{21}H_{26}N_3O_8FS$; $t_R$=0.58 min.

Example 44: (R)-4-(6-((4-(1,1-difluoro-2-hydroxyethyl)phenyl)ethynyl)-3-oxo-1H-pyrrolo[1,2-c]imidazol-2(3H)-yl)-N-hydroxy-2-methyl-2-(methylsulfonyl)butanamide

44.i. (2R)-4-(6-((4-(1,1-difluoro-2-hydroxyethyl)phenyl)ethynyl)-3-oxo-1H-pyrrolo[1,2-c]imidazol-2(3H)-yl)-2-methyl-2-(methylsulfonyl)-N-((tetrahydro-2H-pyran-2-yl)oxy)butanamide Starting from the compound of Preparation H (0.08 g; 0.19 mmol) and the compound of Preparation AI (0.054 g; 0.19 mmol) and proceeding in analogy to Procedure E, the title compound was obtained, after purification by CC (Hept-EA), as a yellow solid (0.030 g; 27% yield).

MS (ESI, m/z): 580.0 for $C_{27}H_{31}N_3O_7F_2S$; $t_R$=0.82 min.

44.ii. (R)-4-(6-((4-(1,1-difluoro-2-hydroxyethyl)phenyl)ethynyl)-3-oxo-1H-pyrrolo[1,2-c]imidazol-2(3H)-yl)-N-hydroxy-2-methyl-2-(methylsulfonyl)butanamide To a solution of intermediate 44.i (0.0301 g; 0.06 mmol) in EtOH (1 mL) was added Amberlyst 15 (0.030 g). The mixture was stirred 1 h at 80° C. The ethanol was evaporated and the mixture was taken in DMF (2 mL). The solids were filtered and the filtrate was evaporated. The residue was purified by prep-HPLC (Method 3) to afford the title compound as an off-white solid (0.0076 g; 30% yield).

$^1$H NMR ($d_6$-DMSO) δ: 7.59 (m, 2H); 7.54 (m, 2H); 7.51 (d, J=0.6 Hz, 1H); 6.30 (d, J=1.2 Hz, 1H); 5.66 (t, J=6.3 Hz, 1H); 4.46 (s, 2H); 3.86 (m, 2H); 3.47-3.54 (m, 1H); 3.40 (m, 1H); 3.07 (s, 3H); 2.60 (m, 1H); 1.97 (m, 1H); 1.53 (s, 3H).

MS (ESI, m/z): 495.98 [M+H$^+$] for $C_{22}H_{23}N_3O_6F_2S$; $t_R$=0.71 min.

Example 45: (R)-N-hydroxy-4-(6-((4-(2-hydroxyacetyl)phenyl)ethynyl)-3-oxo-1H-pyrrolo[1,2-c]imidazol-2(3H)-yl)-2-methyl-2-(methylsulfonyl)butanamide Starting from the compound of Preparation H (0.07 g; 0.165 mmol) and 2-hydroxy-1-(4-iodophenyl)ethan-1-one (0.044 g; 0.166 mmol) and proceeding successively in analogy to Procedure E (27% yield) and Example 44, step 44.ii (28% yield), the title compound was obtained, after purification by prep-HPLC (Method 3), as a brownish solid (0.006 g).

$^1$H NMR ($d_6$-DMSO) δ: 10.96 (s, 1H); 9.19 (br. s, 1H); 7.94 (m, 2H); 7.62 (m, 2H); 7.55 (d, J=0.8 Hz, 1H); 6.32 (d, J=1.2 Hz, 1H); 5.15 (br. s, 1H); 4.80 (s, 2H); 4.48 (s, 2H); 3.51 (m, 1H); 3.41 (m, 1H); 3.08 (s, 3H); 2.61 (m, 1H); 1.99 (m, 1H); 1.54 (s, 3H).

MS (ESI, m/z): 473.95 [M+H$^+$] for $C_{22}H_{23}N_3O_7S$; $t_R$=0.71 min.

Example 46: (R)-4-(6-(5-(dimethylamino)penta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation H (0.08 g; 0.19 mmol) and the compound of Preparation AJ (0.04 g; 0.19 mmol) and proceeding successively in analogy to Procedure E (26% yield) and Example 44, step 44.ii (29% yield), the title compound was obtained, after purification by prep-HPLC (Method 3), as a brownish solid (0.006 g).

¹H NMR (d6-DMSO) δ: 10.93 (br. s, 1H); 9.17 (br. s, 1H); 7.59 (s, 1H); 6.28 (m, 1H); 4.43 (s, 2H); 3.49 (s, 2H); 3.48 (partially overlapped m, 1H); 3.06 (s, 3H); 2.98-3.02 (m, 1H); 2.56-2.61 (overlapped m, 1H); 2.20-2.26 (m, 6H); 1.52 (s, 3H); 1.52 (partially overlapped m, 1H).

MS (ESI, m/z): 420.96 [M+H$^+$] for $C_{19}H_{24}N_4O_5S$; $t_R$=0.49 min.

Example 47: methyl (R)-3-fluoro-4-(2-(4-(hydroxyamino)-3-methyl-3-(methylsulfonyl)-4-oxobutyl)-3-oxo-2,3-dihydro-1H-pyrrolo[1,2-c]imidazol-6-yl)benzoate Starting from the compound of Preparation C (0.150 g; 0.314 mmol) and 2-fluoro-4-(methoxycarbonyl)phenylboronic acid (0.062 g; 0.313 mmol) and proceeding successively in analogy to Procedure A (34% yield) and Procedure B (23% yield), the title compound was obtained, after purification by prep-HPLC (Method 1), as a white solid (0.012 g).

¹H NMR (d6-DMSO) δ: 10.94 (br. s, 1H); 9.20 (br. s, 1H); 7.94 (m, 1H); 7.79 (d, J=8.1 Hz, 1H); 7.75 (d, J=11.9 Hz, 1H); 7.64 (s, 1H); 6.67 (s, 1H); 4.53 (s, 2H); 3.88 (s, 3H); 3.49-3.55 (overlapped m, 1H); 3.40-3.46 (overlapped m, 1H); 3.08 (s, 3H); 2.60-2.63 (overlapped m, 1H); 1.97-2.04 (m, 1H); 1.55 (s, 3H).

MS (ESI, m/z): 467.93 [M+H$^+$] for $C_{20}H_{22}N_3O_7FS$; $t_R$=0.73 min.

Example 48: (R)-4-(6-(4-chloro-2-fluorophenyl)-3-oxo-1H-pyrrolo[1,2-c]imidazol-2(3H)-yl)-N-hydroxy-2-methyl-2-(methylsulfonyl)butanamide Starting from the compound of Preparation C (0.150 g; 0.314 mmol) and 4-chloro-2-fluorophenylboronic acid (0.055 g; 0.315 mmol) and proceeding successively in analogy to Procedure A (66% yield) and Procedure B (33% yield), the title compound was obtained, after purification by prep-HPLC (Method 1), as a white solid (0.031 g).

¹H NMR (d6-DMSO) δ: 10.88-11.00 (br. s, 1H); 9.12-9.23 (br. s, 1H); 7.78 (t, J=8.5 Hz, 1H); 7.51 (s, 1H); 7.48 (dd, J=1.8, 11.2 Hz, 1H); 7.30 (dd, J=1.7, 8.4 Hz, 1H); 6.58 (s, 1H); 4.50 (s, 2H); 3.48-3.55 (m, 1H); 3.38-3.44 (overlapped m, 1H); 3.07 (s, 3H); 2.57-2.62 (overlapped m, 1H); 1.95-2.02 (m, 1H); 1.54 (s, 3H).

MS (ESI, m/z): 443.93 [M+H$^+$] for $C_{18}H_{19}N_3O_5ClFS$; $t_R$=0.77 min.

Example 49: (R)-4-(6-(2-chloro-4-ethoxyphenyl)-3-oxo-1H-pyrrolo[1,2-c]imidazol-2(3H)-yl)-N-hydroxy-2-methyl-2-(methylsulfonyl)butanamide Starting from the compound of Preparation C (0.150 g; 0.314 mmol) and 2-chloro-4-ethoxyphenylboronic acid (0.063 g; 0.314 mmol) and proceeding successively in analogy to Procedure A (74% yield) and Procedure B (28% yield), the title compound was obtained, after purification by prep-HPLC (Method 1), as a white solid (0.031 g).

¹H NMR (d6-DMSO) δ: 10.87-10.99 (br. s, 1H); 9.16-9.22 (br. s, 1H); 7.46 (d, J=8.6 Hz, 1H); 7.36 (s, 1H); 7.06 (d, J=2.6 Hz, 1H); 6.93 (dd, J=2.6, 8.6 Hz, 1H); 6.40 (s, 1H); 4.48 (s, 2H); 4.01-4.10 (m, 2H); 3.46-3.56 (overlapped m, 1H); 3.07 (s, 3H); 2.57-2.62 (overlapped m, 1H); 1.98 (overlapped m, 1H); 1.54 (s, 3H); 1.33 (t, J=6.9 Hz, 3H).

MS (ESI, m/z): 469.92 [M+H$^+$] for $C_{20}H_{24}N_3O_6ClS$; $t_R$=0.77 min.

Example 50: (R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl dimethylglycinate hydrochloride Starting from the compound of Preparation H (0.38 g; 0.89 mmol) and the compound of Preparation AP (0.303 g; 1.17 mmol) and proceeding successively in analogy to Example 12, step 12.i (66% yield) and Procedure D (37% yield), the title compound was obtained, after purification by prep-HPLC (Method 2) and lyophilisation from 1M HCl, as a white foam (0.12 g).

¹H NMR (d6-DMSO) δ: 10.94 (m, 1H); 10.41 (m, 1H); 9.20 (m, 1H); 7.57 (d, J=0.8 Hz, 1H); 6.24 (d, J=1.2 Hz, 1H); 4.44 (m, 2H); 4.31 (m, 2H); 4.17 (m, 2H); 3.48 (m, 1H); 3.30-3.43 (overlapped m, 1H); 3.06 (s, 3H); 2.86 (s, 6H); 2.59 (m, 1H); 1.96 (m, 1H); 1.53 (s, 3H); 1.08-1.14 (m, 4H).

MS (ESI, m/z): 519.0 [M+H$^+$] for $C_{24}H_{30}N_4O_7S$; $t_R$=0.59 min.

Example 51: (R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl dihydrogen phosphate Starting from the compound of Preparation H (0.3 g; 0.7 mmol) and the compound of Preparation AQ (0.338 g; 0.92 mmol) and proceeding successively in analogy to Example 12, step 12.i (84% yield) and Procedure I (59% yield), the title compound was obtained, after purification by prep-HPLC (Method 1), as a white foam (0.13 g).

¹H NMR (d6-DMSO) δ: 10.94 (s, 1H); 9.19 (s, 1H); 7.56 (d, J=0.8 Hz, 1H); 6.25 (d, J=1.2 Hz, 1H); 4.43 (s, 2H); 3.74 (d, J=6.1 Hz, 2H); 3.45-3.53 (m, 2H); 3.22-3.43 (overlapped m, 2H); 3.06 (s, 3H); 2.59 (m, 1H); 1.96 (m, 1H); 1.53 (s, 3H); 0.98-1.07 (m, 4H).

MS (ESI, m/z): 513.9 [M+H$^+$] for $C_{20}H_{24}N_3O_9PS$; $t_R$=0.56 min.

Example 52: (R)-4-(6-(2-chloro-4-methoxyphenyl)-3-oxo-1H-pyrrolo[1,2-c]imidazol-2(3H)-yl)-N-hydroxy-2-methyl-2-(methylsulfonyl)butanamide Starting from the compound of Preparation C (0.150 g; 0.314 mmol) and 2-chloro-4-methoxyphenylboronic acid (0.059 g; 0.317 mmol) and proceeding successively in analogy to Procedure A (58% yield) and Procedure B (35% yield), the title compound was obtained, after purification by prep-HPLC (Method 1), as a white solid (0.029 g).

¹H NMR (d6-DMSO) δ: 10.97 (br. s, 1H); 9.22 (br. s, 1H); 7.49 (d, J=8.7 Hz, 1H); 7.38 (s, 1H); 7.09 (d, J=2.5 Hz, 1H); 6.96 (dd, J=2.5, 8.7 Hz, 1H); 6.41 (d, J=0.9 Hz, 1H); 4.49 (s, 2H); 3.80 (s, 3H); 3.49-3.56 (m, 1H); 3.38-3.42 (overlapped m, 1H); 3.08 (s, 3H); 2.58-2.63 (overlapped m, 2H); 1.96-2.03 (m, 1H); 1.55 (s, 3H).

MS (ESI, m/z): 455.93 [M+H$^+$] for $C_{19}H_{22}N_3O_6ClS$; $t_R$=0.77 min.

Example 53: (R)-4-(6-(2-fluoro-4-(trifluoromethyl)phenyl)-3-oxo-1H-pyrrolo[1,2-c]imidazol-2(3H)-yl)-N-hydroxy-2-methyl-2-(methylsulfonyl)butanamide Starting from the compound of Preparation C (0.150 g; 0.314 mmol) and (2-fluoro-4-(trifluoromethyl)phenyl)boronic acid (0.065 g; 0.317 mmol) and proceeding successively in analogy to Procedure A (62% yield) and Procedure B (26% yield), the title compound was obtained, after purification by prep-HPLC (Method 1), as a white solid (0.014 g).

$^1$H NMR (d6-DMSO) δ: 10.96 (s, 1H), 9.20 (s, 1H), 8.00 (t, J=7.9 Hz, 1H), 7.73 (d, J=11.4 Hz, 1H), 7.65 (s, 1H), 7.59 (d, J=8.7 Hz, 1H), 6.67 (s, 1H), 4.53 (s, 2H), 3.50-3.57 (m, 1H), 3.39-3.46 (overlapped m, 1H), 3.08 (s, 3H), 2.59-2.66 (overlapped m, 1H), 1.97-2.04 (m, 1H), 1.55 (s, 3H).

MS (ESI, m/z): 477.92 [M+H$^+$] for $C_{19}H_{19}N_3O_5P_4S$; $t_R$=0.80 min.

Example 54: (R)-N-hydroxy-2-methyl-2-(methylsulfonyl)-4-(3-oxo-6-(2,3,4-trifluorophenyl)-1H-pyrrolo[1,2-c]imidazol-2(3H)-yl)butanamide Starting from the compound of Preparation C (0.200 g; 0.418 mmol) and (2,3,4-trifluorophenyl)boronic acid (0.073 g; 0.415 mmol) and proceeding successively in analogy to Procedure A (32% yield) and Procedure B (25% yield), the title compound was obtained, after purification by prep-HPLC (Method 1), as a white solid (0.015 g).

$^1$H NMR (d6-DMSO) δ: 10.96 (br. s, 1H); 9.20 (br. s, 1H); 7.57-7.63 (m, 1H); 7.55 (s, 1H); 7.31-7.38 (m, 1H); 6.58 (s, 1H); 4.51 (s, 2H); 3.49-3.56 (m, 1H); 3.38-3.45 (m, 1H); 3.08 (s, 3H); 2.59-2.63 (overlapped m, 1H); 1.96-2.03 (m, 1H); 1.55 (s, 3H).

MS (ESI, m/z): 445.88 [M+H$^+$] for $C_{18}H_{18}N_3O_5F_3S$; $t_R$=0.76 min.

Example 55: (R)-4-(6-(2,3-difluoro-4-methoxyphenyl)-3-oxo-1H-pyrrolo[1,2-c]imidazol-2(3H)-yl)-N-hydroxy-2-methyl-2-(methylsulfonyl)butanamide Starting from the compound of Preparation C (0.150 g, 0.314 mmol) and (2,3-difluoro-4-methoxyphenyl)boronic acid (0.059 g, 0.314 mmol) and proceeding successively in analogy to Procedure A (48% yield) and Procedure B (65% yield), the title compound was obtained, after purification by prep-HPLC (Method 1) to afford the title compound (0.045 g) as a white solid.

$^1$H NMR (d6-DMSO) δ: 10.96 (d, J=1.7 Hz, 1H); 9.20 (d, J=1.8 Hz, 1H); 7.49 (td, J=2.2, 8.8 Hz, 1H); 7.45 (s, 1H); 7.05 (m, 1H); 6.53 (s, 1H); 4.50 (s, 2H); 3.90 (s, 3H); 3.49-3.55 (m, 1H); 3.37-3.44 (m, 1H); 3.08 (s, 3H); 2.59-2.63 (overlapped m, 1H); 1.96-2.02 (m, 1H); 1.55 (s, 3H).

MS (ESI, m/z): 457.93 [M+H$^+$] for $C_{19}H_{21}N_3O_6P_2S$; $t_R$=0.74 min.

Example 56: (R)-N-hydroxy-4-(6-((1-(hydroxymethyl)cyclobutyl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation H (0.1 g; 0.23 mmol) and the compound of Preparation AS (0.131 g; 0.3 mmol), and proceeding successively in analogy to Example 12, step 12.i (63% yield), Example 15, step 15.ii (92% yield) and Procedure D (52% yield), the title compound was obtained, after precipitation from water and drying, as a yellowish solid (0.033 g).

$^1$H NMR (d6-DMSO) δ: 10.90 (br. s, 1H); 9.19 (br. s, 1H); 7.55 (d, J=1.0 Hz, 1H); 6.25 (m, 1H); 5.15 (t, J=5.8 Hz, 1H); 4.43 (s, 2H); 3.45-3.53 (m, 3H); 3.37-3.43 (m, 1H); 3.07 (s, 3H); 2.56-2.63 (m, 1H); 2.07-2.17 (m, 4H); 1.84-2.01 (m, 3H); 1.53 (s, 3H).

MS (ESI, m/z): 448.00 [M+H$^+$] for $C_{21}H_{25}N_3O_6S$; $t_R$=0.70 min.

Example 57: ((R)-N-hydroxy-4-(6-((3-(hydroxymethyl)oxetan-3-yl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation H (0.1 g; 0.23 mmol) and the compound of Preparation AT (0.132 g; 0.3 mmol), and proceeding successively in analogy to Example 12, step 12.i (60% yield), Example 15, step 15.ii (92% yield) and Procedure D (44% yield), the title compound was obtained, after precipitation from water and drying, as a yellowish solid (0.026 g).

$^1$H NMR (d6-DMSO) δ: 10.9 (br. s, 1H); 9.19 (br. s, 1H); 7.59 (m, 1H); 6.28 (m, 1H); 5.46 (t, J=5.9 Hz, 1H); 4.58 (d, J=5.7 Hz, 2H); 4.52 (d, J=5.7 Hz, 2H); 4.44 (s, 2H); 3.70 (d, J=5.9 Hz, 2H); 3.49 (m, 1H); 3.38 (m, 1H); 3.07 (s, 3H); 2.60 (m, 1H); 1.93 (m, 1H); 1.53 (s, 3H).

MS (ESI, m/z): 450.00 [M+H$^+$] for $C_{20}H_{23}N_3O_7S$; $t_R$=0.61 min.

Example 58: (R)-N-hydroxy-2-methyl-4-(6-(5-(methylsulfonamido)penta-1,3-diyn-1-yl)-3-oxo-1H-pyrrolo[1,2-c]imidazol-2(3H)-yl)-2-(methylsulfonyl)butanamide Starting from the compound of Preparation H (0.280 g; 0.754 mmol) and the compound of Preparation BM (0.246 g; 0.58 mmol), and proceeding successively in analogy to Example 12, step 12.i (84% yield) and Procedure D (65% yield), the title compound was obtained, after precipitation and drying, as a greyish solid (0.08 g).

$^1$H NMR (d6-DMSO) δ: 10.91 (s, 1H); 9.15 (s, 1H); 7.67 (t, J=6.0 Hz, 1H); 7.62 (d, J=0.7 Hz, 1H); 6.29 (d, J=1.2 Hz, 1H); 4.44 (s, 2H); 4.04 (d, J=5.9 Hz, 2H); 3.48 (m, 1H); 3.38 (m, 1H); 3.06 (s, 3H); 2.98 (s, 3H); 2.58 (m, 1H); 1.96 (m, 1H); 1.52 (s, 3H).

MS (ESI, m/z): 471.0 [M+H$^+$] for $C_{18}H_{22}N_4O_7S_2$; $t_R$=0.63 min.

Example 59: tert-butyl (R)-3-hydroxy-3-(4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)phenyl)azetidine-1-carboxylate Starting from the compound of Preparation H (0.246 g; 0.58 mmol) and the compound of Preparation BK (0.283 g; 0.76 mmol), and proceeding successively in analogy to Procedure E (70% yield) and Procedure D (35% yield), the title compound was obtained, after purification by prep-HPLC (Method 3), as a yellowish solid (0.024 g).

$^1$H NMR (d6-DMSO) δ: 9.20 (br. s, 1H); 7.47-7.56 (m, 4H); 7.47 (d, J=0.6 Hz, 1H); 6.43 (s, 1H); 6.28 (d, J=1.2 Hz, 1H); 4.47 (s, 2H); 4.03 (s, 4H); 3.50 (m, 1H); 3.39 (m, 1H); 3.08 (s, 3H); 2.60 (m, 1H); 1.98 (m, 1H); 1.54 (s, 3H); 1.42 (s, 9H).

MS (ESI, m/z): 587.1 [M+H$^+$] for $C_{28}H_{34}N_4O_8S$; $t_R$=0.77 min.

Example 60: (2R)-4-(6-((5RS)-5-cyclobutyl-6-hydroxyhexa-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation H (0.1 g; 0.23 mmol) and the compound of Preparation AW (0.136 g; 0.43 mmol), and proceeding successively in analogy to Example 12, step 12.i (56% yield), Example 15, step 15.ii (79% yield) and Procedure D (37% yield), the title compound was obtained, after precipitation from water and drying, as a yellowish solid (0.018 g).

$^1$H NMR (d6-DMSO) δ: 10.9 (br. s, 1H); 9.19 (br. s, 1H); 7.56 (s, 1H); 6.27 (d, J=1.1 Hz, 1H); 4.89 (t, J=5.6 Hz, 1H); 4.44 (s, 2H); 3.49 (m, 1H); 3.36-3.43 (m, 2H); 3.06 (s, 3H); 2.55-2.69 (m, 4H); 1.91-2.05 (m, 3H); 1.72-1.90 (m, 4H); 1.53 (m, 3H).

MS (ESI, m/z): 462.92 [M+H$^+$] for $C_{22}H_{27}N_3O_6S$; $t_R$=0.73 min.

Example 61: (R)-N-hydroxy-4-(6-(((1R,2S)-2-(hydroxymethyl)-2-methylcyclopropyl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation H (0.1 g; 0.23 mmol) and the compound of Preparation AX (0.071 g; 0.3 mmol), and proceeding successively in analogy to Example 12, step 12.i (70% yield) and Procedure D (36% yield), the title compound was obtained, after precipitation from water and drying, as a beige solid (0.025 g).

$^1$H NMR (d6-DMSO) δ: 10.9 (br. s, 1H); 9.18 (br. s, 1H); 7.53 (s, 1H); 6.25 (d, J=1.1 Hz, 1H); 4.74 (t, J=5.8 Hz, 1H); 4.43 (s, 2H); 3.48 (m, 1H); 3.39 (m, 1H); 3.29 (dd, J=5.9, 11.2 Hz, 1H); 3.21 (dd, J=5.6, 11.2 Hz, 1H); 3.06 (s, 3H); 2.59 (m, 1H); 1.96 (m, 1H); 1.54 (overlaid m, 1H); 1.53 (br. s, 3H); 1.17 (s, 3H); 1.03 (m, 1H); 0.61 (m, 1H).

MS (ESI, m/z): 448.00 [M+H$^+$] for $C_{21}H_{25}N_3O_6S$; $t_R$=0.68 min.

Example 62: (R)-N-hydroxy-4-(6-(((1-(2-hydroxyacetyl)azetidin-3-yl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation H (0.1 g; 0.23 mmol) and the compound of Preparation AY (0.067 g; 0.3 mmol), and proceeding in analogy to Example 12, step 12.i (32% yield) and Procedure D (43% yield), the title compound was obtained, after purification by prep-HPLC (Method 1), as a yellow solid (0.015 g).

$^1$H NMR (d6-DMSO) δ: 10.9 (m, 1H); 9.19 (m, 1H); 7.60 (m, 1H); 6.29 (m, 1H); 5.01 (m, 1H); 4.41-4.45 (m, 3H); 4.14-4.21 (m, 2H); 3.89-3.94 (m, 2H); 3.83 (m, 1H); 3.73 (m, 1H); 3.50 (m, 1H); 3.40 (m, 1H); 3.06 (s, 3H); 2.59 (m, 1H); 1.97 (m, 1H); 1.52 (s, 3H).

MS (ESI, m/z): 476.97 [M+H$^+$] for $C_{21}H_{24}N_4O_7S$; $t_R$=0.57 min.

Example 63: (R)-N-hydroxy-4-(6-(5-(3-hydroxyoxetan-3-yl)penta-1,3-diyn-1-yl)-3-oxo-1H-pyrrolo[1,2-c]imidazol-2(3H)-yl)-2-methyl-2-(methylsulfonyl)butanamide Starting from the compound of Preparation H (0.1 g; 0.23 mmol) and the compound of Preparation AZ (0.073 g; 0.3 mmol), and proceeding in analogy to Example 12, step 12.i (54% yield) and Procedure D (25% yield), the title compound was obtained, after purification by prep-HPLC (Method 1), as a yellow solid (0.017 g).

$^1$H NMR (d6-DMSO) δ: 7.57 (s, 1H); 6.27 (d, J=0.9 Hz, 1H); 6.06 (m, 1H); 4.39-4.46 (m, 6H); 3.48 (m, 1H); 3.38 (overlapped m, 1H); 3.06 (s, 3H); 2.83 (s, 2H); 2.59 (m, 1H); 1.95 (m, 1H); 1.52 (m, 3H).

MS (ESI, m/z): 449.97 [M+H$^+$] for $C_{20}H_{23}N_3O_7S$; $t_R$=0.60 min.

Example 64: (R)-N-hydroxy-4-(6-((4-hydroxytetrahydro-2H-pyran-4-yl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation H (0.1 g; 0.23 mmol) and the compound of Preparation BA (0.077 g; 0.3 mmol), and proceeding in analogy to Example 12, step 12.i (66% yield) and Procedure D (60% yield), the title compound was obtained, after purification by prep-HPLC (Method 1), as a yellow solid (0.035 g).

$^1$H NMR (d6-DMSO) δ: 7.61 (d, J=0.6 Hz, 1H); 6.29 (d, J=1.2 Hz, 1H); 5.93 (m, 1H); 4.44 (s, 2H); 3.71-3.80 (m, 2H); 3.45-3.54 (m, 3H); 3.38 (overlapped m, 1H); 3.07 (s, 3H); 2.59 (m, 1H); 1.98 (m, 1H); 1.79-1.87 (m, 2H); 1.63-1.71 (m, 2H); 1.53 (s, 3H).

MS (ESI, m/z): 463.97 [M+H$^+$] for $C_{21}H_{25}N_3O_7S$; $t_R$=0.62 min.

Example 65: (R)-4-(6-(((2S,5R)-5-aminotetrahydro-2H-pyran-2-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation H (0.1 g; 0.23 mmol) and the compound of Preparation BB (0.074 g; 0.3 mmol), and proceeding in analogy to Example 12, step 12.i (37% yield) and Procedure D (71% yield), the title compound was obtained, after purification by prep-HPLC (Method 3), as a yellow solid (0.029 g).

$^1$H NMR (d6-DMSO) δ: 7.62 (s, 1H); 6.29 (d, J=1.2 Hz, 1H); 4.44 (br. s, 2H); 4.27 (m, 1H); 4.11 (br. s, 1H); 3.77 (m, 1H); 3.49 (m, 1H); 3.34-3.42 (overlapped m, 2H); 3.17 (br. s, 2H); 3.06 (s, 3H); 2.98 (m, 1H); 2.56-2.67 (m, 2H); 1.85-1.99 (m, 2H); 1.59 (m, 1H); 1.51 (s, 3H); 1.26 (m, 1H).

MS (ESI, m/z): 504.01 [M+H$^+$] for $C_{21}H_{26}N_4O_6S$; $t_R$=0.51 min.

Examples 66 and 67: (R)-4-(6-(((1R,2R)-1-fluoro-2-(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide and (R)-4-(6-(((1S,2S)-1-fluoro-2-(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide 66/67.i. (R)-4-(6-(((1R*,2R*)-1-fluoro-2-(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation H (0.1 g; 0.23 mmol) and the compound of Preparation AU (0.132 g; 0.3 mmol), and proceeding in analogy to Example 12, step 12.i (65% yield), Example 15, step 15.ii (69% yield) and Procedure D (70% yield), the title compound was obtained, after precipitation from water and drying, as a beige solid (0.034 g).

$^1$H NMR (d6-DMSO) δ: 11.09 (br. s, 1H); 9.19 (br. s, 1H); 7.67 (s, 1H); 6.31 (s, 1H); 4.86-4.93 (m, 1H); 4.45 (s, 2H); 3.62-3.75 (m, 1H); 3.46-3.56 (m, 1H); 3.35-3.44 (m, 2H);

3.06 (m, 3H); 2.56-2.66 (overlapped m, 1H); 1.93-2.04 (m, 1H); 1.59-1.72 (m, 1H); 1.53 (s, 3H); 1.35-1.45 (m, 1H); 1.21-1.31 (m, 1H).

MS (ESI, m/z): 452.00 [M+H$^+$] for $C_{20}H_{22}N_3O_6FS$; $t_R$=0.67 min.

66/67.ii. (R)-4-(6-(((1R,2R)-1-fluoro-2-(hydroxymethyl)cyclopropyl)buta-1,3-diyn-1-yl-3-oxo-1H-pyrrolo[1,2-c]imidazol-2(3H)-yl)-N-hydroxy-2-methyl-2-(methylsulfonyl)butanamide AND (R)-4-(6-(((1S,2S)-1-fluoro-2-(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide Intermediate 66/67.i (0.029 g) was separated by semi-preparative chiral HPLC Method A (EtOH-MeCN (containing 0.1% TFA) 4-1; flow rate: 20 mL/min, UV detection at 213 nm); the respective retention times of the enantiomers (flow rate: 0.8 mL/min) were 5.5 and 9.7 min. The title enantiomers, first-eluting enantiomer (0.009 g) and second-eluting enantiomer (0.01 g) respectively, were obtained as beige solids. The respective absolute configurations of the two diastereomeric compounds have not been determined. Example 66 and Example 67 refer to the first-eluting enantiomer and the second-eluting enantiomer respectively.

First-Eluting Enantiomer:
MS (ESI, m/z): 452.00 [M+H$^+$] for $C_{20}H_{22}N_3O_6FS$; $t_R$=0.67 min.

Second-Eluting Enantiomer:
MS (ESI, m/z): 452.00 [M+H$^+$] for $C_{20}H_{22}N_3O_6FS$; $t_R$=0.67 min.

Example 68: (R)-4-(6-((5-(1-aminocyclopropyl)thiophen-2-yl)ethynyl)-3-oxo-1H-pyrrolo[1,2-c]imidazol-2(3H)-yl)-N-hydroxy-2-methyl-2-(methylsulfonyl)butanamide Starting from the compound of Preparation E (0.11 g; 0.21 mmol) and the compound of Preparation BC (0.039 g; 0.24 mmol), and proceeding successively in analogy to Procedure F (42% yield) and Procedure I (27% yield), the title compound was obtained, after purification by prep-HPLC (Method 3), as a yellowish solid (0.007 g).

$^1$H NMR (d6-DMSO) δ: 10.94 (br. s, 1H); 9.12 (br. s, 1H); 7.45 (s, 1H); 7.10 (d, J=3.7 Hz, 1H); 6.68 (d, J=3.7 Hz, 1H); 6.25 (d, J=0.7 Hz, 1H); 4.45 (s, 2H); 3.49 (m, 1H); 3.39 (m, 1H); 3.06 (s, 3H); 2.59 (m, 1H); 1.97 (m, 1H); 1.52 (s, 3H); 1.05-1.10 (m, 2H); 0.94-0.99 (m, 2H).

MS (ESI, m/z): 518.00 [M+H$^+$] for $C_{21}H_{24}N_4O_5S_2$; $t_R$=0.55 min.

Example 69: (R)-4-(6-((4-(3-aminooxetan-3-yl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation H (0.12 g; 0.28 mmol) and the compound of Preparation BD (0.115 g; 0.37 mmol) and proceeding successively in analogy to Procedure E (63% yield) and Procedure I (77% yield), the title compound was obtained, after purification by prep-HPLC (Method 3), as a brownish solid (0.02 g).

$^1$H NMR (d$_6$-DMSO) δ: 10.96 (s, 1H); 9.19 (br. s, 1H); 7.61-7.64 (m, 2H); 7.49-7.52 (m, 2H); 7.47 (d, J=0.7 Hz, 1H); 6.28 (d, J=1.2 Hz, 1H); 4.64-4.70 (m, 4H); 4.47 (s, 2H); 3.51 (m, 1H); 3.41 (m, 1H); 3.08 (s, 3H); 2.62 (m, 2H); 1.99 (m, 1H); 1.54 (s, 3H).

MS (ESI, m/z): 487.24 [M+H$^+$] for $C_{23}H_{26}N_4O_6S$; $t_R$=0.42 min.

Example 70: (R)-N-hydroxy-4-(6-((4-(3-(hydroxymethyl)oxetan-3-yl)phenyl)ethynyl)-3-oxo-1H-pyrrolo[1,2-c]imidazol-2(3H)-yl)-2-methyl-2-(methylsulfonyl)butanamide Starting from the compound of Preparation H (0.105 g; 0.25 mmol) and the compound of Preparation BE (0.094 g; 0.32 mmol) and proceeding successively in analogy to Procedure E (60% yield) and Procedure B (15% yield), the title compound was obtained, after purification by prep-HPLC (Method 1) as an off-white solid (0.011 g).

$^1$H NMR (d$_6$-DMSO) δ: 10.96 (s, 1H); 9.19 (br. s, 1H); 7.47 (s, 1H); 7.45-7.47 (m, 2H); 7.15-7.20 (m, 2H); 6.28 (s, 1H); 5.16 (m, 1H); 4.71 (s, 4H); 4.46 (s, 2H); 3.72 (d, J=5.4 Hz, 2H); 3.51 (m, 1H); 3.40 (m, 1H); 3.07 (s, 3H); 2.60 (overlapped m, 1H); 1.97 (m, 1H); 1.53 (s, 3H).

MS (ESI, m/z): 502.00 [M+H$^+$] for $C_{24}H_{27}N_3O_7S$; $t_R$=0.64 min.

Example 71: (R)-N-hydroxy-4-(6-((4-(2-hydroxyacetamido)phenyl)ethynyl)-3-oxo-1H-pyrrolo[1,2-c]imidazol-2(3H)-yl)-2-methyl-2-(methylsulfonyl)butanamide Starting from the compound of Preparation H (0.12 g; 0.28 mmol) and 2-hydroxy-N-(4-iodophenyl)acetamide (0.102 g; 0.37 mmol; commercial), and proceeding successively in analogy to Procedure E (57% yield) and Procedure D (31% yield), the title compound was obtained, after purification by prep-HPLC (Method 1), as a white solid (0.024 g).

$^1$H NMR (d$_6$-DMSO) δ: 10.96 (m, 1H); 9.85 (s, 1H); 9.10-9.27 (m, 1H); 7.74-7.78 (m, 2H); 7.40-7.46 (m, 3H); 6.26 (d, J=1.2 Hz, 1H); 5.68 (t, J=6.1 Hz, 1H); 4.46 (s, 2H); 4.01 (d, J=6.0 Hz, 2H); 3.51 (m, 1H); 3.40 (m, 1H); 3.08 (s, 3H); 2.60 (m, 1H); 1.99 (m, 1H); 1.54 (s, 3H).

MS (ESI, m/z): 489.01 [M+H$^+$] for $C_{22}H_{24}N_4O_7S$; $t_R$=0.62 min.

Example 72: (R)-4-(6-((4-(1-aminocyclopropyl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation H (0.122 g; 0.28 mmol) and the compound of Preparation BF (0.11 g; 0.37 mmol), and proceeding successively in analogy to Example 12, step 12.i (32% yield) and Procedure B (21% yield), the title compound was obtained, after precipitation, filtration and drying, as a white solid (0.007 g).

$^1$H NMR (d$_6$-DMSO) δ: 9.24 (s, 1H); 7.44 (s, 1H); 7.37-7.40 (m, 2H); 7.29-7.33 (m, 2H); 6.26 (d, J=1.1 Hz, 1H); 4.46 (s, 2H); 3.50 (m, 1H); 3.40 (m, 1H); 3.08 (s, 3H); 2.61 (m, 1H); 1.98 (m, 1H); 1.54 (s, 3H); 0.92-1.03 (m, 4H).

MS (ESI, m/z): 471.13 [M+H$^+$] for $C_{23}H_{26}N_4O_5S$; $t_R$=0.56 min.

Example 73: (R)-N-hydroxy-4-(6-(5-((1s,3R)-1-hydroxy-3-(hydroxymethyl)cyclobutyl)penta-1,3-diyn-1-yl)-3-oxo-1H-pyrrolo[1,2-c]imidazol-2(3H)-yl)-2-methyl-2-(methylsulfonyl)butanamide Starting from the compound of Preparation H (0.1 g; 0.23 mmol) and the compound of Preparation BG (0.082 g; 0.30 mmol), and proceeding successively in analogy to Example 12, step 12.i (32% yield) and Procedure B (21% yield), the title compound was obtained, after purification by prep-HPLC (Method 1), as a yellowish solid (0.007 g).

$^1$H NMR (d$_6$-DMSO) δ: 10.91 (br. s, 1H); 9.19 (br. s, 1H); 7.55 (s, 1H); 6.26 (d, J=1.2 Hz, 1H); 5.21 (s, 1H); 4.48 (m, 1H); 4.43 (s, 2H); 3.48 (m, 1H); 3.32-3.40 (m, 3H); 3.06 (s, 3H); 2.61 (m, 1H); 2.02-2.09 (m, 2H); 1.90-1.99 (m, 2H); 1.68-1.75 (m, 2H); 1.54 (s, 3H).

MS (ESI, m/z): 478.0 [M+H$^+$] for C$_{22}$H$_{27}$N$_3$O$_7$S; $t_R$=0.60 min.

Example 74: (phosphonooxy)methyl (R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl) carbamate Starting from the compound of Preparation H (0.089 g; 0.21 mmol) and the compound of Preparation BH (0.133 g; 0.28 mmol), and proceeding successively in analogy to Example 12, step 12.i (52% yield) and Procedure I (10% yield), the title compound was obtained, after purification by prep-HPLC (Method 1), as a white solid (0.024 g).

$^1$H NMR (d$_6$-DMSO) δ: 10.94 (s, 1H); 9.18 (s, 1H); 8.33 (s, 1H); 7.55 (s, 1H); 6.25 (s, 1H); 5.34-5.41 (m, 2H); 4.43 (s, 2H); 3.45-3.50 (m, 1H); 3.24-3.43 (overlapped m, 1H); 3.05 (s, 3H); 2.44-2.62 (overlapped m, 1H); 1.96 (m, 1H); 1.52 (s, 3H); 1.20-1.26 (m, 2H); 1.08-1.14 (m, 2H).

MS (ESI, m/z): 573.0 [M+H$^+$] for C$_{21}$H$_{25}$N$_4$O$_{11}$PS; $t_R$=0.53 min.

Example 75: (R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl((phosphonooxy)methyl)carbonate 75.i. Chloromethyl ((1-((2-((3R)-3-methyl-3-(methylsulfonyl)-4-oxo-4-(((tetrahydro-2H-pyran-2-yl)oxy)amino)butyl)-3-oxo-2,3-dihydro-1H-pyrrolo[1,2-c]imidazol-6-yl)buta-1,3-diyn-1-yl)cyclopropyl)methyl)carbonate To a solution of intermediate 15.i (0.14 g; 0.27 mmol) in DCM (5 mL), cooled at 0° C., were added Pyr (0.044 mL; 0.54 mmol) and chloromethyl chloroformate (0.03 mL; 0.33 mmol). The reaction mixture was stirred at 0° C. for 1.75 h. Sat. aq. NaHCO$_3$ (10 mL) was added and the mixture was extracted with DCM (10 mL). The org. layer was washed with brine (10 mL), dried over MgSO$_4$, filtered and evaporated under reduced pressure. The reaction mixture was purified by CC (Hept-EA) to afford the title compound as a yellow gum (0.041 g; 25% yield).

MS (ESI, m/z): 610.0 [M+H$^+$] for C$_{27}$H$_{32}$N$_3$O$_9$ClS; $t_R$=0.90 min.

75.ii. ((Di-tert-butoxyphosphoryl)oxy)methyl ((1-((2-((3R)-3-methyl-3-(methylsulfonyl)-4-oxo-4-(((tetrahydro-2H-pyran-2-yl)oxy)amino)butyl)-3-oxo-2,3-dihydro-1H-pyrrolo[1,2-c]imidazol-6-yl)buta-1,3-diyn-1-yl)cyclopropyl)methyl)carbonate To a solution of intermediate 75.i (0.041 g; 0.067 mmol) in DME (1 mL) was added tetra-n-butylammonium di-tert-butylphosphate (0.042 g; 0.094 mmol). The reaction mixture was heated at 80° C. for 4 h. Water (5 mL) was added and the mixture was extracted with EA (10 mL). The aq. layer was extracted with EA (5 mL). The combined org. layers were washed with brine (5 mL), dried over MgSO$_4$ and concentrated to dryness. The residue was purified by CC (Hept-EA) to afford the title compound as a yellow solid (0.024 g; 46% yield).

$^1$H NMR (d6-DMSO) δ (mixture of diastereomers): 11.36 (s, 0.5H); 11.31 (s, 0.5H); 7.53 (s, 0.5H); 7.52 (s, 0.5H); 6.23 (s, 1H); 5.54 (s, 1H); 5.51 (s, 1H); 4.84 (m, 0.5H); 4.46 (m, 0.5H); 4.36-4.44 (m, 2H); 4.12 (s, 2H); 4.03 (m, 0.5H); 3.95 (m, 0.5H); 3.45-3.52 (m, 1H); 3.37-3.43 (m, 2H); 3.05 (s, 1.5H); 3.03 (s, 1.5H); 2.57 (m, 1H); 1.95 (m, 1H); 1.60-1.66 (m, 2H); 1.55 (s, 1.5H); 1.54 (s, 1.5H); 1.47-1.49 (m, 4H); 1.42 (s, 18H); 1.05-1.12 (m, 4H).

MS (ESI, m/z): 784.0 [M+H$^+$] for C$_{35}$H$_{50}$N$_3$O$_{13}$PS; $t_R$=0.94 min.

75.iii. (R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl ((phosphonooxy)methyl) carbonate Starting from the intermediate 75.ii (0.02 g; 0.025 mmol) and proceeding in analogy to Procedure I, the title compound was obtained, after purification by prep-HPLC (Method 1), as a white solid (0.024 g; 28% yield).

$^1$H NMR (d6-DMSO) δ: 10.94 (s, 1H); 9.18 (m, 1H); 7.55 (s, 1H); 6.25 (s, 1H); 5.45 (d, J=13.2 Hz, 2H); 4.42 (s, 2H); 4.09 (s, 2H); 3.48 (m, 1H); 3.37 (m, 1H); 3.05 (s, 3H); 2.46-2.62 (overlapped m, 1H); 1.96 (m, 1H); 1.52 (s, 3H); 1.08 (d, J=3.8 Hz, 4H).

MS (ESI, m/z): 588.0 [M+H$^+$] for C$_{22}$H$_{26}$N$_3$O$_{12}$PS; $t_R$=0.59 min.

Example 76: (R)-N-hydroxy-4-(6-((2-(2-hydroxypropan-2-yl)thiazol-5-yl)ethynyl)-3-oxo-1H-pyrrolo[1,2-c]imidazol-2(3H)-yl)-2-methyl-2-(methylsulfonyl)butanamide Starting from the compound of Preparation E (0.113 g; 0.21 mmol) and the compound of Preparation BI (0.073 g; 0.43 mmol), and proceeding successively in analogy to Procedure F (73% yield) and Procedure B (64% yield), the title compound was obtained, after purification by CC (EA-MeOH), as a white solid (0.049 g).

$^1$H NMR (d6-DMSO) δ: 10.95 (s, 1H); 9.18 (s, 1H); 7.88 (s, 1H); 7.52 (d, J=0.6 Hz, 1H); 6.29 (m, 1H); 6.14 (s, 1H); 4.46 (s, 2H); 3.49 (m, 1H); 3.39 (m, 1H); 3.07 (s, 3H); 2.60 (m, 1H); 1.97 (m, 1H); 1.53 (s, 3H); 1.50 (s, 6H).

MS (ESI, m/z): 481.01 [M+H$^+$] for C$_{20}$H$_{24}$N$_4$O$_6$S$_2$; $t_R$=0.65 min.

Example 77: (R)-4-(6-((4-((4-aminopiperidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide dihydrochloride Starting from the compound of Preparation H (0.2 g; 0.472 mmol) and tert-butyl (1-(4-iodobenzyl)piperidin-4-yl)carbamate (0.102 g; 0.37 mmol; prepared as described in WO 2013/092674), and proceeding successively in analogy to Procedure E (71% yield) and Procedure I (37% yield), the title compound was obtained, after purification by prep-HPLC (Method 3), as a white solid (0.014 g).

$^1$H NMR (d6-DMSO) δ: 7.45 (s, 1H); 7.44 (d, J=8.2 Hz, 2H); 7.30 (d, J=8.2 Hz, 2H); 6.26 (d, J=1.2 Hz, 1H); 4.46 (s,

2H); 3.47-3.53 (m, 1H); 3.45 (s, 2H); 3.37-3.41 (m, 1H); 3.07 (s, 3H); 2.73 (m, 2H); 2.64-2.66 (m, 1H); 2.58 (m, 1H); 1.93-1.98 (m, 3H); 1.72 (m, 2H); 1.50 (s, 3H); 1.29-1.35 (m, 2H).

MS (ESI, m/z): 528.11 [M+H$^+$] for $C_{26}H_{33}N_5O_5S$; $t_R$=0.49 min.

Examples 78 and 79: (R)-4-(6-(((1R,2R)-2-fluoro-2-(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide AND (R)-4-(6-(((1S,2S)-2-fluoro-2-(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation H (0.15 g; 0.354 mmol) and either the first-eluting enantiomer ("1$^{st}$ variant") or the second-eluting enantiomer ("2$^{nd}$ variant") of Preparation BJ (each time 0.116 g (0.39 mmol)), and proceeding in analogy to Example 12, step 12.i (1$^{st}$ variant: 76% yield; 2$^{nd}$ variant: 84% yield) and Procedure D (1$^{st}$ variant: 85% yield; 2$^{nd}$ variant: 85% yield), the title compounds were obtained, after purification by CC (DCM-MeOH), in the 1$^{st}$ variant case, as a yellow solid (0.103 g), and, in the 2$^{nd}$ variant case, as a yellow solid (0.115 g).
1$^{st}$ Variant Product:
$^1$H NMR (d6-DMSO) δ: 10.94 (s, 1H); 9.18 (s, 1H); 7.56 (d, J=0.9 Hz, 1H); 6.25 (d, J=1.2 Hz, 1H); 5.23 (t, J=6.1 Hz, 1H); 4.42 (s, 2H); 3.59-3.71 (m, 2H); 3.49 (m, 1H); 3.38 (m, 1H); 3.06 (s, 3H); 2.59 (m, 1H); 1.90-1.97 (m, 2H); 1.52 (s, 3H); 1.31-1.36 (m, 2H).

MS (ESI, m/z): 451.99 [M+H$^+$] for $C_{20}H_{22}N_3O_6FS$; $t_R$=0.67 min.
2$^{nd}$ Variant Product:
$^1$H NMR (d6-DMSO) δ: 10.94 (s, 1H); 9.18 (s, 1H); 7.57 (d, J=0.9 Hz, 1H); 6.26 (d, J=1.2 Hz, 1H); 5.23 (t, J=6.1 Hz, 1H); 4.43 (s, 2H); 3.58-3.71 (m, 2H); 3.48 (m, 1H); 3.39 (m, 1H); 3.06 (s, 3H); 2.59 (m, 1H); 1.91-1.98 (m, 2H); 1.53 (s, 3H); 1.32-1.37 (m, 2H).

MS (ESI, m/z): 452.03 [M+H$^+$] for $C_{20}H_{22}N_3O_6FS$; $t_R$=0.65 min.

Example 80: (R)-N-hydroxy-4-(6-((4-((4-hydroxypiperidin-1-yl)methyl)phenyl)ethynyl)-3-oxo-1H-pyrrolo[1,2-c]imidazol-2(3H)-yl)-2-methyl-2-(methylsulfonyl)butanamide Starting from the compound of Preparation H (0.2 g; 0.47 mmol) and 1-(4-iodobenzyl)piperidin-4-ol (0.165 g; 0.52 mmol; commercial), and proceeding successively in analogy to Procedure E (89% yield) and Procedure I (35% yield), the title compound was obtained, after purification by prep-HPLC (Method 3), as a beige solid (0.047 g).

MS (ESI, m/z): 529.1 [M+H$^+$] for $C_{26}H_{32}N_4O_6S$; $t_R$=0.54 min.

Example 81: (R)-4-(6-((4-(4-aminopiperidin-1-yl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation H (0.113 g; 0.26 mmol) and 1-(4-iodophenyl)piperidin-4-amine trifluoroacetate (0.118 g; 0.28 mmol), and proceeding successively in analogy to Procedure E (100% yield) and Procedure I (41% yield), the title compound was obtained, after purification by prep-HPLC (Method 1), as a beige solid (0.051 g).

MS (ESI, m/z): 514.10 [M+H$^+$] for $C_{25}H_{31}N_5O_5S$; $t_R$=0.56 min.

Example 82: (R)-N-hydroxy-2-methyl-4-(6-((4-(methylsulfonamidomethyl)phenyl)ethynyl)-3-oxo-1H-pyrrolo[1,2-c]imidazol-2(3H)-yl)-2-(methylsulfonyl)butanamide Starting from the compound of Preparation H (0.2 g; 0.47 mmol) and N-(4-iodobenzyl)methanesulfonamide (0.237 g; 0.71 mmol), and proceeding successively in analogy to Procedure E (70% yield), and Procedure D (81% yield), the title compound was obtained as a greyish solid (0.11 g).

$^1$H NMR (d6-DMSO) δ: 10.96 (s, 1H); 9.19 (s, 1H); 7.62 (t, J=6.4 Hz, 1H); 7.46-7.50 (overlapped m, 2H); 7.47 (s, 1H); 7.38 (d, J=8.2 Hz, 2H); 6.28 (m, 1H); 4.47 (s, 2H); 4.18 (d, J=6.3 Hz, 2H); 3.50 (m, 1H); 3.41 (m, 1H); 3.08 (s, 3H); 2.88 (s, 3H); 2.60 (m, 1H); 1.99 (m, 1H); 1.54 (s, 3H).

MS (ESI, m/z): 523.0 [M+H$^+$] for $C_{22}H_{26}N_4O_7S_2$; $t_R$=0.67 min.

Example 83: (R)-N-hydroxy-2-methyl-2-(methylsulfonyl)-4-(6-((1-(oxetan-3-yl)azetidin-3-yl)buta-1,3-diyn-1-yl)-3-oxo-1H-pyrrolo[1,2-c]imidazol-2(3H)-yl)butanamide 83.i. 4-iodo-1H-pyrrole-2-carbaldehyde oxime To a solution of NH$_2$OH.HCl (17.61 g, 253.42 mmol) in MeOH (600 mL) was added NaOAc.3H$_2$O (35.1 g; 257.94 mmol) and the mixture is stirred at rt for 5 min. 4-iodo-1H-pyrrole-2-carbaldehyde (50.00 g; 226.25 mmol) was added portion-wise and the reaction mixture was stirred for 1 h. The mixture was evaporated under reduced pressure to dryness, the residue was dissolved in EA, washed with water (5×100 mL), filtered and dried over Na$_2$SO$_4$. The solvent was evaporated to give the title compound as a white solid (53 g; 99% yield).

$^1$H NMR (d6-DMSO) δ: 11.42-11.53 (br. s, 1H); 10.80 [major] and 11.34 (both s, total 1H); 7.24 and 7.89 [major] (both s, 1H); 6.93 [major] and 7.00 (both dd, J=1.5, 2.7 Hz, total 1H); 6.40 [major] and 6.73 (both t, J=1.8 Hz, total 1H).

83.ii. (4-iodo-1H-pyrrol-2-yl)methanamine

To a solution of intermediate 83.i (10.0 g; 42.37 mmol) in AcOH (250 mL) under argon was added a first portion (approximately ⅔) of Zn powder (total amount: 16.62 g (254.24 mmol)) and the mixture was stirred for 20 min. Then the remaining portion of Zn powder was added and stirring was continued for an additional 15 min. The solids were filtered off and the filtrate was evaporated under reduced pressure (bath temperature below 40° C.). The residue was dissolved in EA (200 mL), washed with 5-7% aq. NaOH (50 mL) and brine (50 mL), and dried over anhydrous MgSO$_4$. After filtration and evaporation to dryness, the title compound was obtained as a brown solid (7.7 g; 81.7% yield).

$^1$H NMR (d6-DMSO) δ: 10.89 (br. s, 1H); 6.74 (d, J=1.5 Hz, 1H); 5.93 (m, 1H); 3.58 (s, 2H).

83.iii. 6-iodo-1H-pyrrolo[1,2-c]imidazol-3(2H)-one

To a solution of CDI (4.69 g; 28.92 mmol) in THF (150 mL), cooled with an ice-water bath, was added dropwise a solution of intermediate 83.ii (6.112 g; 27.53 mmol) in THF (20 mL). Immediately after addition completed, NaH (2.36 g; 60% in mineral oil; 59.0 mmol) was added and the mixture is stirred for 4 h. Then, water (2 mL) was added and the solvent was evaporated under reduced pressure. The residue was purified by CC (DCM-EA) to give the title compound as a pale yellow solid (3.35 g; 49% yield).

$^1$H NMR (d6-DMSO) δ: 8.55 (br. s, 1H); 7.27 (d, J=1.6 Hz, 1H); 6.17 (d, J=1.6 Hz, 1H); 4.34 (s, 2H).

MS (ESI, m/z): 248.9 [M+H$^+$] for $C_6H_5N_2OI$; $t_R$=0.66 min.

83.iv. Ethyl 4-(6-iodo-3-oxo-1H-pyrrolo[1,2-c]imidazol-2(3H)-yl)-2-methyl-2-(methylsulfonyl)butanoate To a solution of intermediate 83.iii (1.55 g; 6.25 mmol) in DMF (30 mL) was added NaH (0.275 g; 60% in mineral oil; 6.88 mmol). The mixture was stirred at rt for 1.5 h. (R)-ethyl 4-bromo-2-methyl-2-(methylsulfonyl)butanoate (1.88 g; 6.5 mmol) was added. The reaction proceeded at rt for 2 h. Aq. NH$_4$Cl (2 mL) was added and the solvent was removed under reduced pressure. The residue was dissolved in EA (150 mL), washed with water (50 mL) and brine (50 mL), and dried over Na$_2$SO$_4$. After filtration and evaporation to dryness, the residue was purified by CC (PE-EA) to afford the title compound as a pale yellow semi-solid (1.58 g, 55% yield).

$^1$H NMR (d6-DMSO) δ: 7.32 (d, J=1.0 Hz, 1H); 6.24 (m, 1H); 3.89-4.00 (m, 2H); 3.60 (m, 1H); 3.47 (m, 1H); 3.13 (s, 3H); 2.61 (m, 1H); 2.06 (m, 1H); 1.57 (s, 3H); 1.12 (t, J=7.1 Hz, 3H).

MS (ESI, m/z): 455.00 [M+H$^+$] for $C_{14}H_{19}N_2O_5IS$; $t_R$=0.82 min.

83.v. Ethyl 4-(6-ethynyl-3-oxo-1H-pyrrolo[1,2-c]imidazol-2(3H)-yl)-2-methyl-2-(methylsulfonyl)butanoate Starting from intermediate 83.iv (2 g; 4.4 mmol) and proceeding in analogy to Procedure C (quant.) and Preparation H, step H.ii (83% yield), the title compound was obtained, after purification by CC (Hept-EA), as a beige foam (1.28 g).

$^1$H NMR (d6-DMSO) δ: 7.41 (s, 1H); 6.20 (d, J=1.2 Hz, 1H); 4.36 (s, 2H); 3.99 (s, 1H); 3.89-3.98 (m, 2H); 3.62 (m, 1H); 3.47 (m, 1H); 3.12 (s, 3H); 2.61 (m, 1H); 2.06 (m, 1H); 1.57 (s, 3H); 1.11 (t, J=7.1 Hz, 3H).

MS (ESI, m/z): 352.93 [M+H$^+$] for $C_{16}H_{20}N_2O_5S$; $t_R$=0.77 min.

83.vi. Ethyl 4-(6-(azetidin-3-ylbuta-1,3-diyn-1-yl)-3-oxo-1H-pyrrolo[1,2-c]imidazol-2(3H)-yl)-2-methyl-2-(methylsulfonyl)butanoate Starting from the intermediate 83.v (0.48 g; 1.36 mmol) and intermediate AY.ii (0.375 g; 1.9 mmol) and proceeding in analogy to Example 12, step 12.i, the title compound was obtained, after purification by CC (DCM-MeOH), as a beige foam (0.257 g; 44% yield).

$^1$H NMR (d6-DMSO) δ: 7.61 (s, 1H); 6.28 (d, J=1.1 Hz, 1H); 4.38 (s, 2H); 4.05-4.15 (m, 2H); 3.90-3.99 (m, 3H); 3.58-3.66 (m, 3H); 3.44-3.51 (m, 2H); 3.12 (s, 3H); 2.60 (m, 1H); 2.07 (m, 1H); 1.57 (s, 3H); 1.11 (t, J=7.1 Hz, 3H).

MS (ESI, m/z): 432.2 [M+H$^+$] for $C_{21}H_{25}N_3O_5S$; $t_R$=0.62 min.

83.vii. Ethyl 2-methyl-2-(methylsulfonyl)-4-(6-((1-(oxetan-3-yl)azetidin-3-yl)buta-1,3-diyn-1-yl)-3-oxo-1H-pyrrolo[1,2-c]imidazol-2(3H)-yl)butanoate To a solution of intermediate 83.vi (0.237 g; 0.549 mmol) in DCM (7.2 mL) were added oxetan-3-one (0.119 g; 1.65 mmol) and NaBH(OAc)$_3$ (0.706 g; 3.33 mmol). The reaction mixture was stirred at rt for 2 h. Sat. aq. NaHCO$_3$ (10 mL) and DCM (10 mL) were added. The aq. layer was extracted 3 times with DCM-MeOH (9-1, 3×10 mL). The combined org. layers were dried over MgSO$_4$, filtered and concentrated down. The residue was purified by CC (DCM-MeOH) to afford the title compound as an orange oil (0.272 g).

$^1$H NMR (d6-DMSO) δ: 7.59 (d, J=1.2 Hz, 1H); 6.27 (d, J=1.2 Hz, 1H); 4.51-4.54 (m, 2H); 4.45 (m, 1H); 4.37 (s, 2H); 4.31 (m, 3H); 3.90-3.99 (m, 2H); 3.41-3.69 (m, 6H); 3.12 (s, 3H); 2.56-2.65 (m, 1H); 2.02-2.11 (m, 1H); 1.57 (s, 3H); 1.11 (t, J=7.1 Hz, 3H).

MS (ESI, m/z): 488.0 [M+H$^+$] for $C_{24}H_{29}N_3O_6S$; $t_R$=0.60 min.

83.viii. (R)-2-methyl-2-(methylsulfonyl)-4-(6-(0-(oxetan-3-yl)azetidin-3-yl)buta-1,3-diyn-1-yl)-3-oxo-1H-pyrrolo[1,2-c]imidazol-2(3H)-yl)butanoic acid lithium salt To an ice-chilled solution of intermediate 83.vii (0.140 g; 0.288 mmol) in a THF-MeOH—H$_2$O mixture (2-2-1; 0.75 mL) was added lithium hydroxide (0.0277 g; 0.37 mmol). The reaction mixture was warmed to rt (about 15 min) and stirred at rt for 1 h. The compound was concentrated to dryness to afford the title salt as an orange gum (0.134 g; quant.).

MS (ESI, m/z): 460.0 [M+H$^+$] for $C_{22}H_{25}N_3O_6S$; $t_R$=0.53 min.

83.ix. (R)-N-hydroxy-2-methyl-2-(methylsulfonyl)-4-(6-(((1-(oxetan-3-yl)azetidin-3-yl)buta-1,3-diyn-1-yl)-3-oxo-1H-pyrrolo[1,2-c]imidazol-2(3H)-yl)butanamide Starting from intermediate 83.viii (0.134 g; 0.288 mmol) and proceeding in analogy to Preparation C, step C.iv (67% yield) and Procedure I (12% yield), the title compound was obtained, after purification by prep-HPLC (Method 1), as a white solid (0.001 g).

$^1$H NMR (d$_6$-DMSO) δ: 9.06-9.14 (br. s, 1H); 7.56 (d, J=1.2 Hz, 1H); 6.26 (d, J=1.2 Hz, 1H); 4.53 (t, J=6.6 Hz, 2H); 4.43 (s, 2H); 4.31 (dd, J=5.3, 6.4 Hz, 2H); 3.67 (m, 1H); 3.52 (overlapped t, J=7.6 Hz, 2H); 3.30-3.49 (overlapped m, 3H); 3.10-3.13 (m, 2H); 3.05 (s, 3H); 2.58 (m, 1H); 1.95 (m, 1H); 1.51 (s, 3H).

MS (ESI, m/z): 475.08 [M+H$^+$] for $C_{22}H_{26}N_4O_6S$; $t_R$=0.51 min.

The racemic mixtures of Reference Examples 1 to 10 can be separated into their enantiomers using, for example, chiral HPLC. Thus the following further invention compounds or salts would be obtained:

(R)-N-hydroxy-4-(6-(4-(3-hydroxyoxetan-3-yl)phenyl)-3-oxo-1H-pyrrolo[1,2-c]imidazol-2(3H)-yl)-2-methyl-2-(methylsulfonyl)butanamide;

(R)-4-(6-((4-(2-ethoxypropan-2-yl)phenyl)ethynyl)-3-oxo-1H-pyrrolo[1,2-c]imidazol-2(3H)-yl)-N-hydroxy-2-methyl-2-(methylsulfonyl)butanamide;

(R)-4-(6-((2-fluoro-4-(hydroxymethyl)phenyl)ethynyl)-3-oxo-1H-pyrrolo[1,2-c]imidazol-2(3H)-yl)-N-hydroxy-2-methyl-2-(methylsulfonyl)butanamide;

(R)-N-hydroxy-4-(6-(4-(3-hydroxy-3-methylbut-1-yn-1-yl)phenyl)-3-oxo-1H-pyrrolo[1,2-c]imidazol-2(3H)-yl)-2-methyl-2-(methylsulfonyl)butanamide;

(R)-N-hydroxy-4-(6-(5-hydroxy-5-methylhexa-1,3-diyn-1-yl)-3-oxo-1H-pyrrolo[1,2-c]imidazol-2(3H)-yl)-2-methyl-2-(methylsulfonyl)butanamide;

(R)-N-hydroxy-2-methyl-4-(6-((4-((4-methylpiperazin-1-yl)methyl)phenyl)ethynyl)-3-oxo-1H-pyrrolo[1,2-c]imidazol-2(3H)-yl)-2-(methylsulfonyl)butanamide;

(R)-N-hydroxy-4-(6-(4-(2-hydroxyethoxy)phenyl)-3-oxo-1H-pyrrolo[1,2-c]imidazol-2(3H)-yl)-2-methyl-2-(methylsulfonyl)butanamide;

(R)-N-hydroxy-4-(6-(4-(2-methoxyethoxy)phenyl)-3-oxo-1H-pyrrolo[1,2-c]imidazol-2(3H)-yl)-2-methyl-2-(methylsulfonyl)butanamide.

(R)-4-(6-(2-fluoro-4-methylphenyl)-3-oxo-1H-pyrrolo[1,2-c]imidazol-2(3H)-yl)-N-hydroxy-2-methyl-2-(methylsulfonyl)butanamide; and (R)-4-(6-(3-fluoro-4-isopropoxyphenyl)-3-oxo-1H-pyrrolo[1,2-c]imidazol-2(3H)-yl)-N-hydroxy-2-methyl-2-(methylsulfonyl)butanamide.

Pharmacological Properties of the Invention Compounds
In Vitro Assays
Bacterial Growth Minimal Inhibitory Concentrations:
Experimental Methods:

Minimal Inhibitory Concentrations (MICs; mg/L) were determined in cation-adjusted Mueller-Hinton Broth by a microdilution method following the description given in "*Methods for Dilution Antimicrobial Susceptibility Tests for Bacteria that Grow Aerobically*", Approved standard, $7^{th}$ ed., a Clinical and Laboratory Standards Institute (CLSI) Document M7-A7, Wayne, Pa., USA (2006).

Results:

All Example compounds were tested against several Gram-positive and Gram-negative bacteria. Typical antibacterial test results are given in Table 1 hereafter (MICs in mg/L). *K. pneumoniae* A-651 is a multiply-resistant strain (in particular quinolone-resistant), while *E. coli* ATCC25922 and *P. aeruginosa* ATCC27853 are quinolone-sensitive strains.

TABLE 1

| Example No. | MIC for E. coli ATCC25922 | MIC for P. aeruginosa ATCC27853 | MIC for K. Pneumoniae A-651 |
|---|---|---|---|
| RE1 | 8 | 16 | 16 |
| RE2 | 2 | 8 | 2 |
| RE3 | 0.5 | 4 | 1 |
| RE4 | 0.25 | 2 | 0.5 |
| RE5 | 2 | 4 | 8 |
| RE6 | 2 | 2 | 8 |
| RE7 | 4 | 8 | 8 |
| RE8 | 2 | 8 | 2 |
| RE9 | 0.125 | 0.5 | 2 |
| RE10 | 0.25 | 2 | 8 |
| 1 | 0.125 | 1 | ≤0.063 |
| 2 | 0.5 | 1 | 1 |
| 3 | 0.125 | 2 | 0.5 |
| 4 | 2 | 4 | 2 |
| 5 | ≤0.063 | 0.5 | 0.125 |
| 6 | 0.031 | 0.5 | 0.125 |
| 7 | 0.125 | 0.5 | 0.25 |
| 8 | 8 | 4 | 8 |
| 9 | 0.25 | 0.5 | 0.5 |
| 10 | 0.25 | 0.5 | 0.25 |
| 11 | 8 | 8 | 16 |
| 12 | 0.25 | 0.25 | 0.25 |
| 13 | 0.125 | 0.5 | 0.25 |
| 14 | 0.125 | 1 | 0.25 |
| 15 | 0.5 | 1 | 1 |
| 16 | ≤0.063 | 0.5 | 0.25 |
| 17 | 1 | 1 | 1 |
| 18 | 0.5 | 1 | 1 |
| 19 | 0.25 | 1 | 0.5 |
| 20 | 1 | 4 | 4 |
| 21 | 0.25 | 1 | 1 |
| 22 | 0.125 | 1 | 0.5 |
| 23 | 1 | 4 | 4 |
| 24 | 8 | 8 | 32 |
| 25 | 0.125 | 1 | 0.25 |
| 26 | 1 | 4 | 1 |
| 27 | ≤0.063 | 0.5 | 0.25 |
| 28 | ≤0.063 | 1 | 0.25 |
| 29 | 0.25 | 2 | 0.5 |
| 30 | 0.125 | 0.5 | 0.25 |
| 31 | 1 | 1 | 1 |
| 32 | ≤0.063 | 0.5 | 0.25 |
| 33 | 0.5 | 1 | 0.5 |
| 34 | 0.125 | 16 | 1 |
| 35 | 0.25 | 2 | 0.5 |
| 36 | 0.125 | 0.5 | 0.25 |
| 37 | 0.5 | 4 | 1 |
| 38 | 0.25 | 1 | 0.25 |
| 39 | 2 | 4 | 4 |
| 40 | ≤0.063 | 1 | 0.25 |
| 41 | 1 | 4 | 2 |
| 42 | 8 | 4 | 8 |
| 43 | 8 | 8 | 16 |
| 44 | ≤0.063 | 1 | 0.25 |
| 45 | 0.25 | 4 | 1 |
| 46 | 1 | 4 | 2 |
| 47 | ≤0.063 | 8 | 0.25 |
| 48 | ≤0.063 | 1 | 0.25 |
| 49 | ≤0.063 | 4 | 0.125 |
| 52 | ≤0.063 | 2 | ≤0.063 |
| 53 | 0.25 | 8 | 0.25 |
| 54 | 0.125 | 1 | 1 |
| 55 | 0.125 | 4 | 1 |
| 56 | 0.25 | 2 | 1 |
| 57 | 1 | 4 | 2 |
| 58 | 4 | 4 | 8 |
| 59 | 1 | 8 | 1 |
| 60 | 0.5 | 4 | 1 |
| 61 | 0.25 | 0.25 | 0.25 |
| 62 | 1 | 1 | 4 |
| 63 | 2 | 4 | 4 |
| 64 | 4 | 4 | 8 |
| 65 | 2 | 1 | 8 |
| 66 | 0.125 | 1 | 0.5 |
| 67 | 0.125 | 0.5 | 0.5 |
| 68 | 0.125 | 1 | 0.125 |
| 69 | 0.5 | 2 | 2 |
| 70 | 1 | 2 | 2 |
| 71 | 0.25 | 1 | 1 |
| 72 | 0.125 | 0.5 | 0.25 |
| 73 | 8 | 4 | 16 |
| 75 | 1 | 2 | 2 |
| 76 | 1 | 2 | 2 |
| 77 | 8 | 2 | 16 |
| 78 | 0.25 | 0.5 | 0.5 |
| 79 | 0.25 | 0.5 | 0.25 |
| 80 | 1 | 1 | 2 |
| 81 | 8 | 2 | 16 |
| 82 | 0.5 | 1 | 1 |
| 83 | 0.5 | 1 | 0.5 |
| Cipro | 0.5 | >32 | >32 |

The compounds of Examples 37, 50, 51 and 74 were tested against wild-type *E. coli* A-1261 in the absence of alkaline phosphatase or esterase, in the presence of an alkaline phosphatase and in the presence of an esterase. The corresponding antibacterial test results are given in Table 2 hereafter (MICs in mg/L).

TABLE 2

| | MIC for E. coli A-1261 | | |
|---|---|---|---|
| Example No. | In the absence of alkaline phosphatase or esterase | In the presence of an alkaline phosphatase (2 i.U./mL) | In the presence of an esterase (10 i.U./mL) |
| 37 | 0.25 | 0.125 | 0.25 |
| 50 | 2 | 1 | 0.5 |
| 51 | >16 | 0.5 | 16 |
| 74 | 4 | 0.25 | 4 |

The invention claimed is:
1. A compound of formula I

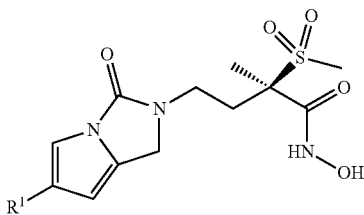

I wherein
$R^1$ represents the group M;
M is one of the groups $M^A$, $M^B$ and $M^C$ represented below

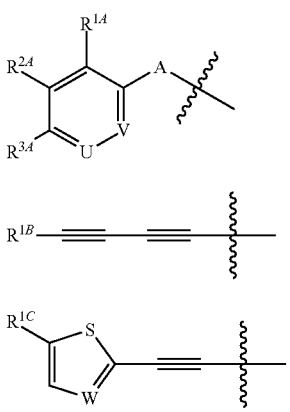

wherein A represents a bond, CH=CH or C≡C;
U represents N or CH;
V represents N or CH;
W represents N or CH;
$R^{1A}$ represents H or halogen;
$R^{2A}$ represents H, $(C_1-C_3)$alkoxy or halogen;
$R^{3A}$ represents H, halogen, $(C_1-C_3)$alkoxy, hydroxy$(C_2-C_4)$alkoxy, dihydroxy$(C_3-C_4)$alkoxy, $(C_1-C_3)$alkoxy$(C_1-C_3)$alkoxy, $(C_1-C_3)$thioalkoxy, trifluoromethoxy, trifluoromethyl, amino, hydroxy$(C_1-C_4)$alkyl, 1,2-dihydroxyethyl, 1-hydroxy-2,2-difluoroethyl, $(C_1-C_3)$alkoxy$(C_1-C_4)$alkyl, 2-hydroxy-1-oxoethyl, [$(C_1-C_4)$alkoxy]carbonyl, methylsulfonamidomethyl, 3-hydroxy-3-methylbut-1-yn-1-yl, 2-hydroxyacetamido, (carbamoyloxy)methyl, 1-aminocyclopropyl, 1-hydroxymethyl-cycloprop-1-yl, 1-(((dimethylglycyl)oxy)methyl)cyclopropyl, 1-aminomethyl-cycloprop-1-yl, 1-(carbamoyloxy)methyl-cycloprop-1-yl, 1-(morpholin-4-yl)methylcycloprop-1-yl, trans-2-hydroxymethyl-cycloprop-1-yl, 1-(hydroxymethyl)-cyclobut-1-yl, 1-(2-hydroxyacetyl)azetidin-3-yl, (1-tert-butyloxycarbonyl)-3-hydroxyazetidin-3-yl, 3-hydroxyoxetan-3-yl, 3-(hydroxy$(C_1-C_3)$alkyl)oxetan-3-yl, 3-aminooxetan-3-yl, 3-hydroxythietan-3-yl, 4-aminopiperidin-1-yl, morpholin-4-yl$(C_2-C_3)$alkoxy, [4-N—$(C_1-C_3)$alkylpiperazin-1-yl]$(C_1-C_3)$alkyl, morpholin-4-yl-$(C_1-C_2)$alkyl, [1,2,3]triazol-2-yl, 3-[hydroxy$(C_2-C_3)$alkyl]-2-oxo-imidazolidin-1-yl, (1s,3r)-(1-hydroxy-3-(hydroxymethyl)cyclobutyl)methyl, (4-hydroxypiperidinyl)methyl or (4-aminopiperidinyl)methyl;
$R^{1B}$ represents 3-hydroxyoxetan-3-yl, 3-hydroxythietan-3-yl, 3-(hydroxy$(C_1-C_3)$alkyl)oxetan-3-yl, hydroxy$(C_1-C_3)$alkyl, 1,2-dihydroxyethyl, amino$(C_1-C_3)$alkyl, (dimethylamino)methyl, methylsulfonamidomethyl, 1-aminocyclopropyl, 1-hydroxymethyl-cycloprop-1-yl, 1-(carbamoyloxy)methyl-cycloprop-1-yl, 1-(((dimethylglycyl)oxy)methyl)cycloprop-1-yl, 1-((phosphonooxy)methyl)-cycloprop-1-yl, 1-((((phosphonooxy)methoxy)carbonyl)oxymethyl)cycloprop-1-yl, 1-(((((phosphonooxy)methoxy)carbonyl)amino)-cycloprop-1-yl, trans-2-hydroxymethyl-cycloprop-1-yl, 1-fluoro-2-hydroxymethyl-cycloprop-1-yl, 2-fluoro-2-hydroxymethyl-cycloprop-1-yl, 1-methyl-2-hydroxymethyl-cycloprop-1-yl, 2-hydroxymethyl-2-methylcycloprop-1-yl, (1R*,2S*,3s*)-1,2-bis-(hydroxymethyl)-cycloprop-3-yl, 1-(hydroxymethyl)cyclobut-1-yl, 3-amino-oxetan-3-yl, 3-(hydroxy$(C_1-C_3)$alkyl)oxetan-3-yl, 1-(2-hydroxyacetyl)-azetidin-3-yl, trans-(cis-3,4-dihydroxy)-cyclopent-1-yl, 3-hydroxymethyl-bicyclo[1,1,1]pentan-1-yl, 4-hydroxy-tetrahydro-2H-pyran-4-yl, 5-amino-tetrahydro-2H-pyran-2-yl, 3-hydroxyoxetan-3-ylmethyl, 1-cyclobutyl-2-hydroxyethyl or 1-(oxetan-3-yl)-azetidin-3-yl; and
$R^{1C}$ represents 1-aminocyclopropyl or hydroxy$(C_1-C_3)$alkyl;
or a salt thereof.

2. The compound of formula I according to claim 1, which is also a compound of formula $I_P$

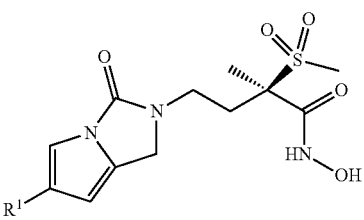

$I_P$ wherein
$R^1$ represents the group M;
M is one of the groups $M^A$ and $M^B$ represented below

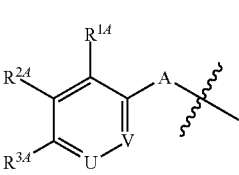

$M^A$

-continued $M^B$

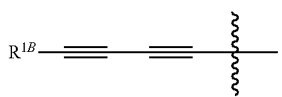

wherein A represents a bond, CH=CH or C≡C;
U represents N or CH;
V represents N or CH;
$R^{1A}$ represents H or halogen;
$R^{2A}$ represents H, ($C_1$-$C_3$)alkoxy or halogen;
$R^{3A}$ represents H, ($C_1$-$C_3$)alkoxy, hydroxy($C_2$-$C_4$)alkoxy, ($C_1$-$C_3$)alkoxy($C_1$-$C_3$)alkoxy, ($C_1$-$C_3$)thioalkoxy, trifluoromethoxy, amino, hydroxy($C_1$-$C_4$)alkyl, ($C_1$-$C_3$)alkoxy($C_1$-$C_4$)alkyl, 3-hydroxy-3-methylbut-1-yn-1-yl, 2-hydroxyacetamido, (carbamoyloxy)methyl, 1-hydroxymethyl-cycloprop-1-yl, 1-aminomethyl-cycloprop-1-yl, 1-(carbamoyloxy)methyl-cycloprop-1-yl, 1-(morpholin-4-yl)methylcycloprop-1-yl, trans-2-hydroxymethyl-cycloprop-1-yl, 1,2-dihydroxyethyl, 3-hydroxyoxetan-3-yl, 3-(hydroxy($C_1$-$C_3$)alkyl)oxetan-3-yl, 3-aminooxetan-3-yl, 3-hydroxythietan-3-yl, morpholin-4-yl($C_2$-$C_3$)alkoxy, [4-N—($C_1$-$C_3$)alkylpiperazin-1-yl]($C_1$-$C_3$)alkyl, morpholin-4-yl-($C_1$-$C_2$)alkyl, [1,2,3]triazol-2-yl or 3-[hydroxy($C_2$-$C_3$)alkyl]-2-oxo-imidazolidin-1-yl; and
$R^{1B}$ represents 3-hydroxyoxetan-3-yl, 3-hydroxythietan-3-yl, 3-(hydroxy($C_1$-$C_3$)alkyl)oxetan-3-yl, hydroxy($C_1$-$C_3$)alkyl, 1,2-dihydroxyethyl, amino($C_1$-$C_3$)alkyl, 1-hydroxymethyl-cycloprop-1-yl, trans-2-hydroxymethyl-cycloprop-1-yl, trans-(cis-3,4-dihydroxy)-cyclopent-1-yl or 3-hydroxymethylbicyclo[1,1,1]pentan-1-yl;
or a salt of this compound thereof.

3. The compound of formula I according to claim 1, which is a compound of formula $I_{CE}$

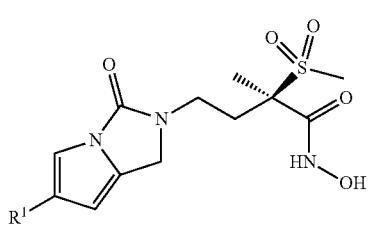

$I_{CE}$ wherein
$R^1$ represents the group M;
M is one of the groups $M^A$, $M^B$ and $M^C$ represented below $M^A$

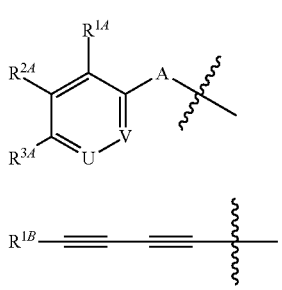

$M^B$

-continued $M^C$

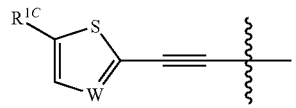

wherein A represents a bond, CH=CH or C≡C;
U represents CH or N;
V represents CH or N;
W represents CH or N;
$R^{1A}$ represents H or halogen;
$R^{2A}$ represents H, ($C_1$-$C_3$)alkoxy or halogen;
$R^{3A}$ represents H, halogen, ($C_1$-$C_3$)alkoxy, hydroxy($C_2$-$C_4$)alkoxy, dihydroxy($C_3$-$C_4$)alkoxy, ($C_1$-$C_3$)alkoxy($C_1$-$C_3$)alkoxy, trifluoromethyl, hydroxy($C_1$-$C_4$)alkyl, 1,2-dihydroxyethyl, 1-hydroxy-2,2-difluoroethyl, ($C_1$-$C_3$)alkoxy($C_1$-$C_4$)alkyl, 2-hydroxy-1-oxoethyl, [($C_1$-$C_4$)alkoxy]carbonyl, methylsulfonamidomethyl, 3-hydroxy-3-methylbut-1-yn-1-yl, 2-hydroxyacetamido, (carbamoyloxy)methyl, 1-aminocyclopropyl, 1-hydroxymethyl-cycloprop-1-yl, 1-(((dimethylglycyl)oxy)methyl)-cyclopropyl, 1-aminomethyl-cycloprop-1-yl, 1-(carbamoyloxy)methyl-cycloprop-1-yl, 1-(morpholin-4-yl)methyl-cycloprop-1-yl, trans-2-hydroxymethyl-cycloprop-1-yl, 1-(hydroxymethyl)-cyclobut-1-yl, 1-(2-hydroxyacetyl)azetidin-3-yl, (1-tert-butyloxycarbonyl)-3-hydroxyazetidin-3-yl, 3-hydroxyoxetan-3-yl, 3-(hydroxy($C_1$-$C_3$)alkyl)oxetan-3-yl, 3-aminooxetan-3-yl, 4-aminopiperidin-1-yl, [4-N—($C_1$-$C_3$)alkylpiperazin-1-yl]($C_1$-$C_3$)alkyl, morpholin-4-yl-($C_1$-$C_2$)alkyl, 3-[hydroxy($C_2$-$C_3$)alkyl]-2-oxo-imidazolidin-1-yl, (1s,3r)-(1-hydroxy-3-(hydroxymethyl)cyclobutyl)methyl, (4-hydroxypiperidinyl)methyl or (4-aminopiperidinyl)methyl; and
$R^{1B}$ represents 3-hydroxyoxetan-3-yl, hydroxy($C_1$-$C_3$)alkyl, 1,2-dihydroxyethyl, amino($C_1$-$C_3$)alkyl, (dimethylamino)methyl, methylsulfonamidomethyl, 1-aminocyclopropyl, 1-hydroxymethyl-cycloprop-1-yl, 1-(carbamoyloxy)methyl-cycloprop-1-yl, 1-(((dimethylglycyl)oxy)methyl)cycloprop-1-yl, 1-((phosphonooxy)methyl)-cycloprop-1-yl, 1-((((phosphonooxy)methoxy)carbonyl)oxymethyl)-cycloprop-1-yl, 1-((((phosphonooxy)methoxy)carbonyl)amino)-cycloprop-1-yl, trans-2-hydroxymethyl-cycloprop-1-yl, 1-fluoro-2-hydroxymethyl-cycloprop-1-yl, 2-fluoro-2-hydroxymethyl-cycloprop-1-yl, 1-methyl-2-hydroxymethyl-cycloprop-1-yl, 2-hydroxymethyl-2-methylcycloprop-1-yl, (1R*,2S*,3s*)-1,2-bis-(hydroxymethyl)-cycloprop-3-yl, 1-(hydroxymethyl)cyclobut-1-yl, 3-amino-oxetan-3-yl, 3-(hydroxy($C_1$-$C_3$)alkyl)oxetan-3-yl, 1-(2-hydroxy-acetyl)azetidin-3-yl, trans-(cis-3,4-dihydroxy)-cyclopent-1-yl, 3-hydroxymethylbicyclo[1,1,1]pentan-1-yl, 4-hydroxy-tetrahydro-2H-pyran-4-yl, 5-amino-tetrahydro-2H-pyran-2-yl, 3-hydroxyoxetan-3-ylmethyl, 1-cyclobutyl-2-hydroxyethyl or 1-(oxetan-3-yl)-azetidin-3-yl;
$R^{1C}$ represents 1-aminocyclopropyl or hydroxy($C_1$-$C_3$)alkyl;
or a salt thereof.

4. The compound of formula I according to claim 1, wherein $R^1$ represents the group $M^A$;
or a salt thereof.

5. The compound of formula I according to claim 4, wherein A represents a bond;
or a salt thereof.

6. The compound of formula I according to claim 4, wherein A represents C≡C;
or a salt thereof.

7. The compound of formula I according to claim 6, wherein
U represents CH,
V represents CH,
$R^{1A}$ represents H or fluorine,
$R^{2A}$ represents H or fluorine and
$R^{3A}$ represents hydroxy($C_2$-$C_4$)alkoxy, hydroxy($C_1$-$C_4$) alkyl, 1,2-dihydroxyethyl, 1-hydroxy-2,2-difluoroethyl, methylsulfonamidomethyl, 2-hydroxyacetamido, (carbamoyloxy)methyl, 1-aminocyclopropyl, 1-hydroxymethyl-cycloprop-1-yl, 1-(carbamoyloxy)methyl-cycloprop-1-yl, trans-2-hydroxymethyl-cycloprop-1-yl, 1-(hydroxymethyl)-cyclobut-1-yl, 3-hydroxyoxetan-3-yl, morpholin-4-ylmethyl or (4-hydroxypiperidinyl)methyl;
or a salt thereof.

8. The compound of formula I according to claim 1, wherein $R^1$ represents the group $M^B$;
or a salt thereof.

9. The compound of formula I according to claim 8, wherein $R^{1B}$ represents amino($C_1$-$C_3$)alkyl, 1-aminocyclopropyl, 1-hydroxymethyl-cycloprop-1-yl, trans-2-hydroxymethyl-cycloprop-1-yl, 1-fluoro-2-hydroxymethyl-cycloprop-1-yl, 2-fluoro-2-hydroxymethyl-cycloprop-1-yl, 1-methyl-2-hydroxymethyl-cycloprop-1-yl, 2-hydroxymethyl-2-methylcycloprop-1-yl, 1-(2-hydroxyacetyl)-azetidin-3-yl, trans-(cis-3,4-dihydroxy)-cyclopent-1-yl, 3-hydroxymethylbicyclo[1,1,1]pentan-1-yl, 5-amino-tetrahydro-2H-pyran-2-yl or 1-(oxetan-3-yl)-azetidin-3-yl;
or a salt thereof.

10. The compound of formula I according to claim 1, wherein $R^1$ represents the group $M^C$;
or a salt thereof.

11. The compound of formula I according to claim 1, wherein the compound is:
(R)-4-(6-(2-fluoro-4-methoxyphenyl)-3-oxo-1H-pyrrolo[1,2-c]imidazol-2(3H)-yl)-N-hydroxy-2-methyl-2-(methylsulfonyl)butanamide;
(R)-N-hydroxy-4-(6-((4-(3-hydroxyoxetan-3-yl)phenyl)ethynyl)-3-oxo-1H-pyrrolo[1,2-c]imidazol-2(3H)-yl)-2-methyl-2-(methylsulfonyl)butanamide;
(R)-N-hydroxy-4-(6-((4-(hydroxymethyl)phenyl)ethynyl)-3-oxo-1H-pyrrolo[1,2-c]imidazol-2(3H)-yl)-2-methyl-2-(methylsulfonyl)butanamide;
(R)-N-hydroxy-4-(6-((3-hydroxyoxetan-3-yl)buta-1,3-diyn-1-yl)-3-oxo-1H-pyrrolo[1,2-c]imidazol-2(3H)-yl)-2-methyl-2-(methylsulfonyl)butanamide;
(R)-N-hydroxy-4-(6-((4-((1R,2R)-2-(hydroxymethyl)cyclopropyl)phenyl)ethynyl)-3-oxo-1H-pyrrolo[1,2-c]imidazol-2(3H)-yl)-2-methyl-2-(methylsulfonyl)butanamide;
(R)-N-hydroxy-4-(6-((4-((1S,2S)-2-(hydroxymethyl)cyclopropyl)phenyl)ethynyl)-3-oxo-1H-pyrrolo[1,2-c]imidazol-2(3H)-yl)-2-methyl-2-(methylsulfonyl)butanamide;
(R)-N-hydroxy-4-(6-((4-(1-(hydroxymethyl)cyclopropyl)phenyl)ethynyl)-3-oxo-1H-pyrrolo[1,2-c]imidazol-2(3H)-yl)-2-methyl-2-(methylsulfonyl)butanamide;
(R)-4-(6-((4-(1-(aminomethyl)cyclopropyl)phenyl)ethynyl)-3-oxo-1H-pyrrolo[1,2-c]imidazol-2(3H)-yl)-N-hydroxy-2-methyl-2-(methylsulfonyl)butanamide;
(R)-N-hydroxy-4-(6-((4-(1-hydroxy-2-methylpropan-2-yl)phenyl)ethynyl)-3-oxo-1H-pyrrolo[1,2-c]imidazol-2(3H)-yl)-2-methyl-2-(methylsulfonyl)butanamide;
(R)-N-hydroxy-4-(6-((4-(2-hydroxypropan-2-yl)phenyl)ethynyl)-3-oxo-1H-pyrrolo[1,2-c]imidazol-2(3H)-yl)-2-methyl-2-(methylsulfonyl)butanamide;
(R)-4-(6-((S)-5,6-dihydroxyhexa-1,3-diyn-1-yl)-3-oxo-1H-pyrrolo[1,2-c]imidazol-2(3H)-yl)-N-hydroxy-2-methyl-2-(methylsulfonyl)butanamide;
(R)-N-hydroxy-4-(6-(5-((1S,2S)-2-(hydroxymethyl)cyclopropyl)penta-1,3-diyn-1-yl)-3-oxo-1H-pyrrolo[1,2-c]imidazol-2(3H)-yl)-2-methyl-2-(methylsulfonyl)butanamide;
(R)-N-hydroxy-4-(6-((4-((R)-1-hydroxyethyl)phenyl)ethynyl)-3-oxo-1H-pyrrolo[1,2-c]imidazol-2(3H)-yl)-2-methyl-2-(methylsulfonyl)butanamide;
(R)-N-hydroxy-4-(6-((4-((S)-1-hydroxyethyl)phenyl)ethynyl)-3-oxo-1H-pyrrolo[1,2-c]imidazol-2(3H)-yl)-2-methyl-2-(methylsulfonyl)butanamide;
(R)-N-hydroxy-4-(6-((1-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)butanamide;
(R)-N-hydroxy-4-(6-((4-(2-hydroxyethyl)phenyl)ethynyl)-3-oxo-1H-pyrrolo[1,2-c]imidazol-2(3H)-yl)-2-methyl-2-(methylsulfonyl)butanamide;
(R)-4-(6-((4-((R)-1,2-dihydroxyethyl)phenyl)ethynyl)-3-oxo-1H-pyrrolo[1,2-c]imidazol-2(3H)-yl)-N-hydroxy-2-methyl-2-(methylsulfonyl)butanamide;
(R)-4-(6-((4-((S)-1,2-dihydroxyethyl)phenyl)ethynyl)-3-oxo-1H-pyrrolo[1,2-c]imidazol-2(3H)-yl)-N-hydroxy-2-methyl-2-(methylsulfonyl)butanamide;
(R)-4-(6-((2-fluoro-4-(1-(hydroxymethyl)cyclopropyl)phenyl)ethynyl)-3-oxo-1H-pyrrolo[1,2-c]imidazol-2(3H)-yl)-N-hydroxy-2-methyl-2-(methylsulfonyl)butanamide;
(R)-N-hydroxy-4-(6-((4-(3-(2-hydroxyethyl)-2-oxoimidazolidin-1-yl)phenyl)ethynyl)-3-oxo-1H-pyrrolo[1,2-c]imidazol-2(3H)-yl)-2-methyl-2-(methylsulfonyl)butanamide;
(R)-4-(6-((3-fluoro-4-(2-hydroxyacetamido)phenyl)ethynyl)-3-oxo-1H-pyrrolo[1,2-c]imidazol-2(3H)-yl)-N-hydroxy-2-methyl-2-(methylsulfonyl)butanamide;
(R)-N-hydroxy-4-(6-((4-(2-hydroxyethoxy)phenyl)ethynyl)-3-oxo-1H-pyrrolo[1,2-c]imidazol-2(3H)-yl)-2-methyl-2-(methylsulfonyl)butanamide;
(R)-N-hydroxy-4-(6-((6-(1-(hydroxymethyl)cyclopropyl)pyridin-3-yl)ethynyl)-3-oxo-1H-pyrrolo[1,2-c]imidazol-2(3H)-yl)-2-methyl-2-(methylsulfonyl)butanamide;
(R)-N-hydroxy-4-(6-((5-(1-(hydroxymethyl)cyclopropyl)pyridin-2-yl)ethynyl)-3-oxo-1H-pyrrolo[1,2-c]imidazol-2(3H)-yl)-2-methyl-2-(methylsulfonyl)butanamide;
(R)-N-hydroxy-2-methyl-2-(methylsulfonyl)-4-(6-((4-(morpholinomethyl)phenyl)ethynyl)-3-oxo-1H-pyrrolo[1,2-c]imidazol-2(3H)-yl)butanamide;
(R)-N-hydroxy-2-methyl-2-(methylsulfonyl)-4-(6-((4-(1-(morpholinomethyl)cyclopropyl)phenyl)ethynyl)-3-oxo-1H-pyrrolo[1,2-c]imidazol-2(3H)-yl)butanamide;
(R)-N-hydroxy-4-(6-(((1R,2R)-2-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)butanamide;
(R)-4-(6-(2-fluoro-3-methoxyphenyl)-3-oxo-1H-pyrrolo[1,2-c]imidazol-2(3H)-yl)-N-hydroxy-2-methyl-2-(methylsulfonyl)butanamide;
(R)-(E)-N-hydroxy-4-(6-(4-(hydroxymethyl)styryl)-3-oxo-1H-pyrrolo[1,2-c]imidazol-2(3H)-yl)-2-methyl-2-(methylsulfonyl)butanamide;

(R)-N-hydroxy-4-(6-(4-(3-(hydroxymethyl)bicyclo[1.1.1]pentan-1-yl)buta-1,3-diyn-1-yl)-3-oxo-1H-pyrrolo[1,2-c]imidazol-2(3H)-yl)-2-methyl-2-(methylsulfonyl)butanamide;

(R)-4-(6-(5-amino-5-methylhexa-1,3-diyn-1-yl)-3-oxo-1H-pyrrolo[1,2-c]imidazol-2(3H)-yl)-N-hydroxy-2-methyl-2-(methylsulfonyl)butanamide;

(R)-4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl carbamate;

(R)-4-(6-(((1S,3R,4S)-3,4-dihydroxycyclopentyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-(1-(4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)phenyl)cyclopropyl)methyl carbamate;

(R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl carbamate;

(R)-N-hydroxy-4-(6-(((1R,2R)-2-(hydroxymethyl)-1-methylcyclopropyl)buta-1,3-diyn-1-yl)-3-oxo-1H-pyrrolo[1,2-c]imidazol-2(3H)-yl)-2-methyl-2-(methylsulfonyl)butanamide;

(R)-(1-(4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)phenyl)cyclopropyl)methyl dimethylglycinate;

(R)-4-(6-((1-aminocyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-4-(6-((3-aminooxetan-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-N-hydroxy-4-(6-((4-(1-(hydroxymethyl)cyclobutyl)phenyl)ethynyl)-3-oxo-1H-pyrrolo[1,2-c]imidazol-2(3H)-yl)-2-methyl-2-(methylsulfonyl)butanamide;

(R)-4-(6-(2-fluoro-4-(2-hydroxyethoxy)phenyl)-3-oxo-1H-pyrrolo[1,2-c]imidazol-2(3H)-yl)-N-hydroxy-2-methyl-2-(methylsulfonyl)butanamide;

(R)-4-(6-(((2R,3S)-2,3-bis(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-4-(6-(4-((R)-2,3-dihydroxypropoxy)-2-fluorophenyl)-3-oxo-1H-pyrrolo[1,2-c]imidazol-2(3H)-yl)-N-hydroxy-2-methyl-2-(methylsulfonyl)butanamide;

(R)-4-(6-((4-(1,1-difluoro-2-hydroxyethyl)phenyl)ethynyl)-3-oxo-1H-pyrrolo[1,2-c]imidazol-2(3H)-yl)-N-hydroxy-2-methyl-2-(methylsulfonyl)butanamide;

(R)-N-hydroxy-4-(6-((4-(2-hydroxyacetyl)phenyl)ethynyl)-3-oxo-1H-pyrrolo[1,2-c]imidazol-2(3H)-yl)-2-methyl-2-(methylsulfonyl)butanamide;

(R)-4-(6-(5-(dimethylamino)penta-1,3-diyn-1-yl)-3-oxo-1H-pyrrolo[1,2-c]imidazol-2(3H)-yl)-N-hydroxy-2-methyl-2-(methylsulfonyl)butanamide;

methyl (R)-3-fluoro-4-(2-(4-(hydroxyamino)-3-methyl-3-(methylsulfonyl)-4-oxobutyl)-3-oxo-2,3-dihydro-1H-pyrrolo[1,2-c]imidazol-6-yl)benzoate;

(R)-4-(6-(4-chloro-2-fluorophenyl)-3-oxo-1H-pyrrolo[1,2-c]imidazol-2(3H)-yl)-N-hydroxy-2-methyl-2-(methylsulfonyl)butanamide;

(R)-4-(6-(2-chloro-4-ethoxyphenyl)-3-oxo-1H-pyrrolo[1,2-c]imidazol-2(3H)-yl)-N-hydroxy-2-methyl-2-(methylsulfonyl)butanamide;

(R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl dimethylglycinate;

(R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl dihydrogen phosphate;

(R)-4-(6-(2-chloro-4-methoxyphenyl)-3-oxo-1H-pyrrolo[1,2-c]imidazol-2(3H)-yl)-N-hydroxy-2-methyl-2-(methylsulfonyl)butanamide;

(R)-4-(6-(2-fluoro-4-(trifluoromethyl)phenyl)-3-oxo-1H-pyrrolo[1,2-c]imidazol-2(3H)-yl)-N-hydroxy-2-methyl-2-(methylsulfonyl)butanamide;

(R)-N-hydroxy-2-methyl-2-(methylsulfonyl)-4-(3-oxo-6-(2,3,4-trifluorophenyl)-1H-pyrrolo[1,2-c]imidazol-2(3H)-yl)butanamide;

(R)-4-(6-(2,3-difluoro-4-methoxyphenyl)-3-oxo-1H-pyrrolo[1,2-c]imidazol-2(3H)-yl)-N-hydroxy-2-methyl-2-(methylsulfonyl)butanamide, (R)-N-hydroxy-4-(6-((1-(hydroxymethyl)cyclobutyl)buta-1,3-diyn-1-yl)-3-oxo-1H-pyrrolo[1,2-c]imidazol-2(3H)-yl)-2-methyl-2-(methylsulfonyl)butanamide;

((R)-N-hydroxy-4-(6-((3-(hydroxymethyl)oxetan-3-yl)buta-1,3-diyn-1-yl)-3-oxo-1H-pyrrolo[1,2-c]imidazol-2(3H)-yl)-2-methyl-2-(methylsulfonyl)butanamide;

(R)-N-hydroxy-2-methyl-4-(6-(5-(methylsulfonamido)penta-1,3-diyn-1-yl)-3-oxo-1H-pyrrolo[1,2-c]imidazol-2(3H)-yl)-2-(methylsulfonyl)butanamide;

tert-butyl (R)-3-hydroxy-3-(4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)phenyl)azetidine-1-carboxylate;

(2R)-4-(6-(5-cyclobutyl-6-hydroxyhexa-1,3-diyn-1-yl)-3-oxo-1H-pyrrolo[1,2-c]imidazol-2(3H)-yl)-N-hydroxy-2-methyl-2-(methylsulfonyl)butanamide;

(R)-N-hydroxy-4-(6-(((1R,2S)-2-(hydroxymethyl)-2-methylcyclopropyl)buta-1,3-diyn-1-yl)-3-oxo-1H-pyrrolo[1,2-c]imidazol-2(3H)-yl)-2-methyl-2-(methylsulfonyl)butanamide, (R)-N-hydroxy-4-(6-((1-(2-hydroxyacetyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;

(R)-N-hydroxy-4-(6-(5-(3-hydroxyoxetan-3-yl)penta-1,3-diyn-1-yl)-3-oxo-1H-pyrrolo[1,2-c]imidazol-2(3H)-yl)-2-methyl-2-(methylsulfonyl)butanamide;

(R)-N-hydroxy-4-(6-((4-hydroxytetrahydro-2H-pyran-4-yl)buta-1,3-diyn-1-yl)-3-oxo-1H-pyrrolo[1,2-c]imidazol-2(3H)-yl)-2-methyl-2-(methylsulfonyl)butanamide;

(R)-4-(6-(((2S,5R)-5-aminotetrahydro-2H-pyran-2-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-4-(6-(((1R,2R)-1-fluoro-2-(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide, (R)-4-(6-(((1S,2S)-1-fluoro-2-(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-4-(6-((5-(1-aminocyclopropyl)thiophen-2-yl)ethynyl)-3-oxo-1H-pyrrolo[1,2-c]imidazol-2(3H)-yl)-N-hydroxy-2-methyl-2-(methylsulfonyl)butanamide;

(R)-4-(6-((4-(3-aminooxetan-3-yl)phenyl)ethynyl)-3-oxo-1H-pyrrolo[1,2-c]imidazol-2(3H)-yl)-N-hydroxy-2-methyl-2-(methylsulfonyl)butanamide;

(R)-N-hydroxy-4-(6-((4-(3-(hydroxymethyl)oxetan-3-yl)phenyl)ethynyl)-3-oxo-1H-pyrrolo[1,2-c]imidazol-2(3H)-yl)-2-methyl-2-(methylsulfonyl)butanamide;

(R)-N-hydroxy-4-(6-((4-(2-hydroxyacetamido)phenyl)ethynyl)-3-oxo-1H-pyrrolo[1,2-c]imidazol-2(3H)-yl)-2-methyl-2-(methylsulfonyl)butanamide;

(R)-4-(6-((4-(1-aminocyclopropyl)phenyl)ethynyl)-3-oxo-1H-pyrrolo[1,2-c]imidazol-2(3H)-yl)-N-hydroxy-2-methyl-2-(methylsulfonyl)butanamide;

(R)-N-hydroxy-4-(6-(5-((1s,3R)-1-hydroxy-3-(hydroxymethyl)cyclobutyl)penta-1,3-diyn-1-yl)-3-oxo-1H-pyrrolo[1,2-c]imidazol-2(3H)-yl)-2-methyl-2-(methylsulfonyl)butanamide;

(phosphonooxy)methyl (R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)carbamate;

(R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl ((phosphonooxy)methyl) carbonate;

(R)-N-hydroxy-4-(6-((2-(2-hydroxypropan-2-yl)thiazol-5-yl)ethynyl)-3-oxo-1H-pyrrolo[1,2-c]imidazol-2(3H)-yl)-2-methyl-2-(methylsulfonyl)butanamide;

(R)-4-(6-((4-((4-aminopiperidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide;

(R)-4-(6-(((1R,2R)-2-fluoro-2-(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(R)-4-(6-(((1S,2S)-2-fluoro-2-(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide, (R)-N-hydroxy-4-(6-((4-((4-hydroxypiperidin-1-yl)methyl)phenyl)ethynyl)-3-oxo-1H-pyrrolo[1,2-c]imidazol-2(3H)-yl)-2-methyl-2-(methylsulfonyl)butanamide;

(R)-4-(6-((4-(4-aminopiperidin-1-yl)phenyl)ethynyl)-3-oxo-1H-pyrrolo[1,2-c]imidazol-2(3H)-yl)-N-hydroxy-2-methyl-2-(methylsulfonyl)butanamide;

(R)-N-hydroxy-2-methyl-4-(6-((4-(methylsulfonamidomethyl)phenyl)ethynyl)-3-oxo-1H-pyrrolo[1,2-c]imidazol-2(3H)-yl)-2-(methylsulfonyl)butanamide;

(R)-N-hydroxy-2-methyl-2-(methylsulfonyl)-4-(6-((1-(oxetan-3-yl)azetidin-3-yl)buta-1,3-diyn-1-yl)-3-oxo-1H-pyrrolo[1,2-c]imidazol-2(3H)-yl)butanamide;

(R)-N-hydroxy-4-(6-(4-(3-hydroxyoxetan-3-yl)phenyl)-3-oxo-1H-pyrrolo[1,2-c]imidazol-2(3H)-yl)-2-methyl-2-(methylsulfonyl)butanamide;

(R)-4-(6-((4-(2-ethoxypropan-2-yl)phenyl)ethynyl)-3-oxo-1H-pyrrolo[1,2-c]imidazol-2(3H)-yl)-N-hydroxy-2-methyl-2-(methylsulfonyl)butanamide;

(R)-4-(6-((2-fluoro-4-(hydroxymethyl)phenyl)ethynyl)-3-oxo-1H-pyrrolo[1,2-c]imidazol-2(3H)-yl)-N-hydroxy-2-methyl-2-(methylsulfonyl)butanamide;

(R)-N-hydroxy-4-(6-(4-(3-hydroxy-3-methylbut-1-yn-1-yl)phenyl)-3-oxo-1H-pyrrolo[1,2-c]imidazol-2(3H)-yl)-2-methyl-2-(methylsulfonyl)butanamide;

(R)-N-hydroxy-4-(6-(5-hydroxy-5-methylhexa-1,3-diyn-1-yl)-3-oxo-1H-pyrrolo[1,2-c]imidazol-2(3H)-yl)-2-methyl-2-(methylsulfonyl)butanamide;

(R)-N-hydroxy-2-methyl-4-(6-((4-((4-methylpiperazin-1-yl)methyl)phenyl)ethynyl)-3-oxo-1H-pyrrolo[1,2-c]imidazol-2(3H)-yl)-2-(methylsulfonyl)butanamide;

(R)-N-hydroxy-4-(6-(4-(2-hydroxyethoxy)phenyl)-3-oxo-1H-pyrrolo[1,2-c]imidazol-2(3H)-yl)-2-methyl-2-(methylsulfonyl)butanamide;

(R)-N-hydroxy-4-(6-(4-(2-methoxyethoxy)phenyl)-3-oxo-1H-pyrrolo[1,2-c]imidazol-2(3H)-yl)-2-methyl-2-(methylsulfonyl)butanamide;

(R)-4-(6-(2-fluoro-4-methylphenyl)-3-oxo-1H-pyrrolo[1,2-c]imidazol-2(3H)-yl)-N-hydroxy-2-methyl-2-(methylsulfonyl)butanamide; or (R)-4-(6-(3-fluoro-4-isopropoxyphenyl)-3-oxo-1H-pyrrolo[1,2-c]imidazol-2(3H)-yl)-N-hydroxy-2-methyl-2-(methylsulfonyl)butanamide;

or a salt thereof.

12. The compound of formula I according to claim 1, or a pharmaceutically acceptable salt thereof, formulated as a medicament.

13. A pharmaceutical composition comprising, as active ingredient, a compound of formula I according to claim 1, or a pharmaceutically acceptable salt thereof, and at least one therapeutically inert excipient.

14. A method of preventing or treating a bacterial infection comprising administering to a subject in need thereof, the compound according to claim 1 or a salt thereof.

15. A method of preventing or treating a Gram-negative bacterial infection comprising administering to a subject in need thereof a compound according to claim 1 or a salt thereof.

* * * * *